(12) United States Patent
Hinuma et al.

(10) Patent No.: US 6,538,107 B1
(45) Date of Patent: Mar. 25, 2003

(54) G PROTEIN COUPLED RECEPTOR PROTEIN PRODUCTION, AND USE THEREOF

(75) Inventors: Shuji Hinuma, Ibaraki (JP); Yasuaki Ito, Ibaraki (JP); Ryo Fujii, Ibaraki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/461,436

(22) Filed: Dec. 14, 1999

Related U.S. Application Data

(62) Division of application No. 09/038,572, filed on Mar. 11, 1998, which is a division of application No. 08/513,974, filed as application No. PCT/JP95/01599 on Aug. 10, 1995, now Pat. No. 6,114,139.

(30) Foreign Application Priority Data

| Sep. 30, 1994 | (JP) | 6-236356 |
| Sep. 30, 1994 | (JP) | 6-236357 |
| Nov. 2, 1994 | (JP) | 6-270017 |
| Dec. 28, 1994 | (JP) | 6-326611 |
| Jan. 20, 1995 | (JP) | 7-007177 |
| Mar. 16, 1995 | (JP) | 7-057186 |
| Apr. 19, 1995 | (JP) | 7-093989 |

(51) Int. Cl.$^7$ .................... C07K 14/435; C07K 14/705
(52) U.S. Cl. ..................................... 530/350
(58) Field of Search ......................... 530/350

*Primary Examiner*—Michael Pak
(74) *Attorney, Agent, or Firm*—David G. Conlin; Edwards & Angell, LLP; Intellectual Property Practice Group

(57) ABSTRACT

DNA primers effective in screening G protein coupled receptor protein-encoding DNA fragments are provided. The primers which are complementary to nucleotide sequences that are in community with (homologous to) the nucleotide sequences encoding amino acid sequences corresponding to or near the first membrane-spanning domain or the sixth membrane-spanning domain each of known various G protein coupled receptor proteins were designed and synthesized. Methods of amplifying G protein coupled receptor protein-encoding DNAs using the above DNA primers, and novel target G protein coupled receptor protein-encoding DNAs are also provided. Screening of DNA libraries can be efficiently carried out. Human pituitary gland or amygdala-derived and mouse pancreas-derived G protein coupled receptor proteins, etc. or salts thereof, partial peptides thereof, DNAs coding for the above G protein coupled receptor proteins, processes for producing the above G protein coupled receptor proteins, methods of determining ligands for the above G protein coupled receptor proteins, methods of screening compounds that inhibit the binding between the ligand and the G protein coupled receptor proteins or screening kits therefor, compounds or salts thereof obtained by the above screening method or the screening kit, pharmaceutical compositions containing the above compounds or salts thereof, and antibodies against the above protein coupled receptor proteins or partial peptides thereof are provided.

1 Claim, 79 Drawing Sheets

FIGURE 1

OLIGODEOXYNUCLEOTIDE SEQUENCE FOR 5' SIDE PRIMER

```
Primer HS-1              CGTGGCCATCCTGGGCAACACCCTG
                            G C GG         CT
                                            G
                                            T
```

```
HTRHR              CCTGGGCATTGTAGGCAACATCATGGT
HUMRANTES          CATTGGCCTGGTTGGAAACATCCTGGT
HSBLR1A            CCTGGGCGTGATCGGCAACGTCCTGGT
HUMSOMAT           GGTGGGGCTGGTGGGCAACGCCCTGGT
RNU02083           AGTGGGCCTCTTCGGAAACTTCCTGGT
U00442             GGTGGGCTTAGTGGGCAATTCCCTGGT
HUMNMBR            CGTGGGCTTGCTGGGCAACATCATGCT
HSHM4              GGTGACCATCATCGGCAACATCCTGGT
RATAADRE01         CTTGCCATCGTGGGCAACATCTTGGT
HUMSSTR3X          GGTGGGCCTGCTGGGTAACTCGCTGGT
HUMC5AAR           GGTGGGAGTGCTGGGCAATGCCCTGGT
HUMRDC1A           CATCGGCATGATTGCCAACTCCGTGGT
HUMOPIODRE         CGTGGCGGTGCTCGGCAACCTCGTGGT
RATA2BAR           GCTGGCAGTGGCGGGCAACGTGCTGGT
```

FIGURE 2

OLIGODEOXYNUCLEOTIDE SEQUENCE FOR 3' SIDE PRIMER

```
Complementary Sequence     TTTGCCATCTGCTGGATGCCCCACAAC
to Primer HS-2                     C         C    TTT C
                                             G        G
                                             T        T HUMSGIR        TTTGCCCTCTGCTGGTTCCCTCTCAAC
    HUMBOMB3S      TTTGCCCTCTGCTGGTTGCCAAATCAC
    S46950         TTTGCCCTCTGCTGGCTGCCCCTACAC
    MUSGPCR        TTTGCCCTCGTCTGGTGCCCTCTCAAC
    S43387         TTTGCCCTTTTATGGATGCCCTACAGG
    RATNEURA       TTTGCCATCTGCTGGCTGCCCTATCAC
    RATA1ARA       TTTGCCCTCAGCTGGCTGCCGCTGCAT
    HUMOPIODRE     TTTGCCATCTGCTGGCTGCCCTATCAC
    HUMNEKAR       TTTGCCATCTGCTGGCTGCCCTACCAC
    RATADENREC     TTTGCCTTGTGCTGGCTGCCTTTGTCC
    HUMSRI1A       TTTGTCATCTGCTGGATGCCTTTCTAC
    S8637154       TTTGCTATCTGCTGGCTGCCCTATCAT
    RNCGPCR        TTTGCCGCCTGCTGGATGCCTTTTACC
    HUMSSTR4Z      TTTGTGCTCTGCTGGATGCCTTTCTAC
    RATGNRHA       TTTGCACACTGGTCGAAGCCAGACAAA
```

FIGURE 3

OLIGODEOXYNUCLEOTIDE SEQUENCE FOR 5' SIDE PRIMER

```
Primer 3A          CTGACCGCTCTIACIACTGACCGATAC
                     T T      GG GT     A C
                                          G Primer 3B          CTGACCGCTCTIACIACTGACCGATAT
                     T T      GG GT     A C
                                          G L11064             CTCACCATGATGAGCGTGGACCGCTAC
L11065             TTGACCATGATGGAGTGTGACCGCTAC
D16349             CTCTGCACCATGAGCGTGGACCGCTAC
X69676             CTGATGCTCGTGAGTATCGACCGCTAC
M35328             CTTACGGCACTGTCAGCTGACAGGTAC
M73482             CTCACTGCCCTCAGCGCCGACAGGTAC
M73481             CTCACGGCGCTCTCGGCAGACAGATAC
L08893             TTAACAATTCTCAGCGCTGACAGATAC
X62933             ATGACCGCCATCGCCGCTGACAGGTAC
X62934             ATGACAACTGTGGCCTTTGACAGATAC
J05189             ATGACAGCCATTGCAGTGGACAGGTAT
M60786             CTCTGCGCTCTCAGTGTGGACAGGTAC
L04672             CTCACCTGCCTCAGCATTGACCGCTAC
X61496             TTGCTGGCTATCACTGTGGACCGCTAC
X59249             TTGCTGGCCATTGCTGTAGACCGATAC
L09249             CTCACCTGCCTCAGCATTGACCGCTAC
P30731             CTGACAGCTATCGCAGTGGACCGCCAC
M31210             CTCCTCGCCATCGCCATTGAGCGCTAT
U03642             CTCACCGGCCTCAGCTTCGACCGCTAC
```

FIGURE 4

OLIGODEOXYNUCLEOTIDE SEQUENCE FOR 5' SIDE PRIMER

Primer 3C        CTCGCCGCTATIAGCATGGACCGITAC
                    G   CC   G T       T Primer 3D        CTCGCCGCTATIAGCATGGACCGITAT
                    G   CC   G T       T L32840           ATTACCTGCATGAGTGTCGATAGGTAC
X64052           CTCACGTGTCTCAGCATCGATCGCTAC
M90065           CTCACGTGTCTCAGCATCGATCGCTAC
M91464           CTCACGTGTCTCAGCATTGATCGATAC
M88096           CTGGTAGCCATCTCTCTGGAGAGATAT
M99418           CTCGTGGCCATAGCCCTGGAGCGATAC
L04473           CTCGTGGCCATCGCACTGGAGCGGTAC
M73969           CTGGCCTGCATCAGTGTGGACCGTTAC
X65858           TTGGCCTGCATCAGTGTGGACCGTTAC
S46665           CTGGCTACCATTAGTGCCGACCGTTTC
M60626           ATCGCCCTCATTGCTCTGGACCGCTGT

FIGURE 5

OLIGODEOXYNUCLEOTIDE SEQUENCE FOR 3' SIDE PRIMER

```
Complementary Sequence    TTTACCITCTGTTGGICGCCCTACCACATC
to Primer 6A                 GT           TC   T   T Complementary Sequence    TTCACCITCTGTTGGICGCCCTACCACATC
to Primer 6B                 GT           TC   T   T
```

```
L11064      TTCGTGGTGTGCTGGGCGCCCATCCACATC
L11065      TTCATCATCTGTTGGACCCCATTCACATC
D16349      TTTATCGTCTGCTGGACCCCCATCCACATC
X69676      TTTGTGCTGTGTTGGGTGCCTTTCCAGATC
M35328      TTTGCCTTCTGCTGGCTCCCCAACCATGTC
M73482      TTCATCTTCTGTTGGTTTCCAAACCACATC
M73481      TTCGCCTTCTGCTGGCTCCCCAATCATGTC
L08893      TTTGCCCTCTGCTGGTTGCCAAATCACCTC
X62933      TTTGCCATCTGCTGGCTGCCCTACCACCTC
X62934      TTCGCCATCTGCTGGCTGCCCTTCCACATC
J05189      TTTGCCATCTGCTGGCTGCCCTATCACGTG
M60786      TTCGCCCTGTGCTGGTTCCCTCTTCACTTA
L04672      TTTGTCATCTGCTGGCTGCCCTACCACGTG
X61496      TTTGCCGCCTGCTGGATGCCTTTTACCCTC
X59249      TTTGCCTTGTGCTGGCTGCCTTTGTCCATC
L09249      TTTGCCATCTGCTGGCTGCCCTACCACGTG
P30731      TTTGCCCTCTGCTGGTTCCCTCTCAACTGC
M31210      TTCATCGCCTGCTGGGCACCGCTCTTCATC
U03642      TTTGCCCTGTGCTGGATGCCCTACCACCTG
```

FIGURE 6

OLIGODEOXYNUCLEOTIDE SEQUENCE FOR 3' SIDE PRIMER

```
Complementary Sequence    TTTTTCITTTGCTGGITTCCCTACCACATG
to Primer 6C                CC T   G C            T T L32840               TTCATCATTTGCTGGCTTCCCTTCCATGTT
      X64052               TTCTTCTTTTCCTGGGTTCCCCACCAAATA
      M90065               TTCTTCTTTTCCTGGGTTCCCCACCAAATA
      M91464               TTTTTCTTTTCCTGGATTCCCCACCAAATA
      M88096               TTCTTCCTGTGCTGGATGCCCATCTTCAGC
      M99418               TTCTTCCTGTGTTGGCTGCCAGTGTACAGC
      L04473               TTTTTCTGTGTTGGTTGCCAGTTTATAGT
      M73969               TTCCTGCTTTGCTGGCTGCCCTACAACCTG
      X65858               TTCCTGCTTTGCTGGCTGCCCTACAACCTG
      S46665               TTCTTTATCTTCTGGCTGCCCTATCAGGTG
      M60626               TTTTTCTCTGCTGGTCCCCATATCAGGTG
```

FIGURE 7

OLIGODEOXYNUCLEOTIDE SEQUENCE FOR 5' SIDE PRIMER

```
Primer T2A           GTCACCAACITGTTCATCCTCAICCTG
                      C          AC          GT T
                                              A HUMGALAREC           ACCACCAACCTGTTCATCCTCAACCTG
RATADRA1B            CCCACCAACTACTTTATCGTCAACCTG
HUMADRB1             ACCACCAACCTGTTCATCCTCAACCTG
RABIL8RSB            GTCACCGACGTCTACCTGCTGAACCTG
HUMOPIODRE           GTCACCAACTCCTTCCTCGTGAACCTG
BTSKR                GTGACCAACTACTTCATCGTCAACCTG
HUMSRI2A             ATCACCAACATTTACATCCTCAACCTG
HUMSSTR3Y            GTCACCAACGTCTACATCCTCAACCTG
HUMGARE              GTCACCAACGCCTTCCTCCTCTCACTG
HUMCCKAR             GTCACCAACATCTTCCTCCTCTCCCTG
HUMSHTR              CCCTCCAACTACCTGATCGTGTCCCTG
HUMD1B               ATGACCAACGTCTTCATCGTGTCTCTG
HUM5HT1E             CCTGCCAACTACCTAATCTGTTCTCTG
HUMD4C               CCCACCAACTCCTTCATCGTGAGCCTG
MMSERO               GCCACCAACTATTCCTGATGTCACTT
RATADRA1A            GTCACCAACTATTTCATCGTGAACCTG
S57565               CTGACCAATTGCTTCATTGTGTCCCTG
```

FIGURE 8

COMPLEMENTARY OLIGODEOXYNUCLEOTIDE SEQUENCE TO 3' SIDE PRIMER

```
Complementary Sequence    AACCCCITCITCTATTGCTTTITCICT
to Primer T7A                  T  T       C C   C  G G HUMGALAREC                AATCCTATCATTTATGCATTTCTCTCT
RATA1ADREC                AACCCCATCGTCTATGCCTTCCGGATC
PIGA2R                    AATCCTCTCTTTTATGGCTTTCTGGGG
RAT5HTRTC                 AACCCTATCATCTACCCGCTCTTTATG
S58541                    AACCCCATCATTTATGCCTTTAATGCT
HUMGRPR                   AACCCCTTTGCCCTCTACCTGCTGAGC
MUSGRPBOM                 AACCCCTTTGCTCTTTATCTGCTGAGC
RRVT1AIIR                 AACCCTCTGTTCTACGGCTTTCTGGGG
HUMADRB1                  AACCCCATCATCTACTGCCGCAGCCCC
HSHM4                     AACCCCGTGTGCTATGCTCTGTGCAAC
HUMGARE                   AACCCCCTGGTCTACTGCTTCATGCAC
RATCCKAR                  AACCCCATCATCTATTGCTTCATGAAC
S59749                    AATCCCATGCTCTACACCTTCGCTGGC
HUMSST28A                 AACCCCGTCCTCTACGGCTTCCTCTCG
RNGPROCR                  AACCCCATCCTCTACGGCTTCCTCTCC
MUSSSRI1A                 AACCCCATACTCTACGGCTTCCTGTCG
HUMA1AADR                 AACCCGCTCATCTACCCCTGTTCCAGC
S66181                    AACCCGGTTCTCTACGCCTTCCTGGAC
HUMSSTR3Y                 AACCCCATCCTTTATGGCTTCCTCTCC
```

FIGURE 9

OLIGODEOXYNUCLEOTIDE SEQUENCE FOR 5' SIDE PRIMER

```
Primer TM1-A2         TGITGGTTATIGGIGTTGTIGGIAA
                        CC GC    C    G MUSBB2R               TGGTGGTGGTGGTGGTGGTGGGCAA
BTSKR                 TGGTGCTGGTGGCTGTGATGGGCAA
BOVEETBR              TGTTCGTGCTGGGCATCATCGGAAA
HUMNEUYREC            TGATCATTCTTGGTGTCTCTGGAAA
MMSUBKREC             TGGTGCTGGTGGCTGTAACAGGCAA
HUMPGE2R              TGTTCATCTTCGGGGTGGTGGGCAA
HUMPIR                TGTTCGTGGCCGGTGTGGTGGGCAA
HSU11053              TGTTCGTCGTGGGCTTGGTGGGCAA
RRMC3RA               TGGTGATCCTGGCTGTGGTGAGGAA
HUMMR                 TGGTTATCCTGGCCGTGGTCAGGAA
MUSGRPBOM             TCATCGTGATAGGTCTTATTGGCAA
RATCHOLREC            TCTTTCTGATGAGTGTTGGCGGAAA
RATCCKAR              TATTCCTTCTCAGTGTGCGGGGGAA
```

FIGURE 10

COMPLEMENTARY OLIGODEOXYNUCLEOTIDE SEQUENCE TO 3' SIDE PRIMER

```
Complementary Sequence    GCCATIACCITGGACAGATACCGAT
to Primer TM3-B2              A  T A      C G   A G HUMCCKR                GCCATCGCACTGGAGCGGTACAG
   HUMCCKBGR              GCCATCGCACTGGAGCGGTACAG
   MMGMC5R                GCCATTGCGGTGGACAGGTACA
   HUMV2R                 GCCATGACGCTGGACCGCCACCG
   RATNEURA               GCCATTGCAGTGGACAGGTA
   DOGGSTRN               GCCATCGCCCTGGAGCGATACAG
   RAT5HT5A               GCAATAGCTTTGGACCGCTACTGGT
   MUSALP2ADA             GCCATTAGTCTGGACCGCTACTGGT
   HUMADORA1X             GCAATTGCTGTGGACCGCTACC
   HUMOPIODRE             GCCATCGCGGTGGACAGATACA
   MUSGRPBOM              GCACTGTCAGCTGACAGGTACAAA
   RATCCKAR               GCCATCTCTCTGGAGAGATATGG
   HSTRHREC               GCCTTTACCATTGAGAGGTACATA
```

FIGURE 11

OLIGODEOXYNUCLEOTIDE SEQUENCE FOR 5' SIDE PRIMER

```
Primer TM3-C2              CATGGCCGTGGAGAGITACITGGC
                              TT  C     C     T  A HUMNK3R                    CATTGCGGTGGACAGGTATATGGC
HSMRNAOXY                  CATGTCCCTGGACCGCTGCCTGGC
S68242                     CATATCGCTGGAGAGATACGGAGC
CFGPCR4                    CATCGCTCTGGACAGGTACTGGGC
MMSUBPREC                      TGGCCTTTGACAGATACATGGC
HUMOPIODRE                .CATCGCGGTGGACAGATACATGGC
HUMGALAREC                  ATGTCCGTGGACCGCTACGTGGC
HSS31G                     CATTGCCCTGGACAGGTACTGGGC
HUMARB3A                   CCTGGCCGTGGACCGCTACCTGGC
HUMHPR                     CATGGCCGTGGAGCGCTGCCTGGC
RATCCKAR                   CATCTCTCTGGAGAGATATGGCGC
```

FIGURE 12

COMPLEMENTARY OLIGODEOXYNUCLEOTIDE SEQUENCE TO 3' SIDE PRIMER

```
Complementary Sequence    TTTGCCITCTGCTGGATCCCCAAC
to Primer TM6-E2             C    G       C G   TT HUMNEKAR              TTTGCCATCTGCTGGCTGCCCTAC
   HUMSUBPRA             TTCGCCATCTGCTGGCTGCCCTTC
   RATSKR                TTTGCCATCTGCTGGCTGCCCTAC
   MUSGRPBOM             TTTGCCTTCTGCTGGCTCCCCAAC
   HUMOPIODRE            TTTGCCATCTGCTGGCTGCCCTA
   HUMA2XXX              TTTGCCCTCTGCTGGCTGCCCCT
   HUMADRBR              TTCACCCTCTGCTGGCTGCCCTTC
   CFGPCR8               TTCGCCCCTCTGTGGCTGCCCCT
   HUMETSR               TTTGCCCTCTGCTGGCTTCCCCT
   MMNPY1CDS             TTCGCCGTCTGCTGGCTGCCCCT
   HSMRNAOXY             TTCATCGTGTGCTGGACGCCTTTC
   RATCCKAR              TTCTTCCTGTGCTGGATGCCCATC
```

FIGURE 13

OLIGODEOXYNUCLEOTIDE SEQUENCE FOR 5' SIDE PRIMER

Primer TM2F18          ARYYTIGCIITIGCNGAY

| | |
|---|---|
| HUMTSHX | AACCTGGCCTTTGCGGAT |
| HUMNEKAR | AATCTGGCGCTGGCTGAC |
| HUMFMLP | AACCTGGCCGTGGCTGAC |
| HUMINTLEU8 | AACCTAGCCTTGGCCGAC |
| HUMA1AADR | AACCTGGCCGTGGCCGAC |
| HUMIL8RA | AACCTGGCCTTGGCCGAC |
| HSDD2 | AGCCTCGCAGTGGCCGAC |
| HUMANTIR | AATTTAGCACTGGCTGAC |
| HUMSOMAT | AACCTGGCCGTAGCCGAC |
| HUMEL4REC | AGCTTGGCTGTGGCTGAT |
| HSTRHREC | AGCCTGGCAGTAGCTGAT |
| HSU07882 | AACCTGGCCTTAGCCGAT |

( R = A or G, Y = C or T, N = A, C, G or T, and
  I = Inosine )

FIGURE 14

COMPLEMENTARY OLIGODEOXYNUCLEOTIDE SEQUENCE TO 3' SIDE PRIMER

Complementary Sequence      TTYNYNNTNTGYTGGITICCI
to Primer TM6R21

| | |
|---|---|
| HSBAR | TTCACCCTCTGCTGGCTGCCC |
| HUMNEKAR | TTTGCCATCTGCTGGCTGCCC |
| HUMETN1R | TTTGCTCTTTGCTGGTTCCCT |
| HUMHISH2R | TTCATCATCTGCTGGTTTCCC |
| HUMA1AADR | TTCGTGCTCTGCTGGTTCCCT |
| HUMIL8RA | TTCCTGCTTTGCTGGCTGCCC |
| HUMNMBR | TTCATCTTCTGTTGGTTTCCT |
| HUMNKIRX | TTCGCCATCTGCTGGCTGCCC |
| HUMSUBPRA | TTCGCCATCTGCTGGCTGCCC |
| HUM5HT1DA | TTTATCATCTGCTGGCTGCCC |
| HUMPFPR2A | TTCTTCATCTGTTGGTTTCCC |
| HSDD2 | TTCATCATCTGCTGGCTGCCC |
| HUMNEUYREC | TTTGCAGTCTGCTGGCTCCCT |
| HUM2XXX | TTTGCCCTCTGCTGGCTGCCC |
| HUMBK2A | TTCATCATCTGCTGGCTGCCC |
| HUMFMLPX | TTCTTCATCTGTTGGTTTCCC |
| HUMSSTR3X | TTCGTGCTCTGCTGGATGCCC |
| HUMCCKR | TTTTTTCTGTGTTGGTTGCCA |
| HSNEURA | TTTGTGGTCTGCTGGCTGCCC |

( Y = C or T, N = A, C, G or T, and I = Inosine )

FIGURE 15

OLIGODEOXYNUCLEOTIDE SEQUENCE FOR 5' SIDE PRIMER

```
Primer S3A          GCCTGITIAIGATGAGTGTGGAIAGIT
                        C    G C    TC         C HUMGALAREC          CCCTGGCCGCGATGTCCGTGGACCGCT
S70057              GCCTCGTGGCCATCGCACTGGAGCGGT
S67127              ACCTCTGCGCTCTTAGTGTTGACAGGT
S44866              GTCTATGTGCTCTGAGTATTGACAGAT
HUMC5AAR            TCCTGGCCACCATCAGCGCCGACCGCT
HUMANTIR            TACTCACGTGTCTCAGCATTGATCGAT
HUMBK2A             TCCTGATGCTGGTGAGCATCGACCGCT
HSNEURA             ACGTGGCCAGCCTGAGTGTGGAGCGCT
HUMGRPR             CACTCACGGCGCTCTCGGCAGACAGAT
HUMFSRS             GCCTGACAGTCATGAGCGTGGACCGCT
HUMIL8RA            TGTTGGCCTGCATCAGTGTGGACCGTT
HUMNEKAR            CCATGACCGCCATTGCTGCCGACAGGT
```

FIGURE 16

COMPLEMENTARY OLIGODEOXYNUCLEOTIDE SEQUENCE TO 3' SIDE PRIMER

```
Complementary Sequence      TGGITICCCTACCACITIATCAICATC
to Primer S6A                  T   T    GG   GT HUMGALAREC            TGGCTGCCGCACCACATCATCCATCTC
     S70057                TGGTTGCCAGTTTATAGTGCCAACACG
     S67127                TGGTTCCCTCTTCATTTAAGCCGTATA
     S44866                TGGCTTCCCCTTCACCTCAGCAGGATT
     HUMC5AAR              TGGTTGCCCTACCAGGTGACGGGGATA
     HUMANTIR              TGGATTCCCCACCAAATATTCACTTTT
     HUMBK2A               TGGCTGCCCTTCCAGATCAGCACCTTC
     HSNEURA               TGGACTCCGTTCCTCTATGACTTCTAC
     HUMGRPR               TGGCTCCCCAATCATGTCATCTACCTG
     HUMFSRS               TGGCTGCCCTTCTTCACCGTCAACATC
     HUMIL8RA              TGGCTGCCCTACAACCTGGTCCTGCTG
     HUMNEKAR              TGGCTGCCCTACCACCTCTACTTCATC
```

FIGURE 18

```
                   10        20        30        40        50
A58-T7-2   GTGGGCATGGTGGGCAACCCCCTGGTCATCTTCGTGATCCTTCGCTACGC
           ::::::::::::::::::::::::::::::::::::::::::::::::::
X::::
HUMSOMAT   GTGGGGCTGGTGGGCAACGCCCTGGTCATCTTCGTGATCCTTCGCTACGC
                   285       295       305       315       325
                   60        70        80        90        100

A58-T7-2   CAAGATGAAGACGGCTACCAACATCTACCTGCTCAACCTGGCCGTAGCCG
           ::::::::::::::::::::::::::::::::::::::::::::::::::
HUMSOMAT   CAAGATGAAGACGGCTACCAACATCTACCTGCTCAACCTGGCCGTAGCCG
                   335       345       355       365       375
                   110       120       130       140       150

A58-T7-2   ACGAGCTCTTCATGCTGAGCGTGCCCTTCGTGGCCTCGTGCCGCCCCTG
           ::::::::::::::::::::::::::::::::::::::::::::::::::
HUMSOMAT   ACGAGCTCTTCATGCTGAGCGTGCCCTTCGTGGCCTCGTGCCGCCCCTG
                   385       395       405       415       425
                   160       170       180       190       200

A58-T7-2   CGCCACTGGCCCTTCGGCTCCGTGCTGTGCCGGGTCTCAGCGTCGA
           ::::::::::::::::::::::::::::::::::::::::::::::::::
HUMSOMAT   CGCCACTGGCCCTTCGGCTCCGTGCTGTGCCGGGTCTCAGCGTCGA
                   435       445       455       465       475
                   210       220       230       240

A58-T7-2   CGGCCTCAACATGTTCACCAGCGTCTTCTGTCTCACCGTGCTCAGCGT
           ::::::::::::::::::::::::::::::::::::::::::::::X
HUMSOMAT   CGGCCTCAACATGTTCACCAGCGTCTTCTGTCTCACCGTGCTCAGCGT
                   485       495       505       515
```

FIGURE 19

```
                    10        20        30        40        50
A58-SP6   CAGTGTCCACACCCGGCCTGTCGGCAGTCTTCGTGTTCTACACTTTCCT
          X::: :::::::::::::::::::::::::::::::::::::::::::::
HUMSOMATA CAGTGGCCACACCCGGCCTGTCGGCAGTCTTCGTGTTCTACACTTTCCT
              706       716       726       736       746
               60        70        80        90       100

A58-SP6   GCTGGGCTTCCTGCTGTCCGTGCTGTCCATTGGCCTGTGCTACCTGCTCA
          :::::::::::::::::::::: :::::: :::::::::::::::::::
HUMSOMATA GCTGGGCTTCCTGCTGCCCGTGCCATTGGCCTGTGCTACCTGCTCA
              756       766       776       786       796
              110       120       130       140       150

A58-SP6   TCGTGGGCAAGATGCGCGCCCGTGTCCCTGCGCGCTGGCTGGCAGCAGCGC
          ::::::::::::::::::::::::::::::::::::::::::::::::::
HUMSOMATA TCGTGGGCAAGATGCGCGCCCGTGTCCCTGCGCGCTGGCTGGCAGCAGCGC
              806       816       826       836       846
              160       170       180       190       200

A58-SP6   AGGCGCTCGGAGAAGAAATCACCAGGCTGGTGCTGATGTCGTGATGGTCGT
          ::::::::::::::::::::::::::::::::::::::::::::::::::
HUMSOMATA AGGCGCTCGGAGAAGAAATCACCAGGCTGGTGCTGATGTCGTGATGGTCGT
              856       866       876       886       896
              210       220

A58-SP6   CTTTGCCCCTCTGCTGGTTGCCTCTCCAC
          ::: :::::: :::: :: ::  ::::X
HUMSOMATA CTTTGTGCTCTGCTGGATGCCTTTCTAC
              906       916
```

FIGURE 20

```
                   10         20         30         40         50
57-A-2     GTGGGCATGCTGGGCAACCTCCTGGAAGGCAGTCGCCGAGGTGGCCGGTT
           X:::       ::::: ::    : :::::::::::::::::::::::::::::
HUMDRD5A   GTGGCGCTGCTGGTCATGC-CCTGGAAGGCAGTCGCCGAGGTGGCCGGTT
               424        434        444        454
                   60         70         80         90        100
57-A-2     ACTGGCCCTTTGGAGCGTTCTGCGACGTCTGGGTGGCCTTCGACATCATG
           ::::::::::::::::::::::::::::::::::::::::::::::::::
HUMDRD5A   ACTGGCCCTTTGGAGCGTTCTGCGACGTCTGGGTGGCCTTCGACATCATG
               464        474        484        494        504
                  110        120        130        140        150
57-A-2     TGCTCCACTGCCTCCATCCTGAACCTGTGCGTCATCAGCGTGGACCGCTA
           ::::::::::::::::::::::::::::::::::::::::::::::::::
HUMDRD5A   TGCTCCACTGCCTCCATCCTGAACCTGTGCGTCATCAGCGTGGACCGCTA
               514        524        534        544        554
                  160        170        180        190        200
57-A-2     CTGGGCCATCTCCAGGCCCTTCCGCTACAAGCGCAAGATGACTCAGCGCA
           ::::::::::::::::::::::::::::::::::::::::::::::::::
HUMDRD5A   CTGGGCCATCTCCAGGCCCTTCCGCTACAAGCGCAAGATGACTCAGCGCA
               564        574        584        594        604
                  210        220        230        240        250
57-A-2     TGGCCTTGGTCATGGTCGGCCTGGCATGGACCTTGTCCATCCTCATCTCC
           ::::::::::::::::::::::::::::::::::::::::::::::::::
HUMDRD5A   TGGCCTTGGTCATGGTCGGCCTGGCATGGACCTTGTCCATCCTCATCTCC
               614        624        634        644        654
                  260        270        280        290        300
57-A-2     TTCATTCCGGTCCAGGTCAACTGGGACAGGGACCAGGCGGGCTCTTGGGG
           :::::::::::::::::   :::::::::: ::::::::::::: :::::::::
HUMDRD5A   TTCATTCCGGTCCAGCTCAACTGGCACAGGGACCAGGCGGCCTCTTGGGG
               664        674        684        694        704
                  310
57-A-2     GGGGCTGGACCTGCCAAA
           :::::::::::::::::X
HUMDRD5A   CGGGCTGGACCTGCCAAA
               714        724
```

FIGURE 21

```
                        10         20         30         40         50
B54       GTGGGCATCGTGGGCAACATCCTGGTCATATTCGTGATCCTACGCTATGC
          ::::::  ::  :::  :::::::::::::::::::::::::::::::::
RNU04738  X:::::::GTGGGCCTGGTAGGAAACGCCCTGGTCATATTCGTGATCCTACGCTATGC
          233        243        253        263        273
          60         70         80         90         100

B54       CAAAATGAAGACAGCCCACCAACATCTACCTGCTCAACCTGGCCGTCGCTG
          ::::::::::::::::::::::::::::::::::::::::::::::::::
RNU04738  CAAAATGAAGACAGCCCACCAACATCTACCTGCTCAACCTGGCCGTCGCTG
          283        293        303        313        323
          110        120        130        140        150

B54       ATGAGCTCTTCATGCTCAGTGTGCCATTTGTGGCCTCGGCGGCTGCCCTG
          ::::::::::::::::::::::::::::::::::::::::::::::::::
RNU04738  ATGAGCTCTTCATGCTCAGTGTGCCATTTGTGGCCTCGGCGGCTGCCCTG
          333        343        353        363        373
          160        170        180

B54       CGCCACTGGCCGTTCGGGGCGGTGCTGTGCCGC
          ::::::::::::::::::::::::::::::::X
RNU04738  CGCCACTGGCCGTTCGGGGCGGTGCTGTGCCGC
          383        393        403
```

FIGURE 22

```
                                                                                 54
5' GTG GGC ATG GTG GGC AAC GTC CTG GTG CTG GTG ATC GCG CGG GTG CGC CGG
   Val Gly Met Val Gly Asn Val Leu Val Leu Val Ile Ala Arg Val Arg Arg

108
   CTG CAC AAC GTG ACG AAC TTC CTC ATC GGC AAC CTG GCC TTG TCC GAC GTG CTC
   Leu His Asn Val Thr Asn Phe Leu Ile Gly Asn Leu Ala Leu Ser Asp Val Leu

162
   ATG TGC ACC GCC TGC GTG CCG CTC ACG CTG TAT GCC TTC CTG GAG CCA CGC GGC
   Met Cys Thr Ala Cys Val Pro Leu Thr Leu Tyr Ala Phe Leu Glu Pro Arg Gly

216
   TGG GTG TTC GGC GGC CTG GGC CTG TGC CAC CTG TTC TTC CTG CAG CCG GTC ACC
   Trp Val Phe Gly Gly Leu Gly Leu Cys His Leu Phe Phe Leu Gln Pro Val Thr

270
   GTC TAT GTG TCG TTC ACG GTG TTC ACG CTC ACC ATC GAA GTG GAC CGG TAC GTC GGT
   Val Tyr Val Ser Val Phe Thr Val Phe Thr Leu Thr Ile Glu Val Asp Arg Tyr Val Gly

297
   GCT GGT GCA CCC GCT GAG GCG GGG CAT 3'
   Ala Gly Ala Pro Ala Glu Ala Gly His
```

FIGURE 23

```
                9            18           27           36           45           54
5' GGC CTG CTG GTC ACC TAC CTC CCT CTG GTC ATC CTC CTG TCT TAC
   --- --- --- --- --- --- --- --- --- --- --- --- --- --- ---
   Gly Leu Leu Val Thr Tyr Leu Leu Pro Leu Val Ile Leu Leu Ser Tyr 63           72           81           90           99          108
   GTC CGG GTG TCA GTG AAG CTC CGC AAC CCG GTG CCG GTC TGC GTG ACC CAG
   --- --- --- --- --- --- --- --- --- --- --- --- --- --- --- --- ---
   Val Arg Val Ser Val Lys Leu Arg Asn Pro Val Pro Val Cys Val Thr Gln 117          126          135          144          153          162
   AGC CAG GCC GAC TGG GAC CGC GCT CGG CGC CGG ACC TTC TGC TTG CTG GTG
   --- --- --- --- --- --- --- --- --- --- --- --- --- --- --- --- ---
   Ser Gln Ala Asp Trp Asp Arg Ala Arg Arg Arg Thr Phe Cys Leu Leu Val 171          180          189          198
   GTG GTC GTG GTG TTT GCC ATC TGC TGG TTG CCT TAC TAC 3'
   --- --- --- --- --- --- --- --- --- --- --- --- ---
   Val Val Val Val Phe Ala Ile Cys Trp Leu Pro Tyr Tyr
```

FIGURE 26

```
                   10          20          30          40          50
p19P2     1  VGMVGNVLLV LVIARVRRLH NVTNFLIGNL ALSDVLMCTA CVPLTLAYAF   50
S12863    1  LGVSGNLALI IIILKQKEMR NVTNILIVNL SFSDLLVAVM CLPFTFVYTL   50

60          70          80          90         100
p19P2    51  EPRGWVFGGG LCHLVFFLQP VTVYYSVFTL TTIEVDRYVG AGAPAEAGH   100
S12863   51  MDH-WVFGET MCKLNPFVQC VSITVSIFSL VLIAVERHQL IINPRGWRPN  100

110         120         130         140         150
p19P2   101  NRHAYIGITV IWVLAVASSL PFVIYQILTD EPFQNVSLAA FKDKYVCFDK   150
S12863  101

160         170         180         190         200
p19P2   151  GLLLV TYLLPLLVIL LS------Y VRSVKLRNPV VPVCVTQSQA         200
S12863  151  FPSDSHRLSY TTLLLVLQYF GPLCFIFICM FKIYIRLKRR NNMMDKIRDS   200

210         220         230         240         250
p19P2   201  DWDRARRRRT FCLLVVVVV FAICWLPYY. .......... ..........   250
S12863  201  KYRSSETKRI NVMLLSIVVA FAVCWLPLT. .......... ..........   250
```

FIGURE 27

```
            9              18             27             36             45             54
5'  GTG GGC ATG GTG GGC AAC ATC CTG CTG GTG CTG GTG ATC GCG CGG GTG CGC CGG
    --- --- --- --- --- --- --- --- --- --- --- --- --- --- --- --- --- ---
    Val Gly Met Val Gly Asn Ile Leu Leu Val Leu Val Ile Ala Arg Val Arg Arg 63             72             81             90             99            108
    CTG TAC AAC GTG ACG AAT TTC CTC ATC GGC AAC CTG GCC TTG TCC GAC GTG CTC
    --- --- --- --- --- --- --- --- --- --- --- --- --- --- --- --- --- ---
    Leu Tyr Asn Val Thr Asn Phe Leu Ile Gly Asn Leu Ala Leu Ser Asp Val Leu 117            126            135            144            153            162
    ATG TGC ACC GCC TGC GTG CCG CTC ACG CTG GCC TAT GCC TTC GAG CCA CGC GGC
    --- --- --- --- --- --- --- --- --- --- --- --- --- --- --- --- --- ---
    Met Cys Thr Ala Cys Val Pro Leu Thr Leu Ala Tyr Ala Phe Glu Pro Arg Gly 171            180            189            198            207            216
    TGG GTG TTC GGC GGC GGC CTG TGC CAC CTG GTC TTC TTC CTG CAG GCG GTC ACC
    --- --- --- --- --- --- --- --- --- --- --- --- --- --- --- --- --- ---
    Trp Val Phe Gly Gly Gly Leu Cys His Leu Val Phe Phe Leu Gln Ala Val Thr 225            234            243            252            261            270
    GTC TAT GTG TCG GTG TTC ACG CTC ACC ACC ATC GCA GTG GAC CGC TAC GTC GTG
    --- --- --- --- --- --- --- --- --- --- --- --- --- --- --- --- --- ---
    Val Tyr Val Ser Val Phe Thr Leu Thr Thr Ile Ala Val Asp Arg Tyr Val Val 279            288            297            306            315            324
    CTG GTG CAC CCG CTG AGG CGG CGC ATC TCG CTG CGC CTC AGC GCC TAC GCT GTG
    --- --- --- --- --- --- --- --- --- --- --- --- --- --- --- --- --- ---
    Leu Val His Pro Leu Arg Arg Arg Ile Ser Leu Arg Leu Ser Ala Tyr Ala Val 333            342            351            360            369            378
    CTG GCC ATC TGG GTG CTG TCC GCG GTG CTG GCG CTG CCC GCC GCC GTG CAC ACC
    --- --- --- --- --- --- --- --- --- --- --- --- --- --- --- --- --- ---
    Leu Ala Ile Trp Val Leu Ser Ala Val Leu Ala Leu Pro Ala Ala Val His Thr 387            396            405            414            423            432
    TAT CAC GTG GAG CTC AAG CCG CAC GAC GTG CGC CTC TGC GAG GAG TTC TGG GGC
    --- --- --- --- --- --- --- --- --- --- --- --- --- --- --- --- --- ---
    Tyr His Val Glu Leu Lys Pro His Asp Val Arg Leu Cys Glu Glu Phe Trp Gly 441            450            459            468            477            486
    TCC CAG GAG CGC CAG CGC CAG CTC TAC GCC TGG GGG CTG CTG CTG GTC ACC TAC
    --- --- --- --- --- --- --- --- --- --- --- --- --- --- --- --- --- ---
    Ser Gln Glu Arg Gln Arg Gln Leu Tyr Ala Trp Gly Leu Leu Leu Val Thr Tyr 495            504            513            522            531            540
    CTG CTC CCT CTG CTG GTC ATC CTC CTG TCT TAC GCC CGG GTG TCA GTG AAG CTC
    --- --- --- --- --- --- --- --- --- --- --- --- --- --- --- --- --- ---
    Leu Leu Pro Leu Leu Val Ile Leu Leu Ser Tyr Ala Arg Val Ser Val Lys Leu 549            558            567            576            585            594
    CGC AAC CGC GTG GTG CCG GGC CGC GTG ACC CAG AGC CAG GCC GAC TGG GAC CGC
    --- --- --- --- --- --- --- --- --- --- --- --- --- --- --- --- --- ---
    Arg Asn Arg Val Val Pro Gly Arg Val Thr Gln Ser Gln Ala Asp Trp Asp Arg 603            612            621            630            639            648
    GCT CGG CGC CGG CGC ACC TTC TGC TTG CTG GTG GTG GTC GTG GTG TTC ACC
    --- --- --- --- --- --- --- --- --- --- --- --- --- --- --- --- --- ---
    Ala Arg Arg Arg Arg Thr Phe Cys Leu Leu Val Val Val Val Val Val Phe Thr 657            666
    CTC TGC TGG CTG CCC TTC TTC 3'
    --- --- --- --- --- --- ---
    Leu Cys Trp Leu Pro Phe Phe
```

FIGURE 29

```
      10           19        28        37        46        55
5' GTG GGC ATG CTG GGC AAC GCC CTG GTC TGT CAT ATC TTC AAG AAC CAG CGA
                               Val Cys His Val Ile Phe Lys Asn Gln Arg 64        73        82        91       100       109
ATG CAC TCG GCC ACC AGC CTC TTC ATC GTC AAC CTG GCA GTT GCC GAC ATA ATG
Met His Ser Ala Thr Ser Leu Phe Ile Val Asn Leu Ala Val Ala Asp Ile Met 118       127       136       145       154       163
ATC ACG CTG CTC AAC ACC CCC TTC ACT TTG GTT CGC TTT GTG AAC AGC ACA TGG
Ile Thr Leu Leu Asn Thr Pro Phe Thr Leu Val Arg Phe Val Asn Ser Thr Trp 172       181       190       199       208       217
ATA TTT GGG AAG GGC ATG TGC CAT GTC AGC CGC TTT GCC CAG TAC TCA CTG
Ile Phe Gly Lys Gly Met Cys His Val Ser Arg Phe Ala Gln Tyr Cys Ser Leu 226       235
CAC GTC TCA GCA CTG ACA 3'
His Val Ser Ala Leu Thr
```

FIGURE 30

```
5' GAG CCA GCT GAC CTC TTC TGG AAG AAC CTG GAC TTG CCC ACC TTC ATC CTG CTC      54
    Glu Pro Ala Asp Leu Phe Trp Lys Asn Leu Asp Leu Pro Thr Phe Ile Leu Leu

AAC ATC CTG CCC CTC ATC ATC TCT GTG GCC TAC GTT CGT GTG ACC AAG AAA         108
    Asn Ile Leu Pro Leu Ile Ile Ser Val Ala Tyr Val Arg Val Thr Lys Lys

CTG TGT TGT AAT ATG ATT GTC GAT GTG ACC ACA GAG CAG TAC TTT GCC CTG         162
    Leu Trp Leu Cys Asn Met Ile Val Asp Val Thr Thr Glu Gln Tyr Phe Ala Leu

CGG CCC AAA AAG AAG ACC ATC AAG ATG TTG ATG CTG GTG GTA GTC CTC TTT         216
    Arg Pro Lys Lys Lys Thr Ile Lys Met Leu Met Leu Val Val Leu Phe

GCC CTC TGC TGG TTG CCT CTC GAC 3'                                          234
    Ala Leu Cys Trp Leu Pro Leu Asp
```

FIGURE 33

```
            10         20         30         40         50
p63A2    1  VCHVIFKNQR MHSATSLFTV NLAVADIMIT LLNTPFFTLVR FVNSTWIFGK   50
P30731   1  VCHVIFKNQR MHSATSLFTV NLAVADIMIT LLNTPFFTLVR FVNSTWVFGK   50

60         70         80         90        100
p63A2   51  GMCHVSRFAQ YCSLHVSALT LTAIAVDRHQ VIMHPLKPRI SITKGVIYIA  100
P30731  51  GMCHVSRFAQ YCSLHVSALT LTAIAVDRHQ VIMHPLKPRI SITKGVIYIA  100

110        120        130        140        150
p63A2  101  VIWWMATFFS LPHAICQKLF TFKYSEDIVR SLCLPDFPEP ADLFWKNIDE  150
P30731 101  VIWWMATFFS LPHAICQKLF TFKYSEDIVR SLCLPDFPEP ADLFWKYLDL  150

160        170        180        190        200
p63A2  151  PTFTLINILP ILITSVAYVR VTKKLMLCNM IVDVTTEQYF ALRPKKKTI   200
P30731  151  ATFILLYLIP LFIISVAYAR VAKKLMLCNF IGDVTTEQYL ALRRKKKTTV  200

210        220        230        240        250
p63A2  201  KMEMIVVVL. .......... .......... .......... ..........  250
P30731 201  KMLVHVVVL. .......... .......... .......... ..........  250
```

FIGURE 34

```
   1 CATCGTCAAGCAGATGAAGATCATCCACGAGGATGGCTACTCCGAGGGCCAGCAGAAATT      60
   1                                                                   1

61 CTGCCCCTTCTTCCCGCGAGTGCTTTCCCGCTCTCCAAACCCCACTCCCAGGTGGCCATG     120
   1                                                            Met     1

121 GCCTCATCGACCACTCGGGGCCCCAGGGTTTCTGACTTATTTTCTGGGCTGCCGCCGGCG     180
   1 AlaSerSerThrThrArgGlyProArgValSerAspLeuPheSerGlyLeuProProAla      21

181 GTCACAACTCCCGCCAACCAGAGCGCAGAGGCCTCGGCGGGCAACGGGTCGGTGGCTGGC     240
  21 ValThrThrProAlaAsnGlnSerAlaGluAlaSerAlaGlyAsnGlySerValAlaGly      41

241 GCGGACGCTCCAGCCGTCACGCCCTTCCAGAGCCTGCAGCTGGTGCATCAGCTGAAGGGG     300
  41 AlaAspAlaProAlaValThrProPheGlnSerLeuGlnLeuValHisGlnLeuLysGly      61

301 CTGATCGTGCTGCTCTACAGCGTCGTGGTGGTCGTGGGGCTGGTGGGCAACTGCCTGCTG     360
  61 LeuIleValLeuLeuTyrSerValValValValGlyLeuValGlyAsnCysLeuLeu        81

361 GTGCTGGTGATCGCGGGTGCGCCGGCTGCACAACGTGACGAACTTCCTCATCGGCAAC       420
  81 ValLeuValIleAlaArgValArgArgLeuHisAsnValThrAsnPheLeuIleGlyAsn    101

421 CTGGCCTTGTCCGACGTGCTCATGTGCACCGCCTGCGTGCCGCTCACGCTGGCCTATGCC     480
 101 LeuAlaLeuSerAspValLeuMetCysThrAlaCysValProLeuThrLeuAlaTyrAla    121

481 TTCGAGCCACGCGGCTGGGTGTTCGGCGGCGGCCTGTGCCACCTGGTCTTCTTCCTGCAG     540
 121 PheGluProArgGlyTrpValPheGlyGlyGlyLeuCysHisLeuValPhePheLeuGln    141

541 CCGGTCACCGTCTATGTGTCGGTGTTCACGCTCACCACCATCGCAGTGGACCGCTACGTC     600
 141 ProValThrValTyrValSerValPheThrLeuThrThrIleAlaValAspArgTyrVal    161

601 GTGCTGGTGCACCCGCTGAGGCGGCGCATCTCGCTGCGCCTCAGCGCCTACGCTGTGCTG     660
 161 ValLeuValHisProLeuArgArgArgIleSerLeuArgLeuSerAlaTyrAlaValLeu    181

661 GCCATCTGGGCGCTGTCCGCGGTGCTGGCGCTGCCCGCCGCCGTGCACACCTATCACGTG     720
 181 AlaIleTrpAlaLeuSerAlaValLeuAlaLeuProAlaAlaValHisThrTyrHisVal    201

721 GAGCTCAAGCCGCACGACGTGCGCCTCTGCGAGGAGTTCTGGGGCTCCCAGGAGCGCCAG     780
 201 GluLeuLysProHisAspValArgLeuCysGluGluPheTrpGlySerGlnGluArgGln    221

781 CGCCAGCTCTACGCCTGGGGGCTGCTGCTGGTCACCTACCTGCTCCCTCTGCTGGTCATC     840
 221 ArgGlnLeuTyrAlaTrpGlyLeuLeuLeuValThrTyrLeuLeuProLeuLeuValIle    241

841 CTCCTGTCTTACGTCCGGGTGTCAGTGAAGCTCCGCAACCGCGTGGTGCCGGGCTGCGTG     900
 241 LeuLeuSerTyrValArgValSerValLysLeuArgAsnArgValValProGlyCysVal    261

901 ACCCAGAGCCAGGCCGACTGGGACCGCGCTCGGCGCCGGCGCACCTTCTGCTTGCTGGTG     960
 261 ThrGlnSerGlnAlaAspTrpAspArgAlaArgArgArgThrPheCysLeuLeuVal       281

961 GTGGTCGTGGTGGTGTTCGCCGTCTGCTGGCTGCCGCTGCACGTCTTCAACCTGCTGCGG    1020
 281 ValValValValValPheAlaValCysTrpLeuProLeuHisValPheAsnLeuLeuArg    301

1021 GACCTCGACCCCCACGCCATCGACCCTTACGCCTTTGGGCTGGTGCAGCTGCTCTGCCAC    1080
 301 AspLeuAspProHisAlaIleAspProTyrAlaPheGlyLeuValGlnLeuLeuCysHis    321

1081 TGGCTCGCCATGAGTTCGGCCTGCTACAACCCCTTCATCTACGCCTGGCTGCACGACAGC    1140
 321 TrpLeuAlaMetSerSerAlaCysTyrAsnProPheIleTyrAlaTrpLeuHisAspSer    341

1141 TTCCGCGAGGAGCTGCGCAAACTGTTGGTCGCTTGGCCCCGCAAGATAGCCCCCCATGGC    1200
 341 PheArgGluGluLeuArgLysLeuLeuValAlaTrpProArgLysIleAlaProHisGly    361

1201 CAGAATATGACCGTCAGCGTGGTCATCTGATGCCACTTAGCCAGGCCTTGGTCAAGGAGC    1260
 361 GlnAsnMetThrValSerValValIle***                                 371

1261 TCCACTTCAACTGGCCTCCTAGGGCACCACTCGAGGTCAATCTGGTGCTTATTCTCAGCA    1320
 371                                                                 371

1321 CCAGAGCTAGC                                                     1331
 371                                                                 371
```

FIGURE 37

```
              9            18            27            36            45            54
5' GTG GGC CTG GTG GGC AAC ATC CTG GCT TCC TGG CAC AAG CGT GGA GGT CGC CGT
   --- --- --- --- --- --- --- --- --- --- --- --- --- --- --- --- --- ---
   Val Gly Leu Val Gly Asn Ile Leu Ala Ser Trp His Lys Arg Gly Gly Arg Arg 63           72            81            90            99           108
   GCT GCT TGG GTA GTG TGT GGA GTC GTG TGG CTG GCT GTG ACA GCC CAG TGC CTG
   --- --- --- --- --- --- --- --- --- --- --- --- --- --- --- --- --- ---
   Ala Ala Trp Val Val Cys Gly Val Val Trp Leu Ala Val Thr Ala Gln Cys Leu 117          126           135           144           153           162
   CCC ACG GCA GTC TTT GCT GCC ACA GGC ATC CAG CGC AAC CGC ACT GTG TGC TAC
   --- --- --- --- --- --- --- --- --- --- --- --- --- --- --- --- --- ---
   Pro Thr Ala Val Phe Ala Ala Thr Gly Ile Gln Arg Asn Arg Thr Val Cys Tyr 171          180           189           198           207           216
   GAC CTG AGC CCA CCC ATC CTG TCT ACT CGC TAC CTG CCC TAT GGT ATG GCC CTC
   --- --- --- --- --- --- --- --- --- --- --- --- --- --- --- --- --- ---
   Asp Leu Ser Pro Pro Ile Leu Ser Thr Arg Tyr Leu Pro Tyr Gly Met Ala Leu 225          234           243           252           261           270
   ACG GTC ATC GGC TTC TTG CTG CCC TTC ATA GCC TTA CTG GCT TGT TAT TGT CGC
   --- --- --- --- --- --- --- --- --- --- --- --- --- --- --- --- --- ---
   Thr Val Ile Gly Phe Leu Leu Pro Phe Ile Ala Leu Leu Ala Cys Tyr Cys Arg 279          288           297           306           315           324
   ATG GCC CGC CGC CTG TGT CGC CAG GAT GGC CCA GCA GGT CCT GTG GCC CAA GAG
   --- --- --- --- --- --- --- --- --- --- --- --- --- --- --- --- --- ---
   Met Ala Arg Arg Leu Cys Arg Gln Asp Gly Pro Ala Gly Pro Val Ala Gln Glu 333          342           351           360           369           378
   CGG CGC AGC AAG GCG GCT CGT ATG GCT GTG GTG GTG GCA GCT GTC TTT GCC CTC
   --- --- --- --- --- --- --- --- --- --- --- --- --- --- --- --- --- ---
   Arg Arg Ser Lys Ala Ala Arg Met Ala Val Val Val Ala Ala Val Phe Ala Leu 387          396
   TGC TGG CTG CCT CTC TAC 3'
   --- --- --- --- --- ---
   Cys Trp Leu Pro Leu Tyr
```

FIGURE 39

```
             10          20          30          40          50
p3H2-17   1  VGLVGNILAS  WHKRGGRRAA  WVVCGVVWLA  VTAQCLPTAV  FAATGIQRN-   50
p34996    1  RYTGVVHPLK  SLGRLKKNA   VYVSSLVWAL  VVAVIAPILF  YSGTGVRRN-   50
A46226    1  RYLAVVHPTR  SARWRTAPVA  RTVSAAVWVA  SAVVVLPVVV  F--SGVPRG-   50
JN0605    1  RYVAVVHPLR  AATYRRPSVA  KLINLGVWLA  SLLVTLPIAI  FADTRPARGG   50
S28787    1  RYLAIVHATN  SQKPRKLLAE  KVVYVGVWLP  AVLLTIPDLI  FADIKEVDF-   50

60          70          80          90          100
p3H2-17  51  RTV-CYDL--  SPPILSTRYL  PYGMALTVIG  FLLPFIALLA  CYCRMARRLC  100
p34996   51  KTITCYDT--  TADEYLRSYF  VYSMCTTVFM  FCIPFIVILG  CYGLIVKALI  100
A46226   51  MST-CHMQWP  EPAAAWRAGE  IIY----TAALG  FFGPLLVIICL  CYLLIVKVR   100
JN0605   51  QAVACNLQWP  HPAWSAFVV   YTF----LLG  FLLPVLAHGL  CYLLIVGKMR  100
S28787   51  RYI-CDRF--  YPSDLWLVVF  QFQ--HIVVG  LLLPGIVILS  CYCIIISKLS  100

110         120         130         140         150
p3H2-17 101  RQDGPA-GPV  AQE-RRS---K  AARMAVVAA  VEALCWLPLY  .........   150
p34996  101  YKDLDN-SPL  ----RR---K  SIYLVILVLT  VFAVSYLPFH  .........   150
A46226  101  SAGRRVWAPS  CRRRRSERR   VTRMVAVVA  LEVLCWMPFY  .........   150
JN0605  101  AVALRA----G  WQQRRRSEKK  ITRLVLMVV   VEVLCWMPFY  .........   150
S28787  101  HSKG------  YQKR-------K  ALKTTVLIL   TEFACWLPYY  .........   150
```

FIGURE 40

```
             10            19            28            37            46            55
5' GTG GGC CTG GTG GGC AAC TTC CTG GCC GCG ATG TCT GTG GAT CGC TAC GTG GCC
   --- --- --- --- --- --- --- --- --- --- --- --- --- --- --- --- --- ---
   Val Gly Leu Val Gly Asn Phe Leu Ala Ala Met Ser Val Asp Arg Tyr Val Ala 64            73            82            91           100           109
   ATT GTG CAC TCG CGG CGC TCC TCC TCC CTC AGG GTG TCC CGC AAC GCA CTG CTG
   --- --- --- --- --- --- --- --- --- --- --- --- --- --- --- --- --- ---
   Ile Val His Ser Arg Arg Ser Ser Ser Leu Arg Val Ser Arg Asn Ala Leu Leu 118           127           136           145           154           163
   GGC GTG GGC TTC ATC TGG GCG CTG TCC ATC GCC ATG GCC TCG CCG GTG GCC TAC
   --- --- --- --- --- --- --- --- --- --- --- --- --- --- --- --- --- ---
   Gly Val Gly Phe Ile Trp Ala Leu Ser Ile Ala Met Ala Ser Pro Val Ala Tyr 172           181           190           199           208           217
   CAC CAG CGT CTT TTC CAT CGG GAC AGC AAC CAG ACC TTC TGC TGG GAG CAG TGG
   --- --- --- --- --- --- --- --- --- --- --- --- --- --- --- --- --- ---
   His Gln Arg Leu Phe His Arg Asp Ser Asn Gln Thr Phe Cys Trp Glu Gln Trp 226           235           244           253           262           271
   CCC AAC AAG CTC CAC AAG AAG GCT TAC GTG GTG TGC ACT TTC GTC TTT GGG TAC
   --- --- --- --- --- --- --- --- --- --- --- --- --- --- --- --- --- ---
   Pro Asn Lys Leu His Lys Lys Ala Tyr Val Val Cys Thr Phe Val Phe Gly Tyr 280           289           298           307           316           325
   CTT CTG CCC TTA CTG CTC ATC TGC TTT TGC TAT GCC AAG GTC CTT AAT CAT CTG
   --- --- --- --- --- --- --- --- --- --- --- --- --- --- --- --- --- ---
   Leu Leu Pro Leu Leu Leu Ile Cys Phe Cys Tyr Ala Lys Val Leu Asn His Leu 334           343           352           361           370           379
   CAT AAA AAG CTG AAA AAC ATG TCA AAA AAG TCT GAA GCA TCC AAG AAA AAG ACT
   --- --- --- --- --- --- --- --- --- --- --- --- --- --- --- --- --- ---
   His Lys Lys Leu Lys Asn Met Ser Lys Lys Ser Glu Ala Ser Lys Lys Lys Thr 388           397           406           415           424           433
   GCA CAG ACC GTC CTG GTG GTC GTT GTA GTA TTT GCC CTC TGC TGG CTG CCT TTC
   --- --- --- --- --- --- --- --- --- --- --- --- --- --- --- --- --- ---
   Ala Gln Thr Val Leu Val Val Val Val Val Phe Ala Leu Cys Trp Leu Pro Phe

TAC 3'
   ---
   Tyr
```

FIGURE 42

```
                 10         20         30         40         50
p3H2-34    1 VGLVGNFLAA MSVDRYVALV HSRRSSLRV SRNALLGVGF IVALSIAMAS      50
JN0605     1 MFTSVFCLTV LSVDRYVAVV HPLRAATYRR FSVAKLINLG VWLASLIVIL      50
B41795     1 QFTSFCHTV MSIDRYLAVV HPIKSAWRR PRIDAKMITMA VWGVSLIVIL       50
A39297     1 MFTSIMCLTV LSVDRYVAVV HPIKAARYRR PIVAKVVNLG VVVLSLIVIL      50

60         70         80         90        100
p3H2-34   51 PVA-YHQRLF HRDSNQTFCW EQWPNKLHK- -KAYVVCTFV FGYLLPLLI      100
JN0605    51 PIAIFADTRP AREGAVACN LQWPHPAWS- -AVFVVYTFL LGFLLPVLAI      100
B41795    51 PIMIYAGLRS NWGRSS--CF INMPGESGAW YTGFLIYTFI LGFLVPLTI       100
A39297    51 PIWVESRTAA NSEGIVA-CN MLMPEPAQRW LVGFVLYTFL MGFLLPVGAI      100

110        120        130        140        150
p3H2-34  101 CFCY-----AK VLNHLHKKLK NMSKKSEASK KKIAQTVLMV VVVFALCWLF      150
JN0605   101 GLCYLIVGK MRAVALRACW QQRRSE---- KKITRLVLMV VVVFVLCVMP       150
B41795   101 CLCYLIIK VKSSGIRVGS SKRKKSE---- KKVTRMVSIV VAVFILFCWLP      150
A39297   101 CLCVLIIAK MRMVALRACM QQRKRSE---- RKITIMVMMV VMVFVICWME      150

```
      10          19          28          37          46          55
5' GTG GGC ATG GTG GGC AAC GTC CTG GTG CTC TGG TTC TTC GGC TTC TCC ATC AAG
   --- --- --- --- --- --- --- --- --- --- --- --- --- --- --- --- --- ---
   Val Gly Met Val Gly Asn Val Leu Val Leu Trp Phe Phe Gly Phe Ser Ile Lys 64          73          82          91         100         109
   AGG ACC CCC TTC TCC GTC TAC TTC CTG CAC CTG GCC AGC GCC GAC GGC GCC TAC
   --- --- --- --- --- --- --- --- --- --- --- --- --- --- --- --- --- ---
   Arg Thr Pro Phe Ser Val Tyr Phe Leu His Leu Ala Ser Ala Asp Gly Ala Tyr 118         127         136         145         154         163
   CTC TTC AGC AAG GCC GTG TTC TCC CTG AAC GCC GGC TTC CTG GGC ACC
   --- --- --- --- --- --- --- --- --- --- --- --- --- --- --- ---
   Leu Phe Ser Lys Ala Val Phe Ser Leu Asn Ala Gly Phe Leu Gly Thr 172         181         190         199         208         217
   TTC GCC CAC TAT GTG CGC AGC GTG GCC CGG GTG CTG GGG CTC TGC TTC GCC TTC GTG
   --- --- --- --- --- --- --- --- --- --- --- --- --- --- --- --- --- --- ---
   Phe Ala His Tyr Val Arg Ser Val Ala Arg Val Leu Gly Leu Cys Phe Ala Phe Val 226         235         244         253         262
   GCG GGC GTG AGC CTC CTG CCG GCC GTG AGC ATG GAG CGC TGC GCG TCT G 3'
   --- --- --- --- --- --- --- --- --- --- --- --- --- --- --- ---
   Ala Gly Val Ser Leu Leu Pro Ala Val Ser Met Glu Arg Cys Ala Ser
```

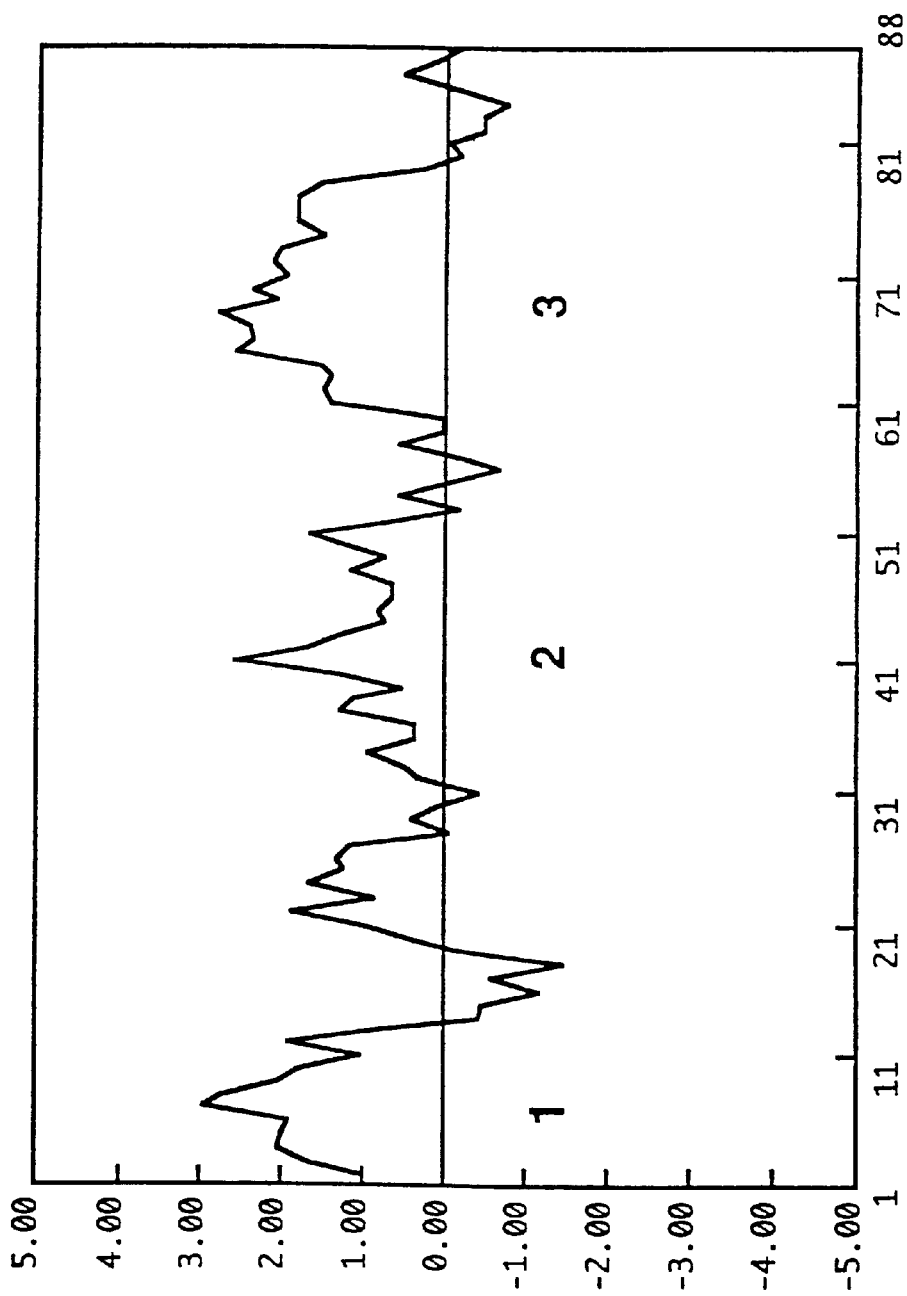

FIGURE 45

```
              10         20         30         40         50
    1  VGMVGNVLVL WFFGFSIKRT PFSVYFLHLA SADGAYLFSK AVFSLLNAGG   50
    1  CGLVGNGLVL WFFGFSIKRT PFSIYFLHLA SADGIYLFSK AVIALLNMGT   50

60         70         80         90        100
   51  FLGTFAHVVR SVARVLGLCA FVAGVSLLPA VSMERCAS.. .........   100
   51  FLGSFPDYVR RVSRIVGLCT FFAGVSLLPA ISIERCVS.. .........   100
``` pMD4
A35639 pMD4
A35639

FIGURE 46

```
   1 CAAAGCAACAGGTGCAACCTCAAGGCACTGAAAGCAAGGGGACGCAGCTCACAAGGGCCAAGGGATTGAACC      72
   1                                                                                1

73 CATAACCGCTCAGAAGATTCTCCGCCTGCGGAGAGCTGCGGAGGAGTCCCACCCGTCCAGCTTGCTGACTGC     144
   1                                                                                1

145 GAGCAGTGAGAGTCGCCTAGACCCGTACCTCTGTGTTCTGGAGCCTGCCGCCCCCGCACGGGAAAGGCTTAG     216
   1                                                                                1

217 CTCGGGACTTGCAGCACCGCCTCCTCTTTAGCCAGGCCAGGCACGAGGATAGTGTGATCGGGCACAGCCAGG     288
   1                                                                                1

289 GTCGCTCTTCCAGGCTTTCTTGCGGGTTGCGGGAGGTACTAGTTGGAGACGCGCGCGCTCGCTCTCGCCGCT     360
   1                                                                                1

361 CTGTCCTGGGCCACTCCGTGATCCTAGGCTACCTCCAGAGCCAGTTTTCCCTGGCTGGCACAACTCTCCAGG     432
   1                                                                                1

433 GCGCTCCGGTCCGTTGCACAGCGCCCAAGGGGGTATCCCAGTAAGTGATGGAACTGGCTATGGTGAACCTC     504
   1                                                              MetGluLeuAlaMetValAsnLeu    8

505 AGTGAAGGGAATGGGAGCGACCCAGAGCCGCCAGCCCCGGAGTCCAGGCCGCTCTTCGGCATTGGCGTGGAG     576
   8 SerGluGlyAsnGlySerAspProGluProProAlaProGluSerArgProLeuPheGlyIleGlyValGlu     32

577 AACTTCATTACGCTGGTAGTGTTTGGCCTGATTTTCGCGATGGGCGTGCTGGGCAACAGCCTGGTGATCACC     648
  32 AsnPheIleThrLeuValValPheGlyLeuIlePheAlaMetGlyValLeuGlyAsnSerLeuValIleThr     56

649 GTGCTGGCGCGCAGCAAACCAGGCAAGCCGCGCAGCACCACCAACCTGTTTATCCTCAATCTGAGCATCGCA     720
  56 ValLeuAlaArgSerLysProGlyLysProArgSerThrThrAsnLeuPheIleLeuAsnLeuSerIleAla     80

721 GACCTGGCCTACCTGCTCTTCTGCATCCCTTTTCAGGCCACCGTGTATGCACTGCCCACCTGGGTGCTGGGC     792
  80 AspLeuAlaTyrLeuLeuPheCysIleProPheGlnAlaThrValTyrAlaLeuProThrTrpValLeuGly    104

793 GCCTTCATCTGCAAGTTTATACACTACTTCTTCACCGTGTCCATGCTGGTGAGCATCTTCACCCTGGCCGCG     864
 104 AlaPheIleCysLysPheIleHisTyrPhePheThrValSerMetLeuValSerIlePheThrLeuAlaAla    128

865 ATGTCTGTGGATCGCTACGTGGCCATTGTGCACTCGCGGCGCTCCTCCTCCCTCAGGGTGTCCCGCAACGCA     936
 128 MetSerValAspArgTyrValAlaIleValHisSerArgArgSerSerSerLeuArgValSerArgAsnAla    152

937 CTGCTGGGCGTGGGCTTCATCTGGGCGCTGTCCATCGCCATGGCCTCGCCGGTGGCCTACCACCAGCGTCTT    1008
 152 LeuLeuGlyValGlyPheIleTrpAlaLeuSerIleAlaMetAlaSerProValAlaTyrHisGlnArgLeu    176

1009 TTCCATCGGGACAGCAACCAGACCTTCTGCTGGGAGCAGTGGCCCAACAAGCTCCACAAGAAGGCTTACGTG    1080
 176 PheHisArgAspSerAsnGlnThrPheCysTrpGluGlnTrpProAsnLysLeuHisLysLysAlaTyrVal    200

1081 GTGTGCACTTTCGTCTTTGGGTACCTTCTGCCCTTACTGCTCATCTGCTTTTGCTATGCCAAGGTCCTTAAT    1152
 200 ValCysThrPheValPheGlyTyrLeuLeuProLeuLeuLeuIleCysPheCysTyrAlaLysValLeuAsn    224

1153 CATCTGCATAAAAAGCTGAAAAACATGTCAAAAAAGTCTGAAGCATCCAAGAAAAAGACTGCACAGACCGTC    1224
 224 HisLeuHisLysLysLeuLysAsnMetSerLysLysSerGluAlaSerLysLysLysThrAlaGlnThrVal    248

1225 CTGGTGGTCGTTGTAGTATTTGGCATATCCTGGCTGCCCCATCATGTCGTCCACCTCTGGGCTGAGTTTGGA    1296
 248 LeuValValValValValPheGlyIleSerTrpLeuProHisHisValValHisLeuTrpAlaGluPheGly    272

1297 GCCTTCCCACTGACGCCAGCTTCCTTCTTCTTCAGAATCACCGCCCATTGCCTGGCATACAGCAACTCCTCA    1368
 272 AlaPheProLeuThrProAlaSerPhePhePheArgIleThrAlaHisCysLeuAlaTyrSerAsnSerSer    296

1369 GTGAACCCCATCATATATGCCTTTCTCTCAGAAAACTTCCGGAAGGCGTACAAGCAAGTGTTCAAGTGTCAT    1440
 296 ValAsnProIleIleTyrAlaPheLeuSerGluAsnPheArgLysAlaTyrLysGlnValPheLysCysHis    320

1441 GTTTGCGATGAATCTCCACGCAGTGAAACTAAGGAAAACAAGAGCCGGATGGACACCCCGCCATCCACCAAC    1512
 320 ValCysAspGluSerProArgSerGluThrLysGluAsnLysSerArgMetAspThrProProSerThrAsn    344

1513 TGCACCCACGTGTGAAGGTTTGCGGGAGCCTCCCGACTTCCAGCTCCCATGTGTGTTAGAGAGAGGAGGGCG    1584
 344 CysThrHisVal***                                                             349

1585 GAGCGAATTATCAAGTAACATGG                                                    1607
 349                                                                            349
```

FIGURE 48

| | | | | | |
|---|---|---|---|---|---|
| MOUSEGALRECE | 1 MELAWNLSE GNGSDPEPPA PESRPLFGIG VENFITHVVF GHIFAMGVLG 50 |
| HUMGALAMI | 1 MELAVGNLSE GNASLPEPPA PERGPLFGIG VENFVLMVF GLIFALGVLG 50 |

| MOUSEGALRECE | 51 NSLVITVFAR SKFGKPRSTT NLFILNLSIA DHAYLLFCIP FQATVVALPT 100 |
| HUMGALAMI | 51 NSLVITVLAR SKFGKPRSTT NLFILNLSIA DLAYLLFCIP FQATVVALPT 100 |

| MOUSEGALRECE | 101 WLGAFICKF IHYFFTVSML VSIFTLAAMS VDRYVAIVHS RRSSSLRVSR 150 |
| HUMGALAMI | 101 WLGAFICKF IHYFFTVSML VSIFTLAAMS VDRYVAIVHS RRSSSLRVSR 150 |

| MOUSEGALRECE | 151 NALLGVGIW ALSIAMASPV AYHORLFH-R DSNQTFCWEQ WPNKLHKKAY 200 |
| HUMGALAMI | 151 NALLGVGIW ALSIAMASPV AYHQLFHPR ASNQTFCWEQ WPDPRHKKAY 200 |

| MOUSEGALRECE | 201 WCTFVFGYL LPLLLICFCY AKVLNHLHKK LKNMSKKSEA SKKKTAQTVL 250 |
| HUMGALAMI | 201 WCTFVFGYL LPLLLICFCY AKVLNHLHKK LKNMSKKSEA SKKKTAQTVL 250 |

| MOUSEGALRECE | 251 VVWVFGISW LPHHVHLMF EFGARPLTPA SFFFRITAHC LAYSNSSVNP 300 |
| HUMGALAMI | 251 VVWVFGISW LPHHIHLWA EFGVFPLTPA SFLFRITAHC LAYSNSSVNP 300 |

| MOUSEGALRECE | 301 IIYAFLSENF RKAYKQVFKC HVCDESPRSE TKENKSRMDT PPSTNCTHVX 350 |
| HUMGALAMI | 301 IIYAFLSENF RKAVKQVFKC HIRKDSHLSD TKENKSRIDT PPSTNCTHVX 350 |

| MOUSEGALRECE | 351 .......... 400 |
| HUMGALAMI | 351 X......... 400 |

FIGURE 49

```
              9              18              27              36              45              54
5' CTC GCG GCT CTG GGT ATG GAT CGG TAT CTT CTC ACC CTT CAC CCA GTG TGG TCC
   ─── ─── ─── ─── ─── ─── ─── ─── ─── ─── ─── ─── ─── ─── ─── ─── ─── ───
                                       Leu Leu Thr Leu His Pro Val Trp Ser 63              72              81              90              99             108
   CAA AAG CAC CGA ACC TCA CAC TGG GCT TCC AGA GTC GTT CTG GGA GTC TGG CTC
   ─── ─── ─── ─── ─── ─── ─── ─── ─── ─── ─── ─── ─── ─── ─── ─── ─── ───
   Gln Lys His Arg Thr Ser His Trp Ala Ser Arg Val Val Leu Gly Val Trp Leu 117             126             135             144             153             162
   TCT GCC ACT GCC TTC AGC GTG CCC TAT TTG GTT TTC AGG GAG ACA TAT GAT GAC
   ─── ─── ─── ─── ─── ─── ─── ─── ─── ─── ─── ─── ─── ─── ─── ─── ─── ───
   Ser Ala Thr Ala Phe Ser Val Pro Tyr Leu Val Phe Arg Glu Thr Tyr Asp Asp 171             180             189             198             207             216
   CGT AAA GGA AGA GTG ACC TGC AGA AAT AAC TAC GCT GTG TCC ACT GAC TGG GAA
   ─── ─── ─── ─── ─── ─── ─── ─── ─── ─── ─── ─── ─── ─── ─── ─── ─── ───
   Arg Lys Gly Arg Val Thr Cys Arg Asn Asn Tyr Ala Val Ser Thr Asp Trp Glu 225             234             243             252             261             270
   AGC AAA GAG ATG CAA ACA GTA AGA CAA TGG ATT CAT GCC ACC TGT TTC ATC AGC
   ─── ─── ─── ─── ─── ─── ─── ─── ─── ─── ─── ─── ─── ─── ─── ─── ─── ───
   Ser Lys Glu Met Gln Thr Val Arg Gln Trp Ile His Ala Thr Cys Phe Ile Ser 279             288             297             306             315             324
   CGC TTC ATA CTG GGC TTC CTT CTG CCT TTC TTA GTC ATT GGC TTT TGT TAT GAA
   ─── ─── ─── ─── ─── ─── ─── ─── ─── ─── ─── ─── ─── ─── ─── ─── ─── ───
   Arg Phe Ile Leu Gly Phe Leu Leu Pro Phe Leu Val Ile Gly Phe Cys Tyr Glu 333             342             351             360             369             378
   AGA GTA GCC CGC AAG ATG AAA GAG AGG GGC CTC TTT AAA TCC AGC AAA CCC TTC
   ─── ─── ─── ─── ─── ─── ─── ─── ─── ─── ─── ─── ─── ─── ─── ─── ─── ───
   Arg Val Ala Arg Lys Met Lys Glu Arg Gly Leu Phe Lys Ser Ser Lys Pro Phe 387             396             405             414             423             432
   AAA GTC ACG ATG ACT GCT GTT ATC TCT TTT TTC TGT CCT GGC TTC CCT ACC ACA
   ─── ─── ─── ─── ─── ─── ─── ─── ─── ─── ─── ─── ─── ─── ─── ─── ─── ───
   Lys Val Thr Met Thr Ala Val Ile

TG 3'
──
```

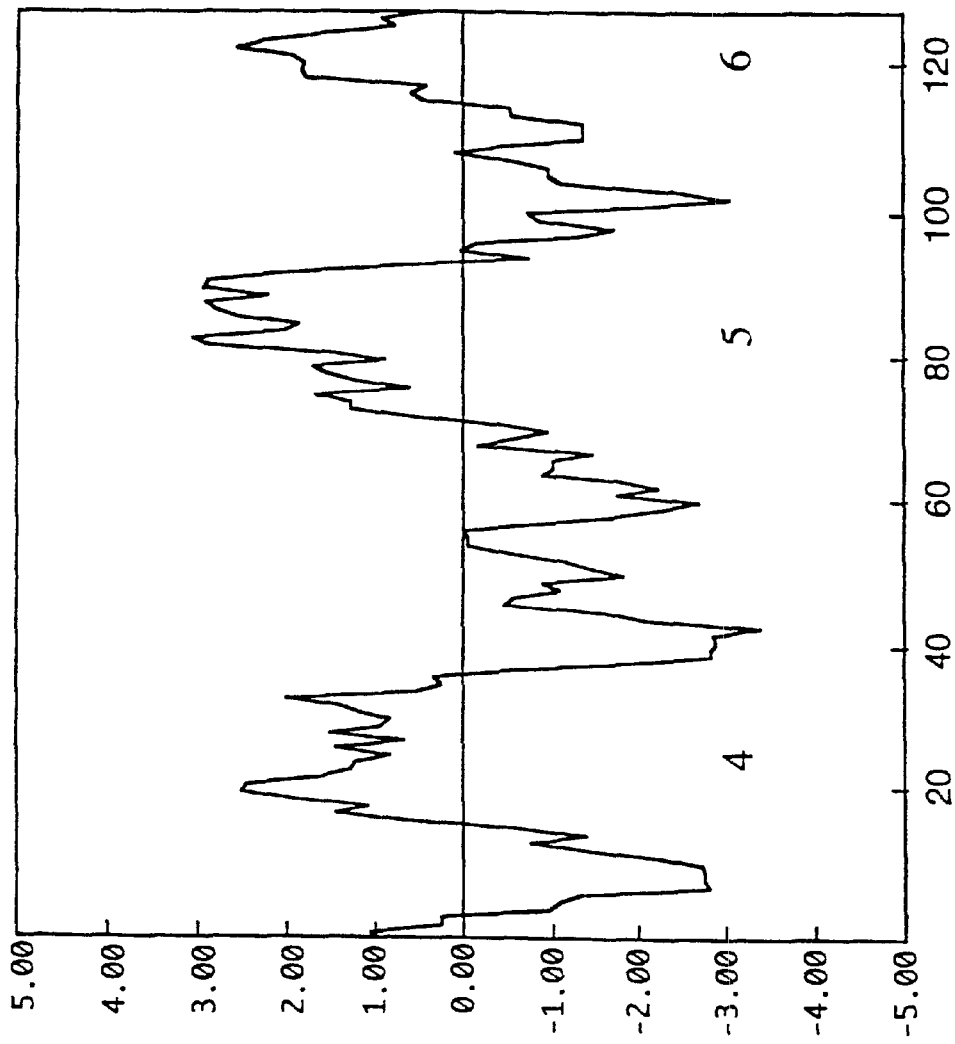

FIGURE 51

```
                  10         20         30         40         50
         1  LLTLRPVWSQ KHRTSHWASR VLGVWLSAI AFSVPYLVER ETYDR-K-G    50
pMJ10
B42009   1  ICVLHPVWAC NHRTVSLAKK VTVGPWILAL VLTLRWFEL TTVIP-N-G     50
JC2014   1  VCVLHPVMIC NHRTVSLAKK VLLGPWMMAL LLTLRPVLRV TTVPGK-T-G    50
A46520   1  ICVLHPVWAC NHRNVSLAKK VLVGPWMMAL LLTLRVIRV TTLSHPRAPG     50
A46525   1  LMFKPIWQ KVR GIGLAWM ACGVAWVLAM LLTPSFVYR EAYKDTYS-E     50
S28787   1  LAIVHATNSC KPRKLLAEKV VYVGWMLPAV LLTPDLIFA DI-KEV-D-E     50

60         70         80         90        100
        51  RVTCRNNYAV STDMESKEMQ TVRQWIHATC FISRFILGFL LPFLVIGFCY  100
pMJ10
B42009  51  DIYCTENFAS WGG-TPEERL KVAATMLIAR GIIRFVIGFS LPMSIVAICY   100
JC2014  51  TVACTFNFSP WTN-DPKERL KVAVAMLTVR GIIRFIIGFS APMSIVAVSY    100
A46520  51  KMACTFDWSE WTE-DPAEKL KVAISMEMVR GIIRFIIGFS TPMSIVAICY    100
A46525  51  HIVCGINYG GS--FPKEKA VA------- -ILRLMVGFV LLLTLNICY      100
S28787  51  RYICRFYP- SDLW------ L VVFQFQH ----IVVGLL LPGIVILSCY      100

110        120        130        140        150
       101  ERVARKMKER GLFKSSKPFK VIMIAVI ........ ........        150
pMJ10
B42009 101  GLTAAKIHHK GMIKSSRPLR VLFAVVA ........ ........          150
JC2014 101  GLIATKIIHQ GLIKSSRPLR VLSFVAA ........ ........          150
A46520 101  GLIATKIIHK GLIKSSRPLR VLSFVVA ........ ........          150
A46525 101  GIIATKIHRQ GLIKSSRPLR VMAVVI ........ ........           150
S28787 101  TFLLRTWSR KATRSTKTEK ........ ........ ........          150
       101  CILISKLSHS KGYQKRKALK TTVILIL.. ........ ........       150
```

FIGURE 52

```
           9               18              27              36              45              54
5' CTG ACT GCT CTG GGG ACT GAC CGG TAT TTC AAG ATT GTG AAG CCC CTT TCC ACG
   --- --- --- --- --- --- --- --- --- --- --- --- --- --- --- --- --- ---
                                           Phe Lys Ile Val Lys Pro Leu Ser Thr 63              72              81              90              99             108
   TCC TTC ATC CAG TCT GTG AAC TAC AGC AAA CTC GTC TCG CTG GTG GTC TGG TTG
   --- --- --- --- --- --- --- --- --- --- --- --- --- --- --- --- --- ---
   Ser Phe Ile Gln Ser Val Asn Tyr Ser Lys Leu Val Ser Leu Val Val Trp Leu 117             126             135             144             153             162
   CTC ATG CTC CTC CTC GCC GTC CCC AAC GTC ATT CTC ACC AAC CAG AGA GTT AAG
   --- --- --- --- --- --- --- --- --- --- --- --- --- --- --- --- --- ---
   Leu Met Leu Leu Leu Ala Val Pro Asn Val Ile Leu Thr Asn Gln Arg Val Lys 171             180             189             198             207             216
   GAC GTG ACG CAG ATA AAA TGC ATG GAA CTT AAA AAC GAA CTG GGC CGC CAG TGG
   --- --- --- --- --- --- --- --- --- --- --- --- --- --- --- --- --- ---
   Asp Val Thr Gln Ile Lys Cys Met Glu Leu Lys Asn Glu Leu Gly Arg Gln Trp 225             234             243             252             261             270
   CAC AAG GCG TCA AAC TAC ATC TTT GTG GGC ATT TTC TGG CTT GTG TTC CTT TTG
   --- --- --- --- --- --- --- --- --- --- --- --- --- --- --- --- --- ---
   His Lys Ala Ser Asn Tyr Ile Phe Val Gly Ile Phe Trp Leu Val Phe Leu Leu 279             288             297             306             315             324
   CTA ATC ATT TTC TAC ACT GCT ATC ACC AGG AAA ATC TTT AAG TCC CAC CTG AAA
   --- --- --- --- --- --- --- --- --- --- --- --- --- --- --- --- --- ---
   Leu Ile Ile Phe Tyr Thr Ala Ile Thr Arg Lys Ile Phe Lys Ser His Leu Lys 333             342             351             360             369             378
   TCC AGA AAG AAT TCC ATC TCG GTC AAA AAG AAA TCT AGC CGC AAC ATC TTC AGC
   --- --- --- --- --- --- --- --- --- --- --- --- --- --- --- --- --- ---
   Ser Arg Lys Asn Ser Ile Ser Val Lys Lys Lys Ser Ser Arg Asn Ile Phe Ser 387             396             405             414
   ATC GTG TTT ATC CTC TGT TGG CCC CCC TAC CAC ATC 3'
   --- --- --- --- --- --- --- --- --- --- --- ---
   Ile Val
```

FIGURE 54

```
                10          20          30          40          50
pMH28     1  FKIVKPLSTS FIQSVNYSKL VSLMVWLLML LLAVPNVLIT NQRVKDVTQI      50
P35343    1  LAMVHATSF- LIQKRHLVKF YCIAMWLHSV IKAIPILILR NPVKVNLSTL      50
A41795    1  VAVVHPLKAA RYRRPTVAKV VNLGVWMESL LVILPIVFS  RTAANSDGIV      50
A47457    1  VAVVHPERAA TYRRBSVAKL INLGVWLASL LVTLRIAIFA DLRPARGGQ-      50

60          70          80          90         100
pMH28    51  KCME-LNEL GRQMHKASNY IFVGIF-WLV FTLLIFYTA IT-RKIFKSH        100
P35343   51  VCYEDVGNNT SRL---RWLR ILPQTFGFLV PLIIMLFCYG FTLRILFKAH        100
A41795   51  AQNM-LMPEP AQRWLVGFV- LYIFLMGFIHL PVGATCLCYV LHILAKVRMVA      100
A47457   51  AVAC-NLQWB HPAMSAVFV- VYTFLGFLL PVLAIGLCYL LLVGKMRAVA         100

110         120         130         140         150
pMH28   101  LKSRKNSI-S VKKKSSRNIF S--IV.....  .......... ..........      150
P35343  101  MG----QKHR AMR-----IF AVVLV..... .......... ..........       150
A41795  101  LKAGWQQRKR SERKITLMVM MVVLV..... .......... ..........       150
A47457  101  LRAGMQQRRR SEKKITRLVL MVVVV..... .......... ..........       150
```

FIGURE 55

```
            9           18          27          36          45          54
5' GCC ACC AAC GTG TTC ATC CTG TGT CTG GTG GAC CTG CTG GCT GCC CTG ACC CTC
   --- --- --- --- --- --- --- --- --- --- --- --- --- --- --- --- --- ---
                                       Val Asp Leu Leu Ala Ala Leu Thr Leu 63          72          81          90          99         108
   ATG CCT CTG GCC ATG CTC TCC AGC TCC GCC CTC TTT GAC CAC GCC CTC TTT GGG
   --- --- --- --- --- --- --- --- --- --- --- --- --- --- --- --- --- ---
   Met Pro Leu Ala Met Leu Ser Ser Ser Ala Leu Phe Asp His Ala Leu Phe Gly 117         126         135         144         153         162
   GAG GTG GCC TGC CGC CTC TAC TTG TTC CTG AGC GTC TGC TTT GTC AGC CTG GCC
   --- --- --- --- --- --- --- --- --- --- --- --- --- --- --- --- --- ---
   Glu Val Ala Cys Arg Leu Tyr Leu Phe Leu Ser Val Cys Phe Val Ser Leu Ala 171         180         189         198         207         216
   ATC CTC TCG GTG TCC GCC ATC AAT GTG GAG CGC TAC TAT TAT GTG GTC CAC CCC
   --- --- --- --- --- --- --- --- --- --- --- --- --- --- --- --- --- ---
   Ile Leu Ser Val Ser Ala Ile Asn Val Glu Arg Tyr Tyr Tyr Val Val His Pro 225         234         243         252         261         270
   ATG CGC TAT GAG GTG CGC ATG AAA CTG GGG CTG GTG GCC TCT GTG CTG GTG GGC
   --- --- --- --- --- --- --- --- --- --- --- --- --- --- --- --- --- ---
   Met Arg Tyr Glu Val Arg Met Lys Leu Gly Leu Val Ala Ser Val Leu Val Gly 279         288         297         306         315         324
   GTG TGG GTG AAG GCC CTG GCC ATG GCT TCT GTG CCA GTG TTG GGA AGG GTG TCC
   --- --- --- --- --- --- --- --- --- --- --- --- --- --- --- --- --- ---
   Val Trp Val Lys Ala Leu Ala Met Ala Ser Val Pro Val Leu Gly Arg Val Ser 333         342         351         360         369         378
   TGG GAG GAA GGC CCT CCC AGT GTC CCC CCA GGC TGT TCA CTC CAA TGG AGC CAC
   --- --- --- --- --- --- --- --- --- --- --- --- --- --- --- --- --- ---
   Trp Glu Glu Gly Pro Pro Ser Val Pro Pro Gly Cys Ser Leu Gln Trp Ser His 387         396         405         414         423         432
   AGT GCC TAC TGC CAG CTT TTC GTG GTG GTC TTC GCC GTC CTC TAC TTC CTG CTG
   --- --- --- --- --- --- --- --- --- --- --- --- --- --- --- --- --- ---
   Ser Ala Tyr Cys Gln Leu Phe Val Val Val Phe Ala Val Leu Tyr Phe Leu Leu 441         450         459         468         477         486
   CCC CTG CTC CTC ATC CTT GTG GTC TAC TGC AGC ATG TTC CGG GTG GCT CGT GTG
   --- --- --- --- --- --- --- --- --- --- --- --- --- --- --- --- --- ---
   Pro Leu Leu Leu Ile Leu Val Val Tyr Cys Ser Met Phe Arg Val Ala Arg Val 495         504         513         522         531         540
   GCT GCC ATG CAG CAC GGG CCG CTG CCC ACG TGG ATG GAG ACG CCC CGG CAA CGC
   --- --- --- --- --- --- --- --- --- --- --- --- --- --- --- --- --- ---
   Ala Ala Met Gln His Gly Pro Leu Pro Thr Trp Met Glu Thr Pro Arg Gln Arg
```

FIGURE 56

```
        549         558         567         576         585         594
TCC GAG TCT CTC AGC AGC CGC TCC ACT ATG GTC ACC AGC TCG GGG GCC CCG CAG
--- --- --- --- --- --- --- --- --- --- --- --- --- --- --- --- --- ---
Ser Glu Ser Leu Ser Ser Arg Ser Thr Met Val Thr Ser Ser Gly Ala Pro Gln 603         612         621         630         639         648
ACC ACC CCT CAC CGG ACG TTT GGC GGA GGG AAG GCA GCA GTG GTC CTC CTG GCT
--- --- --- --- --- --- --- --- --- --- --- --- --- --- --- --- --- ---
Thr Thr Pro His Arg Thr Phe Gly Gly Gly Lys Ala Ala Val Val Leu Leu Ala 657         666         675         684         693         702
GTG GGA GGA CAG TTC CTG CTC TGT TGG TTG CCC TAC TTC TCC TTC CAC CTC TAT
--- --- --- --- --- --- --- --- --- --- --- --- --- --- --- --- --- ---
Val Gly Gly Gln Phe Leu Leu Cys Trp Leu Pro Tyr Phe Ser Phe His Leu Tyr 711         720         729         738         747         756
GTG GCC CTG AGC GCT CAG CCC ATT GCA GCG GGG CAG GTG GAG AAC GTG GTG ACC
--- --- --- --- --- --- --- --- --- --- --- --- --- --- --- --- --- ---
Val Ala Leu Ser Ala Gln Pro Ile Ala Ala Gly Gln Val Glu Asn Val Val Thr 765         774         783         792         801         810
TGG ATT GGC TAC TTC TGC TTC ACC TCC AAC CCT CTC CTC TAT TCC TTC CTC CCT 3'
--- --- --- --- --- --- --- --- ---
Trp Ile Gly Tyr Phe Cys Phe Thr Ser
```

FIGURE 60

```
                 10         20         30         40         50
p19P2     1  VGVWGNVLLV LVIARVRRLH NVIENFLIGNL ALSDVLMCTA CVPLTLAYAF   50
S12863    1  LCVSCNLAEI IILKQKEMRN NVITNLLIVNL SFSDLLAVM  CLPFTFVYTL   50

60         70         80         90        100
p19P2    51  EPRGWVFGGG LCHLVFFLQP VRVYVSVFTL TTIAVDRYVV LVHPLRRRI-   100
S12863   51  MDH-WVFGET MCKLNPFVQC VSITVSIESL VLIAVERHQL IINPRGWRPN   100

110        120        130        140        150
p19P2   101  ---------- NRHAYIGITV IWLAVASSL  PFVIYQILTD EPFQNVSLAA   150
S12863  101  FKDKYVCFDK                                              150

160        170        180        190        200
p19P2   151  -----GLLLV TYLLPLEVIL LS-------Y VRVSVKLRNR VVPGCVTQSQ   200
S12863  151  FPSDSHRLSY TILLVLQYF  GPLCFIFICY FKIYIRLKRR NNMMDKIRDS   200

210        220        230        240        250
p19P2   201  ADWDRARRR  TFCLVVVV   VEAICWLPYY ..........            250
S12863  201  KYRSSETKRI NVMLSIVA   -FAVCMLPLT ..........            250
```

FIGURE 61

```
p19P2        1 VGMVGNVLIV LVIARVRRLH NVINFLIGNL ALSDVLMCTA CVPLTLAYAF    50
pG3-2/pG1-10 1 VGMVGNILIV LVIARVRRLy NVINFLIGNL ALSDVLMCTA CVPLTLAYAF    50 p19P2       51 EPRGMVFGGG LCHLVFFLQP VTVVVSVFTI TTIAVDRYVV LVHPLRRRI           100
pG3-2/pG1-10 51 EPRGMVFGGG LCHLVFFLQA VFVVVSVFTI THFAVDRYVV LVHPLRRRIs         100 p19P2      101 ---------- ---------- ---------- ---------- ----------         150
pG3-2/pG1-10 101 LRLSAYAVLA IWLSAVLAL PAAVHTYHVE LKPHDVRLCE EFWGSQERQR         150 p19P2      151 ------GLLLV TYLLPLLVIL LSYVRVSVKL RNRVVEGCVT QSQADWDRAR         200
pG3-2/pG1-10 151 QLYAWGILIV TYLLPLLVIL LSYARVSVKL RNRVVEGRVI QSQADWDRAR         200 p19P2      201 RRRTFCLLVV VVVFAICWL PYY....... .......... ..........         250
pG3-2/pG1-10 201 RRRTFCLLVV VVVFILCWL PFF....... .......... ..........         250
```

FIGURE 62

```
             9          18          27          36          45          54
5'  CTG TGT GTC ATC GCG GTG GAT AGG TAC GTG GTT CTG GTG CAC CCG CTA CGT CGG
    --- --- --- --- --- --- --- --- --- --- --- --- --- --- --- --- --- ---
    Leu Cys Val Ile Ala Val Asp Arg Tyr Val Val Leu Val His Pro Leu Arg Arg 63          72          81          90          99         108
    CGC ATT TCA CTG AGG CTC AGC GCC TAC GCG GTG CTG GGC ATC TGG GCT CTA TCT
    --- --- --- --- --- --- --- --- --- --- --- --- --- --- --- --- --- ---
    Arg Ile Ser Leu Arg Leu Ser Ala Tyr Ala Val Leu Gly Ile Trp Ala Leu Ser 117         126         135         144         153         162
    GCA GTG CTG GCG CTG CCG GCC GCG GTG CAC ACC TAC CAT GTG GAG CTC AAG CCC
    --- --- --- --- --- --- --- --- --- --- --- --- --- --- --- --- --- ---
    Ala Val Leu Ala Leu Pro Ala Ala Val His Thr Tyr His Val Glu Leu Lys Pro 171         180         189         198         207         216
    CAC GAC GTG AGC CTC TGC GAG GAG TTC TGG GGC TCG CAG GAG CGC CAA CGC CAG
    --- --- --- --- --- --- --- --- --- --- --- --- --- --- --- --- --- ---
    His Asp Val Ser Leu Cys Glu Glu Phe Trp Gly Ser Gln Glu Arg Gln Arg Gln 225         234         243         252         261         270
    ATC TAC GCC TGG GGG CTG CTT CTG GGC ACC TAT TTG CTC CCC CTG CTG GCC ATC
    --- --- --- --- --- --- --- --- --- --- --- --- --- --- --- --- --- ---
    Ile Tyr Ala Trp Gly Leu Leu Leu Gly Thr Tyr Leu Leu Pro Leu Leu Ala Ile 279         288         297         306         315         324
    CTC CTG TCT TAC GTA CGG GTG TCA GTG AAG CTG AGG AAC CGC GTG GTG CCT GGC
    --- --- --- --- --- --- --- --- --- --- --- --- --- --- --- --- --- ---
    Leu Leu Ser Tyr Val Arg Val Ser Val Lys Leu Arg Asn Arg Val Val Pro Gly 333         342         351         360         369         378
    AGC GTG ACC CAG AGT CAA GCT GAC TGG GAC CGA GCG CGT CGC CGC CGC ACT TTC
    --- --- --- --- --- --- --- --- --- --- --- --- --- --- --- --- --- ---
    Ser Val Thr Gln Ser Gln Ala Asp Trp Asp Arg Ala Arg Arg Arg Arg Thr Phe 387         396         405         414         423         432
    TGT CTG CTG GTG GTG GTG GTG GTA GTG TTC ACG CTC TGC TGG CTG CCC TTC TAC
    --- --- --- --- --- --- --- --- --- --- --- --- --- --- --- --- --- ---
    Cys Leu Leu Val Val Val Val Val Val Phe Thr Leu Cys Trp Leu Pro Phe Tyr

```
                      10         20         30         40         50
p19P2          1  VGMVGNVLLV LVIARVRREH NVTNELIGNL ALSDVIMCTA CVPLTLAYAF    50
pG3-2/pG1-10   1  VGMVGNILLV LVIARVRREY NVTNELIGNL ALSDVIMCTA CVPLTLAYAF    50
p5S38        -79  .......... .......... .......... .......... ..........   -30

60         70         80         90        100
p19P2         51  EPRGWVFGGG LCHLVFFLQP VIVVVSVETI LTIAVDRYVV LVHPLRRRI    100
pG3-2/pG1-10  51  EPRGWVFGGG LCHLVFFLQA VIVVVSVETI LTIAVDRYVV LVHPLRRRI    100
p5S38        -29  .......... .......... .....L.... CVIAVDRYVV LVHPLRRHIS    21

110        120        130        140        150
p19P2        101  LRLSAYAVLA IWVLSAVIAL PAAVHTYHVE LKPHDVRLCE EFWGSQERQR   150
pG3-2/pG1-10 101  LRLSAYAVLG IWALSAVIAL PAAVHTYHVE LKPHDVSLCE EFWGSQERQR   150
p5S38         22  .......... .......... .......... .......... ..........    71

160        170        180        190        200
p19P2        151  ----GLLLV QLYAMGLIIL TYILPLLVIL LSYVRVSVKL RNRVVPGCVT   200
pG3-2/pG1-10 151  ----GLLLV QIVAMGLIIG TYILPLLVEL LSYARVSVKT RNRVVPGRVT   200
p5S38         72  .......... .......... .......... .......... ..........   121

210        220        230        240        250
p19P2        201  RRRTFCLLVV VVVFAICML PFY....... .......... ..........   250
pG3-2/pG1-10 201  RRRTFCLLVV VVVFTLCML PFF....... .......... ..........   250
p5S38        122  RRRTFCLLVV VVVFTLCML PFY....... .......... ..........   171
```

FIGURE 69

```
  1 GAGCATAGGAAAGGCTGACAGGCAGTTATGGAGCAGGACAATGGCACCATCCAGGCTCCA   60
  1                         MetGluGlnAspAsnGlyThrIleGlnAlaPro      11

61 GGCTTGCCGCCCACCACCTGCGTCTACCGTGAGGATTTCAAGCGACTGCTGCTAACCCCG  120
 11 GlyLeuProProThrThrCysValTyrArgGluAspPheLysArgLeuLeuLeuThrPro   31

121 GTATACTCGGTGGTGCTGGTGGTCGGCCTGCCACTGAACATCTGCGTCATTGCCCAGATC  180
 31 ValTyrSerValValLeuValValGlyLeuProLeuAsnIleCysValIleAlaGlnIle   51

181 TGCGCATCCCGCCGGACCCTGACCCGTTCCGCTGTGTACACCCTGAACCTGGCACTGGCG  240
 51 CysAlaSerArgArgThrLeuThrArgSerAlaValTyrThrLeuAsnLeuAlaLeuAla   71

241 GACCTGATGTATGCCTGTTCACTACCCCTACTTATCTATAACTACGCCAGAGGGACCAC   300
 71 AspLeuMetTyrAlaCysSerLeuProLeuLeuIleTyrAsnTyrAlaArgGlyAspHis   91

301 TGGCCCTTCGGAGACCTCGCCTGCCGCTTTGTACGCTTCCTCTTCTATGCCAATCTACAT  360
 91 TrpProPheGlyAspLeuAlaCysArgPheValArgPheLeuPheTyrAlaAsnLeuHis  111

361 GGCAGCATCCTGTTCCTCACCTGCATTAGCTTCCAGCGCTACCTGGGCATCTGCCACCCC  420
111 GlySerIleLeuPheLeuThrCysIleSerPheGlnArgTyrLeuGlyIleCysHisPro  131

421 CTGGCTTCCTGGCACAAGCGTGGAGGTCGCCGTGCTGCTTGGGTAGTGTGTGGAGTCGTG  480
131 LeuAlaSerTrpHisLysArgGlyGlyArgArgAlaAlaTrpValValCysGlyValVal  151

481 TGGCTGGCTGTGACAGCCCAGTGCCTGCCCACGGCAGTCTTTGCTGCCACAGGCATCCAG  540
151 TrpLeuAlaValThrAlaGlnCysLeuProThrAlaValPheAlaAlaThrGlyIleGln  171

541 CGCAACCGCACTGTGTGCTACGACCTGAGCCCACCCATCCTGTCTACTCGCTACCTGCCC  600
171 ArgAsnArgThrValCysTyrAspLeuSerProProIleLeuSerThrArgTyrLeuPro  191

601 TATGGTATGGCCCTCACGGTCATCGGCTTCTTGCTGCCCTTCATAGCCTTACTGGCTTGT  660
191 TyrGlyMetAlaLeuThrValIleGlyPheLeuLeuProPheIleAlaLeuLeuAlaCys  211

661 TATTGTCGCATGGCCCGCCGCCTGTGTCGCCAGGATGGCCCAGCAGGTCCTGTGGCCCAA  720
211 TyrCysArgMetAlaArgArgLeuCysArgGlnAspGlyProAlaGlyProValAlaGln  231

721 GAGCGGCGCAGCAAGGCGGCTCGTATGGCTGTGGTGGTGGCAGCTGTCTTTGCCATCAGC  780
231 GluArgArgSerLysAlaAlaArgMetAlaValValValAlaAlaValPheAlaIleSer  251

781 TTCCTGCCTTTCCACATCACCAAGACAGCCTACTTGGCTGTGCGCTCCACGCCCGGTGTC  840
251 PheLeuProPheHisIleThrLysThrAlaTyrLeuAlaValArgSerThrProGlyVal  271

841 TCTTGCCCTGTGCTGGAGACCTTCGCTGCTGCCTACAAAGGCACTCGGCCCTTCGCCAGT  900
271 SerCysProValLeuGluThrPheAlaAlaAlaTyrLysGlyThrArgProPheAlaSer  291

901 GTCAACAGTGTTCTGGACCCCATTCTCTTCTACTTCACACAACAGAAGTTCCGGCGGCAA  960
291 ValAsnSerValLeuAspProIleLeuPheTyrPheThrGlnGlnLysPheArgArgGln  311

961 CCCCACGATCTCTTACAGAGGCTCACAGCCAAGTGGCAGAGGCAGAGAGTCTGAGGCCCC 1020
311 ProHisAspLeuLeuGlnArgLeuThrAlaLysTrpGlnArgGlnArgVal***        329
```

FIGURE 71

```
                         10         20         30         40         50
75+13,CODING    1  MPQL------ --NGIISAEG PPP------- -TI-SVYR-E DFKRLLIP-    50
P2UR_MOUSE      1  VAADLEPWNS TINGIWEGDE PGY------- ---KCRFN-E DEKYVLL-P-   50
P2YR_CHICK      1  STEALISAAL --NGI-S-PE LAGGWAAGN AITKCSLTKT GEQFYYL-ET    50

60         70         80         90        100
75+13,CODING    51 V-YSWVLWT -PLNICVLA QL--CASRRT LTR-SAVVIL NLALADLMYA    100
P2UR_MOUSE      51 VSYGVVCVLC -LCNVVALY -LFLG-RLKI WNA-STYMF HLAVSDSLYA    100
P2YR_CHICK      51 V-YLLVFTTS FLG-NSVAIW M-E-VFHMRP WSGIS-VYMF NLALADFLYV   100

110        120        130        140        150
75+13,CODING    101 CSLPLLIYNY ARG-DHNPFC ELACRFVRFL FYANL-HSSI FLTCISFQRY   150
P2UR_MOUSE      101 ASLPLLVYYY ARG-DHNPFS TVLCKLVRFL FYINLVCSIL FLTCISVHRC   150
P2YR_CHICK      101 LTLPALIFYY FNKTE-KISG DVMCKLQRFI SHVNLYGSII FLTCISVHRY   150

160        170        180        190        200
75+13,CODING    151 LGICHPLASW HKEGEE-RAA WVLCGVVWLA VTAQCL-ETA VFAA-IGIQR   200
P2UR_MOUSE      151 LGVLRPLHSL --RWGRAIWA RRVAAVVWVL VLACQAPVL YFVT-ISVRG    200
P2YR_CHICK      151 TSWHPLKSL G-SLKKQN-A VYVSSLVWAL WAVIA-PTL -SYSGIGVRR    200

210        220        230        240        250
75+13,CODING    201 NRT-VCYDLS PPI-I-STRY LPYSALIVI GSLLPFIALL ACYCRSARRI   250
P2UR_MOUSE      201 TH-ITCHDTS ARE-LFSHGV A-YSSVMLGL LFAVPFSVIL VCYVLMARRL    250
P2YR_CHICK      201 NKTITCYDTT ADSYLRSMSV --YSMCTIVF MGCIPFIVIL GCYGLIVKAL    250

260        270        280        290        300
75+13,CODING    251 CRODGPA-EE VAQERRSKAA --RMAVVAA VFAISFLPFH ITKTAVLAVR   300
P2UR_MOUSE      251 -LN--PAYGT TGGLPRARRK SVRTIALVLA VFALCFLPFH VTRTLYYSFR    300
P2YR_CHICK      251 IYKD-LDNSE ---L-FRK-- SIYLVIIVLT VFAVSYLPFH VMKTLNLRAR    300

310        320        330        340        350
75+13,CODING    301 STP---GVSC PVLETFA-AAY KGTRP-ASVN SVLDPILYF TQQKFRRQPH   350
P2UR_MOUSE      301 SLD----LSC HTLNAINMAV RITRPLASAN SCLDPVLYFL AGQRLVRFAR   350
P2YR_CHICK      301 -LDFQTPQMC AFNDKVYSTY QVTRGLASLN SCVDPILYFL AGDTFRRRLS   350

360        370        380        390        400
75+13,CODING    351 DLLQRLTAKW QRQRV*.... .......... .......... ..........   400
P2UR_MOUSE      351 DAKPPTEPTP SPCARRRLGL HRPNRTVRKD LSVSSDDSRR TESTPAGSET    400
P2YR_CHICK      351 RNTRKSSRRS EPNVQSKSEE MTLNILTEYK QNGDTSL... ..........   400

410        420        430        440        450
75+13,CODING    401 .......... .......... .......... .......... ..........   450
P2UR_MOUSE      401 KDIRL..... .......... .......... .......... ..........   450
P2YR_CHICK      401 .......... .......... .......... .......... ..........   450
```

FIGURE 72

```
            9          18         27         36         45         54
5' GCC ACC AAC GTG TTC ATC CTG TCA CTG GCC GAT GTG CTG GTG ACA GCC ATC TGC
   --- --- --- --- --- --- --- --- --- --- --- --- --- --- --- --- --- ---
                                           Ala Asp Val Leu Val Thr Ala Ile Cys 63         72         81         90         99        108
   CTG CCG GCC AGT CTG CTG GTA GAC ATC ACG GAA TCC TGG CTC TTT GGC CAT GCC
   --- --- --- --- --- --- --- --- --- --- --- --- --- --- --- --- --- ---
   Leu Pro Ala Ser Leu Leu Val Asp Ile Thr Glu Ser Trp Leu Phe Gly His Ala 117        126        135        144        153        162
   CTC TGC AAG GTC ATC CCC TAT CTA CAG GCC GTG TCC GTG TCA GTG GTC GTG CTG
   --- --- --- --- --- --- --- --- --- --- --- --- --- --- --- --- --- ---
   Leu Cys Lys Val Ile Pro Tyr Leu Gln Ala Val Ser Val Ser Val Val Val Leu 171        180        189        198        207        216
   ACT CTC AGC TCC ATC GCC CTG GAC CGC TGG TAC GCC ATC TGC CAC CCG CTG TTG
   --- --- --- --- --- --- --- --- --- --- --- --- --- --- --- --- --- ---
   Thr Leu Ser Ser Ile Ala Leu Asp Arg Trp Tyr Ala Ile Cys His Pro Leu Leu 225        234        243        252        261        270
   TTC AAG AGC ACT GCC CGG CGC GCC CGC GGC TCC ATC CTC GGC ATC TGG GCG GTG
   --- --- --- --- --- --- --- --- --- --- --- --- --- --- --- --- --- ---
   Phe Lys Ser Thr Ala Arg Arg Ala Arg Gly Ser Ile Leu Gly Ile Trp Ala Val 279        288        297        306        315        324
   TCG CTG GCT GTC ATG GTG CCT CAG GCT GCT GTC ATG GAG TGT AGC AGC GTG CTG
   --- --- --- --- --- --- --- --- --- --- --- --- --- --- --- --- --- ---
   Ser Leu Ala Val Met Val Pro Gln Ala Ala Val Met Glu Cys Ser Ser Val Leu 333        342        351        360        369        378
   CCC GAG CTG GCC AAC CGC ACC CGC CTC CTG TCT GTC TGT GAT GAG CGC TGG GCA
   --- --- --- --- --- --- --- --- --- --- --- --- --- --- --- --- --- ---
   Pro Glu Leu Ala Asn Arg Thr Arg Leu Leu Ser Val Cys Asp Glu Arg Trp Ala 387        396        405        414        423        432
   GAC GAC CTG TAC CCC AAG ATC TAC CAC AGC TGC TTC TTC ATT GTC ACC TAC CTG
   --- --- --- --- --- --- --- --- --- --- --- --- --- --- --- --- --- ---
   Asp Asp Leu Tyr Pro Lys Ile Tyr His Ser Cys Phe Phe Ile Val Thr Tyr Leu 441        450        459        468        477        486
   GCC CCA CTG GGC CTC ATG GCC ATG GCC TAT TTC CAG ATC TTC CGC AAG CTC TGG
   --- --- --- --- --- --- --- --- --- --- --- --- --- --- --- --- --- ---
   Ala Pro Leu Gly Leu Met Ala Met Ala Tyr Phe Gln Ile Phe Arg Lys Leu Trp 495        504        513        522        531        540
   GGC CGC CAG ATC CCC GGC ACC ACC TCG GCC CTG GTG CGC AAC TGG AAG CGG CCC
```

FIGURE 73

```
    ---  ---  ---  ---  ---  ---  ---  ---  ---  ---  ---  ---  ---  ---  ---  ---  ---
    Gly  Arg  Gln  Ile  Pro  Gly  Thr  Thr  Ser  Ala  Leu  Val  Arg  Asn  Trp  Lys  Arg  Pro 549            558            567            576            585            594
    TCA  GAC  CAG  CTG  GAC  GAC  CAG  GGC  CAG  GGC  CTG  AGC  TCA  GAG  CCC  CAG  CCC  CGG
    ---  ---  ---  ---  ---  ---  ---  ---  ---  ---  ---  ---  ---  ---  ---  ---  ---  ---
    Ser  Asp  Gln  Leu  Asp  Asp  Gln  Gly  Gln  Gly  Leu  Ser  Ser  Glu  Pro  Gln  Pro  Arg 603            612            621            630            639            648
    GCC  CGC  GCC  TTC  CTG  GCC  GAG  GTG  AAA  CAG  ATG  CGA  GCC  CGG  AGG  AAG  ACG  GCC
    ---  ---  ---  ---  ---  ---  ---  ---  ---  ---  ---  ---  ---  ---  ---  ---  ---  ---
    Ala  Arg  Ala  Phe  Leu  Ala  Glu  Val  Lys  Gln  Met  Arg  Ala  Arg  Arg  Lys  Thr  Ala 657            666            675            684            693            702
    AAG  ATG  CTG  ATG  GTG  GTG  CTG  CTG  GTC  TTC  GCC  CTC  TGC  TAC  CTG  CCC  ATC  AGT
    ---  ---  ---  ---  ---  ---  ---  ---  ---  ---  ---  ---  ---  ---  ---  ---  ---  ---
    Lys  Met  Leu  Met  Val  Val  Leu  Leu  Val  Phe  Ala  Leu  Cys  Tyr  Leu  Pro  Ile  Ser 711            720            729            738            747            756
    GTC  CTC  AAC  GTC  CTC  AAG  AGG  GTC  TTC  GGG  ATG  TTC  CGC  CAA  GCC  AGC  GAC  CGA
    ---  ---  ---  ---  ---  ---  ---  ---  ---  ---  ---  ---  ---  ---  ---  ---  ---  ---
    Val  Leu  Asn  Val  Leu  Lys  Arg  Val  Phe  Gly  Met  Phe  Arg  Gln  Ala  Ser  Asp  Arg 765            774            783            792            801            810
    GAG  GCC  ATC  TAC  GCC  TGC  TTC  ACC  TTC  TCC  CAC  TGG  CTG  GTG  TAC  GCC  AAC  AGC
    ---  ---  ---  ---  ---  ---  ---  ---  ---  ---  ---  ---  ---  ---  ---  ---  ---  ---
    Glu  Ala  Ile  Tyr  Ala  Cys  Phe  Thr  Phe  Ser  His  Trp  Leu  Val  Tyr  Ala  Asn  Ser 819            828            837
    GCC  GCC  AAT  CCC  CTC  CTC  TAC  TCC  TTC  CTC  CCT  3'
    ---  ---
    Ala  Ala
```

FIGURE 76

| | | 10 | 20 | 30 | 40 | 50 | |
|---|---|---|---|---|---|---|---|
| h3H2-17(5-3) | 1 | | | | | | |
| p3H2-17(5') | 1 | GTGGGCCTGG | TGGGCAACAT | CCTGGCTTCC | TGGCACAAGC | GTGGAGTCG | 50 |

| | | 60 | 70 | 80 | 90 | 100 | |
|---|---|---|---|---|---|---|---|
| h3H2-17(5-3) | 51 | | | | | TGACAACCC | 100 |
| p3H2-17(5') | 51 | CCGTGCTGCT | TGGTAGTGT | GTGGAGTCGT | GTGGCTGGCT | GTGACAGCCC | 100 |

| | | 110 | 120 | 130 | 140 | 150 | |
|---|---|---|---|---|---|---|---|
| h3H2-17(5-3) | 101 | AGTGGCTGCC | CACAGCCATC | TTTGCTGCCA | CAGGCATCCA | GCGTAACCGC | 150 |
| p3H2-17(5') | 101 | AGTGCCCTGCC | CACGGCAGTC | TTTGCTGCCA | CAGGCATCCA | GCGCAACCGC | 150 |

| | | 160 | 170 | 180 | 190 | 200 | |
|---|---|---|---|---|---|---|---|
| h3H2-17(5-3) | 151 | ACTGTCTGCT | ATGACCTCAG | CCGGCCTGCC | CTGCCACCC | ACTATATGCC | 200 |
| p3H2-17(5') | 151 | ACTGTGTGCT | ACGACCTGAG | CCCACCATC | CTGTGTACTC | GCTACCTGCC | 200 |

| | | 210 | 220 | 230 | 240 | 250 | |
|---|---|---|---|---|---|---|---|
| h3H2-17(5-3) | 201 | CTATGCATG | GCTCTCTACTG | TCATCGGCTT | CCTGCTTGCCC | TTTGCTGCT | 250 |
| p3H2-17(5') | 201 | CTATGTATG | GCCCTCAGG | TCATCGGCTT | CTTGCTGCCC | TTTCATAGCT | 250 |

| | | 260 | 270 | 280 | 290 | 300 | |
|---|---|---|---|---|---|---|---|
| h3H2-17(5-3) | 251 | TGCTGGCTG | CTACTGTCTC | CTGGCTGCC | GCC....... | .......... | 300 |
| p3H2-17(5') | 251 | TACTGGCTTG | TTATTGTGCC | ATGGCTTGCC | GCCTGTGTG | CCAGGATGGC | 300 |

| | | 310 | 320 | 330 | 340 | 350 | |
|---|---|---|---|---|---|---|---|
| h3H2-17(5-3) | 301 | .......... | CTGTGGCCTG | .......... | .......... | .......... | 350 |
| p3H2-17(5') | 301 | CCAGCAGGTC | CTGTGGCCCA | AGAGCCGGCG | AGCAAGGCGG | CTCGTATGGC | 350 |

| | | 360 | 370 | 380 | 390 | 400 | |
|---|---|---|---|---|---|---|---|
| h3H2-17(5-3) | 351 | .......... | .......... | .......... | .......... | .......... | 400 |
| p3H2-17(5') | 351 | TGTGGTGGTG | GCAGCTGTCT | TTGCCCTCTG | CTGGCTGCCT | CTCTAC..... | 400 |

FIGURE 77

```
   1 TGACTCCCTGAACATAGGAAACCCACCTGGGCAGCCATGGAATGGGACAATGGCACAGGC        60
   1                                           MetGluTrpAspAsnGlyThrGly    8

61 CAGGCTCTGGGCTTGCCACCCACCACCTGTGTCTACCGCGAGAACTTCAAGCAACTGCTG       120
   8 GlnAlaLeuGlyLeuProProThrThrCysValTyrArgGluAsnPheLysGlnLeuLeu        28

121 CTGCCACCTGTGTATTCGGCGGTGCTGGCGGCTGGCCTGCCGCTGAACATCTGTGTCATT       180
  28 LeuProProValTyrSerAlaValLeuAlaAlaGlyLeuProLeuAsnIleCysValIle        48

181 ACCCAGATCTGCACGTCCCGCCGGGCCCTGACCCGCACGGCCGTGTACACCCTAAACCTT       240
  48 ThrGlnIleCysThrSerArgArgAlaLeuThrArgThrAlaValTyrThrLeuAsnLeu        68

241 GCTCTGGCTGACCTGCTATATGCCTGCTCCCTGCCCCTGCTCATCTACAACTATGCCCAA       300
  68 AlaLeuAlaAspLeuLeuTyrAlaCysSerLeuProLeuLeuIleTyrAsnTyrAlaGln        88

301 GGTGATCACTGGCCCTTTGGCGACTTCGCCTGCCGCCTGGTCCGCTTCCTCTTCTATGCC       360
  88 GlyAspHisTrpProPheGlyAspPheAlaCysArgLeuValArgPheLeuPheTyrAla       108

361 AACCTGCACGGCAGCATCCTCTTCCTCACCTGCATCAGCTTCCAGCGCTACCTGGGCATC       420
 108 AsnLeuHisGlySerIleLeuPheLeuThrCysIleSerPheGlnArgTyrLeuGlyIle       128

421 TGCCACCCGCTGGCCCCTGGCACAAACGTGGGGGCCGCCGGGCTGCCTGGCTAGTGTGT       480
 128 CysHisProLeuAlaProTrpHisLysArgGlyGlyArgArgAlaAlaTrpLeuValCys       148

481 GTAACCGTGTGGCTGGCCGTGACAACCCAGTGCCTGCCCACAGCCATCTTCGCTGCCACA       540
 148 ValThrValTrpLeuAlaValThrThrGlnCysLeuProThrAlaIlePheAlaAlaThr       168

541 GGCATCCAGCGTAACCGCACTGTCTGCTATGACCTCAGCCCGCCTGCCCTGGCCACCCAC       600
 168 GlyIleGlnArgAsnArgThrValCysTyrAspLeuSerProProAlaLeuAlaThrHis       188

601 TATATGCCCTATGGCATGGCTCTCACTGTCATCGGCTTCCTGCTGCCCTTTGCTGCCCTG       660
 188 TyrMetProTyrGlyMetAlaLeuThrValIleGlyPheLeuLeuProPheAlaAlaLeu       208

661 CTGGCCTGCTACTGTCTCCTGGCCTGCCGCCTGTGCCGCCAGGATGGCCCGGCAGAGCCT       720
 208 LeuAlaCysTyrCysLeuLeuAlaCysArgLeuCysArgGlnAspGlyProAlaGluPro       228

721 GTGGCCCAGGAGCGGCGTGGCAAGGCGGCCCGCATGGCCGTGGTGGTGGCTGCTGCCTTT       780
 228 ValAlaGlnGluArgArgGlyLysAlaAlaArgMetAlaValValValAlaAlaAlaPhe       248

781 GCCATCAGCTTCCTGCCTTTTCACATCACCAAGACAGCCTACCTGGCAGTGGGCTCGACG       840
 248 AlaIleSerPheLeuProPheHisIleThrLysThrAlaTyrLeuAlaValGlySerThr       268

841 CCGGGCGTCCCCTGCACTGTATTGGAGGCCTTTGCAGCGGCCTACAAAGGCACGCGGCCG       900
 268 ProGlyValProCysThrValLeuGluAlaPheAlaAlaAlaTyrLysGlyThrArgPro       288

901 TTTGCCAGTGCCAACAGCGTGCTGGACCCCATCCTCTTCTACTTCACCCAGAAGAAGTTC       960
 288 PheAlaSerAlaAsnSerValLeuAspProIleLeuPheTyrPheThrGlnLysLysPhe       308

961 CGCCGGCGACCACATGAGCTCCTACAGAAACTCACAGCCAAATGGCAGAGGCAGGGTCGC      1020
 308 ArgArgArgProHisGluLeuLeuGlnLysLeuThrAlaLysTrpGlnArgGlnGlyArg       328

1021 TGA                                                              1023
 328 ***                                                               329
```

FIGURE 79

```
human prino,   1 MEWDNGTIQA LGLPPTICVY RENFKQLLIP PVYSAVTAAG LPLNICVIIG   50
mouseFULL3H2   1 MEQDNGTIQA PGLPPTICVY REDFKRLLLT PVYSVVLVVG LPLNICVIIG   50 human prino,  51 ICTSRRALTR TAVYTLNIAL ADLVACSLF  LIIYNYAQGE HWPFGDFACR  100
mouseFULL3H2  51 ICASRRFLTR SAVYTLNIAL ADLMACSLF  LIIYNYARGD HWPFGDLACR  100 human prino, 101 LVRFLFYANL HGSILFLTCI SFQRYLGICH PLASMWHKRGG RRAAMLCVT   150
mouseFULL3H2 101 FVRFLFYANL HGSILFLTCI SFQRYLGICH PLASMWHKRGG RRAAMVCGV   150 human prino, 151 VMLAVTIQCL PTAIFAATGI QRNRTVCYDI SPPALTHYM  SPPALTHYM  PYGMALTVIG 200
mouseFULL3H2 151 VMLAVTAQCL PTAVFAATGI QRNRTVCYDL SPPILSIRVL            PYGMALTVIG 200 human prino, 201 FLLPFAALLA CYCILFCRLC RQDGPAEFVA QERRGKAARM AVVVAAFFAI  250
mouseFULL3H2 201 FLLPFLALLA CYCMARRLC  RQDGPAFVA  QERRSKAARM AVVVAAVFAI  250 human prino, 251 SFLPFHITKT AYLAVGSTFG VPCTVLEAFA AAYKGTRPFA SANSVLDPIL  300
mouseFULL3H2 251 SFLPFHITKT AMLAVRSTFG VSCPMLEFFA AAYKGTRPFA EVNSVLDPIL  300 human prino, 301 FYFTQKKFRR RPHELLQKLT AKMQRCGR*.  ..........  ..........  350
mouseFULL3H2 301 FYFTQKNFRR QPHDLLQRLT AKMQRQRV*.  ..........  ..........  350
```

G PROTEIN COUPLED RECEPTOR PROTEIN PRODUCTION, AND USE THEREOF

This application is a DIV of Ser. No. 09/038,572 Mar. 11, 1998 which is a DIV of Ser. No. 08/513,974 Sep. 14, 1995 U.S. Pat. No. 6,114,139 which is a 371 of PCT/J95/01599 Aug. 10, 1995.

FIELD OF THE INVENTION

The present invention relates to novel DNAs which are useful as DNA primers for a polymerase chain reaction (PCR); methods for amplifying DNAs each coding for a G protein coupled receptor protein via PCR techniques using said DNA; screening methods for DNAs each encoding a G protein coupled receptor protein via PCR techniques using said DNA; G protein coupled receptor protein-encoding DNAs obtained by said screening method; G protein coupled receptor proteins which are encoded by the DNA obtained via said screening method, peptide fragments or segments thereof, and modified peptide derivatives thereof; etc.

The present invention also relates to novel G protein coupled receptor proteins; novel G protein coupled receptor protein-encoding DNAs; processes for producing said G protein coupled receptor protein; use of said receptor protein and said protein-encoding DNA; etc.

The present invention also relates to novel human amygdaloid nucleus-derived G protein coupled receptor proteins;

novel DNAs each coding for said G protein coupled receptor protein; processes for producing said G protein coupled receptor protein; use of said receptor protein and said protein-encoding DNA; etc.

The present invention also relates to novel mouse pancreatic β cell line MIN6-derived G protein coupled receptor proteins; novel DNAs each coding for said G protein coupled receptor protein; processes for producing said G protein coupled receptor protein; use of said receptor protein and aid protein-encoding DNA; etc. Further, the present invention relates to novel human-derived G protein coupled receptor proteins (human prinoceptors); novel DNAs each coding for said G protein coupled receptor protein; processes for producing said G protein coupled receptor protein; use of said receptor protein and said protein-encoding DNA; etc.

BACKGROUND OF THE INVENTION

A variety of hormones, neurotransmitters and the like control, regulate or adjust the functions of living bodies via specific receptors located in cell membranes. Many of these receptors mediate the transmission of intracellular signals via activation of guanine nucleotide-binding proteins (hereinafter, sometimes referred to as G proteins) with which the receptor is coupled and possess the common (homologous) structure, i.e. seven transmembranes (membrane-spanning regions (domains)). Therefore, such receptors are generically referred to as G protein coupled receptors or seven transmembrane (membrane-spanning) receptors.

G protein coupled receptor proteins have a very important role as targets for molecules such as hormones, neurotransmitters and physiologically active substances, which molecules control, regulate or adjust the functions of living bodies. Each molecule has its own receptor protein which is specific thereto, whereby the specificities of individual physiologically active substances, including specific target cells and organs, specific pharmacological actions, specific action strength, action time, etc., are decided. Accordingly, it has been believed that, if G protein coupled receptor genes or cDNA can be cloned, those will be helpful not only for the clarification of structure, function, physiological action, etc. of the G protein coupled receptor but also for the development of pharmaceuticals by investigating the substances which act on the receptor. Until now, only several G protein coupled receptor genes or cDNAs have been cloned but it is believed that there are many unknown G protein coupled receptor genes which have not been recognized yet.

The characteristic feature of the G protein coupled receptor proteins which have been known up to now is that seven clusters of hydrophobic amino acid residues are located in the primary structure and pass through (span) the cell membrane at each region thereof. It has been known that such a structure is common among all of the known G protein coupled receptor proteins and further that the amino acid sequences corresponding to the area where the protein passes through the membrane (membrane-spanning region or transmembrane region) and the amino acid sequences near the membrane-spanning region are often highly conserved among the receptors. When an unknown protein has such a structure, it is strongly suggested that said protein is within a category of the G protein coupled receptor proteins. In addition, some amino acid residue alinements are common (homologous) and, by taking it as a characteristic feature, it is further strongly suggested that said protein is a G protein coupled receptor protein.

Libert, F, et al. (Science, 244:569–571; 1989) reported a method for cloning novel receptor genes by means of a polymerase chain reaction (hereinafter, sometimes referred to as PCR or a PCR technique) for a synthetic DNA primer which was synthesized based upon the information of common amino acid sequences obtained from a comparison among known G protein coupled receptor proteins. Libert, F. et al. used a pair of synthetic DNA primers corresponding to the portions of the third and the sixth membrane-spanning regions. However, in general, the design of primers used for the PCR regulates the molecular species of DNAs which are to be amplified. In addition, when a similarity (homology) in the amino acid sequence level is used as a basis, the use of different codons affects on the binding (hybridization) of the primer thereby resulting in a decrease in the amplifying efficiency. Accordingly, although various novel receptor protein DNAs have been obtained using said DNA primers, it is not possible to succeed in amplifying DNAs for all receptor proteins in the prior art.

Further, the amino acid sequence which is common to from the first to the seventh membrane-spanning regions among 74 G protein coupled receptor proteins was reported by William C. Probst, et al. (DNA and Cell Biology, Vol. 11, No. 1, 1992, pp. 1–20). In this report, however, there is no suggestion for a method in which DNA coding for a novel G protein coupled receptor protein is screened by means of PCR using DNA primers which are complementary to the DNA coding for those amino acid sequences.

It would be desirable to develop DNA primers for PCR techniques which allow selective and efficient screenings of DNAs coding for the areas (regions) more nearer the full length of novel G protein coupled receptor proteins by utilizing the common (homologous) sequence(s) of the G protein coupled receptor protein or the DNA coding therefor.

It would also be desirable to develop synthetic DNA primers corresponding to the portions of the third and the sixth membrane-spanning regions, said primer being useful in screening for DNA coding for G protein coupled receptor proteins in more selective and efficient manner as compared with a series of the synthetic DNA primers corresponding to the sequences of the third to the sixth membrane-spanning regions as reported by Libert, F. et al.

G protein coupled receptor proteins are important for investigating substances which control the function of living organisms and proceeding developments thereof as pharmaceuticals. Finding and development of candidate compounds for new pharmaceuticals can be efficiently proceeded by using G protein coupled receptor proteins and by conducting receptor binding experiments and evaluating experiments on agonists/antagonists using intracellular information transmittance systems as indexes. Especially when the presence of a novel G protein coupled receptor protein can be clarified, the presence of a substance having a specific action thereon can be suggested.

If a novel DNA which codes for a novel G protein coupled receptor protein can be efficiently screened and isolated, it will now be possible to proceed with the isolation of DNA having an entire coding region, the construction of an expression system therefor and the screening of an acting ligand.

A hypothalamo-hypophysial system is one of the passages for controlling, regulating or adjusting the functions of organisms relying upon interactions of hormones and neurotransmitters with G protein coupled receptors. In the hypothalamo-hypophysial system, the secretion of pituitary hormones from the pituitary body (hypophysis) is regulated by hypothalamic hormones (hypophysiotropic releasing factors), and the functions of target cells and organs are controlled by pituitary hormones released into the blood. Functions which are important for the living body are regulated through this system, such as maintenance of homeostasis and control of development and growth of a genital system and an individual organism. Representative examples of the hypothalamic hormones include TRH, LH-RH, CRF, GRF, somatostatin, galanin, etc. Representative examples of the pituitary hormones include TSH, ACTH, FSH, LH, prolactin, growth hormone, oxytocin, vasopressin, etc. In particular, the secretion of pituitary hormones is regulated according to a positive feedback mechanism or a negative feedback mechanism relied on the hypothalamic hormones and peripheral hormones secreted from the target endocrine glands. A variety of receptor proteins present in the pituitary gland play a major role for regulating the hypothalamo-hypophysial system.

It has been widely known that these hormones, factors and receptors are widely distributed in the brain instead of existing only locally in the hypothalamo-hypophysial system. This fact suggests that the substances which are called "hypothalamic hormones" are working as neurotransmitters or neuroregulators in the central nervous system. It is further considered that these substances are similarly distributed even in the peripheral tissues to play the role of important functions. The pancreas plays an important role of carrying out the carbohydrate metabolism by secreting not only a digestive fluid but also glucagon and insulin. Insulin is secreted from the β cells and its secretion is promoted chiefly by glucose. It has, however, been known that a variety of receptors exist in the β cells, and the secretion of insulin is controlled by various factors such as peptide hormones (galanin, somatostatin, gastric inhibitory polypeptide, glucagon, amylin, etc.), sugars (mannose, etc.), amino acids, and neurotransmitters in addition to glucose.

It has thus been known that in the pituitary gland and in the pancreas are present receptor proteins for many hormones and neurotransmitters, said receptor proteins playing important roles for regulating the functions. As for the galanin and amylin, however, there has not yet been reported any discovery concerning the structure of their receptor protein cDNAs. It is not known whether there exist any unknown receptor proteins or receptor protein subtypes.

For substances regulating the functions of the pituitary gland and pancreas, there exist receptor proteins specific to said substance on the surfaces of various functional cells of the pituitary gland and pancreas. The pituitary gland and the pancreas are associations of a plurality of functional cells, and the actions of the individual substances are defined by the distributions of their target receptor proteins among the functional cells. Accordingly, a substance, in many cases, exhibits an extensive variety of actions. To comprehend such complex systems, it is necessary to clarify the relations between the acting substances and the specific receptor proteins. It is further necessary to efficiently screen for receptor protein agonists and antagonists capable of regulating the pituitary gland and pancreas, to clarify the structures of genes of receptor proteins from the standpoint of investigating and developing pharmaceuticals, and further to express them in a suitable expression system.

By utilizing the fact that a G protein coupled receptor protein exhibits homology in part of the structure thereof at the amino acid sequence level, an experiment of looking at DNAs coding for novel receptor proteins relying upon a polymerase chain reaction (hereinafter simply referred to as "PCR") has recently been made.

In the central nervous system, many receptor proteins such as dopamine receptor protein, LH-RH receptor protein, neurotensin receptor protein, opioid receptor protein, CRF receptor protein, CRF receptor protein, somatostatin receptor protein, galanin receptor protein, TRH receptor protein, etc. are G protein coupled receptor proteins, and it has been clarified that ligands to these receptors exert a variety of effects in the central nervous system.

In the immune system, an α- or a β-chemokine receptor protein, an MIPIα receptor protein, an IL-8 receptor protein, a C5a receptor protein, etc. have been known as such G protein coupled receptor proteins, and are working as receptor proteins responsive to immunoregulating substances to play important roles for regulating the functions of the living body. There is, for example, an IL-6 receptor protein that acts both in the above-mentioned central nervous system and in the immune system. IL-6 is both a β-cell differentiating factor and a biologically active factor related to the proliferation and differentiation of nerve cells.

It has been widely known that these hormones, factors and receptor proteins are usually widely distributed up to the peripheral tissues instead of existing only locally in the central nervous system and in the immune system and are producing important functions, respectively. Agonists and antagonists for these receptor proteins are now being developed as various useful pharmaceuticals.

For substances regulating the functions of the central nervous system and the immune system, there exist receptor proteins specific to said substance on the surfaces of various functional cells of the central nervous system and the immune system. The central nervous system and the immune system are associations of a plurality of functional cells, and the actions of the individual substances are defined by the distributions of their target receptor proteins among the functional cells. Accordingly, a substance, in many cases, exhibits an extensive variety of actions. Moreover, there is an example wherein many factors play a part in a physiological phenomenon. To comprehend such complex systems, it is necessary to clarify relations between the acting substances and the specific receptor proteins.

As discussed herein above, the G protein coupled receptor protein is present on the cell surface of living body cells and organs and has a very important role as a target for molecules such as hormones, neurotransmitters and physiologically active substances, which molecules control, regulate or adjust the functions of living body cells and organs.

SUMMARY OF THE INVENTION

One object of the present invention is to provide novel DNAs which are useful as DNA primers for a polymerase chain reaction; methods for amplifying a DNA coding for a G protein coupled receptor protein using said DNA; screening methods for the DNA coding for a G protein coupled receptor protein using said DNA; DNAs obtained by said screening method; and G protein coupled receptor proteins encoded by the DNA obtained by said screening method, peptide fragments or segments thereof, modified peptide derivatives thereof or salts thereof.

Another object of the present invention is to provide processes for producing said receptor protein; transformants capable of expressing said receptor protein; cell membrane fractions obtained from said transformant; methods for determining a ligand to the receptor protein; screening methods for a compound or a salt thereof capable of inhibiting the binding of the ligand with the receptor protein; kits for said screening method, pharmaceutical compositions comprising an effective amount of the inhibitory compound; antibodies against said receptor protein; immunoassays using said receptor protein or said antibody and use of said receptor protein and encoding DNA.

Yet another object of the present invention is to provide novel G protein coupled receptor proteins which are expressed in pituitary glands or pancreatic β cells; DNAs comprising a DNA coding for said G protein coupled receptor protein; processes for producing said receptor protein; transformants capable of expressing said receptor protein; cell membrane fractions obtained from said transformant; methods for determining a ligand to the receptor protein; screening methods for a compound or a salt thereof capable of inhibiting the binding of the ligand with the receptor protein; kits for said screening method, pharmaceutical compositions comprising the inhibitory compound; antibodies against said receptor protein; immunoassays using said receptor protein or said antibody and use of said receptor protein and encoding DNA.

Still another object of the present invention is to provide novel human amygdaloid nucleus-derived G protein coupled receptor proteins; DNAs comprising a DNA coding for said G protein coupled receptor protein; processes for producing said receptor protein; transformants capable of expressing said receptor protein; cell membrane fractions obtained from said transformant; methods for determining a ligand to the receptor protein; screening methods for a compound or a salt thereof capable of inhibiting the binding of the ligand with the receptor protein; kits for said screening method, pharmaceutical compositions comprising the inhibitory compound; antibodies against said receptor protein; immunoassays using said receptor protein or said antibody and use of said receptor protein and encoding DNA.

Yet another object of the present invention is to provide novel mouse pancreatic β cell line MIN6-derived G protein coupled receptor proteins; DNAs comprising a DNA coding for said G protein coupled receptor protein; processes for producing said receptor protein; transformants capable of expressing said receptor protein; cell membrane fractions obtained from said transformant; methods for determining a ligand to the receptor protein; screening methods for a compound or a salt thereof capable of inhibiting the binding of the ligand with the receptor protein; kits for said screening method, pharmaceutical compositions comprising the inhibitory compound; antibodies against said receptor protein; immunoassays using said receptor protein or said antibody and use of said receptor protein and encoding DNA.

The present inventors have succeeded in synthesizing novel DNA primers based upon the similarity (homology) with the base sequences coding for the first membrane-spanning region or the sixth membrane-spanning region each of known G protein coupled receptor proteins. It is to be particularly noted that there has been no report of a DNA primer pair which has been synthesized paying attention to the similarity with the base sequence coding for the first and the sixth membrane-spanning region of the known G protein coupled receptor protein.

Next the present inventors have succeeded in synthesizing other novel DNA primers based upon the similarity (homology) with the base sequences coding for the third or the sixth membrane-spanning region each of known G protein coupled receptor proteins. They have also unexpectedly succeeded in efficiently amplifying DNAs (DNA fragments) coding for G protein coupled receptor proteins by means of PCR using those DNA primers.

They have further succeeded in synthesizing novel DNA primers based upon the similarity (homology) with the base sequences coding for the second or the seventh membrane-spanning region each of known G protein coupled receptor proteins; upon the similarity (homology) with the base sequences coding for first or the third membrane-spanning region each of known G protein coupled receptor proteins; and upon the similarity (homology) with the base sequences coding for the second or the sixth membrane-spanning region each of known G protein coupled receptor proteins. They have furthermore and unexpectedly succeeded in efficiently amplifying DNAs (DNA fragments) coding for G protein coupled receptor proteins by conducting PCR using those DNA primers.

Moreover, the present inventors have succeeded in efficiently cloning full-length DNA coding for said G protein coupled receptor protein via using amplified DNAs (DNA fragments) coding for said G protein coupled receptor protein. Thus, they have found that novel DNA coding for novel G protein coupled receptor proteins can be isolated, characterized or prepared via conducting amplifications and analyses of various DNA using said DNA primers.

To be more specific, the present inventors have selected amino acid sequences which are each common to the portion corresponding to or near the first and the sixth membrane-spanning region of the known individual G protein coupled receptor proteins and have designed the DNA primer (SEQ ID NO: 1) coding for the amino acid sequence common (homologous) to the first membrane-spanning region and the DNA primer (SEQ ID NO: 2) which is complementary to the nucleotide sequence coding for the amino acid sequence common (homologous) to the area near the sixth membrane-spanning region. Those DNA primers have a different nucleotide sequence as compared with reported DNA primers (e.g. a set of synthetic DNA primers corresponding to the third and the sixth membrane-spanning regions (SEQ ID NO: 60 and SEQ ID NO: 61) as reported by Libert, F. et al.) and such instant primers are novel and unique.

Especially for an object of conducting an efficient elongation reaction in the PCR, the 3'-terminal region of the instant primers contains the nucleotide sequence which is common (homologous) among many receptor proteins. Even in other areas, the similarity (homology) at the nucleotide sequence level (base sequence level) is utilized for setting the mixed base (nucleotide) parts wherein their nucleotide sequences (base sequences) are matched for as many nucleotides (bases) as possible among many DNA for the receptor proteins. Then the present inventors have amplified cDNA derived from human brain amygdala, human pituitary gland and rat brain, found the amplified products as shown in FIG. 17 and, from those products, obtained the G protein coupled receptor protein cDNAs having the sequence as shown in FIG. 18, FIG. 19, FIG. 20, FIG. 21, FIG. 22, FIG. 23, FIG. 27, FIG. 29, FIG. 34, FIG. 37, FIG. 40, FIG. 43 or FIG. 46. Among them, the G protein coupled receptor protein cDNAs having the sequence as shown in FIG. 22, FIG. 23, FIG. 27, FIG. 29, FIG. 34, FIG. 37, FIG. 40, FIG. 43 or FIG. 46 are novel.

Further, the present inventors have selected the amino acid sequences common (homologous) to the third and the sixth membrane-spanning region each of the known G protein coupled receptor proteins and designed the DNA primers coding for the amino acid sequence common (homologous) to the third membrane-spanning region (SEQ ID NO: β; SEQ ID NO: 5, SEQ ID NO: 6 and SEQ ID NO: 7) and the DNA primers which are complementary to the nucleotide sequence coding for the amino acid sequence common (homologous) to the portion near the sixth membrane-spanning region (SEQ ID NO: 4, SEQ ID NO: 8 and SEQ ID NO: 9). Again, those DNA primers have different base sequences from those of the DNA primers previously reported (e.g., a set of synthetic DNA primers corresponding to the sequence of the third and the sixth membrane-spanning regions (SEQ ID NO: 60 and SEQ ID NO: 61) as reported by Libert, F. et al.) and such instant primers are novel and unique. The present inventors amplified cDNA derived from the smooth muscles of gastric pylorus of rabbits using said DNA primer and obtained G protein coupled receptor protein cDNA having the sequence of FIG. 49 or FIG. 52. Those cDNAs are novel.

Still further, the present inventors have selected the amino acid sequences common (homologous) to the second and the seventh membrane-spanning region each of the known G protein coupled receptor proteins and designed the DNA primer coding for the amino acid sequence common (homologous) to the second membrane-spanning region (SEQ ID NO: 10) and the DNA primer which is complementary to the base sequence coding for the amino acid sequence common (homologous) to the portions near the seventh membrane-spanning region (SEQ ID NO: 11). Those DNA primers have different base sequences from those of DNA primers previously reported (e.g., a set of synthetic DNA primers corresponding to the part of the third and the sixth membrane-spanning regions (SEQ ID NO: 60 and SEQ ID NO: 61) as reported by Libert, F. et al) and such instant primers are novel and unique. The present inventors amplified cDNA derived from the smooth muscles of gastric pylorus of rabbits using said DNA primer and obtained G protein coupled receptor protein cDNAs having each the sequence of FIG. 55, FIG. 56, FIG. 72, or FIG. 73. Those cDNAs are novel.

Furthermore, the present inventors have selected the amino acid sequences common (homologous) to the first and the third membrane-spanning region each of the known G protein coupled receptor proteins and designed the DNA primer coding for the amino acid sequence common (homologous) to the first membrane-spanning region (SEQ ID NO: 12) and the DNA primer which is complementary to the base sequence coding for the amino acid sequence common (homologous) to the portions near the third membrane-spanning region (SEQ ID NO: 13). Still further, the present inventors have selected the amino acid sequences common (homologous) to the third and the sixth membrane-spanning region each of the known G protein coupled receptor proteins and designed the DNA primers coding for the amino acid sequence common (homologous) to the third membrane-spanning region (SEQ ID NO: 10 and SEQ ID NO: 18) and the DNA primers which are complementary to the base sequence coding for the amino acid sequence common (homologous) to the parts near the sixth membrane-spanning region (SEQ ID NO: 15 and SEQ ID NO: 19). Further, the present inventors have selected the amino acid sequences common (homologous) to the second and the sixth membrane-spanning region each of the known G protein coupled receptor proteins and designed the DNA primer coding for the amino acid sequence common (homologous) to the second membrane-spanning region (SEQ ID NO: 16) and the DNA primer which is complementary to the base sequence coding for the amino acid sequence common (homologous) to the parts near the sixth membrane-spanning region (SEQ ID NO: 17). Those DNA primers have different base sequences from those of DNA primers previously reported (e.g., a set of synthetic DNA primers corresponding to the part of the third and the sixth membrane-spanning regions (SEQ ID NO: 60 and SEQ ID NO: 61) as reported by Libert, F. et al) and such instant primers are novel and unique.

Still another object of the present invention is to provide a G protein coupled receptor protein expressed in the pituitary gland and pancreatic β cells, a DNA comprising a DNA coding for said protein, a process for producing said protein, and use of said protein and DNA.

In order to achieve the above-mentioned aims, the present inventors have made extensive investigations. As a result, the present inventors have succeeded in amplifying cDNA derived from the human pituitary gland and the mouse pancreatic β-cell strain, MIN 6, with a synthetic DNA primer for efficiently isolating G protein coupled receptor protein-encoding DNA, and have forwarded the analysis. Thus, the present inventors have succeeded in isolating novel human and mouse-derived G protein coupled receptor protein-encoding cDNAs, in determining the spartial structure thereof, and have considered that these cDNA sequences are preserved very well in the human and in the mouse, and are coding for novel receptor proteins for the same ligand. Based upon the above knowledge, the present inventors have discovered that these DNAs make it possible to obtain a cDNA having a full length open reading frame (ORF) of the receptor protein, hence, to produce the receptor protein. The inventors have further discovered that the above-mentioned receptor protein obtained when the G protein coupled receptor protein-encoding cDNA is expressed by a suitable means permits screening for a ligand to the receptor protein from the living body or from natural or non-natural compounds under guidance of data obtainable in receptor coupling tests or measurements of intracellular second messengers, etc. and further allows screening for a compound that inhibits the binding of the ligand and the receptor protein.

In one embodiment, the present inventors have carried out PCR amplification of novel human pituitary gland-derived cDNA fragments as shown in FIGS. 22 and 23, and have subcloned them to obtain a plasmid vector (p19P2). From analysis of the partial sequence, it has been clarified that the cDNA has been encoded a novel receptor protein. The synthetic DNA primers used for amplifying the cDNA are corresponding to seven hydrophobic clusters that exist in the known G protein coupled receptor proteins in common, i.e., corresponding to the first and sixth membrane-spanning regions among the membrane-spanning domains. The nucleotide sequence (SEQ ID NO: 29) has been determined from the primer region at the 5' side (first membrane-spanning domain side) and has been translated into an amino acid sequence (SEQ ID NO: 24) [FIG. 22]. As a result, the second and third membrane-spanning domains have been confirmed on the hydrophobicity plotting [FIG. 58]. Similarly, the nucleotide sequence (SEQ ID NO: 30) has been determined from the primer region at the 3' side (sixth membrane-spanning domain side) and has been translated into an amino acid sequence (SEQ ID NO: 25) [FIG. 23]. As a results the presence of the sixth and fifth membrane-spanning domains has been confirmed on the hydrophobicity plots [FIG. 59]. The size of the amplified cDNA is about 700 bp which is nearly comparable with the number of bases between the first membrane-spanning domain and the sixth membrane-spanning domain of the known G protein coupled receptor protein.

G protein coupled receptor proteins exert common property to some extent at an amino acid sequence level, and are forming one protein family. Therefore, data base retrieval has been carried out based upon the amino acid sequence of the subject novel receptor protein (protein encoded by cDNA included in p19P2). As a result, a high homology has been exhibited as compared with the known G protein coupled receptor protein (rat neuropeptide Y receptor protein encoded by S12863) that is shown in FIG. 60. This fact tells that the novel receptor protein of the present invention belongs to the G protein coupled receptor protein family. Moreover, the data base has been retrieved using, as a template, the amino acid sequence encoded by the DNA of the invention. It exhibits high homology to the amino acid sequences of the known G protein coupled receptor proteins, mouse-derived ligand unknown RP-23 (B40470), human-derived ligand unknown K-opioid receptor protein (P30098) and human-derived NK-2 receptor protein (JQ1059). However, none of them are in perfect agreement, from which it is learned that a novel receptor protein had been encoded. The aforementioned abbreviations in parentheses are reference numbers that are assigned when they are registered as data to NBRF-PIR/Swiss-PROT and are, usually, each called "Accession Number".

Next, by using the novel G protein coupled receptor protein-encoding cDNA fragment (p19P2) of the present invention, a cDNA having a full-length open reading frame of the receptor protein of the present invention has been obtained from human pituitary gland cDNA libraries. The nucleotide sequence analysis of a plasmid (phGR3) carrying the cDNA having a full length open reading frame of the receptor protein shows that the nucleotide sequence of a coding region of this receptor protein is represented by SEQ ID NO: 31, and the amino acid sequence deduced therefrom is represented by SEQ ID NO: 26 [FIG. 34]. Based upon the amino acid sequence, hydrophobicity plotting has been carried out. The results are shown in FIG. 36. From the hydrophobicity plotting, it has been clarified that the receptor protein of the present invention possessed seven hydrophobic domains. That is, it has been confirmed that the receptor protein encoded by the cDNA obtained according to the present invention is a seven transmembrane (membrane-spanning) G protein coupled receptor protein. An expression of mRNA for receptor genes encoded by the cDNA of the present invention has been checked by northern blotting techniques at a mRNA level, and it has been confirmed that the receptor gene has been expressed in the human pituitary gland [FIG. 35].

The present inventors have further succeeded in PCR amplification of a mouse pancreatic β cell strain, MIN6 derived cDNA fragment, and cloning of pG3-2 and pG1-10. Then, based on the nucleotide sequence of cDNA included in these two plasmid vectors, the nucleotide sequence shown in FIG. 27 has been derived. It was learned from the nucleotide sequence that the cDNA encodes a novel receptor protein. Upon translating the nucleotide sequence into an amino acid sequence, the presence of the third, fourth, fifth and sixth membrane-spanning domains has been confirmed on the hydrophobicity plots [FIG. 28]. The size of the amplified cDNA is about 400 bp which is nearly comparable with the number of bases between the third membrane-spanning domain and the sixth membrane-spanning domain of the known G protein coupled receptor protein. The amino acid sequence has been compared with amino acid sequences [FIGS. 22 and 23] encoded by the G protein coupled receptor protein cDNA included in p19P2 cloned from the human pituitary gland. As a result, homology is more than 95% [FIG. 61]. From this fact, it was estimated that the protein encoded by the cDNA included in pG3-2 is a mouse type G protein coupled receptor protein relative to the human-derived one encoded by the cDNA included in p19P2.

The present inventors have further amplified a mouse pancreatic β-cell strain, MIN6-derived cDNA fragment by the PCR followed by subcloning into a plasmid vector to obtain a clone (p5S38) having a nucleotide sequence as shown in FIG. 62. From the nucleotide sequence (SEQ ID NO: 33), it has been clarified that the cDNA encodes a novel receptor protein. Upon translating the nucleotide sequence into an amino acid sequence (SEQ ID NO: 28), the presence of the third, fourth, fifth and sixth membrane-spanning domains has been confirmed on the hydrophobicity plots [FIG. 64]. The size of the amplified DNA is about 400 bp that is nearly comparable with the known G protein coupled receptor protein. The amino acid sequence has been compared with amino acid sequences [FIGS. 22 and 23] encoded by the G protein coupled receptor protein cDNA included in p19P2 cloned from the human pituitary gland and with amino acid sequences of proteins encoded by pG3-2 and pG1-10 derived from the mouse pancreatic β-cell strain. As a result, homology is more than 95% to them [FIG. 63]. This fact suggests that the protein encoded by the human-derived pituitary gland-derived p19P2, the proteins encoded by the mouse pancreatic β-cell strain-derived pG3-2 and pG1-10, and the protein encoded by the mouse pancreatic β-cell strain-derived p5S38, pertain to a receptor family that recognizes the same ligand.

Another object of the present invention is to provide a novel human amygdaloid nucleus-derived protein coupled receptor protein, a DNA containing a DNA coding for said G protein coupled receptor protein, a process for producing said G protein coupled receptor protein, and use of said protein and DNA.

The present inventors have synthesized DNA primers for efficiently isolating a DNA coding for G protein coupled receptor proteins, amplified an amygdaloid nucleus-derived cDNA with the above primer, and have analyzed it.

As a result, the present inventors have succeeded in isolating, from the human amygdaloid nucleus, a cDNA coding for a novel G protein coupled receptor protein and have determined its partial structure. The nucleotide sequence of the isolated cDNA is preserved very well as compared with that of the mouse glucocorticoid-induced receptor (hereinafter sometimes referred to as "GIR") and is considered to be encoding a receptor protein to the same ligand (Molecular Endocrinology 5:1331–1338, 1991). It is reputed that, in the mouse, the GIR is a receptor which is induced by glucocorticoid and expressed in T-cells and is working as a receptor to immunoregulating factors in the immune system on the T-cells. The present inventors have succeeded in the isolation of this human type GIR from the human amygdaloid nucleus. Accordingly, it is suggested that the isolated GIR is expressed even in the human central nervous system to carry out some function. From these facts, it is considered that the receptor protein is strongly expressed in the human brain and in the immune system and is also functioning therein. These characterized DNAs allow one to obtain a cDNA having a full length open reading frame of the receptor and production of the receptor proteins. The receptor proteins expressed by a suitable means, furthermore, permit screening for a ligand to the receptor proteins from the living body or from natural and non-natural compounds depending on indications obtainable in receptor protein-binding experiments, measurements of intracellular second messengers, etc. It further allows one to screen for compounds capable of inhibiting the binding between the ligand and the receptor protein.

To be more specific, the present inventors have amplified, as a novel human amygdaloid nucleus-derived cDNA, one species, as shown in FIGS. 29 and 30, by PCR, cloned it, and clarified from the analysis of a partial sequence thereof that a novel receptor protein is encoded. The synthetic DNA primers used for amplifying the cDNA are corresponding to seven hydrophobic clusters that exist in the G protein coupled receptor proteins in common, i.e., corresponding to the first and sixth membrane-spanning regions among the membrane-spanning domains. The nucleotide sequence has been determined from the primer region at the 5' side (first membrane-spanning domain side) and has been translated into an amino acid sequence. As a result, the second and third membrane-spanning domains have been confirmed on the hydrophobicity plotting [FIG. 31]. Similarly, the nucleotide sequence has been determined from the primer region at the 3' side (sixth membrane-spanning domain side) and has been translated into an amino acid sequence. As a result, the presence of the fifth and fourth membrane-spanning domains has been confirmed on the hydrophobicity plots [FIG. 32]. The size of the amplified cDNA is about 700 bp which is nearly comparable with the number of bases of the known G protein coupled receptor protein.

The inventors have further retrieved the data base based on, as a template, the nucleotide sequence of the isolated DNA and observed high homology to the DNA that codes for mouse-derived glucocorticoid-induced receptor protein which is a widely known G protein coupled receptor protein [FIG. 33]. This result strongly suggests that the DNA of the present invention is encoding a human-type receptor protein of GIR.

Yet another object of the present invention is to provide a novel mouse pancreatic β-cell strain, MIN6-derived protein coupled receptor protein, a DNA containing a DNA coding for said G protein coupled receptor protein, a process for producing said G protein coupled receptor protein, and use of said protein and DNA. The present inventors have synthesized DNA primers for efficiently isolating a DNA coding for G protein coupled receptor proteins, amplified a mouse pancreatic β-cell strain, MIN6-derived cDNA with the above primer, and have analyzed it.

As a result, the present inventors have succeeded in isolating a mouse-derived cDNA coding for a novel G protein coupled receptor protein and have determined its partial structure. The isolated cDNA is homologous to known G protein coupled receptors at the nucleotide sequence level and at the amino acid sequence level and is considered to be encoding a novel receptor protein which is expressed in the mouse pancreas and is also functioning therein. These characterized DNAs allow one to obtain a cDNA having a full length open reading frame of the receptor and production of the receptor proteins. Human-derived cDNAs may be cloned by using, as a probe, said mouse-derived cDNA. The receptor proteins expressed by a suitable means, furthermore, permit screening for a ligand to the receptor protein from the living body or from natural and non-natural compounds relying on indications obtainable in receptor protein-binding experiments, measurements of intracellular second messengers, etc. It further allows one to screen for compounds capable of inhibiting the binding of the ligand with the receptor protein.

To be more specific, the present inventors have amplified, as a novel mouse pancreatic β-cell strain, MIN6-derived cDNA, p3H2-17, as shown in FIGS. 37, by PCR, cloned it, and clarified from the analysis of a partial sequence thereof that a novel receptor protein is encoded. The nucleotide sequence has been translated into an amino acid sequence. As a result, the presence of the third, fourth, fifth and sixth membrane-spanning domains has been confirmed on the hydrophobicity plots [FIG. 38]. The size of the amplified cDNA is about 400 bp which is nearly comparable with that of the known G protein coupled receptor protein.

The inventors have retrieved the data base based on, as a template, the nucleotide sequence of the isolated DNA and observed 30% homology to chicken ATP receptor (P34996), 25% homology to human somatostatin receptor subtype 3 (A46226), 27% homology to human somatostatin receptor subtype 4 (JN0605), and 28% homology to bovine neuropeptide Y receptor (S28787), respectively (FIG. 39), which are known G protein coupled receptor proteins. The aforementioned abbreviations in parentheses are reference numbers that are assigned when they are registered as data to NBRF-PIR/Swiss-PROT and are, usually, each called "Accession Number".

An expression of receptor genes encoded by the cDNA fragment included in p3H2-17 of the present invention has been checked by northern blotting techniques at a mRNA level, and it has been confirmed that the receptor gene has been intensely expressed in the mouse thymus and spleen. It has been also confirmed that the receptor gene has been expressed in the mouse brain and pancreas (FIG. 65).

Next, by utilizing the information on the nucleotide sequence of the fragment included in p3H2-17, cDNA encoding a full-length open reading frame of the mouse pancreatic β-cell strain, MIN6-derived G protein coupled receptor protein of the present invention has been obtained from mouse thymic and spleenic poly(A) RNA by 5'RACE (5' rapid amplification of cDNA ends) techniques (Frohman M. A. et al., Proc. Natl. Acad. Sci. USA, 85:8998–9002 (1988); Belyavsky A. et al., Nucleic Acids Res., 17:2919–2932 (1989); Edwards J. B. D. M. et al., Nucleic Acids Res., 19:5227–5232 (1991)) and 3'RACE (3' rapid amplification of cDNA ends) techniques (Frohman M. A. et al., Proc. Natl. Acad. Sci. USA, 85:8998–9002 (1988); Belyavsky A. et al., Nucleic Acids Res., 17:2919–2932 (1989)).

The plasmid (pMAH2-17) carrying cDNA encoding a full-length open reading frame of the receptor protein of the present invention has been subjected to sequencing analysis. As a result, the nucleotide sequence of the region coding for the receptor protein is represented by SEQ ID NO: 41 and the amino acid sequence deduced therefrom is represented by SEQ ID NO: 39 (FIG. 69). Based on the amino acid sequence, hydrophobicity plotting has been carried out. The results are shown in FIG. 70.

It has been clarified from the hydrophobicity plotting that the mouse pancreatic β-cell strain, MIN6-derived receptor protein of the present invention has seven hydrophobic domains. Thus, it has been confirmed that the receptor protein encoded by the cDNA Included in pMAH2-17 according to the present invention is a seven transmembrane G protein coupled receptor protein.

Data base retrieval has been carried out based on the full-length amino acid sequence encoded by the cDNA included in pMAH2-17, and it has been observed that the amino acid sequence has 44.0% homology to mouse $P_{2U}$ purinoceptor (P35383) and 38.1% homology to chicken $P_{2Y}$ purinoceptor (P34996), respectively (FIG. 71), which are known G protein coupled receptor proteins. The aforementioned abbreviations in parentheses are reference numbers that are assigned when they are registered as data to NBRF-PIR/SwissPROT and are, usually, each called "Accession Number". Since the receptor protein encoded by pMAH2-17 is highly homologous to prinoceptors, it is considered that there are strong possibility of a subtype within prinoceptor families. Therefore, the present inventors have carried out an electrophysiological analysis of the receptor gene in Xenopus oocytes and found significant inward currents elicited by Xenopus oocytes carrying the subject receptor gene in response to ATP stimulation (FIG. 75). As a result, it has been determined that the receptor encoded by pMAH2-17 is one of the subtypes within prinoceptor families. It has been discussed and expected that there are a variety of subtypes among purinoceptors (Pharmac. Ther., Vol. 64, pp. 445–475 (1994).

All data are supporting that the mouse pancreatic β-cell strain, MIN6-derived receptor protein of the present invention (e.g., SEQ ID NO: 38 and SEQ ID NO: 39, or proteins encoded by pMAH2-17) is a novel purinoceptor subtype which is clearly distinct from chicken $P_{2y1}$ purinoceptor (FEBS LETTERS, Vol. 324(2), 219–225 (1993)); mouse $P_{2y2}$ or $P_{2u}$ purinoceptor (Proc. Natl. Acad. Sci. USA, Vol. 90, pp.5113–5117 (1993)); rat $P_{2u}$ or $P_{2y2}$ purinoceptor (Am. J. Respir. Cell Mol. Biol., Vol. 12, pp. 27–32 (1995)); human $P_{2u}$ or $P_{2y2}$ purinoceptor (Proc. Natl. Acad. Sci. USA, Vol. 91, pp.3275–3279 (1994)); and rat $P_{2x}$ purinoceptor (Nature, Vol. 371.6, pp.516–519 (1994).

It is also strongly suggested that agonists and/or antagonists related to the receptor encoded by pMAH2-17 would be useful in therapeutic or prophylactic treatment of diseases or syndromes in connection with purine ligand compounds. It is expected that the agonists of the receptor encoded by pMAH2-17 are useful as an immunomodulator or an anti-tumor agent, in addition they are useful in therapeutically or prophylactically treating hypertension, diabetes, cystic fibrosis, etc. It is still expected that the antagonists of the receptor encoded by pMAH2-17 are useful as hypotensive agents, analgesics, agents for therapeutically or prophylactically treating incontinence of urine, etc.

Another object of the present invention is to provide a novel human-derived protein coupled receptor protein of prinoceptor type, a DNA containing a DNA coding for said G protein coupled receptor protein, a process for producing said G protein coupled receptor protein, and use of said protein and DNA. The present inventors have synthesized DNA primers for efficiently isolating a DNA coding for prinoceptor type G protein coupled receptor proteins on the basis of the nucleotide sequence of mouse purinoceptor, amplified a human-derived cDNA with the above primer, and have analyzed it.

As a result, the present inventors have succeeded in isolating a human-derived cDNA coding for a novel G protein coupled receptor protein and have determined its full-length structure [FIG. 77]. The isolated cDNA is homologous to mouse G protein coupled receptor (purinoceptor) at the nucleotide sequence level and at the amino acid sequence level (87% homology; FIG. 79) and is considered to be encoding a novel purinoceptor protein. The receptor proteins expressed by a suitable means, furthermore, permit screening for a ligand to the receptor protein from the living body or from natural and non-natural compounds relying on indications obtainable in receptor protein-binding experiments, etc. It further allows one to screen for compounds capable of inhibiting the binding of the ligand with the receptor protein.

It is also strongly suggested that agonists and/or antagonists related to the human receptor encoded by phAH2-17 would be useful in therapeutic or prophylactic treatment of diseases or syndromes in connection with purine ligand compounds. It is expected that the agonists of the human receptor are useful as an immunomodulator or an antitumor agent, in addition they are useful in therapeutically or prophylactically treating hypertension, diabetes, cystic fibrosis, etc. It is still expected that the antagonists of the human receptor are useful as hypotensive agents, analgesics, agents for therapeutically or prophylactically treating incontinence of urine, etc.

Accordingly, one aspect of the present invention is
(1) DNAs comprising a nucleotide sequence represented by a SEQ ID NO selected from the group consisting of SEQ ID NO: 1 to SEQ ID NO: 19;
(2) DNAs according to the above (1) comprising a nucleotide sequence represented by a SEQ ID NO selected from the group consisting of SEQ ID NO: 1 to SEQ ID NO: 9;
(3) DNAs according to the above (1) comprising a nucleotide sequence represented by SEQ ID NO: 1 or SEQ ID NO: 2;
(4) DNAs according to the above (1) wherein the DNA is a primer for polymerase chain reaction in order to amplify a DNA coding for a G protein coupled receptor protein;
(5) a method for amplifying a DNA coding for a G protein coupled receptor protein by polymerase chain reaction techniques, which comprises:
  (i) carrying out a polymerase chain reaction in the presence of a mixture of
   ① a DNA coding for G protein coupled receptor protein, said DNA being capable of acting as a template,
   ② at least one DNA primer selected from the group consisting of DNA primers comprising a nucleotide sequence represented by SEQ ID NO: 1, DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 10, DNA primers comprising a nucleotide sequence represented by SEQ ID NO: 14, DNA primers comprising a nucleotide sequence represented by SEQ ID NO: 16 and DNA primers comprising a nucleotide sequence represented by SEQ ID NO: 18, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 11, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19; or (ii) carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 13;

(6) a method for screening a DNA library for a DNA coding for a G protein coupled receptor protein, which comprises:

carrying out a polymerase chain reaction in the presence of a mixture of

① said DNA library,

② at least one DNA primer selected from the group consisting of DNA primers comprising a nucleotide sequence represented by SEQ ID NO: 1, DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 10, DNA primers comprising a nucleotide sequence represented by SEQ ID NO: 14, DNA primers comprising a nucleotide sequence represented by SEQ ID NO: 16 and DNA primers comprising a nucleotide sequence represented by SEQ ID NO: 18, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 11, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19, to amplify selectively a template DNA coding for G protein coupled receptor protein, contained in the DNA library; or (ii) carrying out a polymerase chain reaction in the presence of a mixture of ① said DNA library ② at least one DNA primer selected from the group consisting of DNA primers comprising a nucleotide sequence represented by SEQ ib NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 13, to amplify selectively a DNA coding for G protein coupled receptor protein, contained in the DNA library;

(7) a DNA coding for a G protein coupled receptor protein, which is obtained by a method according to the above (5) or (6); and (8) G protein coupled receptor proteins encoded by a DNA according to the above (7), their peptide segments or fragments and salts thereof.

Another specific aspect of the invention is:

(9) a method for amplifying a DNA coding for G protein coupled receptor protein (e.g. a region corresponding to from the first to sixth membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primer's comprising a nucleotide sequence represented by SEQ ID NO: 9, DNA primers comprising a nucleotide sequence represented by SEQ ID NO: 15, DNA primers comprising a nucleotide sequence represented by SEQ Ib NO: 17 and DNA primers comprising a nucleotide sequence represented by SEQ ID NO: 19;

(10) a method for amplifying a DNA coding for G protein coupled receptor protein (e.g. a region corresponding to from the first to seventh membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 11;

(11) a method for amplifying a DNA coding for G protein coupled receptor protein (e.g. a region corresponding to from the third to sixth membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 14 and DNA primers comprising a nucleotide sequence represented by SEQ ID NO: 18, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19;

(12) a method for amplifying a DNA coding for G protein coupled receptor protein (e.g. a region corresponding to from the third to seventh membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 14 and DNA primers comprising a nucleotide sequence represented by SEQ ID NO: 18, and ③ at least one DNA primer selected from the group consisting of DNA primers comprising a nucleotide sequence represented by SEQ ID NO: 11;

(13) a method for amplifying a DNA coding for G protein coupled receptor protein (e.g. a region corresponding to from the second to sixth membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 10 and DNA primers comprising a nucleotide sequence represented by SEQ ID NO: 16, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19;

(14) a method for amplifying a DNA coding for G protein coupled receptor protein (e.g. a region corresponding to from the second to seventh membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 10 and DNA primers comprising a nucleotide sequence represented by SEQ ID NO: 16, and ③ at least one DNA primer selected from the group consisting of DNA primers comprising a nucleotide sequence represented by SEQ ID NO: 11;

(15) a method-for amplifying a DNA coding for G protein coupled receptor protein (e.g., a region corresponding to from the first to third membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 13;

(16) a method for amplifying a DNA coding for G protein coupled receptor protein by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 1, and ③ at least one DNA primer selected from the group consisting of DNA primers comprising a nucleotide sequence represented by SEQ ID NO: 2;

(17) a method for amplifying a DNA coding for G protein coupled receptor protein by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 3, and ③ at least one DNA primer selected from the group consisting of DNA primers comprising a nucleotide sequence represented by SEQ ID NO: 4;

(18) a method for amplifying a DNA coding for G protein coupled receptor protein by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 6, and ③ at least one DNA primer selected from the group consisting of DNA primers comprising a nucleotide sequence represented by SEQ ID NO: 8;

(19) a method for amplifying a DNA coding for G protein coupled receptor protein by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 10, and ③ at least one DNA primer selected from the group consisting of DNA primers comprising a nucleotide sequence represented by SEQ ID NO: 11;

(20) a method for amplifying DNA coding for a G protein coupled receptor protein which comprises (i) carrying out a polymerase chain reaction in the presence of a mixture of ① a DNA coding for G protein coupled receptor protein, said DNA being capable of acting as a template, ② at least one DNA primer which is capable of binding with the 3'-side nucleotide sequence of the − chain (minus chain) of the template DNA coding for G protein coupled receptor protein to allow the extension of the + chain (plus chain) in the 5'→3' direction, said DNA primer being selected from the group consisting of DNA primers comprising a nucleotide sequence represented by SEQ ID NO: 1, DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 10, DNA primers comprising a nucleotide sequence represented by SEQ ID NO: 12, DNA primers comprising a nucleotide sequence represented by SEQ ID NO: 14, DNA primers comprising a nucleotide sequence represented by SEQ ID NO: 16 and DNA primers comprising a nucleotide sequence represented by SEQ ID NO: 18, and ③ at least one DNA primer which is capable of binding with the 3'-side nucleotide sequence of the + chain (plus chain) of the template DNA coding for G protein coupled receptor protein to allow the extension of the − chain (minus chain) in the 5'→3' direction, said DNA primer being selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 11, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19, or (ii) carrying out a polymerase chain reaction in the presence of a mixture of ① a DNA coding for G protein coupled receptor protein, said DNA being capable of acting as a template, ② at least one DNA primer which is capable of binding with the 3'-side nucleotide sequence of the − chain (minus chain) of the template DNA coding for G protein coupled receptor protein to allow the extension of the + chain (plus chain) in the 5'→3' direction, said DNA primer being selected from the group consisting of DNA primers comprising a nucleotide sequence represented by SEQ ID NO: 1 and DNA primers comprising a nucleotide sequence represented by SEQ ID NO: 12, and ③ at least one DNA primer which is capable of binding with the 3'-side nucleotide sequence of the + chain (plus chain) of the template DNA coding for G protein coupled receptor protein to allow the extension of the − chain (minus chain) in the 5'→3' direction, said DNA primer being selected from the group consisting of DNA primers comprising a nucleotide sequence represented by SEQ ID NO: 13;

(21) a method for screening DNA libraries for a DNA coding for G protein coupled receptor protein (e.g. from the first to sixth membrane-spanning domains or other domains of G protein coupled receptor protein), which comprises carrying out a polymerase chain reaction in the presence of a mixture of ① said DNA library, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19,
to amplify selectively a template DNA coding for G protein coupled receptor protein (e.g. from the first to sixth membrane-spanning domains or other domains of G protein coupled receptor protein), contained in the DNA library;

(22) a method for screening DNA libraries for a DNA coding for G protein coupled receptor protein (e.g. from the first to seventh membrane-spanning domains or other domains of G protein coupled receptor protein), which comprises carrying out a polymerase chain reaction in the presence of a mixture of
① said DNA library,
② at least one DNA primer selected from the group consisting of DNA primers comprising a nucleotide sequence represented by SEQ ID NO: 1 and DNA primers comprising a nucleotide sequence represented by SEQ ID NO: 12, and
③ at least one DNA primer selected from the group consisting of DNA primers comprising a nucleotide sequence represented by SEQ ID NO: 11,
to amplify selectively a template DNA coding for G protein coupled receptor protein (e.g. from the first to seventh membrane-spanning domains or other domains of G protein coupled receptor protein), contained in the DNA library;

(23) a method for screening DNA libraries for a DNA coding for G protein coupled receptor protein (e.g. from the third to sixth membrane-spanning domains or other domains of G protein coupled receptor protein), which comprises carrying out a polymerase chain reaction in the presence of a mixture of
① said DNA library,
② at least one DNA primer selected from the group consisting of DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 14 and DNA primers comprising a nucleotide sequence represented by SEQ ID NO: 18, and
③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19,
to amplify selectively a template DNA coding for G protein coupled receptor protein (e.g. from the third to sixth membrane-spanning domains or other domains of G protein coupled receptor protein), contained in the DNA library;

(24) a method for screening DNA libraries for a DNA coding for G protein coupled receptor protein (e.g. from the third to seventh membrane-spanning domains or other domains of G protein coupled receptor protein), which comprises carrying out a polymerase chain reaction in the presence of a mixture of
① said DNA library,
② at least one DNA primer selected from the group consisting of DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 14 and DNA primers comprising a nucleotide sequence represented by SEQ ID NO: 18, and
③ at least one DNA primer selected from the group consisting of DNA primers comprising a nucleotide sequence represented by SEQ ID NO: 11,
to amplify selectively a template DNA coding for G protein coupled receptor protein (e.g. from the third to seventh membrane-spanning domains or other domains of G protein coupled receptor protein), contained in the DNA library;

(25) a method for screening DNA libraries for a DNA coding for G protein coupled receptor protein (e.g. from the second to sixth membrane-spanning domains or other domains of G protein coupled receptor protein), which comprises carrying out a polymerase chain reaction in the presence of a mixture of
① said DNA library,
② at least one DNA primer selected from the group consisting of DNA primers comprising a nucleotide sequence represented by SEQ ID NO: 10 and DNA primers comprising a nucleotide sequence represented by SEQ ID NO: 16, and
③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19,
to amplify selectively a template DNA coding for G protein coupled receptor protein (e.g. from the second to sixth membrane-spanning domains or other domains of G protein coupled receptor protein), contained in the DNA library;

(26) a method for screening DNA libraries for a DNA coding for G protein coupled receptor protein (e.g. from the second to seventh membrane-spanning domains or other domains of G protein coupled receptor protein), which comprises carrying out a polymerase chain reaction in the presence of a mixture of
① said DNA library,
② at least one DNA primer selected from the group consisting of DNA primers comprising a nucleotide sequence represented by SEQ ID NO: 10 and DNA primers comprising a nucleotide sequence represented by SEQ ID NO: 16, and
③ at least one DNA primer selected from the group consisting of DNA primers comprising a nucleotide sequence represented by SEQ ID NO: 11, to amplify selectively a template DNA coding for G protein coupled receptor protein (e.g. from the second to seventh membrane-spanning domains or other domains of G protein coupled receptor protein), contained in the DNA library;

(27) a method for screening DNA libraries for a DNA coding for G protein coupled receptor protein (e.g. from the first to third membrane-spanning domains or other domains of G protein coupled receptor protein), which comprises carrying out a polymerase chain reaction in the presence of a mixture of
① said DNA library,
② at least one DNA primer selected from the group consisting of DNA primers comprising a nucleotide sequence represented by SEQ ID NO: 1 and DNA primers comprising a nucleotide sequence represented by SEQ ID NO: 12, and
③ at least one DNA primer selected from the group consisting of DNA primers comprising a nucleotide sequence represented by SEQ ID NO: 13,
to amplify selectively a template DNA coding for G protein coupled receptor protein (e.g. from the first to third membrane-spanning domains or other domains of G protein coupled receptor protein), contained in the DNA library;

(28) a method for screening DNA libraries for a DNA coding for G protein coupled receptor protein, which comprises carrying out a polymerase chain reaction in the presence of a mixture of
① said DNA library,
② at least one DNA primer selected from the group consisting of DNA primers comprising a nucleotide sequence represented by SEQ ID NO: 1, and
③ at least one DNA primer selected from the group consisting of DNA primers comprising a nucleotide sequence represented by SEQ ID NO: 2,
to amplify selectively the template DNA coding for G protein coupled receptor protein, contained in the DNA library;

(29) a method for screening DNA libraries to detect a DNA coding for G protein coupled receptor protein, which comprises carrying out a polymerase chain reaction in the presence of a mixture of
① said DNA library,
② at least one DNA primer selected from the group consisting of DNA primers comprising a nucleotide sequence represented by SEQ ID NO: 3, and
③ at least one DNA primer selected from the group consisting of DNA primers comprising a nucleotide sequence represented by SEQ ID NO: 4,
to amplify selectively a template DNA coding for G protein coupled receptor protein, contained in the DNA library;

(30) a method for screening DNA libraries for a DNA coding for G protein coupled receptor protein, which comprises carrying out a polymerase chain reaction in the presence of a mixture of
① said DNA library,
② at least one DNA primer selected from the group consisting of DNA primers comprising a nucleotide sequence represented by SEQ ID NO: 6, and
③ at least one DNA primer selected from the group consisting of DNA primers comprising a nucleotide sequence represented by SEQ ID NO: 8,
to amplify selectively a template DNA coding for G protein coupled receptor protein, contained in the DNA library;

(31) a method for screening DNA libraries for a DNA coding for G protein coupled receptor protein, which comprises carrying out a polymerase chain reaction in the presence of a mixture of
① said DNA library,
② at least one DNA primer selected from the group consisting of DNA primers comprising a nucleotide sequence represented by SEQ ID NO: 10, and
③ at least one DNA primer selected from the group consisting of DNA primers comprising a nucleotide sequence represented by SEQ ID NO: 11,
to amplify selectively a template DNA coding for G protein coupled receptor protein, contained in the DNA library; and

(32) a method for screening DNA libraries according to any of the above (6), and (21) to (31) wherein said DNA library is derived from an origin selected from the group consisting of human tissues and human cells. Examples of such human tissues include adrenal, umbilical cord, brain, tongue, liver, lymph gland, lung, thymus, placenta, peritoneum, retina, spleen, heart, smooth muscle, intestine, vessel, bone, kidney, skin, fetus, mammary gland, ovary, testis, pituitary gland, pancreas, submandibular gland, spine, prostate gland, stomach, thyroid gland, trachea (windpipe), skeletal muscle, uterus, adipose tissue, urinary bladder, cornea, olfactory bulb, bone marrow, amnion, etc. Examples of such human cells include nerve cells, epithelial cells, endothelial cells, leukocytes, lymphocytes, gliacytes, fibroblasts, keratinized cells, osteoblasts, osteoclasts, astrocytes, melanocytes, various carcinomas, various sarcomas, various cells derived from the above-mentioned human tissues.

Yet another aspect of the present invention is a degenerate deoxynucleotide which has an oligonucleotide sequence to which a SEQ ID NO selected from the group consisting of SEQ ID NO: 1 to SEQ ID NO: 19 is assigned.

Another aspect of the present invention is

(33) a G protein coupled receptor protein comprising an amino acid sequence selected from the group consisting of amino acid sequences represented by SEQ ID NO: 24 and/or SEQ ID NO: 25 and substantial equivalents to the amino acid sequence represented by SEQ ID NO: 24 or SEQ ID NO: 25; or a salt thereof;

(34) a G protein coupled receptor protein according to the above (33) comprising an amino acid sequence selected from the group consisting of an amino acid sequence represented by SEQ ID NO: 26 and substantial equivalents to the amino acid sequence represented by SEQ ID NO: 26; or a salt thereof;

(35) a G protein coupled receptor protein comprising an amino acid sequence selected from the group consisting of an amino acid sequence represented by SEQ ID NO: 27 and substantial equivalents to the amino acid sequence represented by SEQ ID NO: 27; or a salt thereof;

(36) a G protein coupled receptor protein comprising an amino acid sequence selected from the group consisting of an amino acid sequence represented by SEQ ID NO: 28 and substantial equivalents to the amino acid sequence represented by SEQ ID NO: 28; or a salt thereof;

(37) a G protein coupled receptor protein comprising an amino acid sequence selected from the group consisting of amino acid sequences represented by SEQ ID NO: 34 and/or SEQ ID NO: 35 and substantial equivalents to the amino acid sequence represented by SEQ ID NO: 34 or SEQ ID NO: 35; or a salt thereof;

(38) a G protein coupled receptor protein comprising an amino acid sequence selected from the group consisting of an amino acid sequence represented by SEQ ID NO:

38 and substantial equivalents to the amino acid sequence represented by SEQ ID NO: 38; or a salt thereof;

(39) a G protein coupled receptor protein according to the above (38) comprising an amino acid sequence selected from the group consisting of an amino acid sequence represented by SEQ ID NO: 39 and substantial equivalents to the amino acid sequence represented by SEQ ID NO: 39; or a salt thereof;

(40) a G protein coupled receptor protein comprising an amino acid sequence represented by SEQ ID NO: 56 and substantial equivalents to the amino acid sequence represented by SEQ ID NO: 56; or a salt thereof;

(41) a peptide segment or fragment of a G protein coupled receptor protein according to any of the above (33) to (40), a modified derivative thereof or a salt thereof;

(42) a DNA which comprises a nucleotide sequence coding for a G protein coupled receptor protein of the above (33);

(43) a DNA which comprises a nucleotide sequence coding for a G protein coupled receptor protein of the above (34);

(44) a DNA which comprises a nucleotide sequence coding for a G protein coupled receptor protein of the above (35);

(45) a DNA which comprises a nucleotide sequence coding for a G protein coupled receptor protein of the above (36);

(46) a DNA which comprises a nucleotide sequence coding for a G protein coupled receptor protein of the above (37);

(47) a DNA which comprises a nucleotide sequence coding for a G protein coupled receptor protein of the above (38);

(48) a DNA which comprises a nucleotide sequence coding for a G protein coupled receptor protein of the above (39);

(49) a DNA which comprises a nucleotide sequence coding for a G protein coupled receptor protein of the above (40);

(50) a DNA of the above (42) comprising a nucleotide sequence represented by SEQ ID NO: 29 and/or SEQ ID NO: 30;

(51) a DNA of the above (43) comprising a nucleotide sequence represented by SEQ ID NO: 31;

(52) a DNA of the above (44) comprising a nucleotide sequence represented by SEQ ID NO: 32;

(53) a DNA of the above (45) comprising a nucleotide sequence represented by SEQ ID NO: 33;

(54) a DNA of the above (46) comprising a nucleotide sequence represented by SEQ ID NO: 36 and/or SEQ ID NO: 37;

(55) a DNA of the above (47) comprising a nucleotide sequence represented by SEQ ID NO: 40;

(56) a DNA of the above (48) comprising a nucleotide sequence represented by SEQ ID NO: 41;

(57) a DNA of the above (49) comprising a nucleotide sequence represented by SEQ ID NO: 57;

(58) a vector comprising a DNA according to any of the above (42) to (57);

(59) a transformant (including a transfectant) carrying a vector of the above (58);

(60) a process for producing a G protein coupled receptor protein or a salt thereof according to any of the above (33) to (40), which comprises culturing a transformant of the above (59) to express said G protein coupled receptor protein on the membrane of the transformant;

(61) a method for determining a ligand to a G protein coupled receptor protein according to any of the above (33) to (40), which comprises contacting
  (i) at least one component selected from the group consisting of G protein coupled receptor proteins or salts thereof according to any of the above (33) to (40), peptide fragments or segments or salts thereof according to the above (41), and mixtures thereof, with
  (ii) at least one compound to be tested;

(62) a screening method for a compound capable of inhibiting the binding of a G protein coupled receptor protein according to any of the above (33) to (40) with a ligand, which comprises carrying out a comparison between:
  (i) at least one case where said ligand is contacted with at least one component selected from the group consisting of G protein coupled receptor proteins or salts thereof according to any of the above (33) to (40), peptide fragments or segments or salts thereof according to the above (41), and mixtures thereof, and
  (ii) at least one case where said ligand together with a compound to be tested is contacted with at least one component selected from the group consisting of G protein coupled receptor proteins or salts thereof according to any of the above (33) to (40), peptide fragments or segments or salts thereof according to the above (41), and mixtures thereof;

(63) a kit for the screening of one or more compounds capable of inhibiting the binding of a G protein coupled receptor protein according to any of the above (33) to (40), with a ligand, which comprises at least one component selected from the group consisting of G protein coupled receptor proteins or salts thereof according to any of the above (33) to (40), peptide fragments or segments or salts thereof according to the above (41), and mixtures thereof; and

(64) an antibody against at least one component selected from the group consisting of G protein coupled receptor proteins or salts thereof according to any of the above (33) to (40), peptide fragments or segments or salts thereof according to the above (41), and mixtures thereof.

Yet another aspect of the present invention is

(65) a G protein coupled receptor protein according to the above (33) comprising
  (i) an amino acid sequence selected from the group consisting of an amino acid sequence represented by SEQ ID NO: 24, amino acid sequences wherein one or more amino acid residues (preferably from 2 to 30 amino acid residues, more preferably from 2 to 10 amino acid residues) are deleted from the amino acid sequence of SEQ ID NO: 24, amino acid sequences wherein one or more amino acid residues (preferably from 2 to 30 amino acid residues, more preferably from 2 to 10 amino acid residues) are added to the amino acid sequence of SEQ ID NO: 24, and amino acid sequences wherein one or more amino acid residues (preferably from 2 to 30 amino acid residues, more preferably from 2 to 10 amino acid residues) in the amino acid sequence of SEQ ID NO: 24 are substituted with one or more other amino acid residues, or/and (ii) an amino acid sequence selected from the group consisting of an amino acid sequence represented by SEQ ID NO: 25, amino acid sequences wherein one or more amino acid residues (preferably from 2 to 30 amino acid residues, more preferably from 2 to 10 amino acid residues) are deleted from the amino acid sequence of SEQ ID NO: 25, amino acid sequences wherein one or more amino acid residues (preferably from 2 to 30 amino acid residues, more preferably from 2 to 10 amino acid residues) are added to the amino acid sequence of SEQ ID NO: 25, and amino acid sequences wherein one or more amino acid residues (preferably from 2 to 30 amino acid residues, more preferably from 2 to 10 amino acid residues) in the amino acid sequence of SEQ ID NO: 25 are substituted with one or more other amino acid residues, or a salt thereof;

(66) a G protein coupled receptor protein according to the above (34) comprising an amino acid sequence selected from the group consisting of an amino acid sequence represented by SEQ ID NO: 26, amino acid sequences wherein one or more amino acid residues (preferably from 2 to 30 amino acid residues, more preferably from 2 to 10 amino acid residues) are deleted from the amino acid sequence of SEQ ID NO: 26, amino acid sequences wherein one or more amino acid residues (preferably from 2 to 30 amino acid residues, more preferably from 2 to 10 amino acid residues) are added to the amino acid sequence of SEQ ID NO: 26, and amino acid sequences wherein one or more amino acid residues (preferably from 2 to 30 amino acid residues, more preferably from 2 to 10 amino acid residues) in the amino acid sequence of SEQ ID NO: 26 are substituted with one or more other amino acid residues, or a salt thereof;

(67) a G protein coupled receptor protein according to the above (35) comprising an amino acid sequence selected from the group consisting of an amino acid sequence represented by SEQ ID NO: 27, amino acid sequences wherein one or more amino acid residues (preferably from 2 to 30 amino acid residues, more preferably from 2 to 10 amino acid residues) are deleted from the amino acid sequence of SEQ ID NO: 27, amino acid sequences wherein one or more amino acid residues (preferably from 2 to 30 amino acid residues, more preferably from 2 to 10 amino acid residues) are added to the amino acid sequence of SEQ ID NO: 27, and amino acid sequences wherein one or more amino acid residues (preferably from 2 to 30 amino acid residues, more preferably from 2 to 10 amino acid residues) in the amino acid sequence of SEQ ID NO: 27 are substituted with one or more other amino acid residues, or a salt thereof;

(68) a G protein coupled receptor protein according to the above (36) comprising an amino acid sequence selected from the group consisting of an amino acid sequence represented by SEQ ID NO: 28, amino acid sequences wherein one or more amino acid residues (preferably from 2 to 30 amino acid residues, more preferably from 2 to 10 amino acid residues) are deleted from the amino acid sequence of SEQ ID NO: 28, amino acid sequences wherein one or more amino acid residues (preferably from 2 to 30 amino acid residues, more preferably from 2 to 10 amino acid residues) are added to the amino acid sequence of SEQ ID NO: 28, and amino acid sequences wherein one or more amino acid residues (preferably from 2 to 30 amino acid residues, more preferably from 2 to 10 amino acid residues) in the amino acid sequence of SEQ ID NO: 28 are substituted with one or more other amino acid residues, or a salt thereof;

(69) a G protein coupled receptor protein according to the above (37) comprising (i) an amino acid sequence selected from the group consisting of an amino acid sequence represented by SEQ ID NO: 34, amino acid sequences wherein one or more amino acid residues (preferably from 2 to 30 amino acid residues, more preferably from 2 to 10 amino acid residues) are deleted from the amino acid sequence of SEQ ID NO: 34, amino acid sequences wherein one or more amino acid residues (preferably from 2 to 30 amino acid residues, more preferably from 2 to 10 amino acid residues) are added to the amino acid sequence of SEQ ID NO: 34, and amino acid sequences wherein one or more amino acid residues (preferably from 2 to 30 amino acid residues, more preferably from 2 to 10 amino acid residues) in the amino acid sequence of SEQ ID NO: 34 are substituted with one or more other amino acid residues, or/and (ii) an amino acid sequence selected from the group consisting of an amino acid sequence represented by SEQ ID NO: 35, amino acid sequences wherein one or more amino acid residues (preferably from 2 to 30 amino acid residues, more preferably from 2 to 10 amino acid residues) are deleted from the amino acid sequence of SEQ ID NO: 35, amino acid sequences wherein one or more amino acid residues (preferably from 2 to 30 amino acid residues, more preferably from 2 to 10 amino acid residues) are added to the amino acid sequence of SEQ ID NO: 35, and amino acid sequences wherein one or more amino acid residues (preferably from 2 to 30 amino acid residues, more preferably from 2 to 10 amino acid residues) in the amino acid sequence of SEQ ID NO: 35 are substituted with one or more other amino acid residues, or a salt thereof;

(70) a G protein coupled receptor protein according to the above (38) comprising an amino acid sequence selected from the group consisting of an amino acid sequence represented by SEQ ID NO: 38, amino acid sequences wherein one or more amino acid residues (preferably from 2 to 30 amino acid residues, more preferably from 2 to 10 amino acid residues) are deleted from the amino acid sequence of SEQ ID NO: 38, amino acid sequences wherein one or more amino acid residues (preferably from 2 to 30 amino acid residues, more preferably from 2 to 10 amino acid residues) are added to the amino acid sequence of SEQ ID NO: 38, and amino acid sequences wherein one or more amino acid residues (preferably from 2 to 30 amino acid residues, more preferably from 2 to 10 amino acid residues) in the amino acid sequence of SEQ ID NO: 38 are substituted with one or more other amino acid residues, or a salt thereof;

(71) a G protein coupled receptor protein according to the above (39) comprising an amino acid sequence selected from the group consisting of an amino acid sequence represented by SEQ ID NO: 39, amino acid sequences wherein one or more amino acid residues (preferably from 2 to 30 amino acid residues, more preferably from 2 to 10 amino acid residues) are deleted from the amino acid sequence of SEQ ID NO: 39, amino acid sequences wherein one or more amino acid residues (preferably from 2 to 30 amino acid residues, more preferably from 2 to 10 amino acid residues) are added to the amino acid sequence of SEQ ID NO: 39, and amino acid sequences wherein one or more amino acid residues (preferably from 2 to 30 amino acid residues, more preferably from 2 to 10 amino acid residues) in the amino acid sequence of SEQ ID NO: 39 are substituted with one or more other amino acid residues, or a salt thereof;

(72) a G protein coupled receptor protein according to the above (40) comprising an amino acid sequence selected from the group consisting of an amino acid sequence represented by SEQ ID NO: 56, amino acid sequences wherein one or more amino acid residues (preferably from 2 to 30 amino acid residues, more preferably from 2 to 10 amino acid residues) are deleted from the amino acid sequence of SEQ ID NO: 56, amino acid sequences wherein one or more amino acid residues (preferably from 2 to 30 amino acid residues, more preferably from 2 to 10 amino acid residues) are added to the amino acid sequence of SEQ ID NO: 56, and amino acid sequences wherein one or more amino acid residues (preferably from 2 to 30 amino acid residues, more preferably from 2 to 10 amino acid residues) in the amino acid sequence of SEQ ID NO: 56 are substituted with one or more other amino acid residues, or a salt thereof;

(73) a method for determining a ligand according to the above (61) wherein said ligand is selected from the group consisting of angiotensin, bombesin, canavinoid, cholecystokinin, glutamine, serotonin, melatonin, neuropeptide Y, opioid, purine, vasopressin, oxytocin, VIP (vasoactive intestinal and related peptides), somatostatin, dopamine, motilin, amylin, bradykinin, CGRP (calcitonin gene related peptides), adrenomedullin, leukotriene, pancreastatin, prostaglandin, thromboxanes, adenosine, adrenaline, α- and β-chemokine (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptides and galanin;

(74) a method for the screening of a compound or a salt thereof capable of inhibiting the binding of a ligand with a G protein coupled receptor protein according to any of the above (33) to (40), which comprises measuring amounts of a labeled ligand bound to the said G protein coupled receptor protein in at least two cases:
(i) where the labeled ligand is contacted with at least one component selected from the group consisting of G protein coupled receptor proteins or salts thereof according to any of the above (33) to (40), peptide fragments or segments or salts thereof according to the above (41), and mixtures thereof, and
(ii) where the labeled ligand together with a compound to be tested is contacted with at least one component elected from the group consisting of G protein coupled receptor proteins or salts thereof according to any of the above (33) to (40), peptide fragments or segments or salts thereof according to the above (41), and mixtures thereof,
and comparing the measured amounts of the labeled ligand;

(75) a method for the screening of a compound or a salt thereof capable of inhibiting the binding of a ligand with a G protein coupled receptor protein according to any of the above (33) to (40), which comprises measuring amounts of a labeled ligand bound to a cell comprising the said G protein coupled receptor protein in at least two cases:
(i) where the labeled ligand is contacted with the said cell, and
(ii) where the labeled ligand together with a compound to be tested is contacted with the said cell,
and comparing the measured amounts of the labeled ligand;

(76) a method for the screening of a compound or a salt thereof capable of inhibiting the binding of a ligand with a G protein coupled receptor protein according to any of the above (33) to (40), which comprises measuring amounts of a labeled ligand bound to a membrane fraction of a cell comprising the said G protein coupled receptor protein in at least two cases:
(i) where the labeled ligand is contacted with the said membrane fraction, and
(ii) where the labeled ligand together with a compound to be tested is contacted with the membrane fraction,
and comparing the measured amounts of the labeled ligand;

(77) a method for the screening of a compound or a salt thereof capable of inhibiting the binding of a ligand with a G protein coupled receptor protein according to any of the above (33) to (40), which comprises measuring amounts of a labeled ligand bound to said G protein coupled receptor protein in at least two cases:
(i) where the labeled ligand is contacted with a G protein coupled receptor protein according to any of the above (33) to (40) which is expressed on the membrane of a transformant according to the above (59) during incubation of the transformant, and
(ii) where the labeled ligand together with a compound to be tested is contacted with the G protein coupled receptor protein according to any of the above (33) to (40) which is expressed on the membrane of a transformant according to the above (59) during incubation of the transformant, and comparing the measured amounts of the labeled ligand;

(78) a method for the screening of a compound or a salt thereof capable of inhibiting the binding of a ligand with a G protein coupled receptor protein according to any of the above (33) to (40), which comprises measuring G protein coupled receptor protein-mediated cell-stimulating activities in at least two cases:
(i) where a compound capable of activating the G protein coupled receptor protein according to any of the above (33) to (40) is contacted with a cell comprising the said G protein coupled receptor protein, and
(ii) where the compound capable of activating the G protein together with a compound to be tested is contacted with the cell comprising the said G protein coupled receptor protein,
and comparing the measured cell-stimulating activities;

(79) a method for the screening of a compound or a salt thereof capable of inhibiting the binding of a ligand with a G protein coupled receptor protein according to any of the above (33) to (40), which comprises measuring G protein coupled receptor protein-mediated cell-stimulating activities in at least two cases:
(i) where a compound capable of activating the G protein coupled receptor protein according to any of the above (33) to (40) is contacted with a G protein coupled receptor protein according to any of the above (33) to (40) which is expressed on the membrane of a transformant according to the above (59) during incubation of the transformant, and (ii) where the compound capable of activating the G protein together with a compound to be tested is contacted with the G protein coupled receptor protein according to any of the above (33) to (40) which is expressed on the membrane of a transformant according to the above (59) during incubation of the transformant, and comparing the measured cell-stimulating activities;

(80) a method according to the above (78) or (79) wherein said compound capable of activating the G protein coupled receptor protein according to any of the above (33) to (40) is selected from the group consisting of angiotensin, bombesin, canavinoid, cholecystokinin, glutamine, serotonin, melatonin, neuropeptide Y, opioid, purine, vasopressin, oxytocin, VIP (vasoactive intestinal and related peptides), somatostatin, dopamine, motilin, amylin, bradykinin, CGRP (calcitonin gene related peptides), adrenomedullin, leukotriene, pancreastatin, prostaglandin, thromboxane, adenosine, adrenaline, α- and β-chemokine (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptides and galanin;

(81) a compound which is determined through a method according to any of the above (62) and (74) to (80) or a salt thereof;

(82) a pharmaceutical composition comprising an effective amount of a compound according to the above (81) or a salt thereof;

(83) a screening kit according to the above (63), comprising a cell comprising a G protein coupled receptor protein according to any of the above (33) to (40);

(84) a screening kit according to the above (63), comprising a membrane fraction derived from a cell comprising a G protein coupled receptor protein according to any of the above (33) to (40);

(85) a screening kit according to the above (63), comprising a cell of the (59) or (109) mentioned herein below;

(86) a screening kit according to the above (63), comprising a membrane fraction derived from a cell of the (59) or (109);

(87) a compound which is determined by means of a screening kit according to any of the above (63) and (83) to (86) or a salt thereof;

(88) a pharmaceutical composition comprising an effective amount of a compound according to the above (87) or a salt thereof; and

(89) a method for measuring at least one component selected from the group consisting of G protein coupled receptor proteins or salts thereof according to any of the above (33) to (40), peptide fragments or segments or salts thereof according to the above (41), and mixtures thereof, which comprises contacting an antibody according to the above (64) with the component selected from the group consisting of G protein coupled receptor proteins or salts thereof according to the above (33) to (40), peptide segments or salts thereof according to the above (41), and mixtures thereof.

Still another aspect of the present invention is

(90) a ligand to a G protein coupled receptor protein according to any of the above (33) to (40), which is determined through the following step of:

contacting (i) at least one component selected from the group consisting of G protein coupled receptor proteins or salts thereof according to any of the above (33) to (40), peptide fragments or segments or salts thereof according to the above (41), and mixtures thereof, with (ii) at least one compound to be examined; and

(91) a compound capable of inhibiting the binding of a G protein coupled receptor protein according to any of the above (33) to (40) with a ligand, which is determined through carrying out a comparison between:

(i) at least one case where said ligand is contacted with at least one component selected from the group consisting of G protein coupled receptor proteins or salts thereof according to any of the above (33) to (40), peptide fragments or segments or salts thereof according to the above (41), and mixtures thereof, and (ii) at least one case where said ligand together with a compound to be tested is contacted with at least one component selected from the group consisting of G protein coupled receptor proteins or salts thereof according to any of the above (33) to (40), peptide fragments or segments or salts thereof according to the above (41), and mixtures thereof.

Another aspect of the present invention is

(92) a recombinant G protein coupled receptor protein and a salt thereof which is obtained by the expression of a DNA according to any of the above (42) to (57), or a modified or fragmented derivative thereof;

(93) a method for amplifying a DNA coding for G protein coupled receptor protein by polymerase chain reaction techniques, which comprises carrying out a polymerase chain reaction in the presence of a mixture of (1) a DNA coding for G protein coupled receptor protein, said DNA being capable of acting as a template, and (2) at least one DNA primer selected from the group consisting of DNA primers comprising either SEQ ID NO: 1 or SEQ ID NO: 2; and

(94) a method for screening DNA libraries for a DNA coding for G protein coupled receptor protein, which comprises carrying out a polymerase chain reaction in the presence of a mixture of (1) said DNA library, and (2) at least one DNA primer selected from the group consisting of DNA primers comprising either SEQ ID NO: 1 or SEQ ID NO: 2, to amplify selectively the DNA coding for G protein coupled receptor protein, contained in the DNA library.

Yet another aspect of the present invention is

(95) a monoclonal antibody against at least one component selected from the group consisting of G protein coupled receptor proteins or salts thereof according to any of the above (33) to (40), peptide fragments or segments or salts thereof according to the above (41), and mixtures thereof;

(96) a preparation of purified polyclonal antibodies against at least one component selected from the group consisting of G protein coupled receptor proteins or salts thereof according to any of the above (33) to (40), peptide fragments or segments or salts thereof according to the above (41), and mixtures thereof;

(97) an immunoassay for detecting a G protein coupled receptor protein which comprising (i) incubating a sample to be tested with an antibody according to the above (64) to allow formation of an antigen-antibody complex; and (ii) detecting an antigen-antibody complex formed in step (i); and

(98) an immunoassay for detecting antibodies against a G protein coupled receptor protein which comprising
(i) incubating a sample to be tested with at least one component selected from the group consisting of G protein coupled receptor proteins or salts thereof according to any of the above (33) to (40), peptide fragments or segments or salts thereof according to the above (41), and mixtures thereof to allow formation of an antigen-antibody complex; and
(ii) detecting an antigen-antibody complex formed in step (a).

Still another aspect of the present invention is

(99) an antisense DNA or RNA which comprises a nucleotide sequence complementary to at least a portion of a DNA according to any of the above (42) to (57), said antisense DNA or RNA being hybridizable to said DNA according to any of the above (42) to (57);

(100) an antisense DNA or RNA according to the above (99) wherein said antisense DNA or RNA comprises the 5' end hairpin loop, 5' end 6-base-pair repeat, 5' end untranslated region, protein translation initiation site or codon, ORF translation initiation site or codon, 3'-untranslated region, 3' end palindrome region, or 3' end hairpin loop of a G protein coupled receptor protein DNA according to any of the above (42) to (57);

(101) an antisense DNA or RNA according to the above (99) in a pharmaceutically acceptable carrier;

(102) an antisense DNA or RNA according to the above (99) comprising from 2 to 50 nucleotides;

(103) a method for modulating the activity of a G protein coupled receptor protein comprising contacting cells expressing the G protein coupled receptor protein with an antisense DNA or RNA according to the above (99);

(104) a method for producing an antibody against a G protein coupled receptor protein according to any of the above (33) to (40), which comprises administering to an individual at least one component selected from the group consisting of G protein coupled receptor proteins or salts thereof according to any of the above (33) to (40), peptide fragments or segments or salts thereof according to the above (41), and mixtures thereof; and (105) a method for producing a hybridoma which produces a monoclonal antibody against a G protein coupled receptor protein according to any of the above (33) to (40), which comprises
(i) immunizing an individual with at least one component selected from the group consisting of G protein coupled receptor proteins or salts thereof according to any of the above (33) to (40), peptide fragments or segments or salts thereof according to the above (41), and mixtures thereof;
(ii) immortalizing antibody producing cells from the immunized individual;
(iii) selecting an immortal cell which produces antibodies reactive with the G protein coupled receptor protein; and
(iv) growing said immortal cell.

Yet another aspect of the present invention is (106) a PCR screening kit for a DNA (or nucleotide sequence) coding for G protein coupled receptor protein in a DNA library which comprises
(i)
① at least one DNA primer selected from the group consisting of DNA primers comprising a nucleotide sequence represented by SEQ ID NO: 1, DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 10, DNA primers comprising a nucleotide sequence represented by SEQ ID NO: 14, DNA primers comprising a nucleotide sequence represented by SEQ ID NO: 16 and DNA primers comprising a nucleotide sequence represented by SEQ ID NO: 18, and
② at least-one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 11, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19; or
(ii)
① at least one DNA primer selected from the group consisting of DNA primers comprising a nucleotide sequence represented by SEQ ID NO: 1 and DNA primers comprising a nucleotide sequence represented by SEQ ID NO: 12, and
② at least one DNA primer selected from the group consisting of DNA primers comprising a nucleotide sequence represented by SEQ ID NO: 13;

(107) a vector comprising the DNA according to the above (7);

(108) an expression system comprising an open reading frame (ORF) of DNA derived from a G protein coupled receptor protein DNA according to any of the above (7) and (42) to (57), wherein the ORF is operably linked to a control sequence compatible with a desired host cell;

(109) a transformant (including a transfectant) carrying a vector of the above (107) or an expression system of the above (108);

(110) a process for producing a G protein coupled receptor protein or a salt thereof, which comprises culturing the transformant of the above (109) to express said G protein coupled receptor protein on the membrane of the transformant;

(111) a method for expressing a polypeptide of G protein coupled receptor protein, comprising:
(a) providing a transformant of the above (59) or (109); and
(b) incubating the transformant under conditions which allow expression of the polypeptide of G protein coupled receptor protein;

(112) a method for preparing a transformant according to the above (59) or (109), comprising:
(a) providing a host cell capable of transformation;
(b) providing a vector according to the above (58) or (107) or an expression system according to the above (108); and
(c) incubating (a) with (b) under conditions which allow transformation of the host cell with the vector or the expression system;

(113) a pharmaceutical composition according to the above (82) or (88), comprising an effective amount of a compound according to the above (81) or (87) or a pharmaceutically acceptable salt thereof in admixture with a pharmaceutically acceptable carrier, excipient or diluent;

(114) the pharmaceutical composition according to the above (82) or (88), for inhibiting the binding of a G protein coupled receptor protein according to the present invention with a ligand;

(115) a method for inhibiting the binding of a G protein coupled receptor protein according to the present invention with a ligand in a medium which comprises contacting an effective amount of a compound according to the above (81) or (87) or a salt thereof with said medium;

(116) a method for modulating the activity of a G protein coupled receptor protein comprising contacting cells expressing the G protein coupled receptor protein with a an effective amount of a compound according to the above (81) or (87) or a salt thereof;

(117) the ligand according to the above (90) being labeled with a detectable reporter;

(118) the antibody according to the above (64) wherein the antibody is labeled with a detectable reporter;

(119) a pharmaceutical composition for controlling an expression of G protein coupled receptor protein, which comprises an effective amount of the antisense DNA according to the above (99), and (120) a culture product produced by a transformant according to the above (59) or (109).

Yet another aspect of the present invention is (121) a DNA according to the above (1) wherein the DNA is an oligonucleotide having from 8 to 60 base residues;

(122) a DNA according to the above (1) wherein the DNA is synthetic;

(123) a DNA (or nucleotide sequence) coding for a G protein coupled receptor protein or a fragment thereof, which is obtained through the method according to any of the above (5) to (32);

(124) a DNA (or nucleotide sequence) according to the above (123), wherein said G protein coupled receptor protein is selected from the group consisting of angiotensin receptor, bombesin receptor, canavinoid receptor, cholecystokinin receptor, glutamine receptor, serotonin receptor, melatonin receptor, neuropeptide Y receptor, opioid receptor, purine receptor, vasopressin receptor, oxytocin receptor, VIP receptor (vasoactive intestinal and related peptide receptor), somatostatin receptor, dopamine receptor, motilin receptor, amylin receptor, bradykinin receptor, CGRP receptor (calcitonin gene related peptide receptor), adrenomedullin receptor, leukotriene receptor, pancreastatin receptor, prostaglandin receptor, thromboxane receptor, adenosine receptor, adrenaline receptor, α- and β-chemokine receptor including IL-8, GROα, GROβ, GROγ, NAP-2, ENA-78, PF4, IP10, GCP-2, MCP-1, HC14, MCP-3, I-309, MIP1α, MIP-1β, and RANTES receptors, endothelin receptor, enterogastrin receptor, histamine receptor, neurotensin receptor, TRH receptor, pancreatic polypeptide receptor, and galanin receptor; and (125) a culture product produced by a transformant according to the above (59) or (109).

As used herein the term "substantial equivalent(s)" means that the activity of the protein, e.g., nature of the ligand binding activity, and physical characteristics are substantially the same. Substitutions, deletions or insertions of amino acids often do not produce radical changes in the physical and chemical characteristics of a polypeptide, in which case polypeptides containing the substitution, deletion, or insertion would be considered to be substantially equivalent to polypeptides lacking the substitution, deletion, or insertion. Substantially equivalent substitutes for an amino acid within the sequence may be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine, The positively charged (basic) amino acids include arginine, lysine and histidine. The negatively charged (acidic) amino acids include aspartio acid and glutamic acid.

BRIEF DESCRIPTION OF THE DRAWINGS

FIG. 1 depicts the community (homology) of the sequence of 5' side synthetic DNA primers (HS-1) having a nucleotide sequence represented by SEQ ID NO: 1 with the nucleotide sequence each of other G protein coupled receptor protein-encoding cDNAs and genes (SEQ ID NOS: 62–75).

FIG. 2 depicts the community (homology) of the sequence which is complementary to 3' side synthetic DNA primers (HS-2) having a nucleotide sequence represented by SEQ ID NO: 2 with the nucleotide sequence each of other G protein coupled receptor protein-encoding cDNAs and genes (SEQ ID NOS: 76–91).

FIG. 3 depicts the community (homology) of the sequence of 5' side synthetic DNA primers (3A) having a nucleotide sequence represented by SEQ ID NO: 5 or 5' side synthetic DNA primers (3B) having a nucleotide sequence represented by SEQ ID NO: 6 relative to the nucleotide sequence each of other G protein coupled receptor protein-encoding cDNAs and genes (SEQ ID NOS: 92–110).

FIG. 4 depicts the community (homology) of the sequence of 5' side synthetic DNA primers (3C) having a nucleotide sequence represented by SEQ ID NO: 7 or 5' side synthetic DNA primers (3D) having a nucleotide sequence represented by SEQ ID NO: 3 relative to the nucleotide sequence each of other G protein coupled receptor protein-encoding cDNAs and genes (SEQ ID NOS: 111–121).

FIG. 5 depicts the community (homology) of the sequence (6A) which is complementary to 3' side synthetic DNA primers having a nucleotide sequence represented by SEQ ID NO: 8 or the nucleotide sequence (6B) which is complementary to 3' side synthetic DNA primers having a nucleotide sequence represented by SEQ ID NO: 9 relative to the nucleotide sequence each of other G protein coupled receptor protein-encoding cDNAs and genes (SEQ ID NOS: 122–142).

FIG. 6 depicts the community (homology) of the sequence (6C) which is complementary to 3' side synthetic DNA primers having a nucleotide sequence represented by SEQ ID NO: 4 relative to the nucleotide sequence each of other G protein coupled receptor protein-encoding cDNAs and genes (SEQ ID NOS: 143–154).

FIG. 7 depicts the community (homology) of the sequence of 5' side synthetic DNA primers (T2A) having a nucleotide sequence represented by SEQ ID NO: 10 with the nucleotide sequence each of other G protein coupled receptor protein-encoding cDNAs and genes (SEQ ID NOS: 155–171).

FIG. 8 depicts the community (homology) of the sequence which is complementary to 3' side synthetic DNA primers (T7A) having a nucleotide sequence represented by SEQ ID NO: 11 relative to the nucleotide sequence each of other G protein coupled receptor protein-encoding cDNAs and genes (SEQ ID NOS: 172–191).

FIG. 9 depicts the community (homology) of the sequence of 5' side synthetic DNA primers (TM1-A2) having a nucleotide sequence represented by SEQ ID NO: 12 relative to the nucleotide sequence each of other G protein coupled receptor protein-encoding cDNAs and genes (SEQ ID NOS: 192–204).

FIG. 10 depicts the community (homology) of the sequence which is complementary to 3' side synthetic DNA primers (TM3-B2) having a nucleotide sequence represented by SEQ ID NO: 13 relative to the nucleotide sequence each of other G protein coupled receptor protein-encoding cDNAs and genes (SEQ ID NOS: 205–218).

FIG. 11 depicts the community (homology) of the sequence of 5' side synthetic DNA primers (TM3-C2) having a nucleotide sequence represented by SEQ ID NO: 14 relative to the nucleotide sequence each of other G protein coupled receptor protein-encoding cDNAs and genes (SEQ ID NOS: 219–229).

FIG. 12 depicts the community (homology) of the sequence which is complementary to 3' side synthetic DNA primers (TM6-E2) having a nucleotide sequence represented by SEQ ID NO: 15 relative to the nucleotide sequence each of other G protein coupled receptor protein-encoding cDNAs and genes (SEQ ID NOS: 230–242).

FIG. 13 depicts the community (homology) of the sequence of 5' side synthetic DNA primers (TM2F18) having a nucleotide sequence represented by SEQ ID NO: 16 relative to the nucleotide sequence each of other G protein coupled receptor protein-encoding cDNAs and genes (SEQ ID NOS: 243–254).

FIG. 14 depicts the community (homology) of the sequence which is complementary to 3' side synthetic DNA primers (TM6R21) having a nucleotide sequence represented by SEQ ID NO: 17 relative to the nucleotide sequence each of other G protein coupled receptor protein-encoding cDNAs and genes (SEQ ID NOS: 255–274).

FIG. 15 depicts the community (homology) of the sequence of 5' side synthetic DNA primers (S3A) having a nucleotide sequence represented by SEQ ID NO: 18 relative to the nucleotide sequence each of other G protein coupled receptor protein-encoding cDNAs and genes (SEQ ID NOS: 275–286).

FIG. 16 depicts the community (homology) of the sequence which is complementary to 3' side synthetic DNA primers (S6A) having a nucleotide sequence represented by SEQ ID NO: 19 relative to the nucleotide sequence each of other G protein coupled receptor protein-encoding cDNAs and genes (SEQ ID NOS: 287–299).

FIG. 18 shows the nucleotide sequence determined by sequencing of clone A58 (SEQ ID NO: 300), with a T7 primer wherein the clone A58 is obtained by amplifying human brain amygdala-derived cDNA by PCR under mild conditions and subcloning it to pCR™II (HUMSOMATA: SEQ ID NO: 301).

FIG. 19 shows the nucleotide sequence determined by sequencing of clone A58 with an SP6 primer (SEQ ID NO: 302)HUMSOMATA: SEQ.

FIG. 20 shows the nucleotide sequence determined by sequencing of clone 57-A-2 (SEQ ID NO: 304) by using a –21M13 primer wherein the clone 57-A-2 is obtained by amplifying human brain amygdala-derived cDNA by PCR under severe conditions and subcloning it to pCR™II. (HUMDRDSA: SEQ ID NO: 305)

FIG. 21 shows the nucleotide sequence determined by sequencing of clone B54 with a T7 primer wherein the clone B54 (SEQ ID NO: 306) is obtained by amplifying rat whole brain-derived cDNA by PCR under mild conditions and subcloning it to pCR™II.(RNU04738: SEQ ID NO: 307)

FIG. 22 illustrates the nucleotide sequence (SEQ ID NO: 308) of the human pituitary gland-derived G protein coupled receptor protein cDNA fragment included in the cDNA clone p19P2 isolated by PCR using a human pituitary gland-derived cDNA and the amino acid sequence (SEQ ID NO: 309) encoded thereby, wherein the primer used for sequencing is –21M13, and the underlined part corresponds to the synthetic primer.

FIG. 23 illustrates the nucleotide sequence (SEQ ID NO: 310) of the human pituitary gland-derived G protein coupled receptor protein cDNA fragment included in the cDNA clone p19P2 isolated by PCR using a human pituitary gland-derived cDNA and the amino acid sequence (SEQ ID NO: 311) encoded thereby, wherein the primer used for sequencing is M13RV-N (Takara, Japan), and the underlined part corresponds to the synthetic primer.

FIG. 26 shows the partial amino acid sequence (p19P2) (SEQ ID NO: 312) of the protein encoded by the human pituitary gland-derived G protein coupled receptor protein cDNA fragment included in p19P2, as shown in FIGS. 22 and 23, relative to the known G protein coupled receptor protein, S12863 (SEQ ID NO: 313) wherein reverse amino acid residues are in agreement, the 1st to 99th amino acid residues of the p19P2 sequence correspond to the 1st to 99th amino acid residues in FIG. 22, and the 156th to 230th amino acid residues thereof correspond to the 1st to 68th amino acid residues in FIG. 23.

FIG. 27 is the nucleotide sequence (SEQ ID NO: 314) of the MIN6-derived G protein coupled receptor protein cDNA fragment derived based upon the nucleotide sequences of the MIN6-derived G protein coupled receptor protein cDNA fragments each included in the cDNA clones, pG3-2 and pG1-10, isolated by PCR using a MIN6-derived cDNA and the amino acid sequence encoded (SEQ ID NO: 315) thereby, wherein the underlined parts corresponds to the synthetic primers.

FIG. 29 is the partial nucleotide sequence (SEQ ID NO: 316) of the novel receptor protein cDNA clone, p63A2, obtained from the human amygdaloid nucleus by PCR amplification and the amino acid sequence (SEQ ID NO: 317) encoded thereby, wherein the underlined part corresponds to the synthetic primer.

FIG. 30 is the partial nucleotide sequence (SEQ ID NO: 318) of the novel receptor protein cDNA clone, p63A2, obtained from the human amygdaloid nucleus by PCR amplification and the amino acid sequence (SEQ ID NO: 319) encoded thereby, wherein the underlined part corresponds to the synthetic primer.

FIG. 33 is the partial amino acid sequence (p63A2) (SEQ ID NO: 320) of the protein encoded by the novel receptor protein cDNA fragment included in p63A2, relative to the partial amino acid sequence of the G protein coupled receptor protein (P30731) (SEQ ID NO: 321) expressed and induced by a mouse T cell-derived glucocorticoid, wherein reverse amino acid residues are in agreement.

FIG. 34 is the whole nucleotide sequence (SEQ ID NO: 322) of the the human pituitary gland-derived G protein coupled receptor protein cDNA, included in the cDNA clone, phGR3, isolated from the human-derived cDNA library by plaque hybridization using an DNA insert in the p19P2 as a probe, and the amino acid sequence (SEQ ID NO: 323) encoded thereby.

FIG. 37 is the partial nucleotide sequence (SEQ ID NO: 324) of the novel receptor protein cDNA clone, p3H2-17, obtained from mouse pancreatic β-cell strain, MIN6, by PCR amplification and the amino acid sequence (SEQ ID NO: 325) encoded thereby, wherein the underlined part corresponds to the synthetic primer used for the PCR amplification.

FIG. 39 is the partial amino acid sequence encoded by the novel receptor protein cDNA included in p3H2-17 (SEQ ID NO: 326), relative to the partial amino acid sequence each of chicken ATP receptor protein (P34996) (SEQ ID NO: 327), human somatostatin receptor subtype 3 protein (A46226) (SEQ ID NO: 328), human somatostatin receptor subtype 4 protein (JN0605) (SEQ ID NO: 329) and bovine neuropeptide Y receptor protein (S28787) (SEQ ID NO: 330), wherein reverse amino acid residues are in agreement.

FIG. 40 is the partial nucleotide sequence (SEQ ID NO: 331) of the novel receptor protein cDNA clone, p3H2-34, obtained from mouse pancreatic β-cell strain, MIN6, by PCR amplification and the amino acid sequence (SEQ ID NO: 332) encoded thereby, wherein the underlined parts correspond to the synthetic primers used for the PCR amplification.

FIG. 42 is the partial amino acid sequence encoded by the novel receptor protein cDNA included in p3H2-34, (SEQ ID NO: 333), relative to the partial amino acid sequence each of human somatostatin receptor subtype 4 protein (JN0605) (SEQ ID NO: 334), human somatostatin receptor subtype 2 protein (B41795) (SEQ ID NO: 335) and rat-derived ligand unknown receptor protein (A39297) (SEQ ID NO: 336), wherein reverse amino acid residues are in agreement.

FIG. 43 is the nucleotide sequence (SEQ ID NO: 337) of the rabbit gastropyrolic part smooth muscle-derived G protein coupled receptor protein cDNA fragment included in the novel receptor protein cDNA clone, pMD4, obtained from rabbit gastropyrolic part smooth muscles by PCR amplification, and the amino acid sequence (SEQ ID NO: 338) encoded thereby, wherein the underlined parts correspond to the synthetic primers used for the PCR amplification.

FIG. 44 is the hydrophobicity plotting profile of the protein encoded by the rabbit gastropyrolic part smooth muscle-derived G protein coupled receptor protein cDNA fragment included in pMD4, prepared based upon the amino acid sequence shown in FIG. 35, wherein numerals 1 to 3 suggest the presence of hydrophobic domains.

FIG. 45 is the partial amino acid sequence (pMD4) (SEQ ID NO: 339) of the protein encoded by the rabbit gastropyrolic part smooth muscle-derived G protein coupled receptor protein cDNA fragment included in pMD4 as shown in FIG. 43, relative to the known G protein coupled receptor protein, rat ligand unknown receptor protein (A35639) (SEQ ID NO: 340), wherein reverse amino acid residues are in agreement, the 1st to 88th amino acid residues of the pMD4 sequence correspond to the 1st to 88th amino acid residues in FIG. 43.

FIG. 46 shows the nucleotide sequence (SEQ ID NO: 341) of the mouse-derived galanin receptor protein cDNA clone, pMGR20, which has been cloned with, as a probe, the cDNA insert in p3H2-34 and the amino acid sequence encoded thereby (SEQ ID NO: 342).

FIG. 48 is the amino acid sequence (MOUSEGALRECE) (SEQ ID NO: 343) of the mouse-derived galanin receptor protein encoded by pMGR20, relative to the amino acid sequence (HUMAGALAMI) (SEQ ID NO: 344) of the human-derived galanin receptor protein, wherein reverse amino acid residues are in agreement.

FIG. 49 is the nucleotide sequence (SEQ ID NO: 345) of the rabbit gastropyrolic part smooth muscle-derived G protein coupled receptor protein cDNA fragment included in the novel receptor protein cDNA clone, pMJ10, obtained from rabbit gastropyrolic part smooth muscles by PCR amplification and the amino acid sequence encoded thereby (SEQ ID NO: 346), wherein the underlined parts corresponds to the synthetic primers used for the PCR amplification.

FIG. 50 is the hydrophobicity plotting profile of the protein encoded by the rabbit gastropyrolic part smooth muscle-derived G protein coupled receptor protein cDBA fragment included in pMJ10, prepared based upon the amino acid sequence shown in FIG. 49, wherein numerals 4 to 6 suggest the presence of hydrophobic domains.

FIG. 51 is the partial amino acid sequence (pMJ10) (SEQ ID NO: 347) of the protein encoded by the rabbit gastropyrolic part smooth muscle-derived G protein coupled receptor protein cDNA fragment included in pMJ10 shown in FIG. 49, relative to human ligand unknown receptor protein (B42009) (SEQ ID NO: 348), human N-formylpeptide receptor protein (JC2014) (SEQ ID NO: 349), rabbit N-formylpeptide receptor protein (A46520) (SEQ ID NO: 350), mouse C5a anaphylatoxin receptor protein (A46525) (SEQ ID NO: 351) and bovine neuropeptide Y receptor protein (S28787) (SEQ ID NO: 352) which are known G protein coupled receptor proteins, wherein reverse amino acid residues are in agreement, and the 1st to 125th amino acid residues of pMJ10 correspond to the 1st to 125th amino acid residues in FIG. 49.

FIG. 52 is the nucleotide sequence (SEQ ID NO: 353) of the rabbit gastropyrolic part smooth muscle-derived G protein coupled receptor protein cDNA fragment included in the novel receptor protein cDNA clone, pMH28, obtained from rabbit gastropyrolic part smooth muscles by PCR amplification and the amino acid sequence encoded thereby (SEQ ID NO: 354), wherein the underlined parts correspond to the synthetic primers used for the PCR amplification.

FIG. 54 is the partial amino acid sequence (pMH28) (SEQ ID NO: 355) of the protein encoded by the rabbit gastropyrolic part smooth muscle-derived G protein coupled receptor protein cDNA fragment included in pMH28 shown in FIG. 52, relative to mouse IL-8 receptor protein (P35343) (SEQ ID NO: 356), human somatostatin receptor protein 1 (A41795) (SEQ ID NO: 357) and human somatostatin receptor protein 4 (A47457) (SEQ ID NO: 358) which are known G protein coupled receptor proteins, wherein reverse amino acid residues are in agreement, and the 1st to 119th amino acid residues of pMH28 correspond to the 1st to 119th amino acid residues in FIG. 52.

FIG. 55 is the nucleotide sequence (SEQ ID NO:359) of the rabbit gastropyrolic part smooth muscle-derived G protein coupled receptor protein cDNA fragment included in the novel receptor protein cDNA clone, pMN7, obtained from rabbit gastropyrolic part smooth muscles by PCR amplification and the amino acid sequence encoded thereby (SEQ ID NO:360), wherein the underlined 5'-end nucleotide sequence part corresponds to the synthetic primer used for the PCR amplification.

FIG. 56 is the nucleotide sequence (SEQ ID NO:359) of the rabbit gastropyrolic part smooth muscle-derived G protein coupled receptor protein cDNA fragment included in the novel receptor protein cDNA clone, pMN7, obtained from rabbit gastropyrolic part smooth muscles by PCR amplification and the amino acid sequence encoded thereby (SEQ ID NO:360), wherein the underlined 3'-end nucleotide sequence part corresponds to the synthetic primer used for the PCR amplification.

FIG. 60 shows the partial amino acid sequence (p19P2) (SEQ ID NO:361) of the protein encoded by the human pituitary gland-derived G protein coupled receptor protein cDNA fragment included in p19P2, as shown in FIGS. 22 and 23, relative to, the known G protein coupled receptor protein, S12863 (SEQ ID NO:362), wherein reverse amino acid residues are in agreement, the 1st to 99th amino acid residues of the p19P2 sequence correspond to the 1st to 99th amino acid residues in FIG. 22, and the 156th to 230th amino acid residues thereof correspond to the 1st to 68th amino acid residues in FIG. 23.

FIG. 61 is the partial amino acid sequence (pG3-2/pG1-10) (SEQ ID NO:363) of the MIN6-derived G protein coupled receptor protein, as shown in FIG. 27, relative to the partial amino acid sequence (p19P2) (SEQ ID NO:364) of the protein encoded by p19P2, as shown in FIGS. 22 and 23, wherein reverse amino acid residues are in agreement, the 1st to 99th amino acid residues of the p19P2 sequence correspond to the 1st to 99th amino acid residues in FIG. 22, the 156th to 223rd amino acid residues thereof correspond to the 1st to 68th amino acid residues in FIG. 23, and the 1st to 223rd amino acid residues of the pG3-2/pG1-10 sequence correspond to the 1st to 223rd amino acid residues in FIG. 27.

FIG. 62 is the nucleotide sequence (SEQ ID NO:365) of the MIN6-derived G protein coupled receptor protein cDNA fragment included in the cDNA clone, p5S38, isolated by PCR using a MIN6-derived cDNA and the amino acid sequence (SEQ ID NO:366) encoded thereby, wherein the underlined parts corresponds to the synthetic primers.

FIG. 63 is the partial amino acid sequence (p5S38) (SEQ ID NO:367) of the MIN6-derived G protein coupled receptor protein, as shown in FIG. 62, relative to the partial amino acid sequence (p19P2) (SEQ ID NO:368) of the G protein coupled receptor protein encoded by p19P2, as shown in FIGS. 22 and 23, as well as the partial amino acid sequence (SEQ ID NO:369) of the G protein coupled receptor protein encoded by the nucleotide sequence derived from the nucleotide sequence of the cDNA fragment included in pG3-2 and pG1-10, as shown in FIG. 27, wherein reverse amino acid residues are in agreement, the 1st to 144th amino acid residues of the p5S38 sequence correspond to the 1st to 144th amino acid residues in FIG. 62, the 1st to 99th amino acid residues of the p19P2 sequence correspond to the 1st to 99th amino acid residues in FIG. 22, the 156th to 223rd amino acid residues thereof correspond to the 1st to 68th amino acid residues in FIG. 23, and the 1st to 223rd amino acid residues of the pG3-2/pG1-10 sequence correspond to the 1st to 223rd amino acid residues in FIG. 27.

Lane 1 indicates the size marker 6 (Wako Pure Chemical, Japan).

Lane 2 indicates the internal control which is the thymus-derived PCR product obtained by PCR amplification using the primer having SEQ ID NO: 20 and the primer having SEQ ID NO: 22 with Taq polymerase.

Lane 3 indicates the negative control which is the PCR product obtained by Ex Taq polymerase PCR amplification of thymus cDNA prior to addition of anchors.

Lane 4 indicates the negative control which is the PCR product obtained by Taq polymerase PCR amplification of thymus cDNA prior to addition of anchors.

Lane 5 indicates the PCR product obtained by 5'RACE of thymus poly(A)$^+$ RNA with Pfu polymerase.

Lane 6 indicates the PCR product obtained by 5'RACE of thymus poly(A)$^+$ RNA with Vent polymerase.

Lane 7 indicates the PCR product obtained by 5'RACE of thymus poly(A)$^+$ RNA with Ex Taq polymerase.

Lane 8 indicates the PCR product obtained by 5'RACE of thymus poly(A)$^+$ RNA with Taq polymerase.

Lane 9 indicates the size marker 5 (Wako Pure Chemical, Japan).

Lane 10 indicates the internal control which is the spleen-derived PCR product obtained by PCR amplification using the primer having SEQ ID NO: 20 and the primer having SEQ ID NO: 22 with Taq polymerase.

Lane 11 indicates the negative control which is the PCR product obtained by Ex Taq polymerase PCR amplification of spleen cDNA prior to addition of anchors.

Lane 12 indicates the negative control which is the PCR product obtained by Taq polymerase PCR amplification of spleen cDNA prior to addition of anchors.

Lane 13 indicates the PCR product obtained by 5'RACE of poly(A)RNA$^+$ with Pfu polymerase.

Lane 14 indicates the PCR product obtained by 5'RACE of spleen poly(A)$^+$ RNA with Vent polymerase.

Lane 15 indicates the PCR product obtained by 5'RACE of spleen poly(A)$^+$ RNA with Ex Taq polymerase.

Lane 16 indicates the PCR product obtained by 5'RACE of spleen poly(A)$^+$ RNA with Taq polymerase.

Lane 17 indicates the size marker 5 (Wako Pure Chemical, Japan).

Each blacked triangle indicates the band recovered.

Figure 67:
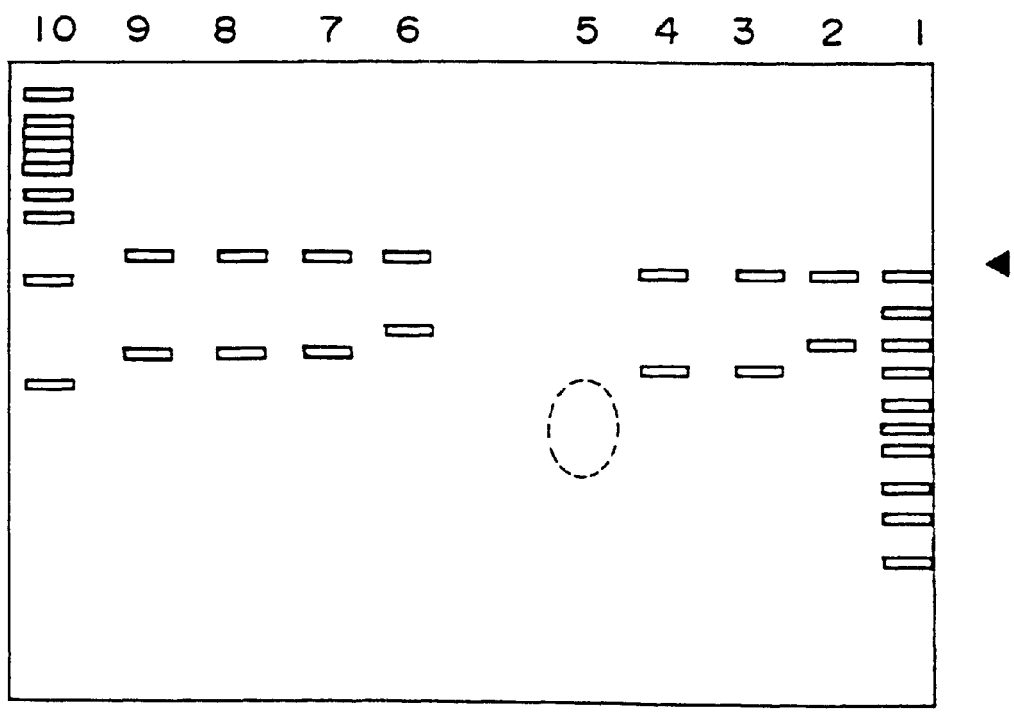

FIG. 67 shows the agarose gel electrophoresis analysis profile of the PCR products obtained by 3'RACE PCR of the receptor gene included in p3H2-17 using mouse thymus and spleen poly(A)$^+$ RNA.

Lane 1 indicates the size marker 5 (Wako Pure Chemical, Japan).

Lane 2 indicates the PCR product obtained by 3'RACE of spleen poly(A)$^+$ RNA with Taq polymerase.

Lane 3 indicates the PCR product obtained by 3'RACE of spleen poly(A)$^+$ RNA with Ex Taq polymerase.

Lane 4 indicates the PCR product obtained by 3'RACE of spleen poly(A)$^+$ RNA with Vent polymerase.

Lane 5 indicates the PCR product obtained by 3'RACE of spleen poly(A)$^+$ RNA with Pfu polymerase.

Lane 6 indicates the PCR product obtained by 3'RACE of thymus poly(A)$^+$ RNA with Taq polymerase.

Lane 7 indicates the PCR product obtained by 3'RACE of thymus poly(A)$^+$ RNA with Ex Taq polymerase.

Lane 8 indicates the PCR product obtained by 3'RACE of thymus poly(A)$^+$ RNA with Vent polymerase.

Lane 9 indicates the PCR product obtained by 3'RACE of thymus poly(A)$^+$ RNA with Pfu polymerase.

Lane 10 indicates the size marker 6 (Wako Pure Chemical, Japan).

Each blacked triangle indicates the band recovered.

Figure 68:
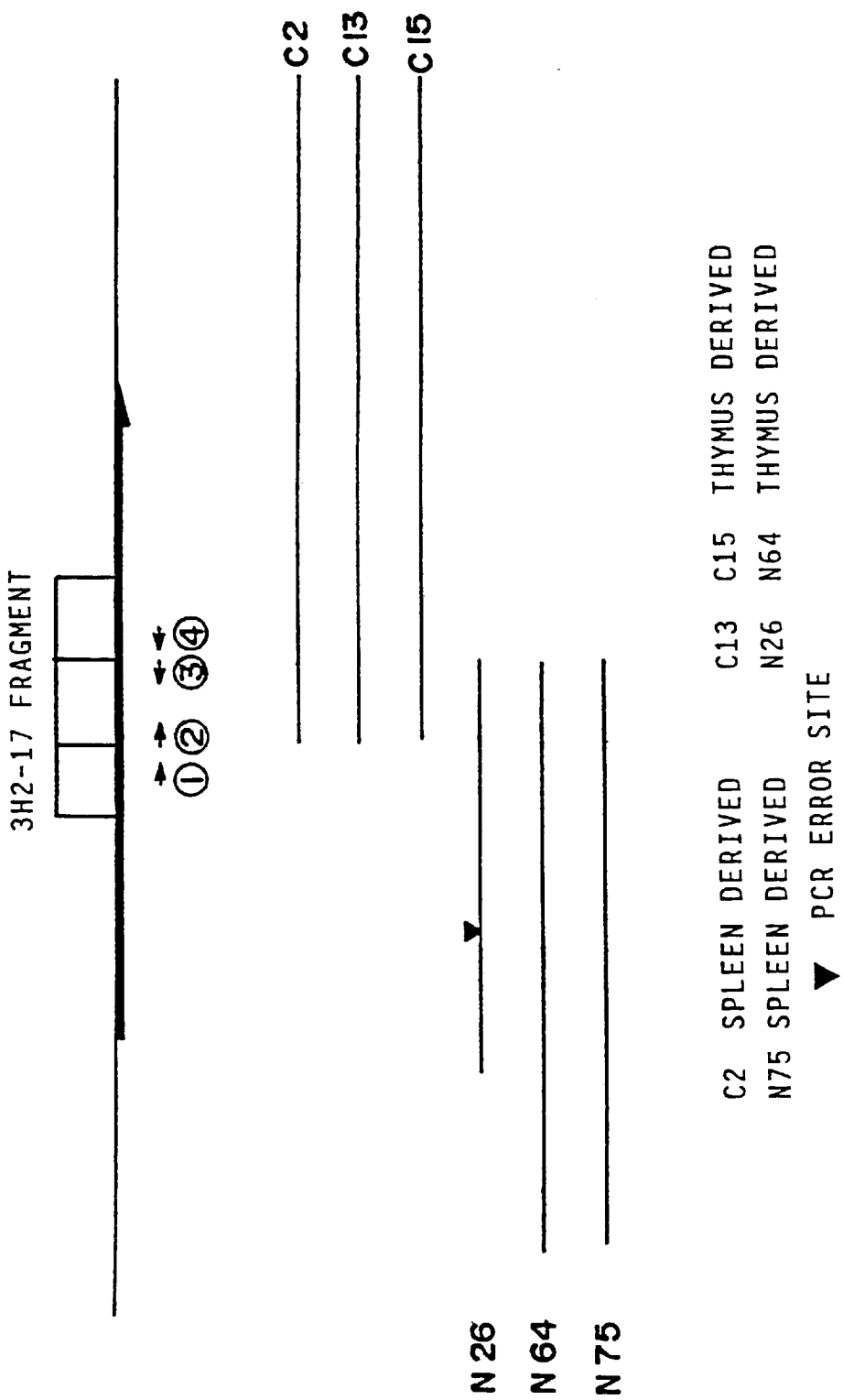

FIG. 68 depicts the model of the RACE products of the receptor protein cDNA fragment included in p3H2-17 obtained by 5'RACE and 3'RACE. Open squares represent regions which have already been isolated and included in p3H2-17. Small arrows, ①, ②, ③, and ④, indicate the positions and directions of the primers designed in Working Example 19. The big arrow shows a predicted full-length open reading frame of the receptor protein held by p3H2-17. Numbers at both ends, N26, N64, N75, C2, C13 and C15, indicate clone numbers of the RACE products obtained. Among these RACE products, N26, N64 and N75 are inserted into pCR™II vector and C2, C13 and C15 are inserted into the SmaI site of pUC18. The solid triangle indicates the PCR error position which has been clarified through sequencing.

FIG. 69 is the nucleotide sequence (SEQ ID NO:370) of the open reading frame and neighboring regions thereof of mouse G protein coupled receptor protein cDNA included in the cDNA clone pMAH2-17 obtained from mouse spleen and thymus poly(A) RNA by RACE techniques based on the nucleotide sequence of the cDNA fragment included in p3H2-17 and the amino acid sequence (SEQ ID NO:371) encoded thereby.

Figure 70:
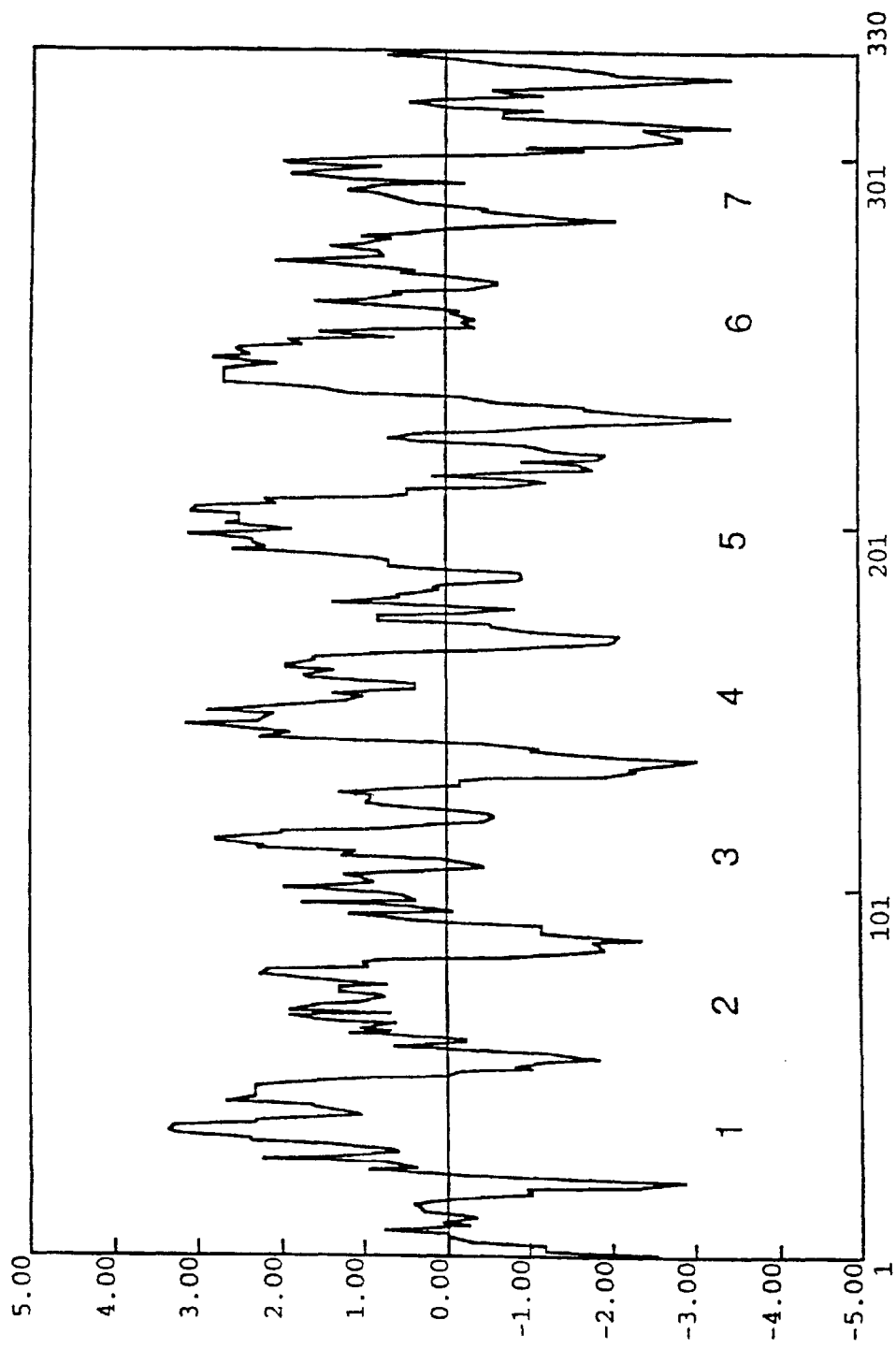

FIG. 70 is the hydrophobicity plotting profile of the protein encoded by the receptor protein cDNA included in pMAH2-17, prepared based upon the amino acid sequence shown in FIG. 69.

FIG. 71 is the amino acid sequence (75+13CODING) (SEQ ID NO:372) of the protein encoded by the mouse-derived G protein coupled receptor protein cDNA fragment included in pMAH2-17, as shown in FIG. 69, relative to the known G protein coupled receptor proteins, mouse P$_{2U}$purinoceptor (P2UR MOUSE) (SEQ ID NO:373) and chicken P$_{2Y}$purinoceptor (P2YR CHICK) (SEQ ID NO:374), wherein reverse amino acid residues are in agreement.

FIG. 72 is the nucleotide sequence (SEQ ID NO:375) (from 1st to 540th nucleotides) of the rabbit gastropyrolic part smooth muscle-derived G protein coupled receptor protein cDNA fragment included in the novel receptor protein cDNA clone, pMN128, obtained from rabbit gastropyrolic part smooth muscles by PCR amplification, and the amino acid sequence (SEQ ID NO:376), encoded thereby, wherein the underlined 5' part corresponds to the synthetic primer used for the PCR amplification.

FIG. 73 is the nucleotide sequence (SEQ ID NO:375) (from 541st to 843rd nucleotides) of the rabbit gastropyrolic part smooth muscle-derived G protein coupled receptor protein cDNA fragment included in the novel receptor protein cDNA clone, pMN128, obtained from rabbit gastropyrolic part smooth muscles by PCR amplification, and the amino acid sequence (SEQ ID NO:376) encoded thereby, wherein the underlined 3' part corresponds to the synthetic primer used for the PCR amplification.

Figure 74:
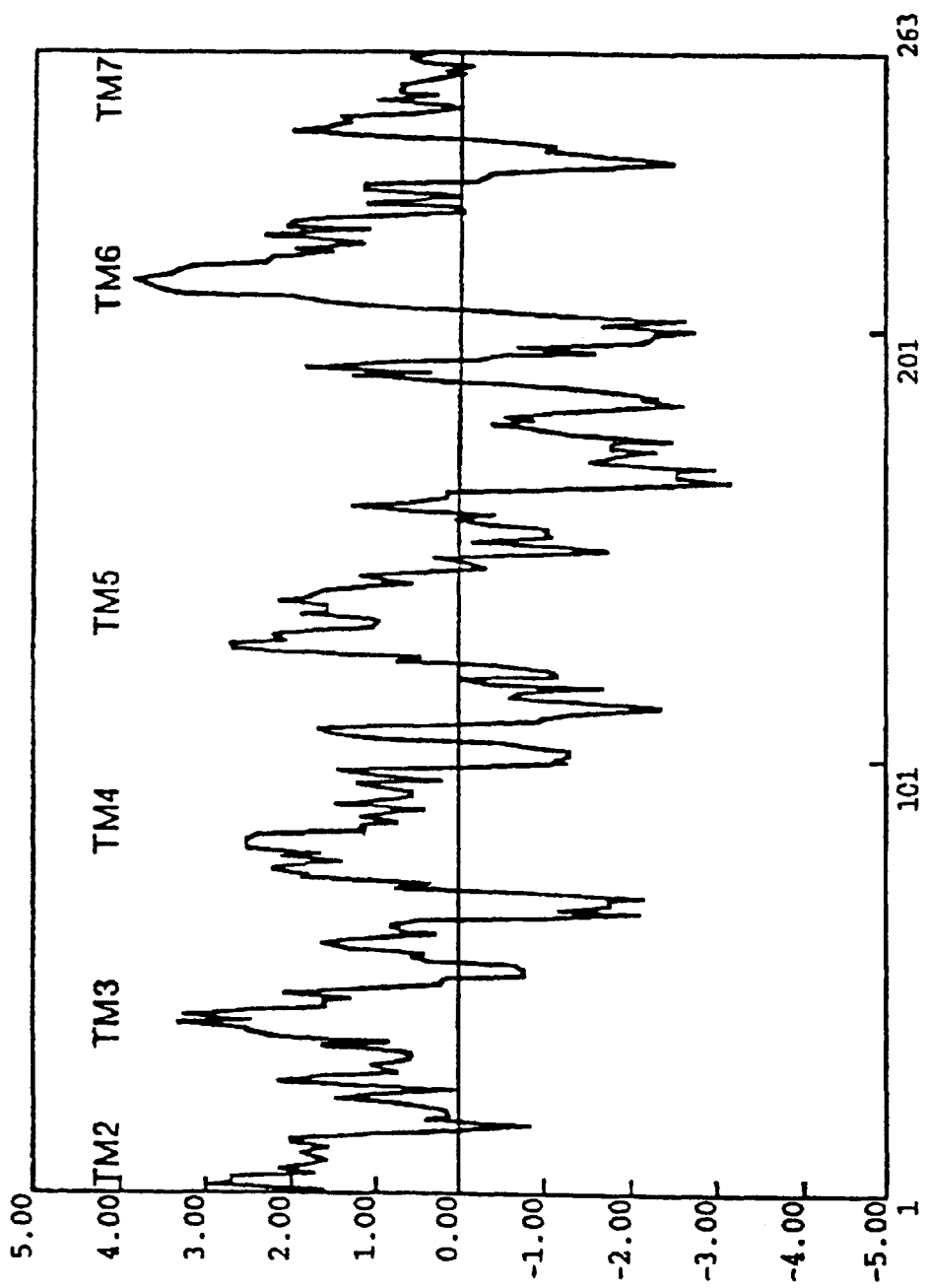

FIG. 74 is the hydrophobicity plotting profile of the protein encoded by the rabbit gastropyrolic part smooth muscle-derived G protein coupled receptor protein cDNA fragment included in pMN128, prepared based upon the amino acid sequences shown in FIGS. 72 and 73, suggesting the presence of hydrophobic domains.

Figure 75:
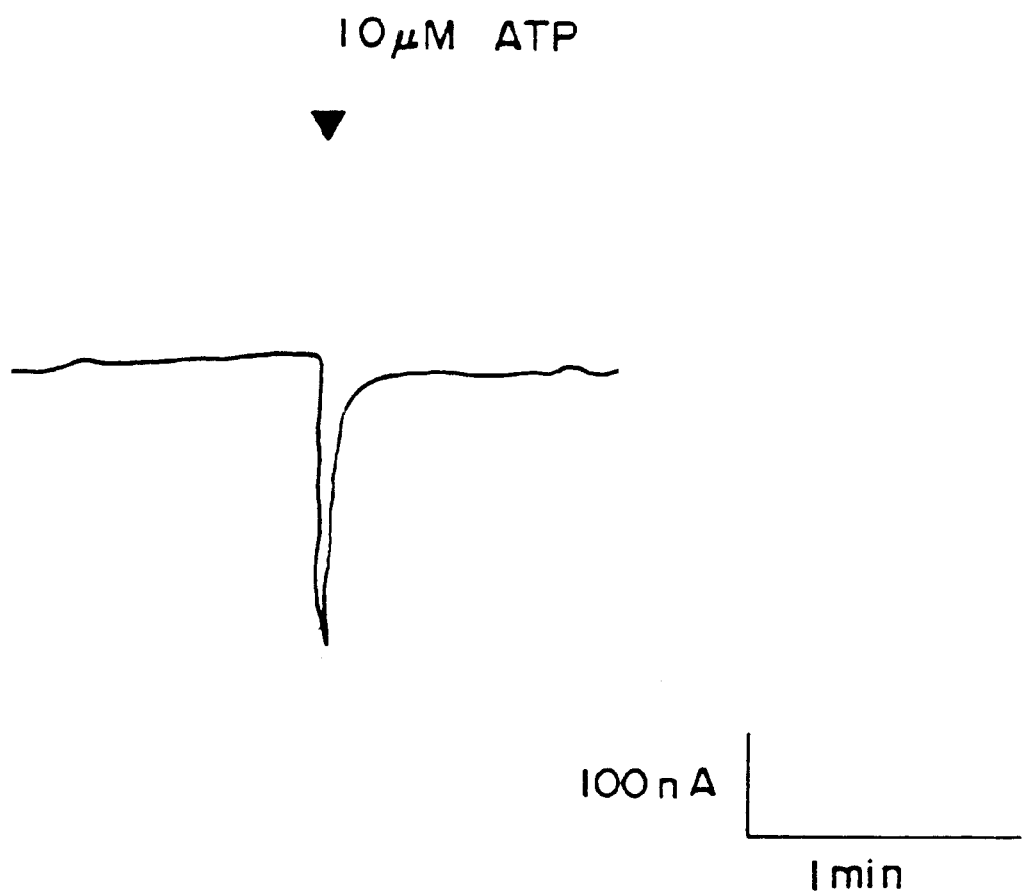

FIG. 75 shows inward currents evoked by ATP in Xenopus oocytes injected with cDNA of pMAH2-17-encoded receptor.

FIG. 76 is the nucleotide sequence (SEQ ID NO:377) of the human-derived G protein coupled receptor protein cDNA fragment included in ph3H2-17, relative to the nucleotide sequence (SEQ ID NO:378) of the mouse-derived G protein coupled receptor protein cDNA fragment included in p3H2-17, wherein reverse base residues are in agreement.

FIG. 77 is the nucleotide sequence (SEQ ID NO:379) of the open reading frame and neighboring regions thereof of human-derived G protein coupled receptor protein cDNA included in phAH2-17 and the amino acid sequence (SEQ ID NO:380) encoded thereby.

Figure 78:
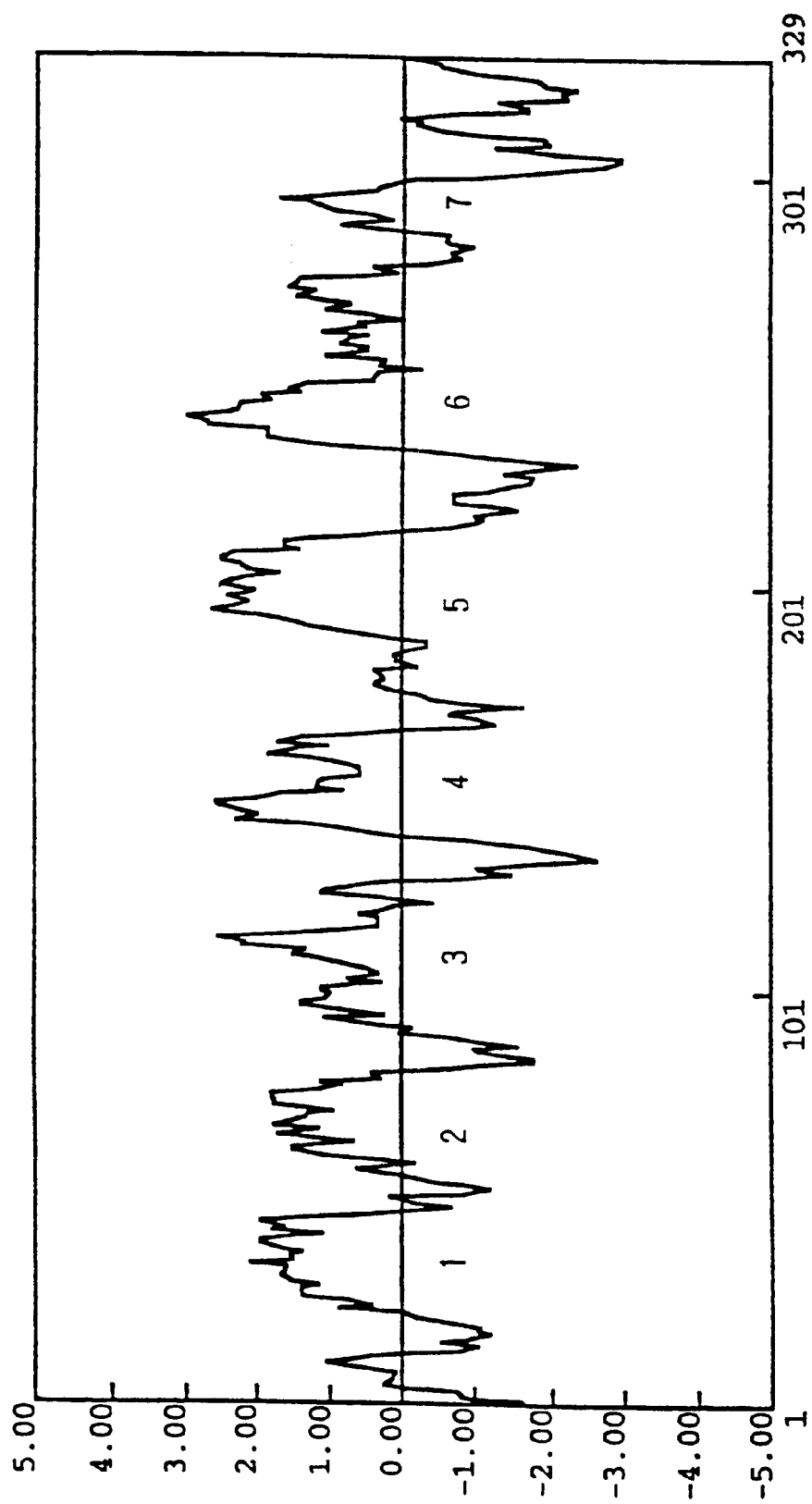

FIG. 78 is the hydrophobicity plotting profile of the protein encoded by the human-derived G protein coupled receptor protein cDNA included in phAH2-17.

FIG. 79 is the amino acid sequence (SEQ ID NO:59) of human type purinoceptor encoded by phAH2-17, relative to the mouse purinoceptor (SEQ ID NO:39) encoded by p3H2-17, wherein reverse amino acid residues are in agreement.

DETAILED DESCRIPTION OF THE PREFERRED EMBODIMENT

According to the present invention, DNA sequences comprising each a nucleotide sequence indicated by a SEQ ID NO selected from the group consisting of SEQ ID NO: 1 to SEQ ID NO: 19 have been synthesized and characterized. The DNA is a potent primer for polymerase chain reaction in order to amplify DNA sequences encoding part or all of the polypeptide sequence of G protein coupled receptor protein. PCR amplification methods of the DNA coding for part or all of the polypeptide sequence of G protein coupled receptor protein can be advantageously carried out with the said primer DNA. Screening of DNA libraries for the DNA encoding part or all of the polypeptide sequence of G protein coupled receptor protein can be successfully carried out through polymerase chain reaction techniques with the said primer DNA. As a result, template DNAs coding for part or all of the polypeptide sequence of G protein coupled receptor protein, contained in the DNA library, can be selectively amplified and various DNA sequences encoding part or all of the polypeptide sequence of G protein coupled receptor protein may be isolated and characterized. Further, G protein coupled receptor proteins, peptide segments or fragments derived from the G protein coupled receptor protein, modified derivatives or analogues thereof, and salts thereof may be recognized, predicted, deduced, produced, expressed, isolated and characterized.

The primer DNA useful in PCR amplification of the DNA sequence encoding part or all of the polypeptide sequence of G protein coupled receptor protein is a degenerate deoxynucleotide which has an oligonucleotide sequence to which a SEQ ID NO selected from the group consisting of SEQ ID NO: 1 to SEQ ID NO: 19 is assigned.

The nucleotide sequence represented by SEQ ID NO: 1 is a base sequence having the following formula:

wherein S is G or C, M is A or C, $N_1$=A, G, C, or T, and Y is T or C (FIG. 1: HS-1).

The nucleotide sequence represented by SEQ ID NO: 2 (HS-2) is a base sequence having the following formula:

wherein $N_1$=A, G, C, or T, W is A or T, R is A or G, and K is G or T, which is complementary to a nucleotide sequence having the following formula:

wherein N=A, C, G, or T, M is A or C, Y is T or C, and W is A or T (FIG. 2).

The nucleotide sequence represented by SEQ ID NO: 3 is a base sequence having the following formula:

wherein S is G or C, Y is C or T, M is A or C, R is A or G, and $N_2$=I (FIG. 4: 3D).

The nucleotide sequence represented by SEQ ID NO: 4 is a base sequence having the following formula:

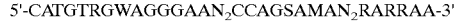

wherein R is A or G, W is T or A, S is G or C, M is A or C, and $N_2$=I, which is complementary to a nucleotide sequence having the following formula:

wherein Y is C or T, $N_1$=A, G, C, or T, K is G or T, S is G or C, W is A or T (FIG. 6: 6C).

The nucleotide sequence represented by SEQ ID NO: 5 is a base sequence having the following formula:

wherein Y is C or T, R is A or G, S is G or C, M is A or C, and V is A, C or G, and $N_2$ is I (FIG. 3: 3A).

The nucleotide sequence represented by SEQ ID NO: 6 is a base sequence having the following formula:

wherein Y is C or T, R is A or G, S is G or C, M is A or C, and V is A, C or G, and $N_2$ is I (FIG. 3: 3B).

The nucleotide sequence represented by SEQ ID NO: 7 is a base sequence having the following formula:

wherein S is G or C, Y is C or T, M is A or C, R is A or G, and $N_2$ is I (FIG. 4: 3C).

The nucleotide sequence represented by SEQ ID NO: 8 is a base sequence having the following formula:

5'-GATGTGRTARGGSRN₂CCAACAGAN₂GRYAAA-3' wherein R is A or G, S is G or C, Y is C or T, and N₂ is I, which is complementary to a nucleotide sequence having the following formula:

5'-TTTRYCN₁TCTGTTGGN₁YSCCYTAYCACATC-3' wherein R is A or G, Y is C or T, S is G or C, and N₁ is A, T, G, or C (FIG. 5: 6A).

The nucleotide sequence represented by SEQ ID NO: 9 is a base sequence having the following formula:

5'-GATGTGRTARGGSRN₂CCAACAGAN₂GRYGAA-3' wherein R is A or G, S is G or C, Y is C or T, and N₂ is I, which is complementary to a nucleotide sequence having the following formula:

5'-TTCRYCN₁TCTGTTGGN₁YSCCYTAYCACATC-3' wherein R is A or G, Y is C or T, S is G or C, and N₁ is A, T, G, or C (FIG. 5: 6B).

The nucleotide sequence represented by SEQ ID NO: 10 is a base sequence having the following formula:

5'-GYCACCAACN₂WSTTCATCCTSWN₂HCTG-3' wherein S is G or C, Y is C or T, W is A or T, H is A, C or T, and N₂ is I (FIG. 7: T2A).

The nucleotide sequence represented by SEQ ID NO: 11 (FIG. 8: T7A) is a base sequence having the following formula:

5'-ASN₂SAN₂RAAGSARTAGAN₂GAN₂RGGRTT-3' wherein R is A or G, S is G or C, and N₂ is I, which is complementary to a nucleotide sequence having the following formula:

5'-AAYCCYN₂TCN₂TCTAYTSCTTYN₂TSN₂ST-3' wherein Y is C or T, N₂ is I, and S is G or C (FIG. 8).

The nucleotide sequence represented by SEQ ID NO: 12 is a base sequence having the following formula:

5'-TGN₂TSSTKMTN₂GSN₂GTKGTN₂GGN₂AA-3' wherein S is G or C, K is G or T, M is A or C, and N₂ is I (FIG. 9: TM1-A2).

The nucleotide sequence represented by SEQ ID NO: 13 (FIG. 10: TM3-B2) is a base sequence having the following formula:

5'-AYCKGTAYCKGTCCAN₂KGWN₂ATKGC-3' wherein Y is C or T, K is G or T, W is A or T, and N₂ is I, which is complementary to a nucleotide sequence having the following formula:

5'-GCMATN₂WCMN₂TGGACMGRTACMGRT-3' wherein M is A or C, W is A or T, R is A or G, and N₂ is I (FIG. 10).

The nucleotide sequence represented by SEQ ID NO: 14 is a base sequence having the following formula:

5'-CATKKCCSTGGASAGN₂TAYN₂TRGC-3' wherein K is G or T, S is G or C, Y is C or T. R is A or G, and N₂ is I (FIG. 11: TM3-C2).

The nucleotide sequence represented by SEQ ID NO: 15 (FIG. 12: TM6-E2) is a base sequence having the following formula:

5'-GWWGGGSAKCCAGCASAN₂GGCRAA-3' wherein W is A or T, S is G or C, K is G or T, R is A or G, and N₂ is I, which is complementary to a nucleotide sequence having the following formula:

5'-TTYGCCN₂TSTGCTGGMTSCCCWWC-3' wherein Y is C or T, S is G or C, M is A or C, W is A or T, and N₂ is I (FIG. 12).

The nucleotide sequence represented by SEQ ID NO: 16 is a base sequence having the following formula:

5'-ARYYTN₂GCN₂N₂TN₂GCN₁GAY-3' wherein R is A or G, Y is C or T, N₁ is A, T, G, or C, and N₂ is I (FIG. 13: TM2F18).

The nucleotide sequence represented by SEQ ID NO: 17 (FIG. 14: TM6R21) is a base sequence having the following formula:

5'-N₂GGN₂AN₂CCARCAN₁AN₁N₁RN₁RAA-3' wherein R is A or G, N₁ is A, T, G, or C, and N₂ is I which is complementary to a nucleotide sequence having the following formula:

5'-TTYN₁YN₁N₁TN₁TGYTGGN₂TN₂CCN₂-3' wherein Y is C or T, N₁ is A, T, G, or C, and N₂ is I (Figure 14).

The nucleotide sequence represented by SEQ ID NO: 18 is a base sequence having the following formula:

5'-GCCTSN₂TN₂RN₂SATGWSTGTGGAN₂MGN₂T-3' wherein S is G or C, R is A or G, W is A or T, M is A or C, and N₂ is I (FIG. 15: S3A).

The nucleotide sequence represented by SEQ ID NO: 19 (FIG. 16: S6A) is a base sequence having the following formula:

5'-GAWSN₂TGMYN₂AN₂RTGGWAGGGN₂AN₂CCA-3' wherein W is A or T, S is G or C, M is A or C, Y is C or T, R is A or G, and N₂ is I, which is complementary to a nucleotide sequence having the following formula:

5'-TGGN₂TN₂CCCTWCCAYN₂TN₂RKCAN₂SWTC-3' wherein W is A or T, Y is C or T, R is A or G, K is G or T, and S is G or C (FIG. 16).

In a specific embodiment, symbols in the aforementioned SEQ ID NOs (R, Y, M, K, S, W, H, V and N) indicate the incorporation of plural bases, leading to multiple oligonucleotides in the primer preparation. In other words, SEQ ID NO: 1 to SEQ ID NO: 19 are degenerate nucleotide primers.

The nucleotide sequence represented by SEQ ID NO: 1 (FIG. 1: HS-1) is a nucleotide sequence highly homologous to the DNA sequence coding for the amino acid sequence corresponding to or near the first membrane-spanning (transmembrane) domain each of known C protein coupled receptor proteins such as human-derived TRH receptor protein (HTRHR), human-derived RANTES receptor protein (L10918, HUMRANTES), human Burkitt's lymphoma-derived receptor protein with an unknown ligand (X68149, HSBLR1A), human-derived somatostatin receptor protein (L14856, HUMSOMAT0), rat-derived μ-opioid receptor protein (U02083, RNU02083), rat-derived κ-opioid receptor protein (U00442, U00442), human-derived neuromedin B receptor protein (M73482, HUMNMBR), human-derived muscarinic acetylcholine receptor protein (X15266, HSHM4), rat-derived adrenaline α₁B receptor protein (L08609, RATAADRE01), human-derived somatostatin 3 receptor protein (M96738, HUMSSTR3X), human-derived C₅a receptor protein (HUMC5AAR), human-derived receptor protein with an unknown ligand (HUMRDC1A), human-derived receptor protein with an unknown ligand (M84605, HUMOPIODRE), rat-derived adrenaline α₂B receptor protein (M91466, RATA2BAR) and the like [FIG. 1].

The nucleotide sequence represented by SEQ ID NO: 2 (HS-2) is a nucleotide sequence which is complementary to the nucleotide sequence (FIG. 2) highly homologous to the DNA sequence coding for the amino acid sequence corresponding to or near the sixth membrane-spanning domain of known G protein coupled receptor proteins such as mouse-derived receptor protein with an unknown ligand (M80481, MUSGIR), human-derived bombesin receptor protein (L08893, HUMBOMB3S), human-derived adenosine A2 receptor protein (S46950, S46950), mouse-derived receptor protein with an unknown ligand (D21061, MUSGPCR), mouse-derived TRH receptor protein (S43387, S43387), rat-derived neuromedin K receptor protein (J05189, RATNEURA), rat-derived adenosine A1 receptor protein (M69045, RATA1ARA), human-derived neurokinin A receptor protein (M57414, HUMNEKAR), rat-derived adenosine A3 receptor protein (M94152, RATADENREC), human-derived somatostatin 1 receptor protein (M81829, HUMSTRI1A), human-derived neurokinin 3 receptor protein (S86390, S86371S4), rat-derived receptor protein with an unknown ligand (X61496, RNCGPCR), human-derived somatostatin 4 receptor protein (L07061, HUMSSTR4Z), rat-derived GnRH receptor protein (M31670, RATGNRHA) and the like [FIG. 2].

The nucleotide sequence represented by SEQ ID NO: 5 (FIG. 3: 3A) or the nucleotide sequence represented by SEQ ID NO: 6 (FIG. 3: 3B) is a nucleotide sequence highly homologous to the DNA sequence coding for the amino acid sequence corresponding to or near the third membrane-spanning domain each of known G protein coupled receptors such as mouse-derived κ-opioid receptor protein (L11064), mouse-derived δ-opioid receptor protein (L11065), rat-derived μ-opioid receptor protein (D16349), mouse-derived bradykinin B2 receptor protein (X69676), rat-derived bradykinin B2 receptor protein (M59967), mouse-derived bombesin receptor protein (M35328), human-derived neuromedin B receptor protein (M73482), human-derived gastrin releasing-peptide receptor protein (M73481), human-derived bombesin receptor protein subtype 3 (L08893), mouse-derived substance K receptor protein (X62933), mouse-derived substance P receptor protein (X62934), rat-derived neurokinin 3 receptor protein (J05189), rat-derived endothelin receptor protein (M60786), rat-derived receptor protein with an unknown ligand (L04672), rat-derived receptor protein with an unknown ligand (X61496), rat-derived receptor protein with an unknown ligand (X59249), rat-derived receptor protein with an unknown ligand (L09249), mouse-derived receptor protein with an unknown ligand (P30731), human-derived receptor protein with an unknown ligand (M31210), human-derived receptor protein with an unknown ligand (U03642) and the like [FIG. 3].

The nucleotide sequence represented by SEQ ID NO: 7 (FIG. 4: 3C) or the nucleotide sequence represented by SEQ ID NO: 3 (FIG. 4: 3D) is a nucleotide sequence highly homologous to the DNA sequence coding for the amino acid sequence corresponding to or near the third membrane-spanning domain each of known G protein coupled receptors such as mouse-derived angiotensin II receptor protein (L32840), rat-derived angiotensin Ib receptor protein (X64052), rat-derived angiotensin receptor protein subtype (M90065), human-derived angiotensin Ia receptor protein (M91464), rat-derived cholecystokinin a receptor protein (M88096), rat-derived cholecystokinin b receptor protein (M99418), human-derived cholecystokinin b receptor protein (L0448), human-derived cholecystokinin b receptor protein (L04473), mouse-derived low affinity interleukin 8 receptor protein (M73969), human-derived high affinity interleukin 8 receptor protein (X65858), mouse-derived C5a anaphylatoxin receptor protein (S46665), human-derived N-formylpeptide receptor protein (M60626) and the like [FIG. 4].

The nucleotide sequence represented by SEQ ID NO: 10 (FIG. 7: T2A) is a nucleotide sequence highly homologous to the DNA sequence coding for the amino acid sequence corresponding to or near the second membrane-spanning domain each of known G protein coupled receptors such as human galanin receptor (HUMGALAREC), rat α-1B-adrenergic receptor (RATADR1B), human β-1-adrenergic receptor (HUMADRB1), rabbit IL-8 receptor (RABIL8RSB), human opioid receptor (HUMOPIODRE), bovine substance K receptor (BTSKR), human somatostatin receptor-2 (HUMSRI2A), human somatostatin receptor-3 (HUMSSTR3Y), human gastrin receptor (HUMGARE), human cholecystokinin A receptor (HUMCCKAR), human dopamine receptor-D5 (HUMD1B), human serotonin receptor 5HT1E (HUM5HT1E), human dopamine receptor D4 (HUMD4C), mouse serotonin receptor-2 (MMSERO), rat α-1A-adrenergic receptor (RATADRA1A), rat histamine H2 receptor (S57565) and the like [FIG. 7].

The nucleotide sequence represented by SEQ ID NO: 8 (complementary to 6A of FIG. 5) or the nucleotide sequence represented by SEQ ID NO: 9 (complementary to 6B of FIG. 5) is a nucleotide sequence which is complementary to the nucleotide sequence (FIG. 5) highly homologous to the DNA sequence coding for the amino acid sequence corresponding to or near the sixth membrane-spanning domain of known G protein coupled receptors such as mouse-derived κ-opioid receptor protein (L11064), mouse-derived 7-opioid receptor protein (L11065), rat-derived μ-opioild receptor protein (D16349), mouse-derived bradykinin B2 receptor protein (X69676), rat-derived bradykinin B2 receptor protein (M59967), mouse-derived bombesin receptor protein (M35328), human-derived neuromedin B receptor protein (M73482), human-derived gastrin releasing peptide receptor protein (M73481), human-derived bombesin receptor protein subtype 3 (L08893), mouse-derived substance K receptor protein (X62933), mouse-derived substance P receptor protein (X62934), rat-derived neurokinin 3 receptor protein (J05189), rat-derived endothelin receptor protein (M60786), rat-derived receptor protein with an unknown ligand (L04672), rat-derived receptor protein with an unknown ligand (X61496), rat-derived receptor protein with an unknown ligand (X59249), rat-derived receptor protein with an unknown ligand (LX9249), mouse-derived receptor protein with an unknown ligand (P30731), human-derived receptor protein with an unknown ligand (M31210) human-derived receptor protein with an unknown ligand (U03642) and the like [FIG. 5].

The nucleotide sequence represented by SEQ ID NO: 4 (complementary to 6C of FIG. 6) is a nucleotide sequence which is complementary to the nucleotide sequence (FIG. 6) highly homologous to the DNA sequence coding for the amino acid sequence corresponding to or near the sixth membrane-spanning domain of known G protein coupled receptors such as mouse-derived angiotensin II receptor protein (L32840), rat-derived angiotensin Ib receptor protein (X64052), rat-derived angiotensin receptor protein subtype (M90065), human-derived angiotensin Ia receptor protein (M91464), rat-derived cholecystokinin a receptor protein (M88096), rat-derived cholecystokinin b receptor protein (M99418), human-derived cholecystokinin 8 receptor protein (L04473), mouse-derived low affinity interleukin 8 receptor protein (M73969), human-derived high affinity interleukin 8 receptor protein (X65858), mouse-derived C5a anaphylatoxin receptor protein (S46665), human-derived N-formylpeptide receptor protein (M60626) and the like [FIG. 6].

The nucleotide sequence represented by SEQ ID NO: 11 (FIG. 8: T7A) is a nucleotide sequence which is complementary to the nucleotide sequence (FIG. 8) highly homologous to the DNA sequence coding for the amino acid sequence corresponding to or near the seventh membrane-spanning domain each of known G protein coupled receptors such as human galanin receptor (HUMGALAREC), rat A1 adenosine receptor (RAT1DREC), porcine angiotensin receptor (PIGA2R), rat serdtonin receptor (RAT5HTRTC), human dopamine receptor (S58541), human gastrin releasing peptide receptor (HUMGRPR), mouse GRP/bombesin receptor (MUSGRPBOM), rat vascular type 1 angiotensin receptor (RRVT1AIIR), human muscarinic acetylcholine receptor (HSHM4), human α-1 adrenergic receptor (HUMDRB1), human gastrin receptor (HUMGARE), rat cholecystokinin receptor (RATCCKAR), rat receptor with an unknown ligand (S59748), human somatostatin receptor (HUMSST28A), rat receptor with an unknown ligand (RNGPROCR), mouse somatostatin receptor-1 (MUSSRI1A), human α-A1-adrenergic receptor (HUMA1AADR), mouse delta-opioid receptor (S66181), human somatostatin receptor-3 (HUMSSTR3Y) and the like [FIG. 8].

The nucleotide sequence represented by SEQ ID NO: 12 (FIG. 9: TM1-A2) is a nucleotide sequence highly homologous to the DNA sequence coding for the amino acid sequence within the first membrane-spanning (transmembrane) domain each of known G protein coupled receptors such as mouse-derived bradykinin $B_2$ receptor (MUSBB2R), bovine-derived substance K receptor (BTSKR), bovine-derived endothelin $ET_B$ receptor (BOVEETBR), human-derived neuropeptide Y receptor (MMSUBKREC), human-derived prostaglandin $E_2$ receptor (HUMPGE2R), human-derived prostacyclin receptor (HUMPIR), human-derived κ-opioid receptor (HSU11053), rat-derived melanocortin 3 receptor (RRMC3RA), human-derived melanocortin receptor (HUMMR), mouse-derived bombesin/GRP receptor (MUSGRPBOM), rat-derived cholecystokinin B receptor (RATCHOLREC), rat-derived cholecystokinin A receptor (RATCCKAR) and the like [FIG. 9].

The nucleotide sequence represented by SEQ ID NO: 13 (FIG. 10: TM3-B2) is a nucleotide sequence which is complementary to the nucleotide sequence (FIG. 10) highly homologous to the DNA sequence coding for the amino acid sequence corresponding to or near the end of the third membrane-spanning domain of known G protein coupled receptors such as human-derived cholecystokinin receptor (HUMCCKR), human-derived cholecystokinin B receptor (HUMCCKBGR), mouse-derived melanocortin 5 receptor (MMGMC5R), human-derived vasopressin receptor (HUMV2R), rat-derived neuromedin K receptor (RATNEURA), dog-derived gastrin receptor (DOGGSTRN), rat-derived serotonin receptor (RAT5HT5A), mouse-derived $α_2$-adrenaline receptor (MUSALP2ADA), human-derived adenosine $A_1$ receptor (HUMADORA1X), human-derived opioid (presumed) receptor (HUMOPIODRE), mouse-derived bombesin/GRP receptor (MUSGRPBOM), rat-derived cholecystokinin A receptor (RATCCKAR), human-derived TRH receptor (HSTRHREC) and the like [FIG. 10].

The nucleotide sequence represented by SEQ ID NO: 14 (FIG. 11: TM3-C2) is a nucleotide sequence highly homologous to the DNA sequence coding for the amino acid sequence corresponding to or near the end of the third membrane-spanning domain of known G protein coupled receptors such as human-derived neurokinin 3 receptor (HUMNK3R), human-derived oxytocin receptor (HSMRNAOXY), guinea pig-derived cholecystokinin A receptor (S68242), dog-derived cholecystokinin A receptor with an unknown ligand (CFGPCR4), mouse-derived substance P receptor (MMSUBPREC), human-derived receptor with an unknown ligand (HUMOPIODRE), human-derived galanin receptor (HUMGALAREC), human-derived serotonin receptor (HSS31G), human-derived $β_3$-adrenaline receptor (HUMARB3A), human-derived prostacyclin receptor (HUMHPR), rat-derived cholecystokinin A receptor (RATCCKAR) and the like [FIG. 11].

The nucleotide sequence represented by SEQ ID NO: 15 (FIG. 12: TM6-E2) is a nucleotide sequence which is complementary to the nucleotide sequence (FIG. 12) highly homologous to the DNA sequence coding,for the amino acid sequence within the sixth membrane-spanning domain of known G protein coupled receptors such as human-derived neurokinin A receptor (HUMNEKAR), human-derived substance P receptor (HUMSUBPRA), rat-derived substance K receptor (RATSKR), mouse-derived bombesin/GRP receptor (MUSGRPBOM), human-derived opioid (presumed) receptor (HUMOPIODRE), human-derived adenosine $A_2$ receptor (HUMA2XXX), human-derived $β_2$-adrenaline receptor (HUMADRBR), canine-derived receptor RDC5 with an unknown ligand (CFGPCR8), human-derived endothelin receptor (HUMETSR), mouse-derived neuropeptide Y1 receptor (MMNPY1CDS), human-derived oxytocin receptor (HSMRNAOXY), rat-derived cholecystokinin A receptor (RATCCKAR) and the like [FIG. 12].

The nucleotide sequence represented by SEQ ID NO: 16 (FIG. 13: TM2F18) is a nucleotide sequence highly homologous to the DNA sequence coding for the amino acid sequence corresponding to or near the second membrane-spanning domain of known G protein coupled receptors such as human-derived TSH receptor (HUMTSHX), human-derived neurokinin A receptor (HUMNEKAR), human-derived FMLP receptor (HUMFMLP), human-derived IL8 receptor B (HUMINTLEU8), human-derived α-A1 adrenergic receptor (HUMA1AADR), human-derived IL8 receptor A (HUMIL8RA), human-derived dopamine D2 receptor (HSDD2), human-derived angiotensin type I receptor (HUMANTIR), human-derived somatostatin receptor (HUSOMAT), human-derived TRH receptor (HSTRHREC), human-derived delta-opioid receptor (HSUO7882) and the like [FIG. 13].

The nucleotide sequence represented by SEQ ID NO: 17 (FIG. 14: TM6R21) is a nucleotide sequence which is complementary to the nucleotide sequence (FIG. 14) highly homologous to the DNA sequence coding for the amino acid sequence corresponding to or near the sixth membrane-spanning domain of known G protein coupled receptors such as human-derived β-adrenergic receptor (HSBAR), human-derived neurokinin A receptor (HUMNEKAR), human-derived endothelin-1receptor (HUMETN1R), human-derived histamine $H_2$ receptor (HUMHISH2R), human-derived α-A1 adrenergic receptor (HUMA1AADR), human-derived IL8 receptor A (HUMIL8RA), human-derived neuromedin B receptor (HUMNMBR), human-derived neurokinin 1 receptor (HUMNKIRX), human-derived substance P receptor (HUMSUBPRA), human-derived 5-HT1D serotonin receptor (HUM5HT1DA), human-derived formylpeptide receptor (HUMPFPR2A), human-derived dopamine D2 receptor (HSDD2), human-derived neuropeptide Y receptor (HUMNEUYREC), human-derived adenosine A2 receptor (HUMA2XXX), human-derived bradykinin receptor BK-2 (HUMBK2A), human-derived FMLP-related receptor II (HUMFMLPX), human-derived somatostatin receptor subtype 3 (HUMSSTR3X), human-derived cholecystokinin receptor (HUMCCKR), human-derived neurotensin receptor (HSNEURA) and the like [FIG. 14].

The nucleotide sequence represented by SEQ ID NO: 18 (FIG. 15: S3A) is a nucleotide sequence highly homologous to the DNA sequence coding for the amino acid sequence corresponding to or near the third membrane-spanning domain of known G protein coupled receptors such as human-derived galanin receptor (HUMGALAREC), human-derived CCK-B receptor (S70057), human-derived $ET_A$ receptor (S67127), human-derived $ET_B$ receptor (S44866), human-derived C5A receptor (HUMC5AAR), human-derived angiotensin II receptor (HUMANTIR), human-derived bradykinin receptor (HUMBK2R), human-derived neurotensin receptor (HSNEURA), human-derived GRP receptor (HUMGRPR), human-derived somatostatin 5 receptor (HUMFSRS), human-derived IL-8 receptor (HUMIL8RA), human-derived neurokinin 2 (neurokinin A) receptor (HUMNEKAR) and the like [FIG. 15].

The nucleotide sequence represented by SEQ ID NO: 19 (FIG. 16: S6A) is a nucleotide sequence which is complementary to the nucleotide sequence (FIG. 16) highly homologous to the DNA sequence coding for the amino acid sequence corresponding to or near the sixth membrane-spanning domain of known G protein coupled receptors such as human-derived galanin receptor (HUMGLAREC), human-derived CCK-B receptor (S70057), human-derived $ET_A$ receptor (S67127), human-derived $ET_B$ receptor (S44866), human-derived C5A receptor (HUMC5AAR), human-derived angiotensiniII receptor (HUMANTIR), human-derived bradykinin receptor (HUMBK2R), human-derived neurotensin receptor (HSNEURA), human-derived GRP receptor (HUMGRPR), human-derived somatostatin 5 receptor (HUMFSRS), human-derived IL-8 receptor (HUMIL8RA), human-derived neurokinin 2 (neurokinin A) receptor (HUMNEKAR) and the like [FIG. 16].

The above-mentioned abbreviations in the parentheses are the identifiers (or reference numbers) which are shown when GenBank/EMBL Data Bank is searched using a DNASIS Gene/Protein Sequence Data Base (CD019; Hitachi Software Engineering, Japan) and are usually called "Accession Numbers" or "Entry Names". HTRHR is, however, the sequence as described in Japanese Patent Application No. Hei 5-286986 (or No. 286986/1993) (EPA 638645).

The DNA (or nucleotides) of the present invention may be manufactured by DNA synthetic methods which are known per se or by methods similar thereto. The DNA (or nucleotides) of the present invention may be an oligonucleotide sequence having 8 to 60 base residues, preferably 12 to 50 base residues, more preferably 15 to 40 residues and most preferably 18 to 30 residues.

Among the DNAs of the present invention, the DNA having the nucleotide sequence represented by SEQ ID NO: 1 or SEQ ID NO: 12 is a nucleotide sequence which is commonly present in the nucleotide sequence of the DNA encoding the amino acid sequence corresponding to or near the first membrane-spanning domain of the above-mentioned known G protein coupled receptor protein. Therefore, it can be complementarily bonded (i.e. is hybridizable) with RNA or DNA (including genome DNA, cDNA) coding for the amino acid sequence corresponding to or near the first membrane-spanning domain of known or unknown G protein coupled receptor proteins and, furthermore, it can be complementarily bonded (i.e. is hybridizable) with nucleotide sequences encoding other membrane-spanning domains as well.

The DNA having a nucleotide sequence represented by SEQ ID NO: 3, SEQ ID NO: 5, SEQ ID NO: 6, SEQ ID NO: 7, SEQ ID NO: 14 or SEQ ID NO:18 is a nucleotide sequence which is commonly present in the nucleotide sequence of the DNA coding for the amino acid sequence corresponding to or near the third membrane-spanning domain of the above-mentioned known G protein coupled receptor protein. Therefore, it can be complementarily bonded with RNA or DNA (including genome DNA, cDNA) coding for the part corresponding to or near the third membrane-spanning domain of known or unknown G protein coupled receptor proteins and, furthermore, it can be complementarily bonded with nucleotide sequences encoding other membrane-spanning domains as well.

The DNA having a nucleotide sequence represented by SEQ ID NO: 10 or SEQ ID NO: 16 is a nucleotide sequence which is commonly present in the nucleotide sequence of the DNA coding for the amino acid sequence corresponding to or near the second membrane-spanning domain of the above-mentioned known G protein coupled receptor protein. Therefore, it can be complementarily bonded with RNA or DNA (including genome DNA, cDNA) coding for the part corresponding to or near the second membrane-spanning domain of known or unknown G protein coupled receptor proteins and, furthermore, it can be complementarily bonded with nucleotide sequences encoding other membrane-spanning domains as well.

The DNA having a nucleotide sequence represented by SEQ ID NO: 2, SEQ ID NO: 4, SEQ ID NO: 8, SEQ ID NO: 9, SEQ ID NO: 15, SEQ ID NO: 17 or SEQ ID NO: 19 is a nucleotide sequence which is commonly present in the nucleotide sequence of the DNA coding for the amino acid sequence corresponding to or near the sixth membrane-spanning domain of the above-mentioned known G protein coupled receptor protein. Therefore, it can be complementarily bonded with RNA or DNA (including genome DNA, cDNA) coding for the part corresponding to or near the sixth membrane-spanning domain of known or unknown G protein coupled receptor proteins and, furthermore, it can be complementarily bonded with nucleotide-sequences encoding other membrane-spanning domains as well.

The DNA having a nucleotide sequence represented by SEQ ID NO: 11 is a nucleotide sequence which is commonly present in the nucleotide sequence of the DNA coding for the amino acid sequence corresponding to or near the seventh membrane-spanning domain of the above-mentioned known G protein coupled receptor protein. Therefore, it can be complementarily bonded with RNA or DNA (including genome DNA, cDNA) coding for the part corresponding to or near the seventh membrane-spanning domain of known or unknown G protein coupled receptor proteins and, furthermore, it can be complementarily bonded with nucleotide sequences encoding other transmembrane domains as well.

The DNA having a nucleotide sequence represented by SEQ ID NO: 13 is a nucleotide sequence which is commonly present in the nucleotide sequence of the DNA coding for the amino acid sequence corresponding to or near the third membrane-spanning domain of the above-mentioned known G protein coupled receptor protein. Therefore, it can be complementarily bonded with RNA or DNA (including genome DNA, cDNA) coding for the part corresponding to or near the third membrane-spanning domain of known or unknown G protein coupled receptor proteins and, furthermore, it can be complementarily bonded with nucleotide sequences encoding other membrane-spanning domains as well.

Accordingly, the DNAs (or nucleotides) of the present invention can be used as DNA primers for a polymerase chain reaction (hereinafter, sometimes referred to as PCR). For example:

(i) a polymerase chain reaction is carried out by mixing
  (1) a small amount of DNA (or DNA fragment(s)) which codes for G protein coupled receptor protein, said DNA (or DNA fragment(s)) acting as a template,
  (2) at least one DNA primer selected from the group consisting of DNA primers having a nucleotide sequence represented by SEQ ID NO: 1, DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA as primers having a nucleotide sequence represented by SEQ ID NO: 10, DNA primers having a nucleotide sequence represented by SEQ ID NO: 12, DNA primers having a nucleotide sequence represented by SEQ ID NO: 14, DNA primers having a nucleotide sequence represented by SEQ ID NO: 16 and DNA primers having a nucleotide sequence represented by SEQ ID NO: 18 and
  (3) at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 11, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19; or (ii) a polymerase chain reaction is carried out by mixing
  (1) a small amount of DNA (or DNA fragment(s)) coding for G protein coupled receptor protein, said DNA (or DNA fragment(s)) acting as a template,
  (2) at least one DNA primer selected from the group consisting of DNA primers having a nucleotide sequence represented by SEQ ID NO: 1 and DNA primers having a nucleotide sequence represented by SEQ ID NO: 12 and
  (3) at least one DNA primer selected from the group consisting of DNA primers having a nucleotide sequence represented by SEQ ID NO: 13 so that it is possible to amplify the target DNA (or DNA fragment(s)) coding for said receptor protein.

When the PCR is carried out using at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 11, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19, said DNA primer(s) is(are) bonded (hybridized) with the nucleotide sequence at the 3'-side of the + chain (plus chain) of template RNA or DNA (or fragment(s) thereof) coding for the sixth membrane-spanning domain or other membrane-spanning domains of G protein coupled receptor protein whereupon an elongation of the − chain (minus chain) proceeds in the 5'→3' direction.

When the PCR is carried out using at least one DNA primer selected from the group consisting of DNA primers having a nucleotide sequence represented by SEQ ID NO: 11, said DNA primer is bonded with the nucleotide sequence at the 3'-side of the + chain (plus chain) of template RNA or DNA (or fragment(s) thereof) coding for the seventh membrane-spanning domain or other membrane-spanning domains of the G protein coupled receptor protein whereupon an elongation of the − chain (minus chain) proceeds in the 5'→3' direction.

When the PCR is carried out using at least one DNA primer selected from the group consisting of DNA primers having a nucleotide sequence represented by SEQ ID NO: 1 and DNA primers having a nucleotide sequence represented by SEQ ID NO: 12, said DNA primer is bonded with the nucleotide sequence at the 3'-side of the − chain (minus chain) of template RNA or DNA (or fragment(s) thereof) coding for the first membrane-spanning domain or other membrane-spanning domains of G protein coupled receptor protein whereupon an elongation of the + chain (plus chain) proceeds in the 5'→3' direction.

When the PCR is carried out, using at least one DNA primer selected from the group consisting of DNA primers having a nucleotide sequence represented by SEQ ID NO: 10 and DNA primers having a nucleotide sequence represented by SEQ ID NO: 16, said DNA primer is bonded with the nucleotide sequence at the 3'-side of the − chain (minus chain) of template RNA or DNA (or fragment(s) thereof) coding for the second membrane-spanning domain or other membrane-spanning domains of G protein coupled receptor protein whereupon an elongation of the + chain (plus chain) proceeds in the 5'→3' direction.

When the PCR is carried out using at least one DNA primer selected from the group consisting of DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 14 and DNA primers having a nucleotide sequence represented by SEQ ID NO: 18, said DNA primer is bonded with the nucleotide sequence at the 3'-side of the − chain (minus chain) of template RNA or DNA (or fragment(s) thereof) coding for the third membrane-spanning domain or other membrane-spanning domains of G protein coupled receptor protein whereupon an elongation of the + chain (plus chain) proceeds in the 5'→3' direction.

Accordingly, when the DNA primers having nucleotide sequences represented by any of SEQ ID NO: 1 to SEQ ID NO: 19 of the present invention are used in combination each other, DNA (or DNA fragment(s)) coding for G protein coupled receptor protein can be successfully amplified.

One embodiment of the present invention provides: (A) a method of amplifying DNA coding for the G protein coupled receptor protein (e.g., from the first to sixth membrane-spanning (transmembrane) domains or other segments of the G protein coupled receptor protein), characterized in that a polymerase chain reaction is carried out by mixing
- ① a DNA coding-for the G protein coupled receptor protein, said DNA acting as a template,
- ② at least one DNA primer selected from the group consisting of DNA primers having a nucleotide sequence represented by SEQ ID NO: 1 and DNA primers having a nucleotide sequence represented by SEQ ID NO: 12 and
- ③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19;

(B) a method of amplifying DNA coding for the G protein coupled receptor protein (e.g., from the first to seventh membrane-spanning (transmembrane) domains or other segments of the G protein coupled receptor protein), characterized in that a polymerase chain reaction is carried out by mixing
- ① a DNA coding for the G protein coupled receptor protein, said DNA acting as a template,
- ② at least one DNA primer selected from the group consisting of DNA primers having a nucleotide sequence represented by SEQ ID NO: 1 and DNA primers having a nucleotide sequence represented by SEQ ID NO: 12 and
- ③ at least one DNA primer selected from the group consisting of DNA primers having a nucleotide sequence represented by SEQ ID NO:11;

(C) a method of amplifying a DNA coding for the G protein coupled receptor protein (e.g., from the second to sixth membrane-spanning (transmembrane) domains or other segments of the G protein coupled receptor protein), characterized in that a polymerase chain reaction is carried out by mixing
- ① a DNA coding for the G protein coupled receptor protein, said DNA acting as a template,
- ② at least one DNA primer selected from the group consisting of DNA primers having a nucleotide sequence represented by SEQ ID NO: 10 and DNA primers having a nucleotide sequence represented by SEQ ID NO: 16 and
- ③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19;

(D) a method of amplifying a DNA coding for the G protein coupled receptor protein (e.g., from the second to seventh membrane-spanning (transmembrane) domains or other segments of the G protein coupled receptor protein), characterized in that a polymerase chain reaction is carried out by mixing
- ① a DNA coding for the G protein coupled receptor protein, said DNA acting as a template,
- ② at least one DNA primer selected from the group consisting of DNA primers having a nucleotide sequence represented by SEQ ID NO: 10 and DNA primers having a nucleotide sequence represented by SEQ ID NO: 16 and
- ③ at least one DNA primer selected from the group consisting of DNA primers having a nucleotide sequence represented by SEQ ID NO: 11;

(E) a method of amplifying a DNA coding for the G protein coupled receptor protein (e.g., from the third to sixth membrane-spanning (transmembrane) domains or other segments of the G protein coupled receptor protein), characterized in that a polymerase chain reaction is carried out by mixing
- ① a DNA coding for the G protein coupled receptor protein, said DNA acting as a template,
- ② at least one DNA primer selected from the group consisting of DNA primers having a nucleotide sequence represented by SEQ ID NO: 3, DNA primers having a nucleotide sequence represented by SEE ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 14 and DNA primers having a nucleotide sequence represented by SEQ ID NO: 18 and
- ③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19;

(F) a method of amplifying a DNA coding for the G protein coupled receptor protein (e.g., from the third to seventh membrane-spanning (transmembrane) domains or other segments of the G protein coupled receptor protein), characterized in that a polymerase chain reaction is carried out by mixing
- ① a DNA coding for the G protein coupled receptor protein, said DNA acting as a template,
- ② at least one DNA primer selected from the group consisting of DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 14 and DNA primers having a nucleotide sequence represented by SEQ ID NO: 18 and ③ at least one DNA primer selected from the group consisting of DNA primers having a nucleotide sequence represented by SEQ ID NO:11; and (G) a method of amplifying a DNA coding for the G protein coupled receptor protein (e.g., from the first to third membrane-spanning (transmembrane) domains or other segments of the G protein coupled receptor protein), characterized in that a polymerase chain reaction is carried out by mixing
① a DNA coding for the G protein coupled receptor protein, said DNA acting as a template,
② at least one DNA primer selected from the group consisting of DNA primers having a nucleotide sequence represented by SEQ ID NO: 1 and DNA primers having a nucleotide sequence represented by SEQ ID NO: 12 and
③ at least one DNA primer selected from the group consisting of DNA primers having a nucleotide sequence represented by SEQ ID NO: 13.

An example of more preferred combination of the DNA primers in the amplification according to the above-mentioned (A) includes a combination of a DNA primer having a nucleotide sequence represented by SEQ ID NO: 1 with a DNA primer having a nucleotide sequence represented by SEQ ID NO: 2 and the like.

An example of more preferred combination of the DNA primers in the amplification according to the above-mentioned (D) includes a combination of a DNA primer having a nucleotide sequence represented by SEQ ID NO: 10 with a DNA primer having a nucleotide sequence represented by SEQ ID NO: 11 and the like.

An example of more preferred combination of the DNA primers in the amplification according to the above-mentioned (E) includes:
(i) a combination of a DNA primer having a nucleotide sequence represented by SEQ ID NO: 5 or a DNA primer having a nucleotide sequence represented by SEQ ID NO: 6 with a DNA primer having a nucleotide sequence represented by SEQ ID-NO: 8 or a DNA primer having a nucleotide sequence represented by SEQ ID NO: 9;
(ii) a combination of a DNA primer having a nucleotide sequence represented by SEQ ID NO: 3 or a DNA primer having a nucleotide sequence represented by SEQ ID NO: 7 with a DNA primer having a nucleotide sequence represented by SEQ ID NO: 4 and the like.

An example of more preferred combination of the DNA primers in the amplification according to the above-mentioned (G) includes a combination of a DNA primer having a nucleotide sequence represented by SEQ ID NO: 12 with a DNA primer having a nucleotide sequence represented by SEQ ID NO: 13 and the like.

The amplification may be carried out in accordance with known PCR techniques. For example, it may be carried out by the method described in Saiki, R. K. et al., Science, 239:487–491 (1988). Temperature, time, buffer, number of reaction cycles, enzyme such as DNA polymerase, addition of 2'-deoxy-7-deazaguanosine triphosphate or inosine, etc. in the PCR amplification may be suitably selected depending upon the type of target DNA and other factors. When RNA is used as a template, PCR amplification may be carried out, for example, by the method described in Saiki, R. K. et al., Science, 239:487–491(1988).

Moreover, the DNA having a nucleotide sequence represented by SEQ ID NO: 1 or SEQ ID NO: 12 of the present invention can be selectively and complementarily bonded (hybridized) with the nucleotide sequence at the 3'-side of the − chain of the DNA coding for the amino acid sequence corresponding to or near the first membrane-spanning domain of the G protein coupled receptor protein; the DNA having a nucleotide sequence represented by SEQ ID NO: 10 or SEQ ID NO: 16 of the present invention can be selectively and complementarily bonded (hybridized) with the nucleotide sequence at the 3'-side of the − chain of the DNA coding for the amino acid sequence corresponding to or near the second membrane-spanning domain of the G protein coupled receptor protein; the DNA having a nucleotide sequence represented by SEQ ID NO: 3, SEQ ID NO: 5, SEQ ID NO: 6, SEQ ID NO: 7, SEQ ID NO: 14 or SEQ ID NO: 18 of the present invention can be selectively and complementarily bonded (hybridized) with the nucleotide sequence at the 3'-side of the − chain of the DNA coding for the amino acid sequence corresponding to or near the third membrane-spanning domain of the G protein coupled receptor protein; the DNA having a nucleotide sequence represented by SEQ ID NO: 2, SEQ ID NO: 4, SEQ ID NO: 8, SEQ ID NO: 9, SEQ ID NO: 15, SEQ ID NO: 17 or SEQ ID NO: 19 of the present invention can be selectively and complementarily bonded (hybridized) with the nucleotide sequence at the 3'-side of the + chain of the DNA coding for the amino acid sequence corresponding to or near the sixth membrane-spanning domain of the G protein coupled receptor protein; the DNA having a nucleotide sequence represented by SEQ ID NO: 11 of the present invention can be selectively and complementarily bonded (hybridized) with the nucleotide sequence at the 3'-side of the + chain of the DNA coding for the amino acid sequence corresponding to or near the third membrane-spanning domain of the G protein coupled receptor protein; and the DNA having a nucleotide sequence represented by SEQ ID NO: 13 of the present invention can be selectively and complementarily bonded (hybridized) with the nucleotide sequence at the 3'-side of the + chain of the DNA coding for the amino acid sequence corresponding to or near the third membrane-spanning domain of the G protein coupled receptor protein and, accordingly, said DNA is also advantageously useful as a probe for screening DNA libraries for DNA (or DNA fragment(s)) encoding part or all of the polypeptide sequence of G protein coupled receptor proteins.

These screening methods for DNA (or DNA fragment(s)) encoding part or all of the polypeptide sequence of G protein coupled receptor proteins from the DNA library by using as a reagent, because it can be used as a probe the DNA of the present invention may be carried out according to DNA cloning methods known per se by those of skill in the art or methods similar thereto. Especially when the DNA of the present invention is used as a DNA primer for the PCR, both amplification and screening of the DNA (or DNA fragment) coding for the G protein coupled receptor protein can be conducted in a single step.

Thus, when the DNAs of the present invention are suitably combined and used as the DNA primer for the PCR, said DNA primer(s) is(are) bonded (hybridized) with RNA or DNA (or fragment(s) thereof) encoding the amino acid sequence of the first membrane-spanning (transmembrane) domain, the second membrane-spanning domain, the third membrane-spanning domain, the sixth membrane-spanning domain, the seventh membrane-spanning domain or other membrane-spanning domains of G protein coupled receptor proteins to amplify, for example,
① RNA or DNA (or fragment(s) thereof) coding for the amino acid sequence of from the first membrane-spanning to the sixth membrane-spanning domains of G protein coupled receptor proteins, ② RNA or DNA (or fragment(s) thereof) coding for the amino acid sequence of from the first membrane-spanning to the seventh membrane-spanning domains of G protein coupled receptor proteins, ③ RNA or DNA (or fragment(s) thereof) coding for the amino acid sequence of from the third membrane-spanning to the sixth membrane-spanning domains of G protein coupled receptor proteins, ④ RNA or DNA (or fragment(s) thereof) coding for the amino acid sequence of from the third membrane-spanning to the seventh membrane-spanning domains of G protein coupled receptor proteins, ⑤ RNA or DNA (or fragment(s) thereof) coding for the amino acid sequence of from the second membrane-spanning to the sixth membrane-spanning domains of G protein coupled receptor proteins or RNA or DNA (or fragment(s) thereof) coding for the amino acid sequence of other domains thereof, ⑥ RNA or DNA (or fragment(s) thereof) coding for the amino acid sequence of from the second membrane-spanning to the seventh membrane-spanning domains of G protein coupled receptor proteins, ⑦ RNA or DNA (or fragment(s) thereof) coding for the amino acid sequence of from the first membrane-spanning to the third membrane-spanning domains of G protein coupled receptor proteins or ⑧ RNA or DNA (or fragment(s) thereof) coding for the amino acid sequence of other domains of G protein coupled receptor proteins.

Through using the DNA primer according to the present invention, therefore, selective amplifications of:

① RNA or DNA (or fragment(s) thereof) coding for the amino acid sequence covering from the first membrane-spanning domain to the sixth membrane-spanning domain of G protein coupled receptor proteins;

② RNA or DNA (or fragment(s) thereof) coding for the amino acid sequence covering from the first membrane-spanning domain to the seventh membrane-spanning domain of G protein coupled receptor proteins;

③ RNA or DNA (or fragment(s) thereof) coding for the amino acid sequence covering from the third membrane-spanning domain to the sixth membrane-spanning domain of G protein coupled receptor proteins;

④ RNA or DNA (or fragment(s) thereof) coding for the amino acid sequence covering from the third membrane-spanning domain to the seventh membrane-spanning domain of G protein coupled receptor proteins;

⑤ RNA or DNA (or fragment(s) thereof) coding for the amino acid sequence covering from the second membrane-spanning domain to the sixth membrane-spanning domain of G protein coupled receptor proteins or RNA or DNA (or fragment(s) thereof) coding for the amino acid sequence covering other areas thereof, ⑥ RNA or DNA (or fragment(s) thereof) coding for the amino acid sequence covering from the second membrane-spanning domain to the seventh membrane-spanning domain of G protein coupled receptor proteins;

⑦ RNA or DNA (or fragment(s) thereof) coding for the amino acid sequence covering from the first membrane-spanning domain to the third membrane-spanning domain of G protein coupled receptor proteins; and the like, from DNA libraries can be successfully achieved.

Among the DNA primers of the present invention, the combination of

① a DNA primer having a nucleotide sequence represented by SEQ ID NO: 1 or SEQ ID NO: 2; with ② at least one DNA primer selected from the group consisting of a DNA primer having a nucleotide sequence represented by SEQ ID NO: 2, a DNA primer having a nucleotide sequence represented by SEQ ID NO: 4, a DNA primer having a nucleotide sequence represented by SEQ ID NO: 8, a DNA primer having a nucleotide sequence represented by SEQ ID NO: 9, a DNA primer having a nucleotide sequence represented by SEQ ID NO: 15, a DNA primer having a nucleotide sequence represented by SEQ ID NO: 17 and a DNA primer having a nucleotide sequence represented by SEQ ID NO: 19;

is, unlike conventional primers, capable of selectively amplifying a broad area covering from the first membrane-spanning domain to the sixth membrane-spanning domain or other domains of G protein coupled receptor proteins.

Among the DNA primers of the present invention, the combination of

① a DNA primer having a nucleotide sequence represented by SEQ ID NO: 1 or SEQ ID NO: 12; with ② a DNA primer having a nucleotide sequence represented by SEQ ID NO: 11;

is, unlike conventional primers, capable of selectively amplifying a broad area covering from the first membrane-spanning domain to the seventh membrane-spanning domain or other domains of G protein coupled receptor proteins.

Among the DNA primers of the present invention, the combination of

① a DNA primer having a nucleotide sequence represented by SEQ ID NO: 10 or SEQ ID NO: 16; with ② at least one DNA primer selected from the group consisting of a DNA primer having a nucleotide sequence represented by SEQ ID NO: 2, a DNA primer having a nucleotide sequence represented by SEQ ID NO: 4, a DNA primer having a nucleotide sequence represented by SEQ ID NO: 8, a DNA primer having a nucleotide sequence represented by SEQ ID NO: 9, a DNA primer having a nucleotide sequence represented by SEQ ID NO: 15, a DNA primer having a nucleotide sequence represented by SEQ ID NO: 17 and a DNA primer having a nucleotide sequence represented by SEQ ID NO: 19;

is, unlike conventional primers, capable of selectively amplifying a broad area covering from the second membrane-spanning domain to the sixth membrane-spanning domain or other domains of G protein coupled receptor proteins.

Among the DNA primers of the present invention, the combination of

① a DNA primer having a nucleotide sequence represented by SEQ ID NO:10 or SEQ ID NO:16; with ② a DNA primer having a nucleotide sequence represented by SEQ ID NO:11;

is, unlike conventional primers, capable of selectively amplifying a broad area covering from the second membrane-spanning domain to the seventh membrane-spanning domain or other domains of G protein coupled receptor proteins.

Among the DNA primers of the present invention, the combination of

① at least one DNA primer selected from the group consisting of a DNA primer having a nucleotide sequence represented by SEQ ID NO: 3, a DNA primer having a nucleotide sequence represented by SEQ ID NO: 5, a DNA primer having a nucleotide sequence represented by SEQ ID NO: 6, a DNA primer having a nucleotide sequence represented by SEQ ID NO: 7, a DNA primer having a nucleotide sequence represented by SEQ ID NO: 14 and a DNA primer having a nucleotide sequence represented by SEQ ID NO: 18; with ② a DNA primer having a nucleotide sequence represented by SEQ ID NO: 11;

is, unlike conventional primers, capable of selectively amplifying a broad area covering from the third membrane-spanning domain to the seventh membrane-spanning domain or other domains of G protein coupled receptor proteins.

Therefore, the protein hydrophobicity plotting of G protein coupled receptor proteins and the homology at the amino acid level or the nucleic acid level between G protein coupled receptor proteins and other similar receptor proteins [said hydrophobicity plotting and homology both serve as standards for determining whether or not RNA or DNA (or fragment(s) thereof) obtained according to the present invention is(are) encoding part or all of the amino acid sequence of G protein coupled receptor protein] can now be more clearly calculated.

Among the DNA primers of the present invention, the combination of

① at least one DNA primer. selected from the group consisting of a DNA primer having a nucleotide sequence represented by SEQ ID NO: 3, a DNA primer having a nucleotide sequence represented by SEQ ID NO: 5, a DNA primer having a nucleotide sequence represented by SEQ ID NO: 6, a DNA primer having a nucleotide sequence represented by SEQ ID NO: 7, a DNA primer having a nucleotide sequence represented by SEQ ID NO: 14 and a DNA primer having a nucleotide sequence represented by SEQ ID NO: 18; with ② at least one DNA primer selected from the group consisting of a DNA primer having a nucleotide sequence represented by SEQ ID NO: 2, a DNA primer having a nucleotide sequence represented by SEQ ID NO: 4, a DNA primer having a nucleotide sequence represented by SEQ ID NO: 8, a DNA primer having a nucleotide sequence represented by SEQ ID NO: 9, a DNA primer having a nucleotide sequence represented by SEQ ID NO: 15, a DNA primer having a nucleotide sequence represented by SEQ IS NO: 17 and a DNA primer having a nucleotide sequence represented by SEQ ID NO: 19;

is capable of amplifying the areas covering from the third membrane-spanning domain to the sixth membrane-spanning domain thereof at once like the conventional DNA primers and, moreover, it is capable of more selectively and efficiently amplifying DNA coding for G protein coupled receptor proteins though it has not been obtained through the conventional DNA primers.

Moreover, among the DNA primers of the present invention, the combination of

① at least one DNA primer selected from DNA primers having a nucleotide sequence of SEQ ID NO: 1 and DNA primers having a nucleotide sequence of SEQ ID NO: 12; with ② a DNA primer having a nucleotide sequence represented by SEQ ID NO: 13;

is capable of amplifying the areas covering from the first membrane-spanning domain to the third membrane-spanning domain thereof at once.

Then (a) the amplified DNA (or fragment(s) thereof) coding for the amino acid sequence of from the first membrane-spanning domain to the sixth membrane-spanning domain of G protein coupled receptor protein, (b) the amplified DNA (or fragment(s) thereof) coding for the amino acid sequence of from the first membrane-spanning domain to the seventh membrane-spanning domain of G protein coupled receptor protein, (c) the amplified DNA (or fragment(s) thereof) coding for the amino acid sequence of from the third membrane-spanning domain to the sixth membrane-spanning domain of G protein coupled receptor protein, (d) the amplified DNA (or fragment(s) thereof) coding for the amino acid sequence of from the third membrane-spanning domain to the seventh membrane-spanning domain of G protein coupled receptor protein, (e) the amplified DNA (or fragment(s) thereof) coding for the amino acid sequence of from the second membrane-spanning domain to the sixth membrane-spanning domain of G protein coupled receptor protein, (f) the amplified DNA (or fragment(s) thereof) coding for the amino acid sequence of from the second membrane-spanning domain to the seventh membrane-spanning domain of G protein coupled receptor protein, (g) the amplified DNA (or fragment(s) thereof) coding for the amino acid sequence of from the first membrane-spanning domain to the third membrane-spanning domain of G protein coupled receptor protein or (h) the amplified DNA (or fragment(s) thereof) coding for the amino acid sequence of other domains of G protein coupled receptor protein may be used as a probe(s) to screen for full-length DNA which completely encodes G protein coupled receptor proteins from DNA libraries according to methods known per se by those of skill in the art or methods similar thereto.

The DNA libraries used in the present invention include any of genome DNA libraries, cDNA libraries and RNA libraries. The term "DNA library" or "DNA libraries" as used herein refers to a DNA library or DNA libraries including all of those libraries.

The present invention further provides screening methods for target DNA (or fragment(s) thereof) coding for G protein coupled receptor protein from the DNA library containing DNA (or fragment(s) thereof) coding for receptor proteins, which comprise employing the DNA of the present invention as a DNA primer for the PCR.

One preferred embodiment of the present invention is a method for cloning full-length DNA which completely encodes an amino acid sequence of G protein coupled receptor protein from DNA libraries which comprises the steps of (i) using the DNA of the present invention as a DNA primer for PCR;

(ii) carrying out PCR in the presence of a mixture of said DNA primer with the DNA library to amplify and select (i.e. screen for) a DNA fragment coding for the amino acid sequence of from the first membrane-spanning domain to the sixth membrane-spanning domain of G protein coupled receptor protein, a DNA fragment coding for the amino acid sequence of from the first membrane-spanning domain to the seventh membrane-spanning domain of G protein coupled receptor protein, a DNA fragment coding for the amino acid sequence of from the third membrane-spanning domain to the sixth membrane-spanning domain of G protein coupled receptor protein, a DNA fragment coding for the amino acid sequence of from the third membrane-spanning domain to the seventh membrane-spanning domain of G protein coupled receptor protein, a DNA fragment coding for the amino acid sequence of from the second membrane-spanning domain to the sixth membrane-spanning domain of G protein coupled receptor protein, a DNA fragment coding for the amino acid sequence of from the second membrane-spanning domain to the seventh membrane-spanning domain of G protein coupled receptor protein, a DNA fragment coding for the amino acid sequence of from the first membrane-spanning domain to the third membrane-spanning domain of G protein coupled receptor protein or a DNA fragment coding for other domains of G protein coupled receptor protein; and (iii) cloning said full-length DNA from the DNA library according to cloning methods known per se by those of skill in the art or methods similar thereto by using, as a probe, the DNA fragment obtained in the above step (ii).

Preferably, an embodiment of the present invention is a screening method of DNA coding for G protein coupled receptor proteins from DNA libraries, which comprises carrying out a polymerase chain reaction in the presence of mixture of ① the DNA library, ② at least one DNA primer selected from the group consisting of DNA primers having a nucleotide sequence represented by SEQ ID NO: 1, DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 10, DNA primers having a nucleotide sequence represented by SEQ ID NO: 14, DNA primers having a nucleotide sequence represented by SEQ ID NO: 16 and DNA primers having a nucleotide sequence represented by SEQ ID NO: 18 and ③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 11, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19 to selectively amplify template DNA coding for G protein coupled receptor protein contained in the DNA library.

More preferably, embodiments of the present invention include:

(1) a screening method of DNA coding for the amino acid sequence of G protein coupled receptor protein and the like (e.g. the regions spanning from the first transmembrane domain to the sixth transmembrane domain of G protein coupled receptor protein or other domains thereof) from a DNA library, which comprises carrying out a polymerase chain reaction in the presence of a mixture of ① the DNA library, ② at least one DNA primer selected from the group consisting of DNA primers having a nucleotide sequence represented by SEQ ID NO: 1 and DNA primers having a nucleotide sequence represented by SEQ ID NO: 12 and ③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19 to selectively amplify the DNA coding for the amino acid sequence of G protein coupled receptor protein and the like (e.g. the regions spanning from the first transmembrane domain to the sixth transmembrane domain of G protein coupled receptor protein or other domains thereof) contained in the DNA library;

(2) a screening method of DNA coding for the amino acid sequence of G protein coupled receptor protein and the like (e.g. the regions spanning from the first transmembrane domain to the seventh transmembrane domain of G protein coupled receptor protein or other domains thereof) from a DNA library, which comprises carrying out a polymerase chain reaction in the presence of a mixture of ① the DNA library, ② at least one DNA primer selected from the group consisting of DNA primers having a nucleotide sequence represented by SEQ ID NO: 1 and DNA primers having a nucleotide sequence represented by SEQ ID NO: 12 and ③ at least one DNA primer selected from the group consisting of DNA primers having a nucleotide sequence represented by SEQ ID NO: 11 to selectively amplify the DNA coding for the amino acid sequence of G protein coupled receptor protein and the like (e.g. the regions spanning from the first transmembrane domain to the seventh transmembrane domain of G protein coupled receptor protein or other domains thereof) contained in the DNA library;

(3) a screening method of DNA coding for the amino acid sequence of G protein coupled receptor protein and the like (e.g. the regions spanning from the second transmembrane domain to the sixth transmembrane domain of G protein coupled receptor protein or other domains thereof) from a DNA library, which comprises carrying out a polymerase chain reaction in the presence of a mixture of ① the DNA library, ② at least one DNA primer selected from the group consisting of DNA primers having a nucleotide sequence represented by SEQ ID NO: 10 and DNA primers having a nucleotide sequence represented by SEQ ID NO: 16 and ③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19 to selectively amplify the DNA coding for the amino acid sequence of G protein coupled receptor protein and the like (e.g. the regions spanning from the second transmembrane domain to the sixth transmembrane domain of G protein coupled receptor protein or other domains thereof) contained in the DNA library;

(4) a screening method of DNA coding for the amino acid sequence of G protein coupled receptor protein and the like (e.g. the regions spanning from the second transmembrane domain to the seventh transmembrane domain of G protein coupled receptor protein or other domains thereof) from a DNA library, which comprises carrying out a polymerase chain reaction in the presence of a mixture of
① the DNA library,
② at least one DNA primer selected from the group consisting of DNA primers having a nucleotide sequence represented by SEQ ID NO: 10 and DNA primers having a nucleotide sequence represented by SEQ ID NO: 16 and
③ at least one DNA primer selected from the group consisting of DNA primers having a nucleotide sequence represented by SEQ ID NO: 11 to selectively amplify the DNA coding for the amino acid sequence of G protein coupled receptor protein and the like (e.g. the regions spanning from the second transmembrane domain to the seventh transmembrane domain of G protein coupled receptor protein or other domains thereof) contained in the DNA library;

(5) a screening method of DNA coding for the amino acid sequence of G protein coupled receptor protein and the like (e.g. the regions spanning from the third transmembrane domain to the sixth transmembrane domain of G protein coupled receptor protein or other domains thereof) from a DNA library, which comprises carrying out a polymerase chain reaction in the presence of a mixture of
① the DNA library,
② at least one DNA primer selected from the group consisting of DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 14 and DNA primers having a nucleotide sequence represented by SEQ ID NO: 18 and
③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19 to selectively amplify the DNA coding for the amino acid sequence of G protein coupled receptor protein and the like (e.g. the regions spanning from the third transmembrane domain to the sixth transmembrane domain of G protein coupled receptor protein or other domains thereof) contained in the DNA library;

(6) a screening method of DNA coding for the amino acid sequence of G protein coupled receptor protein and the like (e.g. the regions spanning from the third transmembrane domain to the seventh transmembrane domain of G protein coupled receptor protein or other domains thereof) from a DNA library, which comprises carrying out a polymerase chain reaction in the presence of a mixture of
① the DNA library,
② at least one DNA primer selected from the group consisting of DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 14 and DNA primers having a nucleotide sequence represented by SEQ ID NO: 18 and
③ at least one DNA primer selected from the group consisting of DNA primers having a,nucleotide sequence represented by SEQ ID NO: 11 to selectively amplify the DNA coding for the amino acid sequence of G protein coupled receptor protein and the like (e.g. the regions spanning from the third transmembrane domain to the seventh transmembrane domain of G protein coupled receptor protein or other domains thereof) contained in the DNA library; and (7) a screening method of DNA coding for the amino acid sequence of G protein coupled receptor protein and the like (e.g. the regions spanning from the first transmembrane domain to the third transmembrane domain of G protein coupled receptor protein or other domains thereof) from a DNA library, which comprises carrying out a polymerase chain reaction in the presence of a mixture of
① the DNA library,
② at least one DNA primer selected from the group consisting of DNA primers having a nucleotide sequence represented by SEQ ID NO: 1 and DNA primers having a nucleotide sequence represented by SEQ ID NO: 12 and
③ at least one DNA primer selected from the group consisting of DNA primers having a nucleotide sequence represented by SEQ ID NO: 13 to selectively amplify the DNA coding for the amino acid sequence of G protein coupled receptor protein and the like (e.g. the regions spanning from the first transmembrane domain to the third transmembrane domain of G protein coupled receptor protein or other domains thereof) contained in the DNA library.

Particularly preferably, embodiments of the present invention include:

(8) a screening method of DNA coding for the amino acid sequence of G protein coupled receptor protein from a DNA library, which comprises carrying out a polymerase chain reaction in the presence of a mixture of
① the DNA library,
② a DNA primer having a nucleotide sequence represented by SEQ ID NO: 1 and (3) a DNA primer having a nucleotide sequence represented by SEQ ID NO: 2 to selectively amplify the DNA coding for the amino acid sequence of G protein coupled receptor protein contained in the DNA library;

(9) a screening method of DNA coding for the amino acid sequence of G protein coupled receptor protein from a DNA library, which comprises carrying out a polymerase chain reaction in the presence of a mixture of
   (1) the DNA library,
   (2) a DNA primer having a nucleotide sequence represented by SEQ ID NO: 3 and
   (3) a DNA primer having a nucleotide sequence represented by SEQ ID NO: 4
to selectively amplify the DNA coding for the amino acid sequence of G protein coupled receptor protein contained in the DNA library;

(10) a screening method of DNA coding for the amino acid sequence of G protein coupled receptor protein from a DNA library, which comprises carrying out a polymerase chain reaction in the presence of a mixture of
   (1) the DNA library,
   (2) a DNA primer having a nucleotide sequence represented by SEQ ID NO: 6 and
   (3) a DNA primer having a nucleotide sequence represented by SEQ ID NO: 8
to selectively amplify the DNA coding for the amino acid sequence of G protein coupled receptor protein contained in the DNA library; and

(11) a screening method of DNA coding for the amino acid sequence of G protein coupled receptor protein from a DNA library, which comprises carrying out a polymerase chain reaction in the presence of a mixture of
   (1) the DNA library,
   (2) a DNA primer having a nucleotide sequence represented by SEQ ID NO: 10 and
   (3) a DNA primer having a nucleotide sequence represented by SEQ ID NO: 11
to selectively amplify the DNA coding for the amino acid sequence of G protein coupled receptor protein contained in the DNA library.

The cloned DNAs can be analyzed, usually by restriction enzyme analysis and/or sequencing.

Target RNA or DNA (or fragment(s) thereof) coding for G protein coupled receptor protein in the amplification and the screening by the PCR techniques wherein the DNA of the present invention is employed may include RNA, DNA or fragments thereof coding for known (or prior art) G protein coupled receptor proteins and RNA, DNA or fragments thereof coding for unknown (novel) G protein coupled receptor proteins.

These target RNA or DNA (or fragment(s) thereof) may include novel nucleotide sequences and even known nucleotide sequences.

Examples of such nucleotide sequences are RNA or DNA (or fragment(s)) coding for a G protein coupled receptor protein, said RNA or DNA (or fragment(s)) being derived from all cells and tissues (e.g. pituitary gland, brain, pancreas, lung, adrenal gland, etc.) of vertebrate animals (e.g. mice, rats, cats, dogs, swines, cattle, horses, monkeys, human beings, etc.), insects or other invertebrate animals (e.g. drosophilae, silkworms, *Barathra brassicae*, etc.), plants (e.g. rice plant, wheat, tomato, etc.) and cultured cell lines derived therefrom, etc.

Specific examples of the nucleotide sequences are RNA or DNA (or fragment(s)) coding for G protein coupled receptor proteins such as receptor proteins to angiotensin, bombesin, canavinoid, cholecystokinin, glutamine, serotonin, melatonin, neuropeptide Y, opioid, putine, vasopressin, oxytocin, VIP (vasoactive intestinal and related peptide), somatostatin, dopamine, motilin, amylin, bradykinin, CGRP (calcitonin gene related peptide), adrenomedullin, leukotriene, pancreastatin, prostaglandin, thromboxane, adenosine, adrenaline, α- and β-chemokine (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptide, galanin, family members thereof, etc.

In the PCR amplification using the DNA of the present invention, the DNA (or DNA fragment) acting as a template may include any DNA so far as it is derived from the above-mentioned tissues and cells. More specifically, the template DNA (or DNA fragment) includes any of genome DNA, genome DNA libraries, cDNA derived from the tissues and cells and cDNA libraries derived from the tissues and cells. cDNA libraries derived from human tissues and cells are particularly suitable. Vectors to be used in the DNA library may include any of bacteriophages, plasmids, cosmids, phagimids, etc. It is also possible to directly amplify the template DNA (or DNA fragment) by reverse transcriptase polymerase chain reaction (RT-PCR) techniques using mRNA fractions prepared from the tissues and cells. The DNA which is to be a template may be either DNA completely coding for G protein coupled receptor proteins or DNA fragments (or segments) thereof.

Preferably, the RNA or DNA (or fragment(s) thereof) obtained via the instant screening method for G protein coupled receptor protein coding DNA wherein said method uses the DNA according to the present invention is a G protein coupled receptor protein-encoding RNA or DNA (or fragment(s) thereof) contained in the used DNA library. More specifically, it is an RNA or DNA (or RNA fragment(s) or DNA fragment(s) (hereinafter, may be often abbreviated as just "DNA") coding for G protein coupled receptor proteins such as angiotensin receptor, bombesin receptor, canavinoid receptor, cholecystokinin receptor, glutamine receptor, serotonin receptor, melatonin receptor, neuropeptide Y receptor, opioid receptor, purine receptor, vasopressin receptor, oxytocin receptor, VIP receptor (vasoactive intestinal and related peptide receptor), somatostatin receptor, dopamine receptor, motilin receptor, amylin receptor, bradykinin receptor, CGRP receptor (calcitonin gene related peptide receptor), adrenomedullin receptor, leukotriene receptor, pancreastatin receptor, prostaglandin receptor, thromboxane receptor, adenosine receptor, adrenaline receptor, α- and β-chemokine receptor (receptors to IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin receptor, enterogastrin receptor, histamine receptor, neurotensin receptor, TRH receptor, pancreatic polypeptide receptor, galanin receptor, their family member receptors, etc.

When the DNA obtained by the screening method of the present invention is the DNA fragment which partially codes for a G protein coupled receptor protein, it is possible to isolate DNA completely encoding said G protein coupled receptor protein from a suitable DNA library according to cloning techniques known per se by using said DNA fragment as a probe.

Means for cloning the DNA completely encoding G protein coupled receptor proteins may include a PCR amplification employing a synthetic DNA primer having the partial nucleotide sequence of the DNA fragment partially coding for the G protein coupled receptor protein and a selection of the target DNA via a hybridization with DNA or synthetic DNA having part or all of the region of said DNA fragments. The hybridization may be conducted, for example, by the methods described in Molecular Cloning, 2nd ed.; J. Sambrook et al., Cold Spring Harbor Lab. Press, 1989. When the commercially available library is used, it may be conducted according to the manners described in the protocols attached thereto.

The DNA completely encoding G protein coupled receptor protein (full-length G protein coupled receptor protein DNA) may be used, depending upon its object, either as it is or after digesting with a restriction enzyme or after ligating with a linker if desired. Said DNA may have ATG at the 5'-terminal as the translation initiation codon and TAA, TGA or TAG at the 3' terminal as the translation termination codon. These translation initiation codons and translation termination codons may be added using a suitable synthetic DNA adaptor. In addition, it is possible to determine said receptor protein-expressing tissues/cells by northern blottings using said DNA as a probe. It is also possible to express target,receptor proteins by introducing DNA having the entire coding region of the receptor protein into animal cells after binding with a suitable promoter.

The G protein coupled receptor protein according to the present invention is a G protein coupled receptor protein encoded by the G protein coupled receptor protein-encoding DNA obtained by the screening method of the present invention. More specifically, the G protein coupled receptor protein according to the present invention includes G protein coupled receptor proteins such as angiotensin receptor protein, bombesin receptor protein, canavinoid receptor protein, cholecystokinin receptor protein, glutamine receptor protein, serotonin receptor protein, melatonin receptor protein, neuropeptide Y receptor protein, opioid receptor protein, purine receptor protein, vasopressin receptor protein, oxytocin receptor protein, VIP receptor protein (vasoactive intestinal and related peptide receptor protein), somatostatin receptor protein, dopamine receptor protein, motilin receptor protein, amylin receptor protein, bradykinin receptor protein, CGRP receptor protein (calcitonin gene related peptide receptor protein), adrenomedullin receptor protein, leukotriene receptor protein, pancreastatin receptor protein, prostaglandin receptor protein, thromboxane receptor protein, adenosine receptor protein, adrenaline receptor protein, α- and β-chemokine receptor protein (receptor protein responsive to IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin receptor protein, enterogastrin receptor protein, histamine receptor protein, neurotensin receptor protein, TRH receptor protein, pancreatic polypeptide receptor protein, galanin receptor protein, family members thereof, etc.

According to the present invention, novel G protein coupled receptors proteins, peptide segments or fragments derived from the G protein coupled receptor protein, modified derivatives or analogues thereof, and salts thereof may be recognized, cloned, produced, isolated or characterized.

These G protein coupled receptor proteins are those derived from all cells and tissues (e.g. pituitary gland, pancreas, brain, kidney, liver, gonad, thyroid gland, cholecyst, bone marrow, adrenal, skin, muscle, lung, digestive duct, blood vessel, heart, etc.) of warm-blooded animals (e.g. guinea pig, rat, mouse, swine, sheep, cattle, monkey, human beings, rabbit, cat, dog, horse, etc.), and any of proteins as long as they comprise an amino acid sequence selected from the group consisting of an amino acid sequence represented by SEQ ID NO: 24, an amino acid sequence represented by SEQ ID NO: 25, an amino acid sequence represented by SEQ ID NO: 26, an amino acid sequence represented by SEQ ID NO: 27, an amino acid sequence represented by SEQ ID NO: 28, an amino acid sequence represented by SEQ ID NO: 34, an amino acid sequence represented by SEQ ID NO: 35, an amino acid sequence represented by SEQ ID NO: 38, an amino acid sequence represented by SEQ ID NO: 39, an amino acid sequence represented by SEQ ID NO: 56, and substantial equivalents to the amino acid sequence represented by SEQ ID NO: 24, SEQ ID NO: 25, SEQ ID NO: 26, SEQ ID NO: 27, SEQ ID NO: 28, SEQ ID NO: 34, SEQ ID NO: 35, SEQ ID NO: 38, SEQ ID NO: 39, and/or SEQ ID NO: 56.

In one embodiment of the present invention, G protein coupled receptor proteins are those derived from all cells and tissues (e.g. pituitary gland, pancreas, brain, kidney, liver, gonad, thyroid gland, cholecyst, bone marrow, adrenal, skin, muscle, lung, digestive duct, blood vessel, heart, etc.) of warm-blooded animals (e.g. guinea pig, rat, mouse, swine, sheep, cattle, monkey, human beings, cat, dog, horse, etc.), and any of proteins as long as they comprise an amino acid sequence selected from the group consisting of an amino acid sequence represented by SEQ ID NO: 24, an amino acid sequence represented by SEQ ID NO: 25, an amino acid sequence represented by SEQ ID NO: 26, an amino acid sequence represented by SEQ ID NO: 27, an amino acid sequence represented by SEQ ID NO: 28, and substantial equivalents to the amino acid sequence represented by SEQ ID NO: 24, SEQ ID NO: 25, SEQ ID NO: 26, SEQ ID NO: 27, or SEQ ID NO: 28. These G protein coupled receptor proteins may include proteins having an amino acid sequence selected from the group consisting of an amino acid sequence represented by SEQ ID NO: 24, an amino acid sequence represented by SEQ ID NO: 25, an amino acid sequence represented by SEQ ID NO: 26, an amino acid sequence represented by SEQ ID NO: 27 and an amino acid sequence represented by SEQ ID NO: 28, proteins wherein the amino acid sequence thereof is about 90% to 99.9% homologous to an amino acid sequence represented by SEQ ID NO: 24, an amino acid sequence represented by SEQ ID NO: 25, an amino acid sequence represented by SEQ ID NO: 26, an amino acid sequence represented by SEQ ID NO: 27 or an amino acid sequence represented by SEQ ID NO: 28 and the activity thereof is substantially equivalent to the protein having an amino acid sequence represented by SEQ ID NO: 24, an amino acid sequence represented by SEQ ID NO: 25, an amino acid sequence represented by SEQ ID NO: 26, an amino acid sequence represented by SEQ ID NO: 27 or an amino acid sequence represented by SEQ ID NO: 28 and the like. The substantially equivalent activity may include ligand binding activity, signal information transmitting, etc. The term "substantially equivalent" or "substantial equivalent" means that the nature of the ligand binding activity and the like is equivalent. Therefore, it is allowable that even differences among grades such as ligand binding affinity grades and ligand binding activity grades and quantitative factors such as molecular weights of receptor proteins are present.

In another embodiment of the present invention, G protein coupled receptor proteins include human pituitary gland-derived G protein coupled receptor proteins comprising an amino acid sequence selected from the group consisting of an amino acid sequence represented by SEQ ID NO: 24, and/or an amino acid sequence represented by SEQ ID NO: 25, mouse pancreas-derived G protein coupled receptor proteins comprising an amino acid sequence represented by SEQ ID NO: 27, mouse pancreas-derived G protein coupled receptor proteins comprising an amino acid sequence represented by SEQ ID NO: 28, etc. Examples of the human pituitary gland-derived G protein coupled receptor protein comprising an amino acid sequence selected from the group consisting of an amino acid sequence represented by SEQ ID NO: 24, and an amino acid sequence represented by SEQ ID NO: 25, are human pituitary gland-derived G protein coupled receptor proteins comprising an amino acid sequence represented by SEQ ID NO: 24, etc. These G protein coupled receptor proteins may include proteins wherein one or more amino acid residues (preferably from 2 to 30 amino acid residues, more preferably from 2 to 10 amino acid residues) are deleted from the amino acid sequence of SEQ ID NO: 24, SEQ ID NO: 25, SEQ ID NO: 26, SEQ ID NO: 27 or SEQ ID NO: 28, proteins wherein one or more amino acid residues (preferably from 2 to 30 amino acid residues, more preferably from 2 to 10 amino acid residues) are added to the amino acid sequence of SEQ ID NO: 24, SEQ ID NO: 25, SEQ ID NO: 26, SEQ ID NO: 27 or SEQ ID NO: 28, proteins wherein one or more amino acid residues (preferably from 2 to 30 amino acid residues, more preferably from 2 to 10 amino acid residues) in the amino acid sequence of SEQ ID NO: 24, SEQ ID NO: 25, SEQ ID NO: 26, SEQ ID NO: 27 or SEQ ID NO: 28, are substituted with one or more amino acid residues, etc.

In yet another embodiment of the present invention, G protein coupled receptor proteins include those derived from all cells and tissues (e.g. amygdaloid nucleus, pituitary gland, pancreas, brain, kidney, liver, gonad, thyroid gland, cholecyst, bone marrow, lung, digestive duct, blood vessel, heart, thymus, spleen, leukocyte, etc.) of warm-blooded animals (e.g. guinea pig, rat, mouse, pig, sheep, cattle, monkey, human beings, etc.), and any of proteins as long as they comprise an amino acid sequence selected from the group consisting of an amino acid sequence represented by SEQ ID NO: 34 and/or an amino acid sequence represented by SEQ ID NO: 35. These G protein coupled receptor proteins may include proteins having an amino acid sequence selected from the group consisting of an amino acid sequence represented by SEQ ID NO: 34 or/and an amino acid sequence represented by SEQ ID NO: 35, proteins wherein the amino acid sequence thereof is about 90% to 99.9% homologous to an amino acid sequence represented by SEQ ID NO: 34 or/and an amino acid sequence represented by SEQ ID NO: 35 and the activity thereof is substantially equivalent to the protein having an amino acid sequence represented by SEQ ID NO: 34 and/or an amino acid sequence represented by SEQ ID NO: 35, and the like. The substantially equivalent activity may include ligand binding activity, signal information transmitting, etc. The term "substantially equivalent" or "substantial equivalent" means that the nature of the ligand binding activity and the like is equivalent. Therefore, it is allowable that even differences among grades such as ligand binding affinity grades and ligand binding activity grades and quantitative factors such as molecular weights of receptor proteins are present. Examples of the G protein coupled receptor protein are human amygdaloid nucleus-derived G protein coupled receptor proteins having an amino acid sequence selected from the group consisting of an amino acid sequence represented by SEQ ID NO: 34 and/or an amino acid sequence represented by SEQ ID NO: 35, etc. These G protein coupled receptor proteins may include proteins wherein one or more amino acid residues (preferably from 2 to 30 amino acid residues, more preferably from 2 to 10 amino acid residues) are deleted from the amino acid sequence of SEQ ID NO: 34 or SEQ ID NO: 35, proteins wherein one or more amino acid residues (preferably from 2 to 30 amino acid residues, more preferably from 2 to 10 amino acid residues) are added to the amino acid sequence of SEQ ID NO: 34 or SEQ ID NO: 35, proteins wherein one or more amino acid residues (preferably from 2 to 30 amino acid residues, more preferably from 2 to 10 amino acid residues) in the amino acid sequence of SEQ ID NO: 34 or SEQ ID NO: 35, are substituted with one or more amino acid residues, etc.

In still another embodiment of the present invention, these G protein coupled receptor proteins are those derived from all cells and tissues (e.g. amygdaloid nucleus, pituitary body, pancreas, brain, kidney, liver, gonad, thyroid gland, cholecyst, bone marrow, lung, digestive duct, blood vessel, heart, thymus, leukocyte, etc.) of warm-blooded animals (e.g. guinea pig, rat, mouse, swine, sheep, cattle, monkey, human beings, etc.), and any of proteins as long as they comprise an amino acid sequence represented by SEQ ID NO: 38, or substantial equivalents to the amino acid sequence represented by SEQ ID NO: 38, preferably an amino acid sequence represented by SEQ ID NO: 39, or substantial equivalents to the amino acid sequence represented by SEQ ID NO: 39. These G protein coupled receptor proteins may include proteins having an amino acid sequence represented by SEQ ID NO: 38, proteins wherein the amino acid sequence thereof is about 90% to 99.9% homologous to an amino acid sequence represented by SEQ ID NO: 38 and the activity thereof is substantially equivalent to the protein having an amino acid sequence represented by SEQ ID NO: 38 and the like. These G protein coupled receptor proteins are preferably proteins having an amino acid sequence represented by SEQ ID NO: 39, proteins wherein the amino acid sequence thereof is about 90% to 99.9% homologous to an amino acid sequence represented by SEQ ID NO: 39 and the activity thereof is substantially equivalent to the protein having an amino acid sequence represented by SEQ ID NO: 39, etc. The substantially equivalent activity may include ligand binding activity, signal information transmitting, etc. The term "substantially equivalent" or "substantial equivalent" means that the nature of the ligand binding activity and the like is equivalent. Therefore, it is allowable that even differences among grades such as ligand binding affinity grades and ligand binding activity grades and quantitative factors such as molecular sizes or weights of receptor proteins are present.

It is suggested by data that the mouse pancreatic β-cell strain, MIN6-derived receptor protein of the present invention (e.g., SEQ ID NO: 38 and SEQ ID NO: 39, or proteins encoded by pMAH2-17) is a novel purinoceptor subtype which is clearly distinct from prior art purinoceptors.

In another more specific embodiment of the present invention, G protein coupled receptor proteins include mouse pancreatic β-cell line, MIN6, derived G protein coupled receptor proteins comprising an amino acid sequence represented by SEQ ID NO: 38, mouse pancreatic β-cell line, MIN6, derived G protein coupled receptor proteins wherein one or more amino acid residues (preferably from 2 to 30 amino acid residues, more preferably from 2 to 10 amino acid residues) are deleted from the amino acid sequence of SEQ ID NO: 38, proteins wherein one or more amino acid residues (preferably from 2 to 30 amino acid residues, more preferably from 2 to 10 amino acid residues) are added to the amino acid sequence of SEQ ID NO: 38, proteins wherein one or more amino acid residues (preferably from 2 to 30 amino acid residues, more preferably from 2 to 10 amino acid residues) are substituted with other amino acid residues in the amino acid sequence of SEQ ID NO: 38, etc. Further preferably these G protein coupled receptor proteins include mouse pancreatic β-cell line, MIN6, derived G protein coupled receptor proteins comprising an amino acid sequence represented by SEQ ID NO: 39, mouse pancreatic β-cell line, MIN6, derived G protein coupled receptor proteins wherein one or more amino acid residues (preferably from 2 to 30 amino acid residues, more preferably from 2 to 10 amino acid residues) are deleted from the amino acid-sequence of SEQ ID NO: 39, proteins wherein one or more amino acid residues (preferably from 2 to 30 amino acid residues, more preferably from 2 to 10 amino acid residues) are added to the amino acid sequence of SEQ ID NO: 39, proteins wherein one or more amino acid residues (preferably from 2 to 30 amino acid residues, more preferably from 2 to 10 amino acid residues) in the amino acid sequence of SEQ ID NO: 39 are substituted with other amino acid residues, etc.

In still another embodiment of the present invention, these G protein coupled receptor proteins are those derived from all cells and tissues (e.g. placenta, gonad, amygdaloid nucleus, pituitary body, pancreas, brain, kidney, liver, thyroid gland, cholecyst, bone marrow, lung, digestive duct, blood vessel, heart, thymus, leukocyte, etc.) of human beings, and any of proteins as long as they comprise an amino acid sequence represented by SEQ ID NO: 56, or substantial equivalents to the amino acid sequence represented by SEQ ID NO: 56. These G protein coupled receptor proteins may include proteins having an amino acid sequence represented by SEQ ID NO: 56, proteins wherein the amino acid sequence thereof is about 90% to 99.9% homologous to an amino acid sequence represented by SEQ ID NO: 56 and the activity thereof is substantially equivalent to the protein having an amino acid sequence represented by SEQ ID NO: 56 and the like. The substantially equivalent activity may include ligand binding activity, signal information transmitting, etc. The term "substantially equivalent" or "substantial equivalent" means that the nature of the ligand binding activity and the like is equivalent. Therefore, it is allowable that even differences among grades such as ligand binding affinity grades and ligand binding activity grades and quantitative factors such as molecular sizes or weights of receptor proteins are present.

In another more specific embodiment of the present invention, G protein coupled receptor proteins include G protein coupled receptor proteins comprising an amino acid sequence represented by SEQ ID NO: 56, G protein coupled receptor proteins wherein one or more amino acid residues (preferably from 2 to 30 amino acid residues, more preferably from 2 to 10 amino acid residues) are deleted from the amino acid sequence of SEQ ID NO: 56, proteins wherein one or more amino acid residues (preferably from 2 to 30 amino acid residues, more preferably from 2 to 10 amino acid residues) are added to the amino acid sequence of SEQ ID NO: 56, proteins wherein one or more amino acid residues (preferably from 2 to 30 amino acid residues, more preferably from 2 to 10 amino acid residues) in the amino acid sequence of SEQ ID NO: 56, are substituted with other amino acid residues, etc.

A portion of the amino acid sequence may be modified (e.g. addition, deletion, substitution with other amino acids, etc.) in the G protein coupled receptor proteins of the present invention.

Furthermore, the G protein coupled receptor proteins of the present invention includes those wherein N-terminal Met is protected with a protecting group (e.g., $C_{1-6}$ acyl group such as formyl, acetyl, etc.), those wherein the N-terminal side of Glu is cleaved in vivo to make said Glu pyroglutaminated, those wherein the intramolecular side chain of amino acids is protected with a suitable protecting group (e.g., $C_{1-6}$ acyl group such as formyl, acetyl, etc.), conjugated proteins such as so-called "glycoproteins" wherein saccharide chains are bonded, etc.

The salt of said G protein coupled receptor protein of the present invention includes preferably physiologically acceptable acid addition salts. Examples of such salts are salts thereof with inorganic acids (e.g. hydrochloric acid, phosphoric acid, hydrobromic acid, sulfuric acid, etc.), salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.), etc.

The G protein coupled receptor protein or its salt of the present invention may be manufactured from the tissues or cells of warm-blooded animals by purifying methods which are known per se by those skilled in the art or methods similar thereto or may be manufactured by culturing the transformant (or transfectant) (as described herein below) containing G protein coupled receptor protein encoding DNA. The protein or its salt of the present invention may be manufactured by the peptide synthesis as described herein below.

The G protein coupled receptor protein fragment (the partial peptide of said G protein coupled receptor protein) may include, for example, the site which is exposed outside cell membranes, among the G protein coupled receptor protein molecule. Examples of the fragment are peptides containing a region which is analyzed as an extracellular area (hydrophilic region or site) in a hydrophobic plotting analysis on the G protein coupled receptor protein represented by any of FIGS. 24, 25, 28, 31, 32, 36, 38, 41, 44, 47, 50, 53, 57, 58, 59, 64, 70, 74, and 78. A peptide which partly contains a hydrophobic region or site may be used as well. Further, a peptide which separately contains each domain may be used too although the partial peptide (peptide fragment) which contains plural domains at the same time will be used as well.

The salt of said G protein coupled receptor protein fragment (partial peptide thereof) includes preferably physiologically acceptable acid addition salts. Examples of such salts are salts thereof with inorganic acids (e.g. hydrochloric acid, phosphoric acid, hydrobromic acid, sulfuric acid, etc.), salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.), etc.

The G protein coupled receptor protein fragment (the partial peptide of the G protein coupled receptor protein) may be manufactured by synthesizing methods for peptides which are known per se by those skilled in the art or methods similar thereto or by cleaving (digesting) G protein coupled receptor proteins by a suitable peptidase. Methods of synthesizing peptide may be any of a solid phase synthesis and a liquid phase synthesis. Thus, a partial peptide (peptide fragment) or amino acids which can construct the protein of the present invention is condensed with the residual part thereof and, when the product has a protective group, said protective group is detached whereupon a desired peptide can be manufactured. Examples of the known methods for condensation and for detachment of protective groups include the following ① to ⑤:

① M. Bodanszky and M. A. Ondetti: Peptide Synthesis, Interscience Publishers, New York (1966).
② Schroeder and Luebke: The Peptide, Academic Press, New York, 1965.

③ Nobuo Izumiya et al.: Fundamentals and Experiments of the Peptide Synthesis, Maruzen KK, Japan (1975).
④ Haruaki Yajima and Shumpei Sakakibara: "Seikagaku Jikken Koza 1" (Experiments of Biochemistry, Part 1), "Tanpakusitu No Kagaku IV" (Chemistry of Protein, IV), p.205 (1977), Japan.
⑤ Haruaki Yajima (ed): Development of Pharmaceuticals (Second Series), Vol. 14, Peptide Synthesis, Hirokawa Shoten, Japan.

After the reaction, conventional purifying techniques such as salting-out, extraction with solvents, distillation, column chromatography, liquid chromatography, electrophoresis, recrystallization, etc. are optionally combined so that the protein of the present invention can be purified and isolated. When the protein obtained as such is a free compound, it may be converted to a suitable salt by known methods while, when it is obtained as a salt, the salt may be converted to a free compound or other salt compounds by known methods.

Furthermore, the product may be manufactured by culturing the transformant (transfectant) containing the DNA coding for said partial peptide.

The G protein coupled receptor protein-encoding DNA obtained by the above-mentioned screening method using the DNA of the present invention and the G protein coupled receptor protein encoded by said DNA or the peptide fragment (partial peptide thereof) encoded by said DNA may, for example, be used for the determination of a ligand to said G protein coupled receptor protein or for the screening of a compound which inhibits the binding of said protein coupled receptor protein with a ligand.

In that case, an expression system for the G protein coupled receptor protein-encoding DNA is at first constructed. Hosts for said DNA may be any of animal cells, insect cells, yeasts, Bacillus subtilis, Escherichia coli, etc. Promoters used therefor may be anyone so far as it is suitable as a promoter for the host used for gene expression. Incidentally, the utilization of enhancers for expression is effective as well.

Then the expressing cells per se which constructed to express the G protein coupled receptor protein or the cell membrane fractions prepared therefrom by methods known per se by those skilled in the art or methods similar thereto may be subjected to a variety of receptor binding experiments. Ligands used therefor may include any of compounds labeled by a commercially available radioisotope, etc., culture supernatants and tissue extracts which are directly labeled by a chloramine T method or by a lactoperoxidase method. Separation of bonded or free ligands may be carried out by a direct washing when cells adhered to substrates are used, while, in the case of floating cells or cell membrane fractions thereof, it may be carried out by means of centrifugal separation or filtration. Nonspecific binding with container, etc. may be estimated by addition of unlabeled ligands which are about 100 times as much concentrated relatively to the poured labeled ligand.

The ligand which is obtained by such a receptor binding experiment may be subjected to a discrimination of agonist versus antagonist.

To be more specific, a natural substance or compound which is presumed to be a ligand with the G protein coupled receptor protein-expressing cell is cultured and, after that, the culture supernatant liquid is collected or the cell is extracted. A change in the components contained therein is measured by, for example, a commercially available measuring kit (e.g. kits for cAMP, diacylglycerol, cGMP, proteinkinase A, etc.). Alternatively, it is possible to measure physiological responses such as liberation of Fura-2, [$^3$H] arachidonic acid and [$^3$H]inositol phosphate metabolites by methods known per se by those skilled in the art or methods similar thereto. The compound or natural substance which is obtained by such a screening is an agonist for said G protein coupled receptor protein or an antagonist for said G protein coupled receptor protein and is presumed to act on the tissues and cells in which said receptor is distributed. Accordingly, it is possible to check the pharmaceutical response (pharmaceutical effect) more efficiently by referring to the distribution disclosed (clarified) by a northern blotting or the like. Moreover, a development of compounds having a novel pharmaceutical response (pharmaceutical effect) in, for example, central nervous tissues, circulatory system, kidney, pancreas, etc. is expected. An efficient development of pharmaceuticals can be proceeded by amplifying G protein coupled receptor protein-encoding DNA selectively from tissues.

The G protein coupled receptor protein-encoding DNA of the present invention may be any coding DNA as long as it contains a nucleotide sequence coding for a G protein coupled receptor protein which contains an amino acid sequence substantially equivalent to the amino acid sequence having SEQ ID NO: 24 and/or which has an activity substantially equivalent to the amino acid sequence having SEQ ID NO: 24, a G protein coupled receptor protein which contains an amino acid sequence substantially equivalent to the amino acid sequence having SEQ ID NO: 25 and/or which has an activity substantially equivalent to the amino acid sequence having SEQ ID NO: 25, a G protein coupled receptor protein which contains an amino acid sequence substantially equivalent to the amino acid sequence having SEQ ID NO: 26 and/or which has an activity substantially equivalent to the amino acid sequence having SEQ ID NO: 26, a G protein coupled receptor protein which contains an amino acid sequence substantially equivalent to the amino acid sequence having SEQ ID NO: 27 and/or which has an activity substantially equivalent to the amino acid sequence having SEQ ID NO: 27, or a G protein coupled receptor protein which contains an amino acid sequence substantially equivalent to the amino acid sequence having SEQ ID NO: 28 and/or which has an activity substantially equivalent to the amino acid sequence having SEQ ID NO: 28.

Still the G protein coupled receptor protein-encoding DNA of the present invention may be any coding DNA as long as it contains a nucleotide sequence coding for a G protein coupled receptor protein which contains an amino acid sequence substantially equivalent to the amino acid sequence having SEQ ID NO: 34 and/or which has an activity substantially equivalent to the amino acid sequence having SEQ ID NO: 34, or a G protein coupled receptor protein which contains an amino acid sequence substantially equivalent to the amino acid sequence having SEQ ID NO: 35 and/or which has an activity substantially equivalent to the amino acid sequence having SEQ ID NO: 35.

Yet the G protein coupled receptor protein-encoding DNA of the present invention may be any coding DNA as long as it contains a nucleotide sequence coding for a G protein coupled receptor protein which contains an amino acid sequence substantially equivalent to the amino acid sequence having SEQ ID NO: 38 and/or which has an activity substantially equivalent to the amino acid sequence having SEQ ID NO: 38, or preferably a G protein coupled receptor protein which contains an amino acid sequence substantially equivalent to the amino acid sequence having SEQ ID NO: 39 and/or which has an activity substantially equivalent to the amino acid sequence having SEQ ID NO: 39.

Yet the G protein coupled receptor protein-encoding DNA of the present invention may be any coding DNA as long as it contains a nucleotide sequence coding for a G protein coupled receptor protein which contains an amino acid sequence substantially equivalent to the amino acid sequence having SEQ ID NO: 56 and/or which. has an activity substantially equivalent to the amino acid sequence having SEQ ID NO: 56, or preferably a G protein coupled receptor protein which contains an amino acid sequence substantially equivalent to the amino acid sequence having SEQ ID NO: 56 and/or which has an activity substantially equivalent to the amino acid sequence having SEQ ID NO: 56.

The DNA of the present invention may be any one of a human genome DNA, a human genome DNA library, a human tissue and cell-derived cDNA, a human tissue and cell-derived cDNA library and a synthetic DNA. The vector used for the library may include bacteriophage, plasmid, cosmid, phagemid, etc. The DNA can be further amplified directly by the reverse transcriptase polymerase chain reaction (hereinafter briefly referred to as "RT-PCR") using mRNA fractions prepared from tissues and cells.

In an embodiment, the DNA coding for the human pituitary gland-derived G protein coupled receptor protein comprising the amino acid sequence of SEQ ID NO: 24 includes DNA having a nucleotide sequence represented by SEQ ID NO: 29, etc. The DNA coding for the human pituitary gland-derived G protein coupled receptor protein comprising the amino acid sequence of SEQ ID NO: 25 includes DNA having a nucleotide sequence represented by SEQ ID NO: 30, etc. The DNA coding for the human pituitary gland-derived G protein coupled receptor protein comprising the amino acid sequence of SEQ ID NO: 26 includes DNA having a nucleotide sequence represented by SEQ ID NO: 31, etc. The DNA coding for the mouse pancreas-derived G protein coupled receptor protein comprising the amino acid sequence of SEQ ID NO: 27 includes DNA having a nucleotide sequence represented by SEQ ID NO: 32, etc. The DNA coding for the mouse pancreas-derived G protein coupled receptor protein comprising the amino acid sequence of SEQ ID NO: 28 includes DNA having a nucleotide sequence represented by SEQ ID NO: 33, etc.

In another embodiment, the DNA coding for the human amygdaloid nucleus-derived G protein coupled receptor protein comprising the amino acid sequence of SEQ ID NO: 34 includes DNA having a nucleotide sequence represented by SEQ ID NO: 36, etc. The DNA coding for the human amygdaloid nucleus-derived G protein coupled receptor protein comprising the amino acid sequence of SEQ ID NO: 35 includes DNA having a nucleotide sequence represented by SEQ ID NO: 37, etc. The DNA coding for the human amygdaloid nucleus-derived G protein coupled receptor protein comprising the amino acid sequence of SEQ ID NO: 34 or the amino acid sequence of SEQ ID NO: 35 includes DNA having a nucleotide sequence represented by SEQ ID NO: 36, DNA having a nucleotide sequence represented by SEQ ID NO: 37, etc. Still in another embodiment, the DNA coding for the mouse pancreatic β-cell line, MIN6-derived G protein coupled receptor protein comprising the amino acid sequence of SEQ ID NO: 38 includes DNA having a nucleotide sequence represented by SEQ ID NO: 40, etc. The DNA coding for the mouse pancreatic β-cell line, MIN6-derived G protein coupled receptor protein comprising the amino acid sequence of SEQ ID NO: 39 includes DNA having a nucleotide sequence represented by SEQ ID NO: 41, etc. Yet in another embodiment, the DNA coding for the human-derived G protein coupled receptor protein comprising the amino acid sequence of SEQ ID NO: 56 includes DNA having a nucleotide sequence represented by SEQ ID NO: 57, etc.

The DNA completely coding for the G protein coupled receptor protein of the present invention can be cloned by (1) carrying out the PCR amplification using a synthetic DNA primer having a partial nucleotide sequence (nucleotide fragment) of the G protein coupled receptor protein; or (2) effecting the selection of a DNA constructed in a suitable vector, based on the hybridization with a labeled DNA fragment having part or all of the region encoding a human G protein coupled receptor protein or a labeled synthetic DNA having part or all of the coding region thereof. The hybridization is carried out according to methods as disclosed in, for example, Molecular Cloning, 2nd Ed., J. Sambrook et al., Cold Spring Harbor Lab. Press, 1989. When a DNA library commercially available in the market is used, the hybridization is carried out according to protocols manuals attached thereto.

The cloned G protein coupled receptor protein-encoding DNA of the present invention can be used as it is, or can be used, as desired, after modifications including digestion with a restriction enzyme or addition of a linker or adapter, etc. depending upon objects. The DNA may have an initiation codon, ATG, on the 5' terminal side and a termination codon, TAA, TGA or TAG, on the 3' terminal side. These initiation and termination codons can be ligated by using a suitable synthetic DNA adapter.

An expression vector for G protein coupled receptor proteins can be produced by, for example, (a) cutting out a target DNA fragment from the G protein coupled receptor protein-encoding DNA of the present invention and (b) ligating the target DNA fragment with the downstream site of a promoter in a suitable expression vector.

The vector may include plasmids derived from *Escherichia coli* (e.g., pBR322, pBR325, pUC12, pUC13, etc.), plasmids derived from *Bacillus subtilis* (e.g., pUB110, pTP5, pC194, etc.), plasmids derived from yeasts (e.g., pSH19, pSH15, etc.), bacteriophages such as λ-phage, and animal virus such as retrovirus, vaccinia virus and baculovirus.

According to the present invention, any promoter can be used as long as it is compatible with a host which is used for expressing a gene. When the host for the transformation is *E. coli*, the promoters are preferably trp promoters, lac promoters, recA promoters, $\lambda_{PL}$ promoters, lpp promoters, etc. When the host for the transformation is the Bacillus, the promoters are preferably SPO1 promoters, SPO2 promoters, penP promoters, etc. When the host is an yeast, the promoters are preferably PHO5 promoters, PGK promoters, GAP promoters, ADH promoters, etc. When the host is an animal cell, the promoters include SV40-derived promoters, retrovirus promoters, metallothionein promoters, heat shock promoters, cytomegalovirus promoters, SRa promoters, etc. An enhancer can be effectively utilized for the expression.

As required, furthermore, a host-compatible signal sequence is added to the N-terminal side of the G protein coupled receptor protein. When the host is *E. coli*, the utilizable signal sequences may include alkaline phosphatase signal sequences, OmpA signal sequences, etc. When the host is the Bacillus, they may include α-amylase signal sequences, subtilisin signal sequences, etc. When the host is an yeast, they may include mating factor α signal sequences, invertase signal sequences, etc. When the host is an animal cell, they may include insulin signal sequences, α-interferon signal sequences, antibody molecule signal sequences, etc.

A transformant or transfectant is produced by using the vector thus constructed, which carries the G protein coupled receptor protein-encoding DNA of the present invention. The host may be, for example, Escherichia microorganisms, Bacillus microorganisms, yeasts, insect cells, animal cells, etc. Examples of the Escherichia and Bacillus microorganisms include *Escherichia coli* K12-DH1 [Proc. Natl. Acad. Sci. USA, Vol. 60, 160 (1968)], JM103 [Nucleic Acids Research, Vol. 9, 309 (1981)], JA221 [Journal of Molecular Biology, Vol. 120, 517 (1978)], HB101 [Journal of Molecular Biology, Vol. 41, 459 (1969)], C600 [Genetics, Vol. 39, 440 (1954)], etc. Examples of the Bacillus microorganism are, for example, *Bacillus subtilis* MI114 [Gene, Vol. 24, 255 (1983)], 207–21 [Journal of Biochemistry, Vol. 95, 87 (1984)], etc. The yeast may be, for example, *Saccharomyces cerevisiae* AH22, AH22R , NA87-11A, DKD-5D, 20B-12, etc. The insect may include a silkworm (*Bombyx mori* larva), [Maeda et al, Nature, Vol. 315, 592 (1985)] etc. The host animal cell may be, for example, monkey-derived cell line, COS-7, Vero, Chinese hamster ovary cell line (CHO cell), DHFR gene-deficient Chinese hamster cell line (dhfr CHO cell), mouse L cell, murine myeloma cell, human FL cell, etc.

Depending on the host cell used, transformation is done using standard techniques appropriate to such cells. Transformation of Escherichia microorganisms can be carried out in accordance with methods as disclosed in, for example, Proc. Natl. Acad. Sci. USA,: Vol. 69, 2110 (1972), Gene, Vol. 17, 107 (1982), etc. Transformation of Bacillus microorganisms can be carried out in accordance with methods as disclosed in, for example, Molecular & General Genetics, Vol. 168, 111 (1979), etc. Transformation of the yeast can be carried out in accordance with methods as disclosed in, for example, Proc. Natl. Acad. Sci. USA, Vol. 75, 1929 (1978), etc. The insect cells can be transformed in accordance with methods as disclosed in, for example, Bio/Technology, 6, 47–55, 1988. The animal cells can be transformed by methods as disclosed in, for example, Virology, Vol. 52, 456, 1973, etc. The transformants or transfectants which are transformed with expression vectors containing a G protein coupled receptor protein-encoding DNA are produced according to the aforementioned techniques.

Cultivation of the transformant (transfectant) in which the host is Escherichia or Bacillus microorganism can be carried out suitably in a liquid culture medium. The culture medium may contains carbon sources, nitrogen sources, minerals, etc. necessary for growing the transformant. The carbon source may include glucose, dextrin, soluble starch, sucrose, etc. The nitrogen source may include organic or inorganic substances such as ammonium salts, nitrates, corn steep liquor, peptone, casein, meat extracts, bean-cakes, potato extracts, etc. Examples of the minerals may include calcium chloride, sodium dihydrogen phosphate, magnesium chloride, etc. It is further allowable to add yeasts, vitamines, growth-promoting factors, etc. It is desired that the culture medium is pH from about 5 to about 8.

The Escherichia microorganism culture medium is preferably an M9 medium containing, for example, glucose and casamino acid (Miller, Journal of Experiments in Molecular Genetics), 431–433, Cold Spring Harbor Laboratory, New York, 1972. Depending on necessity, the medium may be supplemented with drugs such as 3β-indolyl acrylic acid in order to improve efficiency of the promoter. In the case of the Escherichia host, the cultivation is carried out usually at about 15 to 43° C. for about 3 to 24 hours. As required, aeration and stirring may be applied. In the case of the Bacillus host, the cultivation is carried out usually at, about 30 to 40° C. for about 6 to 24 hours. As required, aeration and stirring may be also applied. In the case of the transformant in which the host is an yeast, the culture medium used may include, for example, a Burkholder minimum medium [Bostian, K. L. et al., Proc. Natl. Acad. Sci. USA, Vol. 77, 4505 (1980)], an SD medium containing 0.5% casamino acid [Bitter, G. A. et al., Proc. Natl. Acad. Sci. USA, Vol. 81, 5330 (1984)], etc. It is preferable that pH of the culture medium is adjusted to be from about 5 to about 8. The cultivation is carried out usually at about20 to 35° C. for about 24 to 72 hours. As required, aeration and stirring may be applied. In the case of the transformant in which the host is an insect, the culture medium used may include those obtained by suitably adding additives such as passivated (or immobilized) 10% bovine serum and the like to the Grace's insect medium (Grace, T. C. C., Nature, 195, 788 (1962)). It is preferable that pH of the culture medium is adjusted to be about 6.2 to 6.4. The cultivation is usually carried out at about 27° C. for about 3 to 5 days. As desired, aeration and stirring may be applied. In the case of the transformant in which the host is an animal cell, the culture medium used may include MEM medium [Science, Vol. 122, 501 (1952)], DMEM medium [Virology, Vol. 8, 396 (1959)], RPMI 1640 medium [Journal of the American Medical Association, Vol. 199, 519 (1967)], 199 medium [Proceedings of the Society of the Biological Medicine, Vol. 73, 1 (1950)], etc. which are containing, for example, about 5 to 20% of fetal calf serum. It is preferable that the pH is from about 6 to about 8. The cultivation is usually carried out at about 30 to 40° C. for about 15 to 60 hours. As required, aeration and stirring may be applied.

Separation and purification of the G protein coupled receptor protein from the above-mentioned cultures can be carried out according to methods described herein below.

To extract G protein coupled receptor proteins from the cultured microorganisms or cells, the microorganisms or cells are collected by known methods after the cultivation, suspended in a suitable buffer solution, disrupted by ultrasonic waves, lysozyme and/or freezing and thawing, etc. and, then, a crude extract of the G protein coupled receptor protein is obtained by centrifugation or filtration. Other conventional extracting or isolating methods can be applied. The buffer solution may contain a protein-denaturing agent such as urea or guanidine hydrochloride or a surfactant such as Triton X-100 (registered trademark, hereinafter often referred to as "™").

In case where G protein coupled receptor proteins are secreted into culture media, supernatant liquids are separated from the microorganisms or cells after the cultivation is finished and the resulting supernatant liquid is collected by widely known methods. The culture supernatant liquid and extract containing G protein coupled receptor proteins can be purified by suitable combinations of widely known methods for separation, isolation and purification. The widely known methods of separation, isolation and purification may include methods which utilizes solubility, such as salting out or sedimentation with solvents methods which utilizes chiefly a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as inverse-phase high-performance liquid chromatography, and methods utilizing a difference in the isoelectric point such as isoelectric electrophoresis, etc.

In case where the G protein coupled receptor protein thus obtained is in a free form, the free protein can be converted into a salt thereof by known methods or method analogous thereto. In case where the G protein coupled receptor protein thus obtained is in a salt form vice versa, the protein salt can be converted into a free form or into any other salt thereof by known methods or method analogous thereto.

The G protein coupled receptor protein produced by the transformant can be arbitrarily modified or a polypeptide can be partly removed therefrom, by the action of a suitable protein-modifying enzyme before or after the purification. The protein-modifying enzyme may include trypsin, chymotrypsin, arginyl endopeptidase, protein kinase, glycosidase, etc. The activity of the G protein coupled receptor protein thus formed can be measured by experimenting the coupling (or binding) with a ligand or by enzyme immunoassays (enzyme linked immunoassays) using specific antibodies.

The G protein coupled receptor protein-encoding DNA and the G protein coupled receptor protein of the present invention can be used for:
① methods of determining ligands for the G protein coupled receptor protein of the present invention,
② obtaining an antibody and an antiserum,
③ constructing a system for expressing a recombinant receptor protein,
④ developing a receptor-binding assay system using the above developing system and screening pharmaceutical candidate compounds,
⑤ designing drugs based upon the comparison with ligands and receptors which have a similar or analogous structure,
⑥ preparing a probe in the analysis of genes and preparing a PCR primer, and
⑦ gene manipulating therapy.

In particular, it is allowable to screen a G protein coupled receptor agonist or antagonist specific to a warm-blooded animal such as human being by a receptor-binding assay system which uses a system for expressing a recombinant G protein coupled receptor protein of the present invention. The agonist or antagonist thus screened or characterized permits various applications including prevention and/or therapy of a variety of diseases.

Concretely described below are uses of G protein coupled receptor proteins, partial peptide thereof (peptide fragment thereof), G protein coupled receptor protein-encoding DNAs and antibodies against the G protein coupled receptor protein according to the present invention.

As hereunder, more detailed description will be made on the usefulness of the G protein coupled receptor protein-encoding DNA obtained by the screening method for G protein coupled receptor protein-encoding DNAs according to the present invention, the G protein coupled receptor proteins encoded by said DNA, peptide fragments or segments thereof (including partial peptides thereof) or salts thereof (hereinafter, those including their salts, will be referred to as the "G protein coupled receptor protein or a peptide fragment thereof"), cells or cell membrane fractions thereof each containing the recombinant type G protein coupled receptor protein, etc. Their various applications are also disclosed herein below.

(1) Method for Determining Ligands to the G Protein Coupled Receptor Protein

The G protein coupled receptor protein (or the peptide segment thereof) is useful as a reagent for investigating or determining a ligand to said G protein coupled receptor protein.

According to the present invention, methods for determining a ligand to the G protein coupled receptor protein which comprises contacting the G protein coupled receptor protein or the peptide segment or fragment thereof with the compound to be tested are provided.

The compound to be tested may include not only known ligands such as angiotensins, bombesins, canavinoids, cholecystokinins, glutamine, serotonin, melatonins, neuropeptides Y, opioids, purine, vasopressins, oxytocins, VIP (vasoactive intestinal and related peptides), somatostatins, dopamine, motilins, amylins, bradykinins, CGRP (calcitonin gene related peptides), adrenomedullins, leukotrienes, pancreastatins, prostaglandins, thromboxanes, adenosine, adrenaline, α- and β-chemokines (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelins, enterogastrins, histamine, neurotensins, TRH, pancreatic polypeptides, galanin, modified derivatives thereof, analogues thereof, family members thereof and the like but also tissue extracts, cell culture supernatants, etc. of warm-blooded animals (such as mice, rats, swines, cattle, sheep, monkeys and human being), etc. For example, said tissue extract, said cell culture supernatant, etc. is added to the G protein coupled receptor protein for measurement of the cell stimulating activity, etc. and fractionated by relying on the measurements whereupon a single ligand can be finally obtained.

In one specific embodiment of the present invention, said method for determining the ligand includes a method for determining a compound or a salt thereof capable of stimulating a target cell which comprises binding said compound with the G protein coupled receptor protein either in the presence of the G protein coupled receptor protein or the peptide segment thereof or in a receptor binding assay system in which the expression system for the recombinant type receptor protein is constructed and used; and measuring the receptor-mediated cell stimulating activity, etc. Examples of said cell stimulating activities include promoting activity or inhibiting activity on biological responses, e.g. liberation of arachidonic acid, liberation of acetylcholine, liberation of endocellular $Ca^{2+}$, production of endocellular cAMP, production of endocellular cGMP, production of inositol phosphate, changes in the cell membrane potential, phosphorylation of endocellular protein, activation of c-fos, lowering in pH, activation of G protein, cell promulgation, etc. Examples of said compound or salt capable of stimulating the cell via binding with the G protein coupled receptor protein include peptides, proteins, nonpeptidic compounds, synthetic compounds, fermented products, etc.

In said method for determining the ligand, the characteristic feature is that when the G protein coupled receptor protein or the peptide segment thereof is contacted with the test compound, for example, the binding amount, the cell stimulating activity, etc. of the test compound to the G protein coupled receptor protein or the peptide segment thereof is measured.

In more specific embodiments of the present invention, said methods for determining the ligand includes:
① a method of determining a ligand to a G protein coupled receptor protein, which comprises contacting a labeled test compound with a G protein coupled receptor protein or a peptide segment thereof, and measuring the amount of the labeled test compound binding with said protein or salt thereof or with said peptide fragment or salt thereof;
② a method of determining a ligand to a G protein coupled receptor protein, which comprises contacting a labeled test compound with cells containing the G protein coupled receptor protein or the membrane fraction of said cell, and measuring the amount of the labeled test compound binding with said cells or said cell fraction;

③ a method of determining a ligand to a G protein coupled receptor protein, which comprises contacting a labeled test compound with the G protein coupled receptor protein expressed on cell membranes by culturing transformants containing the DNA coding for the G protein coupled receptor protein, and measuring the amount of the labeled test compound binding with said G protein coupled receptor protein;

④ a method of determining a ligand to a G protein coupled receptor protein, which comprises contacting a test compound with cells containing the G protein coupled receptor protein, and measuring the cell stimulating activity (e.g. promoting or inhibiting activity on biological responses such as liberation of arachidonic acid, liberation of acetylcholine, liberation of endocellular $Ca^{2+}$, production of endocellular cAMP, production of endocellular cGMP, production of inositol phosphate, changes in the cell membrane potential, phosphorylation of endocellular protein, activation of c-fos, lowering in pH, activation of G protein, cell promulgation, etc.) via the G protein coupled receptor protein; and ⑤ a method of determining a ligand to the G protein coupled receptor protein, which comprises contacting a test compound with the G protein coupled receptor protein expressed on the cell membrane by culturing transformants containing the DNA coding for the G protein coupled receptor protein, and measuring the cell stimulating activity (activity for promoting or inhibiting physiological responses such as liberation of arachidonic acid, liberation of acetylcholine, liberation of endocellular $Ca^{2+}$, production of endocellular cAMP, production of endocellular CGMP, production of inositol phosphate, changes in the cell membrane potential, phosphorylation of endocellular protein, activation of c-fos, lowering in pH, activation of G protein, cell promulgation, etc.) via the G protein coupled receptor protein.

Described below are specific explanations on the determining method of ligands according to the present invention which are provided only for illustrative purposes.

First, the G protein coupled receptor protein used for the method for determining the ligand may include any material so far as it contains a G protein coupled receptor protein or a peptide fragment or segment thereof (including a partial peptide thereof) or a salt thereof although it is preferable to express a large amount of G protein coupled receptor proteins in animal cells.

In the manufacture of the G protein coupled receptor protein, the above-mentioned method can be used and it may be carried out by expressing said protein encoding DNA in mammalian cells or in insect cells. With respect to the DNA fragment coding for the aimed region, complementary DNA may be used although it is not limited thereto. For example, gene fragments or synthetic DNA may be used as well.

In order to introduce the G protein coupled receptor protein-encoding DNA fragment into host animal cells and to express it efficiently, it is preferred that said DNA fragment is incorporated into the downstream site of polyhedron promoters derived from nuclear polyhedrosis virus belonging to baculovirus, promoters derived from SV40, promoters derived from retrovirus, metallothionein promoters, human heat shock promoters, cytomegalovirus promoters, SRα promoters, etc. Examinations of the quantity and the quality of the expressed receptor can be carried out by methods per se known to those of skill in the art or methods similar thereto. For example, they may be conducted by methods described in publications such as Nambi, P. et al: The Journal of Biochemical Society, vol.267, pages 19555–19559 (1992).

Accordingly, with respect to the determination of the ligand, the material containing a G protein coupled receptor protein or peptide segment thereof may include products containing G protein coupled receptor proteins which are purified by methods per se known to those of skill in the art or methods similar thereto, peptide fragments of said G protein coupled receptor protein, cells containing said G protein coupled receptor protein, membrane fractions of the cell containing said protein, etc.

When the G protein coupled receptor protein-containing cell is used in the determining method of the ligand, said cell may be immobilized with binding agents including glutaraldehyde, formalin, etc. The immobilization may be carried out by methods per se known to those of skill in the art or methods similar thereto.

The G protein coupled receptor protein-containing cells are host cells expressing the G protein coupled receptor protein. Examples of said host cells are microorganisms such as *Escherichia coli, Bacillus subtilis*, yeasts, insect cells, animal cells, etc.

The cell membrane fraction is a cell membrane-rich fraction which is prepared by methods per se known to those of skill in the art or methods similar thereto after disruption of cells. Examples of cell disruption may include a method for squeezing cells using a Potter-Elvejem homogenizer, a disruption by a Waring blender or a Polytron (manufactured by Kinematica), a disruption by ultrasonic waves, a disruption via blowing out cells from small nozzles together with applying a pressure using a French press or the like, etc. In the fractionation of the cell membrane, a fractionation method by means of centrifugal force such as a fractional centrifugal separation and a density gradient centrifugal separation is mainly used. For example, disrupted cellular liquid is centrifuged at a low speed (500 rpm to 3,000 rpm) for a short period (usually, from about one to ten minutes), the supernatant liquid is further centrifuged at a high speed (1,500 rpm to 3,000 rpm) usually for 30 minutes to two hours and the resulting precipitate is used as a membrane fraction. Said membrane fraction contains a lot of the expressed G protein coupled receptor protein and a lot of membrane components such as phospholipids and membrane proteins derived from the cells.

The amount of the G protein coupled receptor protein in the membrane fraction cell containing said G protein coupled receptor protein is preferably $10^3$–$10^8$ molecules per cell or, suitably, $10^5$ to $10^7$ molecules per cell. Incidentally, the more the expressed amount, the higher the ligand binding activity (specific activity) per membrane fraction whereby the construction of a highly sensitive screening system becomes possible and, moreover, it may enable us to measure the large amount of samples within the same lot.

In conducting the above-mentioned methods ① to ② wherein ligands capable of binding with the G protein coupled receptor protein are determined, a suitable G protein coupled receptor fraction and a labeled test compound are necessary. The G protein coupled receptor fraction is preferably a naturally occurring (natural type) G protein coupled receptor, a recombinant type G protein coupled receptor having the activity equivalent to that of the natural type. Here, the term "activity equivalent to" means the equivalent ligand binding activity, etc.

Suitable examples of the labeled test compound are angiotensin, bombesin, canavinoid, cholecystokinin, glutamine, serotonin, melatonin, neuropeptide Y, opioid, purine, vasopressin, oxytocin, VIP (vasoactive intestinal and related peptides), somatostatin, dopamine, motilin, amylin, bradykinin, CGRP (calcitonin gene related peptides), adrenomedullin, leukotriene, pancreastatin, prostaglandin, thromboxane, adenosine, adrenaline, α- and β-chemokine (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptides, galanin, an analogue derivative thereof, etc. which are labeled with [$^3$H], [$^{125}$I], [$^{14}$C], [$^{35}$S], etc.

Specifically, the determination of ligands capable of binding with G protein coupled receptor proteins is carried out as follows:

First, cells or cell membrane fractions containing the G protein coupled receptor protein are suspended in a buffer suitable for the determining method to prepare the receptor sample in conducting the method of determining the ligand binding with the G protein coupled receptor protein. The buffer may include any buffer such as Tris-HCl buffer or phosphate buffer with pH 4–10 (preferably, pH 6–8), etc., as long as it does not inhibit the binding of the ligand with the receptor. In addition, surface-active agents such as CHAPS, Tween 80™ (Kao-Atlas, Japan), digitonin, deoxycholate, etc. and various proteins such as bovine serum albumin (BSA), gelatin, milk derivatives, etc. may be added to the buffer with an object of decreasing the non-specific binding. Further, a protease inhibitor such as PMSF, leupeptin, E-64 (manufactured by Peptide Laboratory), pepstatin, etc. may be added with an object of inhibiting the decomposition of the receptor and the ligand by protease. A test compound labeled with a predetermined (or certain) amount (5,000 cpm to 500,000 cpm) of [$^3$H], [$^{125}$I], [$^{14}$C], [$^{35}$S], etc. is made copresent in 0.01 ml to 10 ml of said receptor solution. In order to know the non-specific binding amount (NSB), a reaction tube to which a great excessive amount of the unlabeled test compound is added is prepared as well. The reaction is carried out at 0–50° C. (preferably at 4–37° C.) for 20 minutes to 24 hours (preferably 30 minutes to three hours). After the reaction, it is filtered through a glass fiber filter or the like, washed with a suitable amount of the same buffer and the radioactivity remaining in the glass fiber filter is measured by means of a liquid scintillation counter or a gamma-counter. The test compound in which the count (B–NSB) obtained by subtracting the non-specific binding amount (NSB) from the total binding amount (B) is more than 0 cpm can be selected as a ligand to the G protein coupled receptor protein of the present invention.

In conducting the above-mentioned methods ④ to ⑤ wherein ligands capable of binding with the G protein coupled receptor protein are determined, the cell stimulating activity (e.g. the liberation of arachidonic acid, the liberation of acetylcholine, endocellular Ca 2+ liberation, endocellular cAMP production, the production of insitol phosphate, changes in the cell membrane potential, the phosphorylation of endocellular protein, the activation of c-fos, lowering of pH, the activation of G protein, cell promulgation, etc.) mediated by the G protein coupled receptor protein may be measured by known methods or by the use of commercially available measuring kits. To be more specific, G protein coupled receptor protein-containing cells are at first cultured in a multi-well plate or the like.

In conducting the determination of ligand, it is substituted with a fresh medium or a suitable buffer which does not show toxicity to the cells in advance of the experiment, and incubated for certain period after adding a test compound, etc. thereto. Then, the cells are extracted or the supernatant liquid is recovered and the resulting product is determined by each of the methods. When it is difficult to identify the production of the substance (e.g. arachdonic acid) which is to be an index for the cell stimulating activity due to the decomposing enzyme contained in the cell, an assay may be carried out by adding an inhibitor against said decomposing enzyme. With respect to the activity such as an inhibitory action against cAMP production, it may be detected as an inhibitory action against the production of the cells whose fundamental production is increased by forskolin or the like.

The kit used for the method of determining the ligand binding with the G protein coupled receptor protein includes a G protein coupled receptor protein or a peptide fragment thereof, cells containing the G protein coupled receptor protein, a membrane fraction from the cells containing the G protein coupled receptor protein, etc.

Examples of the kit for determining the ligand are as follows:

1. Reagent for Determining the Ligand

① Buffer for Measurement and Buffer for Washing

The buffering product wherein 0.05% of bovine serum albumin (manufactured by Sigma) is added to Hanks' Balanced Salt Solution (manufactured by Gibco).

This product may be sterilized by filtration through a membrane filter with a 0.45 μm pore size, and stored at 4° C. or may be formulated upon use.

② G Protein Coupled Receptor Protein Sample

CHO cells in which G protein coupled receptor proteins are expressed are subcultured at the rate of 5×10$^5$ cells/well in a 12-well plate and cultured at 37° C. in a humidified 5% $CO_2$/95% air atmosphere for two days to prepare the sample.

③ Labeled Test Compound

The compound which is labeled with commercially available [$^3$H], [$^{125}$I], [$^{14}$C], [$^{35}$S], etc. or labeled with a suitable method.

The product in a state of an aqueous solution is stored at 4° C. or at −20° C. and, upon use, diluted to 1 μM with a buffer for the measurement. In the case of the test compound which is hardly soluble in water, it is dissolved in dimethylformamide, DMSO, methanol, etc.

④ Unlabeled Test Compound

The same compound for the labeled one is prepared in a concentration of 100 to 1,000-fold concentrated state.

2. Method of Measurement

① G protein coupled receptor protein-expressing CHO cells cultured in a 12-well tissue culture plate are washed twice with 1 ml of buffer for the measurement and then 490 μl of buffer for the measurement is added to each well.

② Five μl of the labeled test compound is added and the mixture is made to react at room temperature for one hour. For measuring the nonspecific binding amount, 5 μl of the unlabeled test compound is added.

③ The reaction solution is removed from each well, which is washed with 1 ml of a buffer for the measurement three times. The labeled test compound which is binding with the cells is dissolved in 0.2N NaOH-1% SDS and mixed with 4 ml of a liquid scintillator A (manufactured by Wako Pure Chemical, Japan).

④ Radioactivity is measured using a liquid scintillation counter (manufactured by Beckmann).

The ligand which can bind with the G protein coupled receptor protein include substances occurring or existing, for example, in brain, pituitary gland, pancreas, etc. Examples of the ligand are angiotensin, bombesin, canavinoid, cholecystokinin, glutamine, serotonin, melatonin, neuropeptide Y, opioid, purine, vasopressin, oxytocin, VIP (vasoactive intestinal and related peptide), somatostatin, dopamine, motilin, amylin, bradykinin, CGRP (calcitonin gene related peptide), adrenomedullin, leukotriene, pancreastatin, prostaglandin, thromboxane, thromboxatin, adenosine, adrenaline, α- and β-chemokine (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptide, galanin, modified derivatives thereof, analogues thereof, etc.

Since the receptor protein encoded by pMAH2-17 is highly homologous to prinoceptors, it is considered that there are strong possibility of a subtype within prinoceptor families. All data including electrophysiological measurements are supporting that the mouse pancreatic β-cell strain, MIN6-derived receptor protein of the present invention (e.g., SEQ ID NO: 38 and SEQ ID NO: 39, or proteins encoded by pMAH2-17) is a novel purinoceptor subtype. In other words, it is suggested that the ligand capable of binding with the mouse pancreatic β-cell strain, MIN6-derived receptor protein of the present invention (e.g., SEQ ID NO: 38 and SEQ ID NO: 39, or proteins encoded by pMAH2-17) is a purine compound such as ATP. Further, the receptor protein (e.g., SEQ ID NO: 56, or proteins encoded by phAH2-17) is considered to be a novel human type purinoceptor. It is presumed that it is advantageously useful in efficiently screening for agonists or antagonists to receptor proteins which control or regulate functions in the central nervous system or immune system, related to purine compounds, and in developing pharmaceuticals.

(2) Preventive and Therapeutic Agent for of G Protein Conjugated Receptor Protein Deficiency Diseases If a ligand to the G protein coupled receptor protein is disclosed via the aforementioned method (1), the G protein coupled receptor protein-encoding DNA can be used a preventive and/or therapeutic agent for treating said G protein coupled receptor protein deficiency diseases depending upon the action that said ligand exerts.

For example, when there is a patient for whom the physiological action of the ligand cannot be expected because of a decrease in the G protein coupled receptor protein in vivo, the amount of the G protein coupled receptor protein in the brain cells of said patient can be increased whereby the action of the ligand can be fully achieved by:

(a) administering the G protein coupled receptor protein-encoding DNA to the patient to express it; or (b) inserting the G protein coupled receptor protein-encoding DNA into brain cells or the like to express it, followed by transplanting said brain cells or the like to said patient. Accordingly, the G protein coupled receptor protein-encoding DNA can be used as a safe and less toxic preventive and therapeutic agent for the G protein coupled receptor protein deficiency diseases. In an embodiment, it is suggested that the ligands capable of binding with the mouse pancreatic β-cell strain, MIN6-derived receptor protein of the present invention (e.g., SEQ ID NO: 38 and SEQ ID NO: 39, or proteins encoded by pMAH2-17) and further with the human-derived receptor protein of the present invention (e.g., SEQ ID NO: 56, or proteins encoded by phAH2-17) are purine compounds such as ATP. Therefore, the disease to be treated may include diseases or syndromes in connection with purine ligand compounds. Examples of such diseases may include cancer, immunodeficiency, autoimmune disease, rheumatoid arthritis, rejection on internal organ transplant, hypertension, diabetes, cystic fibrosis, hypotension, incontinence of urine, pain, etc.

(3) Preventive and Therapeutic Pharmaceutical Composition for Human-Derived G Protein Conjugated Receptor Protein Deficiency Diseases If the human-derived G protein coupled receptor protein-encoding DNA is screened and a ligand for said human-derived G protein coupled receptor protein can be clarified using the above-mentioned method (1), the human-derived G protein coupled receptor protein-encoding DNA can be used as an agent for the prevention or therapy of the deficiency diseases of said human-derived G protein coupled receptor protein depending upon the action that said ligand exhibits.

For example, when there is a patient for whom the physiological action of the ligand cannot be expected because of a decrease in the G protein coupled receptor protein. in vivo, the amount of the G protein coupled receptor protein in the brain cells of said patient can be increased whereby the action of the ligand can be fully achieved by:

(a) administering the G protein coupled receptor protein-encoding DNA to the patient to express it; or (b) inserting the G protein coupled receptor protein-encoding DNA into brain cells or the like to express it, followed by transplanting said brain cells or the like to said patient. Accordingly, the G protein coupled receptor protein-encoding DNA can be used as a safe and less toxic preventive and therapeutic agent for the G protein coupled receptor protein deficiency diseases.

When the G protein coupled receptor protein-encoding DNA is used as the above-mentioned agent, said DNA may be used alone or after inserting it into a suitable vector such as retrovirus vector, adenovirus vector, adenovirus-associated virus vector, etc. followed by subjecting the product vector to a conventional means. Thus, it may be administered orally parenterally, by inhalation spray, rectally, or topically as pharmaceutical compositions or formulations. Oral formulations include tablets (sugar-coated if necessary), capsules, elixirs, microcapsules, etc. Parenteral formulations include injections such as an aseptic solution or a suspension in water or in other pharmaceutically acceptable liquid. For example, the DNA of the present invention is admixed in a unit dose form which is required for preparing generally approved pharmaceutical preparations together with a physiologically acceptable carriers, flavoring agents, adjuvants, excipients, diluents, fillers, vehicles, antiseptics, stabilizers, binders, etc. whereupon the preparation can be manufactured. The amount of the effective component in those preparations is to be in such an extent that the suitable dose within an indicated range is achieved.

Examples of the additives which can be admixed in the tablets, capsules, etc. are binders such as gelatin, corn starch, tragacanth and gum arabicum; fillers such as crystalline cellulose; swelling agents such as corn starch, gelatin and alginic acid; lubricating agents such as magnesium stearate; sweetening agents such as sucrose, lactose and saccharine; and flavoring agents such as pepper mint, akamono oil and cherry. When the unit dose form of the preparation is a capsule, a liquid carrier such as fat/oil may be further added in addition of the above-mentioned types of materials. The aseptic composition for injection may be formulated by conventional practices for the preparations such as that the active substance in a vehicle such as water for injection is dissolved or suspended in naturally occurring plant oil such as sesame oil and palm oil.

Examples of an aqueous liquid for injection are a physiological saline solution and isotonic solutions containing glucose and other auxiliary agents (e.g. D-sorbitol, D-mannitol, sodium chloride, etc.) wherein a suitable auxiliary solubilizers such as alcohol (e.g. ethanol, etc.), polyalcohol (e.g. propylene glycol polyethylene glycol, etc.), nonionic surface-active agent (e.g. Polysorbate 80™, HCO-50, etc.), etc. may be jointly used. Examples of an oily liquid include sesame oil, soybean oil, etc. wherein benzyl benzoate, benzyl alcohol, etc. may be jointly used as auxiliary solubilizers. In addition, buffers (e.g. phosphate buffer, sodium acetate buffer, etc.), analgesic agents (e.g. benzalkonium chloride, procaine hydrochloride, etc.), stabilizers (e.g. human serum albumin, polyethylene glycol, etc.), stabilizers (e.g. benzyl alcohol phenol, etc.), antioxidants, etc. may be admixed therewith too. The prepared injection solution is filled in suitable ampoules. The preparation prepared as such is safe and less toxic and, therefore, it can be administered to warm-blooded animals (e.g., rat, rabbit, sheep, swine, cattle, cat, dog, monkey, human beings, etc.).

Specific dose levels of said DNA may vary depending upon a variety of factors including the activity of drugs employed, the age, body weight, general health, sex, diet, time of administration, route of administration, drug combination, and the severity of the symptom. In the case of oral administration, it is usually about 0.1–100 mg, preferably about 1.0–50 mg or, more preferably, about 1.0–20 mg per day for adults (as 60 kg). When it is administered parenterally, its dose at a time may vary depending upon the object (patient) to be administered, organs to be administered, symptoms, administering methods, etc. but, in the case of injections, it is usually convenient to give by an intravenous route in an amount of about 0.01–30 mg, preferably about 0.1–20 mg or, more preferably, about 0.1–30 mg per day to adults (as 60 kg). In the case of other animals, the dose calculated for 60 kg may be administered as well.

(4) Quantitative Determination of Ligand to the G Protein Conjugated Receptor Protein of the Present Invention.

The G protein coupled receptor protein or a peptide fragment thereof has a binding property to ligand and, therefore, it is capable of determining quantitatively an amount of ligands in vivo with good sensitivity.

This quantitative determination may be carried out by, for example, combining with a competitive method. Thus, samples to be determined is contacted with G protein coupled receptor proteins or peptide fragments thereof so that the ligand concentration in said sample can be determined. In one embodiment of the quantitative determination, the protocols described in the following ① and ② or the methods similar thereto may be used:

① Hiroshi Irie (ed): "Radioimmunoassay" (Kodansha, Japan, 1974); and

② Hiroshi Irie (ed): "Radioimmunoassay, Second Series" (Kodansha, Japan, 1979).

(5) Screening of Compound Inhibiting the Binding of Ligand with the G Protein Conjugated Receptor Protein of the Present Invention G Protein coupled receptor proteins or peptide fragments thereof are used. Alternatively, expression systems for recombinant type G Protein coupled receptor proteins or peptide fragments thereof are constructed and receptor binding assay systems using said expression system are used. In these assay systems, it is possible to screen compounds (e.g. peptides, proteins, nonpeptidic compounds, synthetic compounds, fermented products, cell extracts, plant extracts, animal tissue extracts, etc.) or salts thereof which inhibits the binding of a ligand with the G protein coupled receptor protein. Such a compound includes a compound exhibiting a G protein coupled receptor-mediated cell stimulating activity (e.g. activity of promoting or activity of inhibiting physiological reactions including liberation of arachdonic acid, liberation of acetylcholine, endocellular $Ca^{2+}$ liberation, endocellular cAMP production, endocellular cGMP production, production of inositol phosphate, changes in cell membrane potential, phosphorylation of endocellular proteins, activation of c-fos, lowering of pH, activation of G protein, cell promulgation, etc.) (so-called "G protein coupled receptor-agonist"), a compound free of such a cell stimulating activity (so-called "G protein coupled receptor-antagonist"), etc.

Thus, the present invention provides a method of screening a compound which inhibits the binding of a ligand with a G protein coupled receptor protein or a salt thereof, characterized in comparing the following two cases:

(i) the case wherein the ligand is contacted with the G protein coupled receptor protein or salt thereof, or a peptide fragment thereof or a salt thereof; and (ii) the case wherein the ligand is contacted with a mixture of the G protein coupled receptor protein or salt thereof or the peptide fragment or salt thereof and said test compound.

In said screening method, one characteristic feature of the present invention resides in that the amount of the ligand bonded with said G protein coupled receptor protein or the peptide fragment thereof, the cell stimulating activity of the ligand, etc. are measured in the case where (i) the ligand is contacted with G protein coupled receptor proteins or peptide fragments thereof and in the case where (ii) the ligand and the test compound are contacted with the G protein coupled receptor protein or the peptide fragment thereof, respectively and then compared therebetween.

In one more specific embodiment of the present invention, the following is provided:

① a method of screening a compound or a salt thereof which inhibits the binding of a ligand with a G protein coupled receptor protein, characterized in that, when a labeled ligand is contacted with a G protein coupled receptor protein or a peptide fragment thereof and when a labeled ligand and a test compound are contacted with a G protein coupled receptor protein or a peptide fragment thereof, the amounts of the labeled ligand bonded with said protein or peptide fragment thereof or salt thereof are measured and compared;

② a method of screening a compound or a salt thereof which inhibits the binding of a ligand with a G protein coupled receptor protein, characterized in that, when a labeled ligand is contacted with cells containing G protein coupled receptor proteins or a membrane fraction of said cells and when a labeled ligand and a test compound are contacted with cells containing G protein coupled receptor proteins or a membrane fraction of said cells, the amounts of the labeled ligand binding with said protein or peptide fragment thereof or salt thereof are measured and compared;

③ a method of screening a compound or a salt thereof which inhibits the binding of a ligand with a G protein coupled receptor protein, characterized in that, when a labeled ligand is contacted with G protein coupled receptor proteins expressed on the cell membrane by culturing a transformant containing a G protein coupled receptor protein encoding DNA and when a labeled ligand and a test compound are contacted with G protein coupled receptor proteins expressed on the cell membrane by culturing a transformant containing a G protein coupled receptor protein encoding DNA, the amounts of the labeled ligand binding with said G protein coupled receptor protein are measured and compared;

④ a method of screening a compound or a salt thereof which inhibits the binding of a ligand with a G protein coupled receptor protein, characterized in that, when a G protein coupled receptor protein-activating compound (e.g. a ligand to the G protein coupled receptor protein) is contacted with cells containing G protein coupled receptor proteins and when the G protein coupled receptor protein-activating compound and a test compound are contacted with cells containing G protein coupled receptor proteins, the resulting G protein coupled receptor protein-mediated cell stimulating activities (e.g. activities of promoting or activities of inhibiting physiological responses including liberation of arachdonic acid, liberation of acetylcholine, endocellular $Ca^{2+}$ liberation, endocellular cAMP production, endocellular cGMP production, production of inositol phosphate, changes in cell membrane potential, phosphorylation of endocellular proteins, activation of c-fos, lowering of pH, activation of G protein, cell promulgation, etc.) are measured and compared; and ⑤ a method of screening a compound or a salt thereof which inhibits the binding of a ligand with a G protein coupled receptor protein, characterized in that, when a G protein coupled receptor protein-activating compound (e.g. a ligand to the G protein coupled receptor protein) is contacted with G protein coupled receptor proteins expressed on cell membranes by culturing transformants containing G protein coupled receptor protein-encoding DNA and when a G protein coupled receptor protein-activating compound and a test compound are contacted with the G protein coupled receptor protein expressed on the cell membrane by culturing the transformant containing the G protein coupled receptor protein-encoding DNA, the resulting G protein coupled receptor protein-mediated cell stimulating activities (activities of promoting or activities of inhibiting physiological responses such as liberation of arachdonic acid, liberation of acetylcholine, endocellular $Ca^{2+}$ liberation, endocellular cAMP production, endocellular cGMP production, production of inositol phosphate, changes in cell membrane potential, phosphorylation of endocellular proteins, activation of c-fos, lowering of pH, activation of G protein, and cell promulgation) are measured and compared.

Before the G protein coupled receptor protein of the present invention was obtained, the G protein coupled receptor agonist or antagonist had to be screened by, first, obtaining a candidate compound by using G protein coupled receptor protein-containing cells, tissues or cell membrane fractions derived from rat or the like (primary screening) and, then, making sure whether the candidate compound really inhibits the binding between human G protein coupled receptor proteins and ligands (secondary screening). Other receptor proteins inevitably exist when the cells, the tissues or the cell membrane fractions are used as they are, whereby they intrinsically make it difficult to screen agonists or antagonists to the desired receptor proteins. By using the human-derived G protein coupled receptor protein, however, there is no need of effecting the primary screening, whereby it is allowable to efficiently screen a compound that inhibits the binding between a ligand and a G protein coupled receptor. Besides, it is allowable to evaluate whether the compound that is screened is a G protein coupled receptor agonist or a G protein coupled receptor antagonist.

Specific explanations of the screening method will be given as hereunder.

First, with respect to the G protein coupled receptor protein used for the screening method of the present invention, any product may be used so far as it contains G protein coupled receptor proteins or peptide fragment thereof although the use of a membrane fraction of mammalian organs is suitable. However, human organs is extremely hardly available and, accordingly, G protein coupled receptor proteins which are expressed in a large amount using a recombinant are suitable for the screening.

In the manufacture of the G protein coupled receptor protein, the above-mentioned method can be used and it may be carried out by expressing the DNA coding for said protein in mammalian cells or in insect cells. With respect to the DNA fragment coding for the target region, complementary DNA may be used although it is not limited thereto. Thus, for example, gene fragments or synthetic DNA may be used as well.

In order to introduce the G protein coupled receptor protein-encoding DNA fragment into host animal cells and to express it efficiently, it is preferred that said DNA fragment is incorporated into the downstream of polyhedron promoter of nuclear polyhedrosis virus belonging to baculovirus, promoter derived from SV40, promoter of retrovirus, metallothionein promoter, human heat shock promoter, cytomegalovirus promoter, SRa promoter, etc. Examinations of the quantity and the quality of expressed receptors can be, carried out by known methods per se or modified methods substantially analogous thereto. For example, they may be conducted by the method described in publications such as Nambi, P. et al.: The Journal of Biochemical Society, vol.267, pages 19555–19559 (1992).

Accordingly, in the screening method, the substance containing a G protein coupled receptor protein or a peptide fragment thereof may be a G protein coupled receptor protein which is purified by known methods per se or a G protein coupled receptor protein fragment which is purified by known methods per se, or a cell containing said protein or a cell membrane fraction of the cell containing said protein, etc.

When the G protein coupled receptor proteincontaining cells are used in the screening method, said cells may be immobilized with glutaraldehyde, formalin, etc. The immobilization may be carried out by known methods per se or modified methods substantially analogous thereto.

The G protein coupled receptor protein-containing cells are host cells expressing the G protein coupled receptor protein. Examples of said host cells may include *Escherichia coli, Bacillus subtilis,* yeasts, insect cells, animal cells such as CHO cell and COS cell, etc.

Cell membrane fractions are fractions which contain a lot of cell membranes prepared by known methods per se or modified methods substantially analogous thereto after disrupting or crushing the cells. Examples of disruptions of the cell may include methods by squeezing the cells with a Potter-Elvejem homogenizer, disrupting or crushing by a Waring blender or a Polytron (manufactured by Kinematica), disrupting or crushing by means of ultrasonic wave, disrupting by blowing out the cells from small nozzles together with applying a pressure with a French press or the like, etc. Fractionation of the cell membrane is carried out mainly by fractionation techniques by means of centrifugal force such as a fractional centrifugal separation and a density gradient centrifugal separation. For example, disrupted liquid of cells is centrifuged at a low speed (500 rpm to 3,000 rpm) for a short period (usually, from about one to ten minutes), the supernatant liquid is further centrifuged at a high speed (1,500 rpm to 3,000 rpm) usually for 30 minutes to two hours and the resulting precipitate is used as a membrane fraction. Said membrane fraction contains a lot of expressed G protein coupled receptor proteins and membrane components such as phospholipids and membrane proteins derived from the cells.

The amount of the G protein coupled receptor protein in the G protein coupled receptor protein-containing cell and in the cell membrane fraction obtained from the cell is preferably $10^3$–$10^8$ molecules per cell or, suitably, $10^5$ to $10^7$ molecules per cell. Incidentally, the more the expressed amount, the higher the ligand binding activity (specific activity) per membrane fraction whereby the construction of a highly sensitive screening system is possible and, moreover, it is possible to measure the large amount of samples in the same lot.

In conducting the above-mentioned methods ① to ③ for screening the compound capable of inhibiting the binding of the ligand with the G protein coupled receptor protein, a suitable G protein coupled receptor fraction and a labeled ligand are necessary. With respect to the G protein coupled receptor fraction, it is preferred to use naturally occurring G protein coupled receptors (natural type G protein coupled receptors) or recombinant type G protein coupled receptor fractions with the activity equivalent to that of the natural type G protein coupled. Here the term "activity equivalent to" means the same ligand binding activity, or the substantially equivalent ligand binding activity.

With respect to the labeled ligand, it is possible to use labeled ligands, labeled ligand analogized compounds, etc. For example, ligands labeled with [$^3$H], [$^{125}$I], [$^{14}$C], [$^{35}$S], etc. and other labeled substances may be utilized.

Specifically, G protein coupled receptor protein-containing cells or cell membrane fractions are first suspended in a buffer which is suitable for the determining method to prepare the receptor sample in conducting the screening for a compound which inhibits the binding of the ligand with the G protein coupled receptor protein. With respect to the buffer, any buffer such as Tris-HCl buffer or phosphate buffer of pH 4–10 (preferably, pH 6–8) which does not inhibit the binding of the ligand with the receptor may be used.

In addition, a surface-active agent such as CHAPS, Tween 80™ (Kao-Atlas, Japan), digitonin, deoxycholate, etc. and/or various proteins such as bovine serum albumin (BSA), gelatine, etc. may be added to the buffer with an object of decreasing the nonspecific binding. Further, a protease inhibitor such as PMSF, leupeptin, E-64 (manufactured by Peptide Laboratory, Japan), pepstatin, etc. may be added with an object of inhibiting the decomposition of the receptor and the ligand by protease. A labeled ligand in a certain amount (5,000 cpm to 500,000 cpm) is added to 0.01 ml to 10 ml of said receptor solution and, at the same time, $10^{-4}$ M to $10^{-10}$ M of a test compound is made copresent. In order to determine the nonspecific binding amount (NSB), a reaction tube to which a great excessive amount of unlabeled test compounds is added is prepared as well.

The reaction is carried out at 0–50° C. (preferably at 4–37° C.) for 20 minutes to 24 hours (preferably 30 minutes to three hours). After the reaction, it is filtered through a glass fiber filter, a filter paper, or the like, washed with a suitable amount of the same buffer and the radioactivity retained in the glass fiber filter, etc. is measured by means of a liquid scintillation counter or a gamma-counter. Supposing that the count ($B_0$–NSB) obtained by subtracting the nonspecific binding amount (NSB) from the total binding amount ($B_0$) wherein an antagonizing substance is not present is set at 100%, the test compound in which the specific binding amount (B–NSB) obtained by subtracting the nonspecific binding amount (NSB) from the total binding amount (B) is, for example, less than 50% may be selected as a candidate ligand to the G protein coupled receptor protein of the present invention.

In conducting the above-mentioned methods ④ to ⑤ for screening the compound which inhibits the binding of the ligand with the G protein coupled receptor protein, the G protein coupled receptor protein-mediated cell stimulating activity (e.g. activities of promoting or activities of inhibiting physiological responses such as liberation of arachidonic acid, liberation of acetylcholine, endocellular $Ca^{2+}$ liberation, endocellular cAMP production, production of insitol phosphate, changes in the cell membrane potential, phosphorylation of endocellular proteins, activation of c-fos, lowering of pH, activation of G protein and cell promulgation, etc.) may be measured by known methods or by the use of commercially available measuring kits. To be more specific, G protein coupled receptor protein-containing cells are at first cultured in a multiwell plate or the like.

In conducting the screening, it is substituted with a suitable buffer which does not show toxicity to fresh media or cells in advance, incubated for a certain period after adding a test compound, etc. thereto. The resultant cells are extracted or the supernatant liquid is recovered and the resulting product is determined, preferably quantitatively, by each of the methods. When it is difficult to identify the production of the index substance (e.g. arachidonic acid, etc.) which is to be an index for the cell stimulating activity due to the presence of decomposing enzymes contained in the cell, an assay may be carried out by adding an inhibitor against said decomposing enzyme. With respect to the activities such as an inhibitory action against cAMP production, it may be detected as an inhibitory action against the cAMP production in the cells whose fundamental production has been increased by forskolin or the like.

In conducting a screening by measuring the cell stimulating activity, cells in which a suitable G protein coupled receptor protein is expressed are necessary. Preferred G protein coupled receptor protein-expressing cells are naturally occurring G protein coupled receptor protein (natural type G protein coupled receptor protein)-containing cell lines or strains (e.g. mouse pancreatic β cell line, MIN6, etc.), the above-mentioned recombinant type G protein coupled receptor protein-expressing cell lines or strains, etc.

Examples of the test compound includes peptides, proteins, non-peptidic compounds, synthesized compounds, fermented products, cell extracts, plant extracts, animal tissue extracts, serum, blood, body fluid, etc. Those compounds may be novel or known.

A kit for screening the compound which inhibits the binding of the ligand with the G protein coupled receptor protein or a salt thereof of the present invention comprises a G protein coupled receptor protein or a peptide fragment thereof, or G protein coupled receptor protein-containing cells or cell membrane fraction thereof.

Examples of the screening kit include as follows:
1. Reagent for Determining Ligand
① Buffer for Measurement and Buffer for Washing The product wherein 0.05% of bovine serum albumin (manufactured by Sigma) is added to Hanks' Balanced Salt Solution (manufactured by Gibco).

This may be sterilized by filtration through a membrane filter with a 0.45 μm pore size, and stored at 4° C. or may be prepared upon use.

② Sample of G Protein Conjugated Receptor Protein

CHO cells in which a G protein coupled receptor protein is expressed are subcultured at the rate of $5 \times 10^5$ cells/well in a 12-well plate and cultured at 37° C. with a 5% $CO_2$ and 95% air atomosphere for two days to prepare the sample.

③ Labeled Ligand

The ligand which is labeled with commercially available $[^3H]$, $[^{125}I]$, $[^{14}C]$, $[^{35}S]$, etc.

The product in a state of an aqueous solution is stored at 4° C. or at −20° C. and, upon use, diluted to 1 μM with a buffer for the measurement.

④ Standard Ligand Solution

Ligand is dissolved in PBS containing 0.1% of bovine serum albumin (manufactured by Sigma) to make 1 mM and stored at −20° C.

2. Method of the Measurement

① CHO cells are cultured in a 12-well tissue culture plate to express G protein coupled receptor proteins. The G protein coupled receptor protein-expressing CHO cells are washed with 1 ml of buffer for the measurement twice. Then 490 μl of buffer for the measurement is added to each well.

② Five μl of a test compound solution of $10^{-3}$ to $10^{-10}$ M is added, then 5 μl of a labeled ligand is added and is made to react at room temperature for one hour. For knowing the non-specific binding amount, 5 μl of the ligand of $10^{-3}$ M is added instead of the test compound.

③ The reaction solution is removed from the well, which is washed with 1 ml of buffer for the measurement three times. The labeled ligand binding with the cells is dissolved in 0.2N NaOH-1% SDS and mixed with 4 ml of a liquid scintillator A (manufactured by Wako Pure Chemical, Japan).

④ Radioactivity is measured using a liquid scintillation counter (manufactured by Beckmann) and PMB (percent of maximum binding) is calculated by the following expression:

$$PMB=[(B-NSB)/(B_0-NSB)] \times 100$$

PMB: Percent of maximum binding
B: Value when a sample is added
NSB: Nonspecific binding
$B_0$: Maximum binding The compound or a salt thereof obtained by the screening method or by the screening kit is a compound which inhibits the binding of a ligand with a G protein coupled receptor protein and, more particularly, it is a compound having a cell stimulating activity mediated via a G protein coupled receptor or a salt thereof (so-called "G protein coupled receptor agonist") or a compound having no said stimulating activity (so-called "G protein coupled receptor antagonist"). Examples of said compound are peptides, proteins, non-peptidic compounds, synthesized compounds, fermented products, etc. and the compound may be novel or known.

Said G protein coupled receptor agonist has the same physiological action as the ligand to the G protein coupled receptor protein has and, therefore, it is useful as a safe and less toxic pharmaceutical composition depending upon said ligand activity.

On the other hand, said G protein coupled receptor antagonist is capable of inhibiting the physiological activity of the ligand to the G protein coupled receptor protein and, there fore, it is useful as a safe and less toxic pharmaceutical composition for inhibiting said ligand activity.

It is also strongly suggested that agonists and/or antagonists related to the receptor encoded by pMAH2-17 obtained in Example 19 and/or the receptor encoded by phAH2-17 obtained in Example 21 would be useful in therapeutic or prophylactic treatment of diseases or syndromes in connection with purine ligand compounds or related analogues. It is expected that the agonists of the receptor encoded by pMAH2-17 and/or of the receptor encoded by phAH2-17 are useful as an immunomodulator or an antitumor agent, in addition they are useful in therapeutically or prophylactically treating hypertension, diabetes, cystic fibrosis, etc. It is still expected that the antagonists of the receptor encoded by pMAH2-17 and/or of the receptor encoded by phAH2-17 are useful as hypotensive agents, analgesics, agents for therapeutically or prophylactically treating incontinence of urine, etc. With regard to purinoceptors, the mutation of conserved basic amino acid residues in the 6th or 7th putative transmembrane domain of purinoceptors introduces alteration into the receptor's responses to ATP (J. Biol. Chem., Vol. 270(9), pp. 4185–4188 (1995)). It is suggested that ATP is related to blood pressure control and circular systems via receptors (Circulation Research, Vol. 58(3), pp. 319–330 (1986)) and that ATP and purinoceptors are closely related (Am. Phys. Soc., pp. C577–C606 (1993)).

When the compound or the salt thereof obtained by the screening method or by the screening kit is used as the above-mentioned pharmaceutical composition, a conventional means may be applied therefor. The compound or the salt thereof may be orally, parenterally, by inhalation spray, rectally, or topically administered as pharmaceutical compositions or formulations (e.g. powders, granules, tablets, pills, capsules, injections, syrups, emulsions, elixirs, suspensions, solutions, etc.). For example, it may be used by an oral route as tablets (sugar-coated if necessary), capsules, elixiers, microcapsules, etc. or by a parenteral route as injections such as an aseptic solution or a suspension in water or in other pharmaceutically acceptable liquid. The pharmaceutical compositions or formulations may comprise at least one such compound alone or in admixture with pharmaceutically acceptable carriers, adjuvants, vehicles, excipients and/or diluents. The pharmaceutical compositions cam be formulated in accordance with conventional methods. For example, said compound or the salt thereof is mixed in a unit dose form which is required for preparing a generally approved pharmaceutical preparations together with a physiologically acceptable carriers, flavoring and/or perfuming agents (fragrances), fillers, vehicles, antiseptics, stabilizers, binders, etc. whereupon the preparation can be manufactured. An amount of the effective component in those preparations is to be in such an extent that the suitable dose within an indicated range is achieved.

Examples of the additives which can be admixed in the tablets, capsules, etc. are binders such as gelatin, corn starch, tragacanth and gum arabicum; fillers such as crystalline cellulose; swelling agents such as corn starch, gelatin and alginic acid; lubricants such as magnesium stearate; sweetening agents such as sucrose, lactose and saccharine; preservatives such as parabens and sorbic acid; antioxidants such as ascorbic acid, α-tocopherol and cysteine; fragrances such as peppermint, akamono oil and cherry; disintegrants; buffering agents; etc. Other additives may include mannitol, maltitol, dextran, agar, chitin, chitosan, pectin, collagen, casein, albumin, synthetic or semi-synthetic polymers, glyceride, lactide,etc. When the unit form of the preparation is a capsule, a liquid carrier such as fat/oil may be further added besides the above-mentioned types of materials. The aseptic composition for injection may be formulated by a conventional technique or practice for the preparations such as that the active substance in a vehicle such as water for injection is dissolved or suspended in a naturally occurring plant oil such as sesame oil and palm oil.

Examples of an aqueous liquid for the injection are a physiological saline solution and isotonic solutions containing glucose and other auxiliary agents (e.g. D-sorbitol, D-mannitol, sodium chloride, etc.) wherein a suitable auxiliary solubilizers such as alcohol (e.g. ethanol, etc.), polyalcohol (e.g. propylene glycol, polyethylene glycol, etc.), nonionic surface-active agent (e.g. Polysorbate 80™, HCO-50, etc.), etc. may be jointly used. In the case of the oily liquid, sesame oil, soybean oil, etc. may be exemplified wherein benzyl benzoate, benzyl alcohol, etc. may be jointly used as auxiliary solubilizers.

In addition, buffers (e.g. phosphate buffer, sodium acetate buffer, etc.), analgesic agents (e.g. benzalkonium chloride, procaine hydrochloride, etc.), stabilizers (e.g. human serum albumin, polyethylene glycol, etc.), stabilizers (e.g. benzyl alcohol, phenol, etc.), antioxidants, etc. may be compounded therewith too. The prepared injection solution is filled in suitable ampoules. The formulation prepared as such is safe and less toxic and, therefore, it can be administered to warm-blooded. mammals such as rats, rabbits, sheep, swines, cattle, cats, dogs, monkeys, human being, etc.

Dose levels of said compound or the salt thereof may vary depending upon the symptom. Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy. In the case of oral administration, it is usually about 0.1–100 mg, preferably about 1.0–50 mg or, more preferably, about 1.0–20 mg per day for adults (as 60 kg). When it is administered parenterally, its dose at a time may vary depending upon the object to be administered, organs to be administered, symptoms, administering methods, etc. The term "parenteral" as used herein includes subcutaneous injections, intravenous, intramuscular, intraperitoneal injections, or infusion techniques. In the case of injections, it is usually convenient to give by an intraveous route in an amount of about 0.01–30 mg, preferably about 0.1–20 mg or, more preferably, about 0.1–10 mg per day to adults (as 60 kg). In the case of other animals, the dose calculated for 60 kg may be administered as well.

(6) Manufacture of Antibody or Antiserum against the G Protein Coupled Receptor Protein of the Present Invention, Its Peptide Fragment or Its Salt Antibodies (e.g. polyclonal antibody and monoclonal antibody) and antisera against the G protein coupled receptor protein or salt thereof of the present invention or against the peptide fragment of the G protein coupled receptor protein or salt thereof of the present invention may be manufactured by antibody or antiserum-manufacturing methods per se known to those of skill in the art or methods similar thereto, using the G protein coupled receptor protein or its salt of the present invention or the peptide fragment of the G protein coupled receptor protein or its salt of the present invention. For example, monoclonal antibodies can be manufactured by the method as given below.

[Preparation of Monoclonal Antibody]

(a) Preparation of Monoclonal Antibody-Producing Cells

The G protein coupled receptor protein of the present invention or its salt or the peptide fragment of the G protein coupled receptor protein of the present invention or its salt (hereinafter, may be abbreviated as the "G protein coupled receptor protein") is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be. administered. The administration is usually carried out once every two to six weeks and two to ten times in total. Examples of the applicable warm-blooded animals are monkeys, rabbits, dogs, guinea pigs, mice, rats, sheep, goats and chickens and the use of mice and rats is preferred.

In the preparation of the cells which produce monoclonal antibodies, an animal wherein the antibody titer is noted is selected from warm-blooded animals (e.g. mice) immunized with antigens, then spleen or lymph node is collected after two to five days from the final immunization and antibody-producing cells contained therein are fused with myeloma cells to give monoclonal antibody-producing hybridomas. Measurement of the antibody titer in antisera may, for example, be carried out by reacting a labeled G protein coupled receptor protein (which will be mentioned later) with the antiserum followed by measuring the binding activity of the labeling agent with the antibody. The operation for fusing may be carried out, for example, by a method of Koehler and Milstein (Nature, 256, 495, 1975). Examples of the fusion accelerator are polyethylene glycol (PEG), Sendai virus, etc. and the use of PEG is preferred.

Examples of the myeloma cells are NS-1, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added in a concentration of about 10–80% followed by incubating at 20–40° C. (preferably, at 30–37°° C.) for one to ten minutes, an efficient cell fusion can be carried out.

Various methods may be applied for screening a hybridoma which produces anti-G protein coupled receptor antibody. For example, a supernatant liquid of hybridoma culture is added to a solid phase (e.g. microplate) to which the G protein coupled receptor protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then anti-G protein coupled receptor monoclonal antibodies bound on the solid phase are detected; or a supernatant liquid of the hybridoma culture is added to the solid phase to which anti-immunoglobulin or protein A is adsorbed, then the G protein coupled receptor labeled with a radioactive substance or an enzyme is added and anti-G protein coupled receptor monoclonal antibodies bonded with the solid phase is detected.

Selection and cloning of the anti-G protein coupled receptor monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1–20% (preferably 10–20%) of fetal calf serum (FCS), a GIT medium (Wako Pure Chemical, Japan) containing 1–20% of fetal calf serum and a serum-free medium for hybridoma culturing (SFM-101; Nissui Seiyaku, Japan). The culturing temperature is usually 20–40° C. and, preferably, about 37° C. The culturing time is usually from five days to three weeks and, preferably, one to two weeks. The culturing is usually carried out in 5% carbon dioxide gas. The antibody titer of the supernatant liquid of the hybridoma culture may be measured by the same manner as in the above-mentioned measurement of the antibody titer of the anti-G protein coupled receptor in the antiserum.

The cloning can be usually carried out by methods known per se such as techniques in semi-solid agar and limiting dilution. The cloned hybridoma is preferably cultured in modern serum-free culture media to obtain optimal amounts of antibody in supernatants. The target monoclonal antibody is also preferably obtained from ascitic fluid derived from a mouse, etc. injected intraperitoneally with live hybridoma cells.

(b) Purification of the Monoclonal Antibody

Like in the separation/purification of conventional polyclonal antibodies, the separation/purification of the anti-G protein coupled receptor monoclonal antibody may be carried out by methods for separating/purifying immunoglobulin (such as salting-out, precipitation with an alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent (such as an antigen-binding solid phase, protein A or protein G) and the bond is dissociated whereupon the antibody is obtained.

The G protein coupled receptor antibody of the present invention which is manufactured by the aforementioned method (a) or (b) is capable of specifically recognizing G protein coupled receptors and, accordingly, it can be used for a quantitative determination of the G protein coupled receptor in test liquid samples and particularly for a quantitative determination by sandwich immunoassays.

Thus, the present invention provides, for example, the following methods:

(i) a quantitative determination of a G protein coupled receptor in a test liquid sample, which comprises
  (a) competitively reacting the test liquid sample and a labeled G protein coupled receptor with an antibody which reacts with the G protein coupled receptor of the present invention, and
  (b) measuring the ratio of the labeled G protein coupled receptor binding with said antibody; and (ii) a quantitative determination of a G protein coupled receptor in a test liquid sample, which comprises
  (a) reacting the test liquid sample with an antibody immobilized on an insoluble carrier and a labeled antibody simultaneously or continuously, and
  (b) measuring the activity of the labeling agent on the insoluble carrier wherein one antibody is capable of recognizing the N-terminal region of the G protein coupled receptor while another antibody is capable of recognizing the C-terminal region of the G protein coupled receptor.

When the monoclonal antibody of the present invention recognizing a G protein coupled receptor (hereinafter, may be referred to as "anti-G protein coupled receptor antibody") is used, G protein coupled receptors can be measured and, moreover, can be detected by means of a tissue staining, etc. as well. For such an object, antibody molecules per se may be used or F(ab')$_2$, Fab' or Fab fractions of the antibody molecule may be used too. There is no particular limitation for the measuring method using the antibody of the present invention and any measuring method may be used so far as it relates to a method in which the amount of antibody, antigen or antibody-antigen complex, depending on or corresponding to the amount of antigen (e.g. the amount of G protein coupled receptor, etc.) in the liquid sample to be measured, is detected by a chemical or a physical means and then calculated using a standard curve prepared by a standard solution containing the known amount of antigen. For example, nephrometry, competitive method, immunometric method and sandwich method are suitably used and, in terms of sensitivity and specificity, the sandwich method which will be described herein later is particularly preferred.

Examples of the labeling agent used in the measuring method using the labeling substance are radioisotopes, enzymes, fluorescent substances, luminescent substances, colloids, magnetic substances, etc. Examples of the radioisotope are [$^{125}$I], [$^{131}$I], [$^{3}$H] and [$^{14}$C]; preferred examples of the enzyme are those which are stable and with big specific activity, such as β-galactosidase, β-glucosidase, alkali phosphatase, peroxidase and malate dehydrogenase; examples of the fluorescent substance are fluorescamine, fluorescein isothiocyanate, etc.; and examples of the luminescent substance are luminol, luminol derivatives, luciferin, lucigenin, etc. Further, a biotin-avidin system may also be used for binding an antibody or antigen with a labeling agent.

In an insolubilization (immobilization) of antigens or antibodies, a physical adsorption may be used or a chemical binding which is usually used for insolubilization or immobilization of proteins or enzymes may be used as well. Examples of the carrier are insoluble polysaccharides such as agarose, dextran and cellulose; synthetic resins such as polystyrene, polyacrylamide and silicone; glass; etc.

In a sandwich (or two-site) method, the test liquid is made to react with an insolubilized anti-G protein coupled receptor antibody (the first reaction), then it is made to react with a labeled anti-G protein coupled receptor antibody (the second reaction) and the activity of the labeling agent on the insoluble carrier is measured whereupon the amount of the G protein coupled receptor in the test liquid can be determined. The first reaction and the second reaction may be conducted reversely or simultaneously or they may be conducted with an interval. The type of the labeling agent and the method of insolubilization (immobilization) may be the same as those mentioned already herein. In the immunoassay by means of a sandwich method, it is not always necessary that the antibody used for the labeled antibody and the antibody for the solid phase is one type or one species but, with an object of improving the measuring sensitivity, etc., a mixture of two or more antibodies may be used too.

In the method of measuring G protein coupled receptors by the sandwich method of the present invention, the preferred anti-G protein coupled receptor antibodies used for the first and the second reactions are antibodies wherein their sites binding to the G protein coupled receptors are different each other. Thus, the antibodies used in the first and the second reactions are those wherein, when the antibody used in the second reaction recognizes the C-terminal region of the G protein coupled receptor, then the antibody recognizing the site other than C-terminal regions, e.g. recognizing the N-terminal region, is preferably used in the first reaction.

The anti-G protein coupled receptor antibody of the present invention may be used in a measuring system other than the sandwich method such as a competitive method, an immunometric method and a nephrometry. In a competitive method, an antigen in the test solution and a labeled antigen are made to react with an antibody in a competitive manner, then an unreacted labeled antigen (F) and a labeled antigen binding with an antibody (B) are separated (i.e. B/F separation) and the labeled amount of any of B and F is measured whereupon the amount of the antigen in the test solution is determined. With respect to a method for such a reaction, there are a liquid phase method in which a soluble antibody is used as the antibody and the B/F separation is conducted by polyethylene glycol, a second antibody to the above-mentioned antibody, etc.; and a solid phase method in which an immobilized antibody is used as the first antibody or a soluble antibody is used as the first antibody while an immobilized antibody is used as the second antibody.

In an immunometric method, an antigen in the test solution and an immobilized antigen are subjected to a competitive reaction with a certain amount of a labeled antibody followed by separating into solid and liquid phases; or the antigen in the test:solution and an excess amount of labeled antibody are made to react, then a immobilized antigen is added to bind an unreacted labeled antibody with the solid phase and separated into solid and liquid phases. After that, the labeled amount of any of the phases is measured to determine the antigen amount in the test solution.

In a nephrometry, the amount of insoluble sediment which is produced as a result of the antigen-antibody reaction in a gel or in a solution is measured. Even when the antigen amount in the test solution is small and only a small amount of the sediment is obtained, a laser nephrometry wherein scattering of laser is utilized can be suitably used.

In applying each of those immunological measuring methods (immunoassays) to the measuring method of the present invention, it is not necessary to set up any special condition, operation, etc. therefor. A measuring system (assay system) for G protein coupled receptor may be constructed taking the technical consideration of the persons skilled in the art into consideration in the conventional conditions and operations for each of the methods. With details of those conventional technical means, a variety of reviews, reference books, etc. may be referred to. They are, for example, Hiroshi Irie (ed): "Radioimmunoassay" (Kodansha, Japan, 1974); Hiroshi Irie (ed): "Radioimmunoassay; Second Series" (Kodansha, Japan, 1979); Eiji Ishikwa et al. (ed): "Enzyme Immunoassay" (Igaku Shoin, Japan, 1978); Eiji Ishikawa et al. (ed): "Enzyme Immunoassay" (Second Edition) (Igaku Shoin, Japan, 1982); Eiji Ishikawa et al. (ed): "Enzyme Immunoassay" (Third Edition) (Igaku Shoin, Japan, 1987); "Methods in Enzymology" Vol. 70 (Immuochemical Techniques (Part A)); ibid. Vol. 73 (Immunochemical Techniques (Part B)); ibid. Vol. 74 (Immunochemical Techniques (Part C)); ibid. Vol. 84 (Immunochemical Techniques (Part b: Selected Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Academic Press); etc.

(7) Preparation of Animals Having the G Protein Coupled Receptor Protein-Encoding DNA of the Present Invention It is possible to prepare transgenic animals expressing G protein coupled receptors using G protein coupled receptor protein-encoding DNA. Examples of the animals are warm-blooded mammals such as rats, rabbit, sheep, swines, cattle, cats, dogs and monkeys.

In transferring the G protein coupled receptor protein-encoding DNA to the aimed animal, it is generally advantageous that said DAN is used by ligating with a site at the downstream of a promoter which is capable of expressing in animal cells. For example, when G protein coupled receptor protein DNA is to be transferred to a rabbit, a gene construct ligated with a site at the downstream of various promoters which are capable of expressing the G protein coupled receptor protein DNA derived from an animal compatible to the animal in animal host cells is subjected to a microinjection to the fertilized ovum (oosperm) of the aimed animal (e.g. fertilized ovum (embryo) of rabbit) whereupon the transgenic animal which produces the G protein coupled receptor protein in a high amount can be prepared.

Examples of the promoters used are promoters derived from virus and ubiquitous expression promoters such as metallothionein promoters may be used but, preferably, enolase gene promoters and NGF gene promoters capable of specifically expressing in brain are used.

Transfer of the G protein coupled receptor protein DNA at a fertilized ovum cell stage is secured in order that the DNA can be present in all of embryonal cells and body somatic cells of an aimed animal. The fact that the G protein coupled receptor protein is present in the fertilized ovum cells of the produced transgenic animal after the DNA transfer means that all progeny of the produced transgenic animal have the G protein coupled receptor protein in all of their embryonal cells and somatic cells. Descendants (offsprings) of the animal of this type which inherited the gene have the G protein coupled receptor protein in all of their embryonal cells and somatic cells.

The transgenic animal to which the G protein coupled receptor protein DNA is transferred can be subjected to a mating and a breeding for generations under a common breeding circumstance as the animal holding said DNA after confirming that the gene can be stably retained. Moreover, male and female animals having the desired DNA are mated to give a homozygote having the transduced gene in both homologous chromosomes and then those male and female animals are mated whereby it is possible to breed for generations so that all descendants have said DNA.

The animal to which the G protein coupled receptor protein DNA is transferred highly expresses the G protein coupled receptor protein and, accordingly, it is useful as the animal for screening for an agonist or an antagonist to said G protein coupled receptor protein.

The DNA-transferred animal can be used as a cell source for a tissue culture. For example, DNA or RNA in the tissue of the DNA-transferred mouse is directly analyzed or protein tissues expressed by gene are analyzed whereupon the G protein coupled receptor protein can be analyzed. Cells of the G protein coupled receptor protein-containing tissue are cultured by standard tissue culture techniques whereupon it is possible to study the function of the cells which are usually difficult to culture (e.g. those derived from brain and peripheral tissues) using the resulting culture. By using said cells, it is also possible to select the pharmaceuticals which can potentiate, for example, the functions of various tissues. Moreover, if a cell strain with a high expression is available, it is possible to separate and purify G protein coupled receptor proteins therefrom.

As such, the amount of G protein coupled receptor proteins can now be determined with a high precision using the anti-G protein coupled receptor antibody of the present invention.

(8) Antisense oligonucleotides Capable of Inhibiting Replication of G Protein Coupled Receptor Protein Gene In another aspect of the present invention, antisense oligonucleotides (nucleic acids) capable of inhibiting the replication or expression of G protein coupled receptor protein gene may be designed and synthesized based on information on the nucleotide sequences of cloned and determined G protein coupled receptor protein-encoding DNAs. Such an antisense oligonucleotide (nucleic acid) is capable of hybridizing with RNA of G protein coupled receptor protein genes to inhibit the synthesis or function of said RNA or of modulating the expression of a G protein coupled receptor protein gene via interaction with G protein coupled receptor protein-related RNA. Oligonucleotides complementary to, and specifically hybridizable with, selected sequences of G protein coupled receptor protein-related RNA are useful in controlling or modulating the expression of a G protein coupled receptor protein gene in vitro and in vivo, and in treating or diagnosing disease states of suspected animals. The term "corresponding" means homologous to or complementary to a particular sequence of the nucleotide sequence or nucleic acid including the gene. As between nucleotides (nucleic acids) and peptides (proteins), "corresponding" usually refers to amino acids of a peptide (protein) in an order derived from the sequence of a nucleotides (nucleic acids) or its complement. The G protein coupled receptor protein gene 5' end hairpin loop, 5' end 6-base-pair repeats, 5' end untranslated region, polypeptide translation initiation codon, protein coding region, ORF translation initiation codon, 3' untranslated region, 3' end palindrome region, and 3' end hairpin loop may be selected as preferred targets though any region may be a target among G protein coupled receptor protein genes. The relationship between the target and oligonucleotides complementary to at least a portion of the target, specifically hybridizable with the target, is denoted as "antisense". The antisense oligonucleotides may be polydeoxynucleotides containing 2-deoxy-D-ribose, polyribonucleotides containing D-ribose, any other type of polynucleotide which is an N-glycoside of a purine or pyrimidine base, or other polymers containing nonnucleotide backbones (e.g., protein nucleic acids and synthetic sequence-specific nucleic acid polymers commercially available) or nonstandard linkages, providing that the polymers contain nucleotides in a configuration which allows for base pairing and base stacking such as is found in DNA and RNA. They may include double- and single-stranded DNA, as well as double- and single-stranded RNA and DNA:RNA hybrids, and also include, as well as unmodified forms of the polynucleotide or oligonucleotide, known types of modifications, for example, labels which are known to those skilled in the art, "caps", methylation, substitution of one or more of the naturally occurring nucleotides with analogue, internucleotide modifications such as, for example, those with uncharged linkages (e.g., methyl phosphonates, phosphotriesters, phosphoramidates, carbamates, etc.) and with charged linkages or sulfur-containing linkages (e.g., phosphorothioates, phosphorodithioates, etc.), those containing pendant moieties, such as, for example, proteins (including nucleases, nuclease inhibitors, toxins, antibodies, signal peptides, poly-L-lysine, etc.) and saccharides (e.g., monosaccharides, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.). The terms "nucleoside", "nucleotide" and "nucleic acid" will include those moieties which contain not only the known purine and pyrimidine bases, but also other heterocyclic bases which have been modified. Such modifications include methylated purines and pyrimidines, acylated purines and pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

The antisense nucleic acid of the present invention is RNA, DNA or a modified nucleic acid. Examples of modified nucleic acid are, but not limited to, degradation-resistant sulfurized and thiophosphate derivatives of nucleic acids, and poly- or oligonucleoside amides. Preferred design modifications of the antisense nucleic acids of the present invention are modifications that are designed to:

(1) increase the intracellular stability of the nucleic acid;
(2) increase the cellular permeability of the nucleic acid;
(3) increase the affinity of the nucleic acid for the target sense strand; or
(4) decrease the toxicity (if any) of the nucleic acid. Many such modifications are known to those skilled in the art, as described in J. Kawakami et al., Pharm Tech Japan, Vol. 8, pp.247, 1992; Vol. 8, pp.395, 1992; S. T. Crooke et al. ed., Antisense Research and Applications, CRC Press, 1993; etc. The nucleic acids may contain altered or modified sugars, bases or linkages, be delivered in specialized systems such as liposomes, microspheres or by gene therapy, or may have attached moieties. Such attached moieties include polycationic moieties such as polylysine that act as charge neutralizers of the phosphate backbone, or hydrophobic moieties such as lipids (e.g., phospholipids, cholesterols, etc.) that enhance interaction with cell membranes or increase uptake of the nucleic acid. Preferred lipids that may attached are cholesterols or derivatives thereof (e.g., cholesteryl chloroformate, cholic acid, etc.). The moieties may be attached at the 3' or 5' ends of the nucleic acids, and also may be attached through a base, sugar, or internucleoside linkage. Other moieties may be capping groups specifically placed at the 3' or 5' ends of the nucleic acids to prevent degradation by nuclease such as exonuclease, RNase, etc. Such capping groups include, but are not limited to, hydroxyl protecting groups known to those skilled in the art, including glycols such as polyethylene glycols, tetraethylene glycol and the like.

The inhibitory activity ofl antisense nucleic acids can be examined using the transformant (or transfectant) of the present invention, the in vitro and in vivo gene expression system of the present invention, or the in vitro and in vivo translation system of G protein coupled receptor proteins. The nucleic acid can be placed in the cell through any number of ways known per se.

In the specification and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.

| | |
|---|---|
| DNA: | Deoxyribonucleic acid |
| cDNA: | Complementary deoxyribonucleic acid |
| A: | Adenine |
| T: | Thymine |

-continued

| | |
|---|---|
| G: | Guanine |
| C: | Cytosine |
| RNA: | Ribonucleic acid |
| mRNA: | Messenger ribonucleic acid |
| dATP: | Deoxyadenosine triphosphate |
| dTTP: | Deoxythymidine triphosphate |
| dGTP: | Deoxyguanosine triphosphate |
| dCTP: | Deoxycytidine triphosphate |
| ATP: | Adenosine triphosphate |
| EDTA: | Ethylenediamine tetraacetic acid |
| SDS: | Sodium dodecyl sulfate |
| EIA: | Enzyme Immunoassay |
| G, Gly: | Glycine (or Glycyl) |
| A, Ala: | Alanine (or Alanyl) |
| V, Val: | Valine (or Valyl) |
| L, Leu: | Leucine (or Leucyl) |
| I, Ile: | Isoleucine (or Isoleucyl) |
| S, Ser: | Serine (or Seryl) |
| T, Thr: | Threonine (or Threonyl) |
| C, Cys: | Cysteine (or Cysteinyl) |
| M, Met: | Methionine (or Methionyl) |
| E, Glu: | Glutamic acid (or Glutamyl) |
| D, Asp: | Aspartic acid (or Aspartyl) |
| K, Lys: | Lysine (or Lysyl) |
| R, Arg: | Arginine (or Arginyl) |
| H, His: | Histidine (or Histidyl) |
| F, Phe: | Pheylalanine (or Pheylalanyl) |
| Y, Tyr: | Tyrossine (or Tyrosyl) |
| W, Trp: | Tryptophan (or Tryptophanyl) |
| P, Pro: | Proline (or Prolyl) |
| N, Asn: | Asparagine (or Asparaginyl) |
| Q, Gln: | Glutainine (or Glutaminyl) |
| NVal: | Norvaline (or Norvalyl) |
| pGlu: | Pyroglutamic acid (or Pyroglutamyl) |
| Blc: | τ-Butyrolacton-7-carbonyl |
| Kpc: | 2-Ketopiperidinyl-6-carbonyl |
| Otc: | 3-Oxoperhydro-1,4-thiazin-5-carbonyl |
| Me: | Methyl |
| Et: | Ethyl |
| Bu: | Butyl |
| Ph: | Phenyl |
| TC: | Thiazolidinyl-4(R)-carboxamide |

The transformant *Escherichia coli*, designated INVα F'/p19P2, which is obtained in the Example 3 mentioned herein below, is on deposit under the terms of the Budapest Treaty from Aug. 9, 1994, with the National Institute of Bioscience and Human-Technology (NIBH), Agency of Industrial Science and Technology, Ministry of International Trade and Industry, Japan and has been assigned the Accession Number FERM BP-4776. It is also on deposit from Aug. 22, 1994 with the Institute for Fermentation, Osaka, Japan (IFO) and has been assigned the Accession Number IFO 15739.

The transformant *Escherichia coli*, designated INVα F'/pG3-2, which is obtained in the Example 4 mentioned herein below, is on deposit under the terms of the Budapest Treaty from Aug. 9, 1994, with NIBH and has been assigned the Accession Number FERM BP-4775. It is also on deposit from Aug. 22, 1994 with IFO and has been assigned the Accession Number IFO 15740.

The transformant *Escherichia coli*, designated INVα F'/p63A2, which is obtained in the Example 5 mentioned herein below, is on deposit under the terms of the Budapest Treaty from Aug. 9, 1994, with NIBH and has been assigned the Accession Number FERM BP-4777. It is also on deposit from Aug. 22, 1994 with IFO aid has been assigned the Accession Number IFO 15738.

The transformant *Escherichia coli*, designated JM109/phGR3, which is obtained in the Example 6 mentioned herein below, is on deposit under the terms of the Budapest Treaty from Sep. 27, 1994, with NIBH and has been assigned the Accession Number FERM BP-4807. It is also on deposit from Sep. 22, 1994 with IFO and has been assigned the Accession Number IFO 15748.

The transformant *Escherichia coli*, designated JM109/p3H2-17, which is obtained in the Example 7 mentioned herein below, is on deposit under the terms of the Budapest Treaty from Sep. 27, 1994, with NIBH and has been assigned the Accession Number FERM BP-4806. It is also on deposit from Sep. 22, 1994 with IFO and has been assigned the Accession Number IFO 15747.

The transformant *Escherichia coli*, designated JM109/p3H2-34, which is obtained in the Example 8 mentioned herein below, is on deposit under the terms of the Budapest Treaty from Oct. 12, 1994, with NIBH and has been assigned the Accession Number FERM BP-4828. It is also on deposit from Oct. 12, 1994 with IFO and has been assigned the Accession Number IFO 15749.

The transformant *Escherichia coli*, designated JM109/pMD4, which is obtained in the Example 9 mentioned herein below, is on deposit under the terms of the Budapest Treaty from Nov. 11, 1994, with NIBH and has been assigned the Accession Number FERM BP-4888. It is also on deposit from Nov. 17, 1994 with IFO and has been assigned the Accession Number IFO 15765.

The transformant *Escherichia coli*, designated JM109/pMGR20, which is obtained in the Example 10 mentioned herein below, is on deposit under the terms of the Budapest Treaty from Dec. 15, 1994, with NIBH and has been assigned the Accession Number FERM BP-4937. It is also on deposit from December 14, 1994 with IFO and has been assigned the Accession Number IFO 15773.

The transformant *Escherichia coli*, designated JM109/pMJ10, which is obtained in the Example 12 mentioned herein below, is on deposit under the terms of the Budapest Treaty from Dec. 15, 1994, with NIBH and has been assigned the Accession Number FERM BP-4936. It is also on deposit from Dec. 16, 1994 with IFO and has been assigned the Accession Number IFO 15784.

The transformant *Escherichia coli*, designated JM109/pMH28, which is obtained in the Example 14 mentioned herein below, is on deposit under the terms of the Budapest Treaty from Jan. 13, 1995, with NIBH and has been assigned the Accession Number FERM BP-4970. It is also on deposit from Jan. 20, 1995 with IFO and has been assigned the Accession Number IFO 15791.

The transformant *Escherichia coli*, designated JM109/pMN7, which is obtained in the Example 16 mentioned herein below, is on deposit under the terms of the Budapest Treaty from Feb. 22, 1995, with NIBH and has been assigned the Accession Number FERM BP-5011. It is also on deposit from Feb. 27, 1995 with IFO and has been assigned the Accession Number IFO 15803.

The transformant *Escherichia coli*, designated JM109/p5S38, which is obtained in the Example 17 mentioned herein below, is on deposit under the terms of the Budapest Treaty from Oct. 27, 1994, with NIBH and has been assigned the Accession Number FERM BP-4856. It is also on deposit from Oct. 25, 1994 with IFO and has been assigned the Accession Number IFO 15754.

The transformant *Escherichia coli*, designated JM109/pMAH2-17, which is obtained in the Example 19 mentioned herein below, is on deposit under the terms of the Budapest Treaty from Apr. 7, 1995, with NIBH and has been assigned the Accession Number FERM BP-5073. It is also on deposit from Mar. 31, 1995 with IFO and has been assigned the Accession Number IFO 15813.

The transformant *Escherichia coli*, designated JM109/pMN128, which is obtained in the Example 20 mentioned herein below, is on deposit under the terms of the Budapest Treaty from Mar. 17, 1995, with NIBH and has been assigned the Accession Number FERM BP-5039. It is also on deposit from Mar. 22, 1995 with IFO and has been assigned the Accession Number IFO 15810.

The transformant *Escherichia coli*, designated JM109/phAH2-17, which is obtained in the Example 21 mentioned herein below, is on deposit under the terms of the Budapest Treaty from Jul. 20, 1995, with NIBH and has been assigned the Accession Number FERM BP-5168. It is also on deposit from Jul. 14, 1995 with IFO and has been assigned the Accession Number IFO 15856.

Each SEQ ID NO set forth in the SEQUENCE LISTING of the specification refers to the following sequence:

[SEQ ID NO: 24] is a partial amino acid sequence of the human pituitary gland-derived G protein coupled receptor protein encoded by the human pituitary gland-derived G protein coupled receptor protein cDNA fragment included in p19P2,

[SEQ ID NO: 25] is a partial amino acid sequence of the human pituitary gland-derived G protein coupled receptor protein encoded by the human pituitary gland-derived G protein coupled receptor protein cDNA fragment included in p19P2,

[SEQ ID NO: 26] is an entire amino acid sequence of the human pituitary gland-derived G protein coupled receptor protein encoded by the human pituitary gland-derived G protein coupled receptor protein cDNA fragment included in phGR3,

[SEQ ID NO: 27] is a partial amino acid sequence of the mouse pancreatic β-cell line, MIN6-derived G protein coupled receptor protein encoded by the mouse pancreatic β-cell line, MIN6-derived G protein coupled receptor protein cDNA fragment having a nucleotide sequence (SEQ ID NO: 32), derived based upon the nucleotide sequences of the mouse pancreatic β-cell line, MIN6-derived G protein coupled receptor protein cDNA fragments each included in pG3-2 and pG1-10,

[SEQ ID NO: 28] is a partial amino acid sequence of the mouse pancreatic β-cell line, MIN6-derived G protein coupled receptor protein encoded by p5S38,

[SEQ ID NO: 29] is a nucleotide sequence of the human pituitary gland-derived G protein coupled receptor protein cDNA fragment included in p19P2,

[SEQ ID NO: 30] is a nucleotide sequence of the human pituitary gland-derived G protein coupled receptor protein cDNA fragment included in p19P2,

[SEQ ID NO: 31] is an entire nucleotide sequence of the human pituitary gland-derived G protein coupled receptor protein cDNA included in phGR3,

[SEQ ID NO: 32] is a nucleotide sequence of the mouse pancreatic β-cell line, MIN6-derived G protein coupled receptor protein cDNA, derived based upon the nucleotide sequences of the mouse pancreatic β-cell line, MIN6-derived G protein coupled receptor protein cDNA fragments each included in pG3-2 and pG1-10,

[SEQ ID NO: 33] is a nucleotide sequence of the mouse pancreatic β-cell line, MIN6-derived G protein cDNA included in p5S38,

[SEQ ID NO: 34] is a partial amino acid sequence of the human amygdaloid nucleus-derived G protein coupled receptor protein encoded by the cDNA fragment included in p63A2,

[SEQ ID NO: 35] is a partial amino acid sequence of the human amygdaloid nucleus-derived G protein coupled receptor protein encoded by the cDNA fragment included in p63A2,

[SEQ ID NO: 36] is a nucleotide sequence of the human amygdaloid nucleus-derived G protein coupled receptor protein cDNA fragment included in p63A2,

[SEQ ID NO: 37] is a nucleotide sequence of the human amygdaloid nucleus-derived G protein coupled receptor protein cDNA fragment included in p63A2,

[SEQ ID NO: 38] is a partial amino acid sequence encoded by the mouse pancreatic β-cell line, MIN6-derived G protein coupled receptor protein cDNA included in p3H2-17,

[SEQ ID NO: 39] is a full-length amino acid sequence encoded by the open reading frame of the mouse pancreatic β-cell line, MIN6-derived G protein coupled receptor protein cDNA included in pMAH2-17,

[SEQ ID NO: 40] is a nucleotide sequence of the mouse pancreatic β-cell line, MIN6-derived G protein coupled receptor protein cDNA included in p3H2-17,

[SEQ ID NO: 41] is a nucleotide sequence of the mouse pancreatic β-cell line, MIN6-derived G protein coupled receptor protein cDNA included in pMAH2-17,

[SEQ ID NO: 42] is a partial amino acid sequence encoded by the mouse pancreatic β-cell line, MIN6-derived G protein coupled receptor protein cDNA included in p3H2-34,

[SEQ ID NO: 43] is a nucleotide sequence of the mouse pancreatic β-cell line, MIN6-derived G protein coupled receptor protein cDNA fragment included in p3H2-34,

[SEQ ID NO: 44] is a partial amino acid sequence encoded by the rabbit gastropyrolic part smooth muscle-derived G protein coupled receptor protein cDNA included in pMD4,

[SEQ ID NO: 45] is a nucleotide sequence of the rabbit gastropyrolic part smooth muscle-derived G protein coupled receptor protein cDNA fragment included in pMD4,

[SEQ ID NO: 46] is an entire amino acid sequence encoded by the mouse pancreatic β-cell line, MIN6-derived G protein coupled receptor protein cDNA included in pMGR20,

[SEQ ID NO: 47] is a nucleotide sequence of the mouse pancreatic β-cell line, MIN6-derived G protein coupled receptor protein cDNA included in PMGR20,

[SEQ ID NO: 48] is a partial amino acid sequence encoded by the rabbit gastropyrolic part smooth muscle-derived G protein coupled receptor protein cDNA included in pMJ10,

[SEQ ID NO: 49] is a nucleotide sequence of the rabbit gastropyrolic part smooth muscle-derived G protein coupled receptor protein cDNA fragment included in pMJ10,

[SEQ ID NO: 50] is a partial amino acid sequence encoded by the rabbit gastropyrolic part smooth muscle-derived G protein coupled receptor protein cDNA included in pMH28,

[SEQ ID NO: 51] is a nucleotide sequence of the rabbit gastropyrolic part smooth muscle-derived G protein coupled receptor protein cDNA fragment included in pMH28,

[SEQ ID NO: 52] is a partial amino acid sequence encoded by the rabbit gastropyrolic part smooth muscle-derived G protein coupled receptor protein cDNA included in pMN7,

[SEQ ID NO: 53] is a nucleotide sequence of the rabbit gastropyrolic part smooth muscle-derived G protein coupled receptor protein cDNA fragment included in pMN7,

[SEQ ID NO: 54] is a partial amino acid sequence encoded by the rabbit gastropyrolic part smooth muscle-derived G protein coupled receptor protein cDNA included in pMN128,

[SEQ ID NO: 55] is a nucleotide sequence of the rabbit gastropyrolic part smooth muscle-derived G protein coupled receptor protein cDNA fragment included in pMN128,

[SEQ ID NO: 56] is a full-length amino acid sequence of the human-derived G protein coupled receptor protein encoded by the human-derived G protein coupled receptor protein cDNA included in phAH2-17, and

[SEQ ID NO: 57] is a nucleotide sequence of the human-derived G protein coupled receptor protein cDNA included in phAH2-17.

EXAMPLES

Described below are working examples of the present invention which are provided only for illustrative purposes, and not to limit the scope of the present invention. In light of the present disclosure, numerous embodiments within the scope of the claims will be apparent to those of ordinary skill in the art.

Example 1

Preparation of Synthetic DNA Primer for Amplifying DNA Coding for G Protein Coupled Receptor Protein A comparison of deoxyribonucleotide sequences coding for the known amino acid sequences corresponding to or near the first membrane-spanning domain each of human-derived TRH receptor protein (HTRHR), human-derived RANTES receptor protein (L10918, HUMRANTES), human Burkitt's lymphoma-derived unknown ligand receptor protein (X68149, HSBLR1A), human-derived somatostatin receptor protein (L14856, HUMSOMAT), rat-derived μ-opioid receptor protein (U02083, RNU02083), rat-derived κ-opioid receptor protein (U00442, U00442), human-derived neuromedin B receptor protein (M73482, HUMNMBR), human-derived muscarinic acetylcholine receptor protein (X15266, HSHM4), rat-derived adrenaline $α_1B$ receptor protein (L08609, RATAADRE01), human-derived somatostatin 3 receptor protein (M96738, HUMSSTR3X), human-derived $C_5a$ receptor protein (HUMC5AAR), human-derived unknown ligand receptor protein (HUMRDC1A), human-derived unknown ligand receptor protein (M84605, HUMOPIODRE) and rat-derived adrenaline $α_2B$ receptor protein (M91466, RATA2BAR) was made. As a result, highly homologous regions or parts were found (FIG. 1).

Further, a comparison of deoxynucleotide sequences coding for the known amino acid sequences corresponding to or near the sixth membrane-spanning domain each of mouse-derived unknown ligand receptor protein (M80481, MUSGIR), human-derived bombesin receptor protein (L08893, HUMBOMB3S), human-derived adenosine A2 receptor protein (S46950, S46950), mouse-derived unknown ligand receptor protein (D21061, MUSGPCR), mouse-derived TRH receptor protein (S43387, S43387), rat-derived neuromedin K receptor protein (J05189, RATNEURA), rat-derived adenosine A1 receptor protein (M69045, RATAIARA), human-derived neurokinin A receptor protein (M57414, HUMNEKAR), rat-derived adenosine A3 receptor protein (M94152, RATADENREC), human-derived somatostatin 1 receptor protein (M81829, HUMSRI1A), human-derived neurokinin 3-receptor protein (S86390, S86371S4), rat-derived unknown ligand receptor protein (X61496, RNCGPCR), human-derived somatostatin 4 receptor protein (L07061, HUMSSTR4Z) and rat-derived GnRH receptor protein (M31670, RATGNRHA) was made. As a result, highly homologous regions or parts were found (FIG. 2).

The aforementioned abbreviations in the parentheses are identifiers (reference numbers) which are indicated when GenBank/EMBL Data Bank is retrieved by using DNASIS Gene/Protein Sequencing Data Base (CD019, Hitachi Software Engineering, Japan) and are usually called "Accession Numbers" or "Entry Names". HTRHR is, however, the sequence as disclosed in Japanese Unexamined Patent Publication No. 286986/1993 (EPA 638645).

Specifically, it was planned to incorporate mixed bases relying upon the base regions that were in agreement with cDNAs coding for a large number of receptor proteins in order to enhance base agreement of sequences with as many receptor cDNAs as possible even in other regions. Based upon these sequences, the degenerate synthetic DNA having a nucleotide sequence represented by SEQ ID NO: 1 which is complementary to the homologous nucleotide sequence of FIG. 1 and the degenerate synthetic DNA having a nucleotide sequence represented by SEQ ID NO: 2 which is complementary to the homologous nucleotide sequence of FIG. 2 were produced. Nucleotide synthesis was carried out by a DNA synthesizer.

[Synthetic DNAs]

5'-CGTGG (G or C) C (A or C) T (G or C) (G or C) TGGGCAAC (A, G, C or T) (C or T) CCTG-3'                          (SEQ ID NO: 1)

5'-GT (A, G, C or T) G (A or T) (A or G) (A or G) GGCA (A, G, C or T) CCAGCAGA (G or T) GGCAAA-3'   (SEQ ID NO: 2)

The parentheses indicate the incorporation of a plurality of bases, leading to multiple oligonucleotides in the primer preparation. In other words, nucleotide residues in parentheses of the aforementioned DNAs were incorporated in the presence of a mixture of plural bases at the time of synthesis.

Example 2

Figure 17:
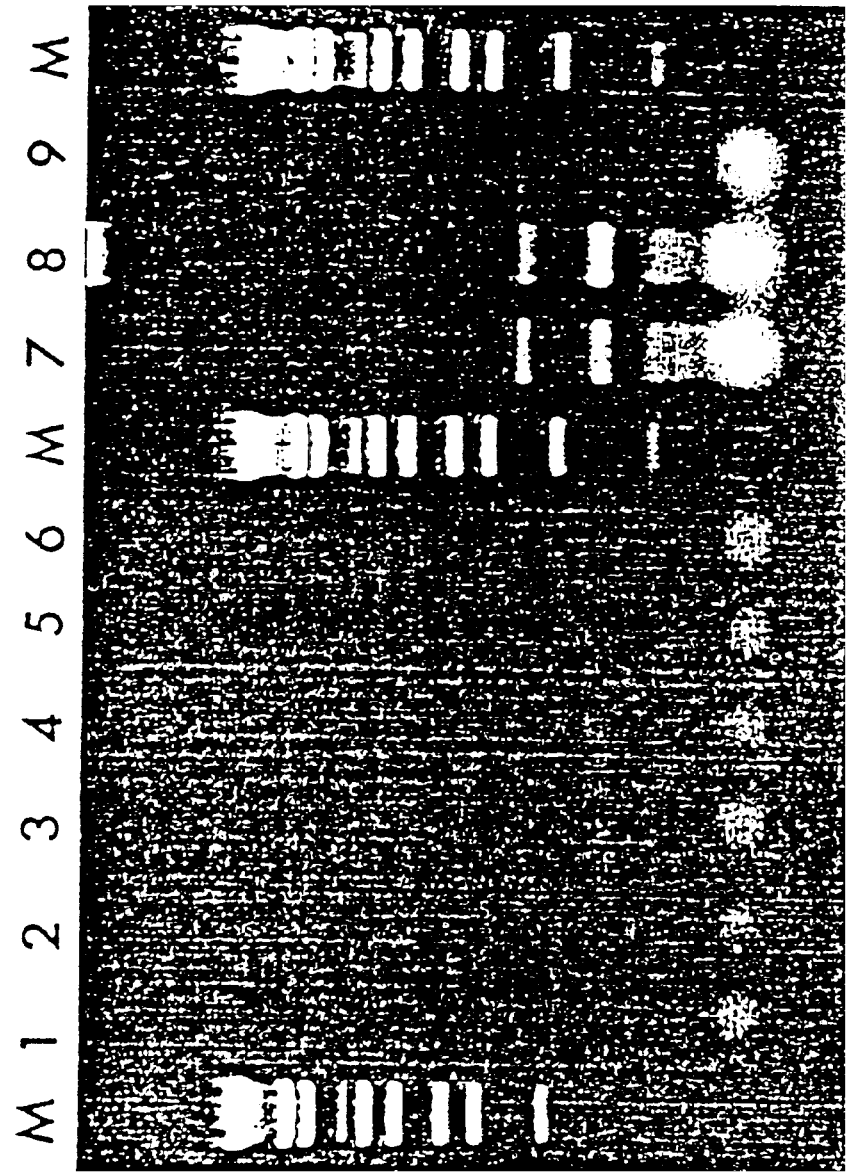
FIG. 17 is the 1.2% agarose gel electrophoresis profile of cDNA products each obtained from human brain amygdala (1, 2, 7), human pituitary body (3, 4, 8) and rat brain (5, 6, 9) by PCR amplification using the synthetic DNA primers having a nucleotide sequence represented by SEQ ID NO: 1 and the synthetic DNA primers having a nucleotide sequence represented by SEQ ID NO: 2, wherein lanes 1 to 6 show the results of when PCR is carried out under severe conditions as disclosed in Examples, lanes 7 to 9 show the results of when PCR is carried out under mild conditions, and M denotes a size marker which is obtained by cutting λ-phage DNA with restriction enzyme, EcoT14I.
Figure 24:
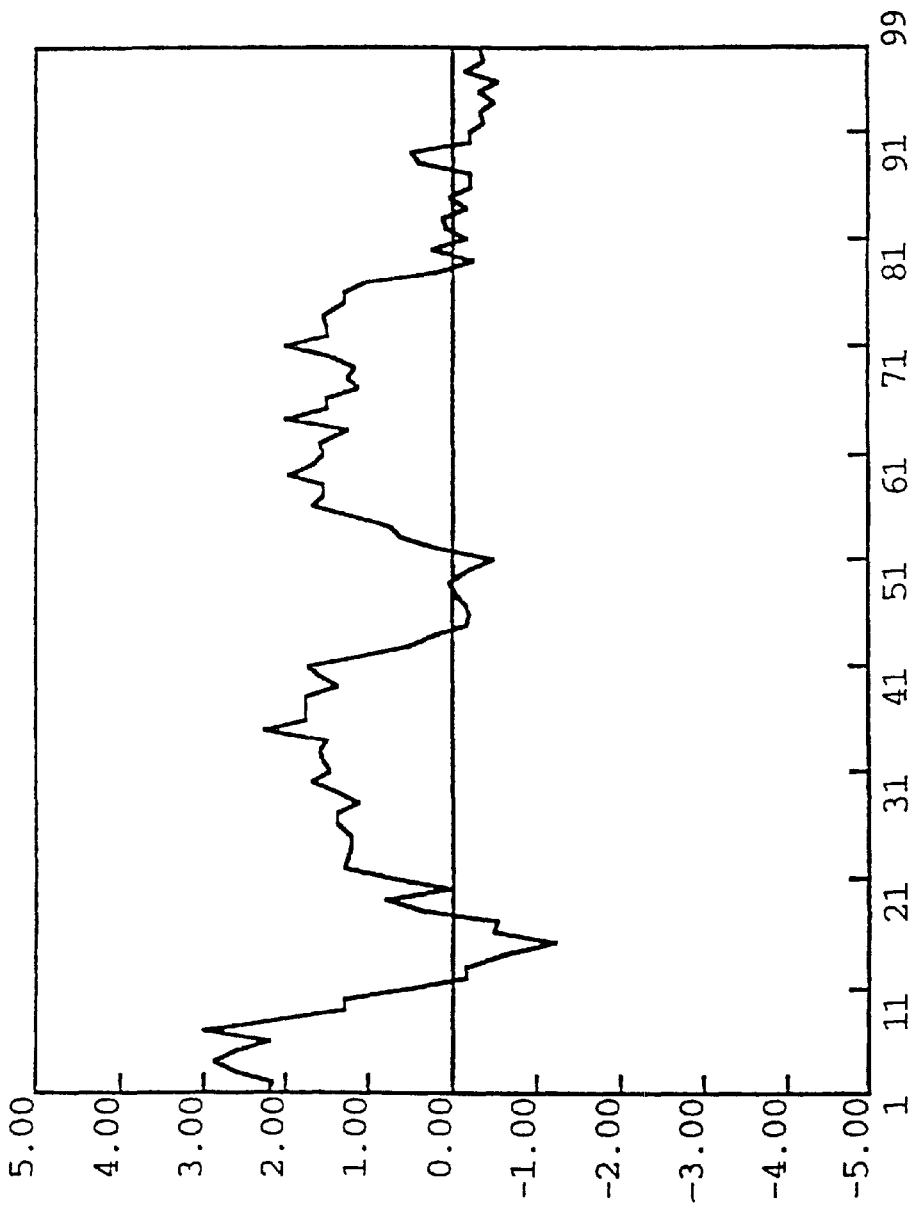
FIG. 24 is the partial hydrophobicity plotting profile of the protein encoded by the human pituitary gland-derived G protein coupled receptor protein cDNA fragment included in p19P2, prepared based upon the amino acid sequence shown in FIG. 22.
Figure 25:
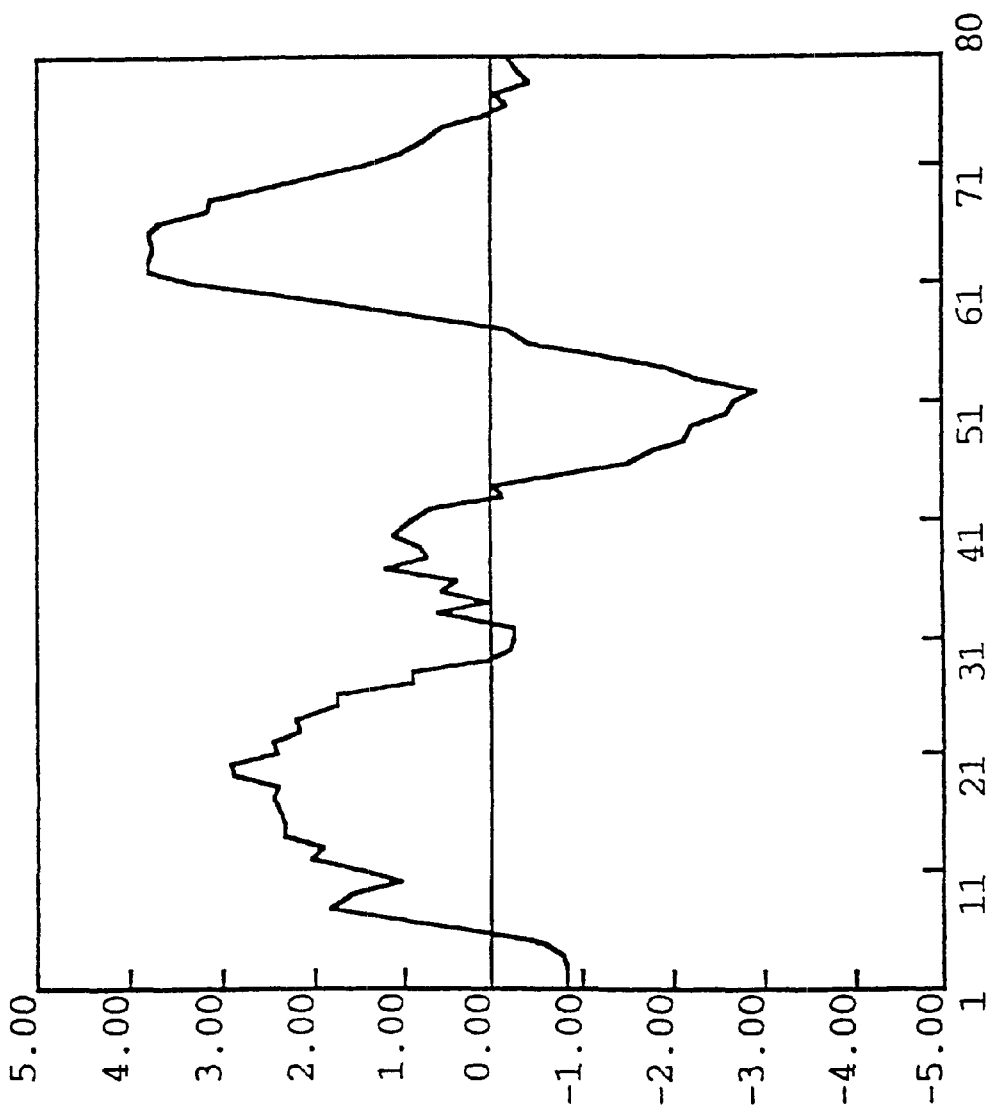
FIG. 25 is the partial hydrophobicity plotting profile of the protein encoded by the human pituitary gland-derived G protein coupled receptor protein cDNA fragment included in p19P2, prepared based upon the amino acid sequence shown in FIG. 23.
Figure 28:
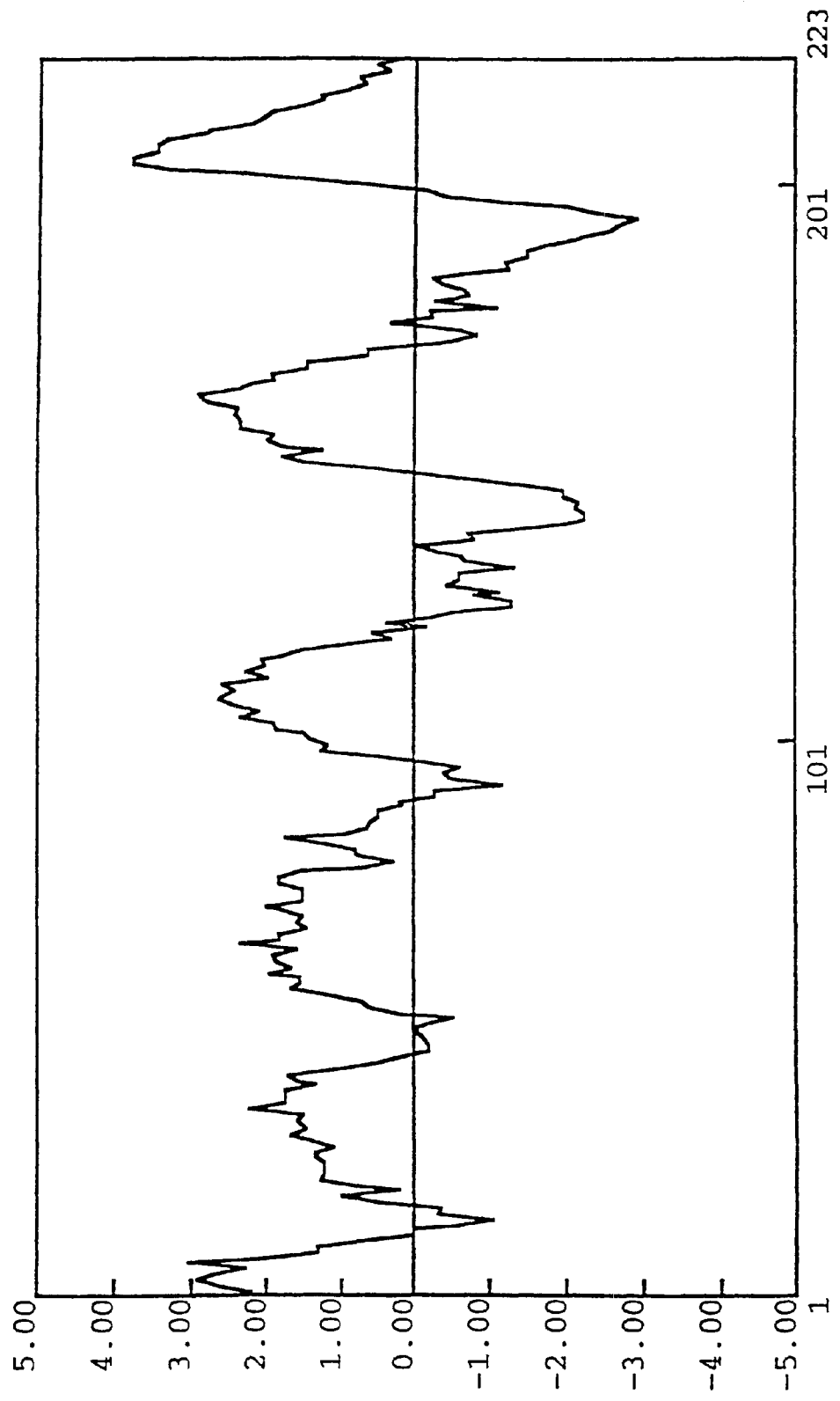
FIG. 28 is the partial hydrophobicity plotting profile of the MIN6-derived G protein coupled receptor protein, prepared based upon the partial amino acid sequence shown in FIG. 27.
Figure 31:
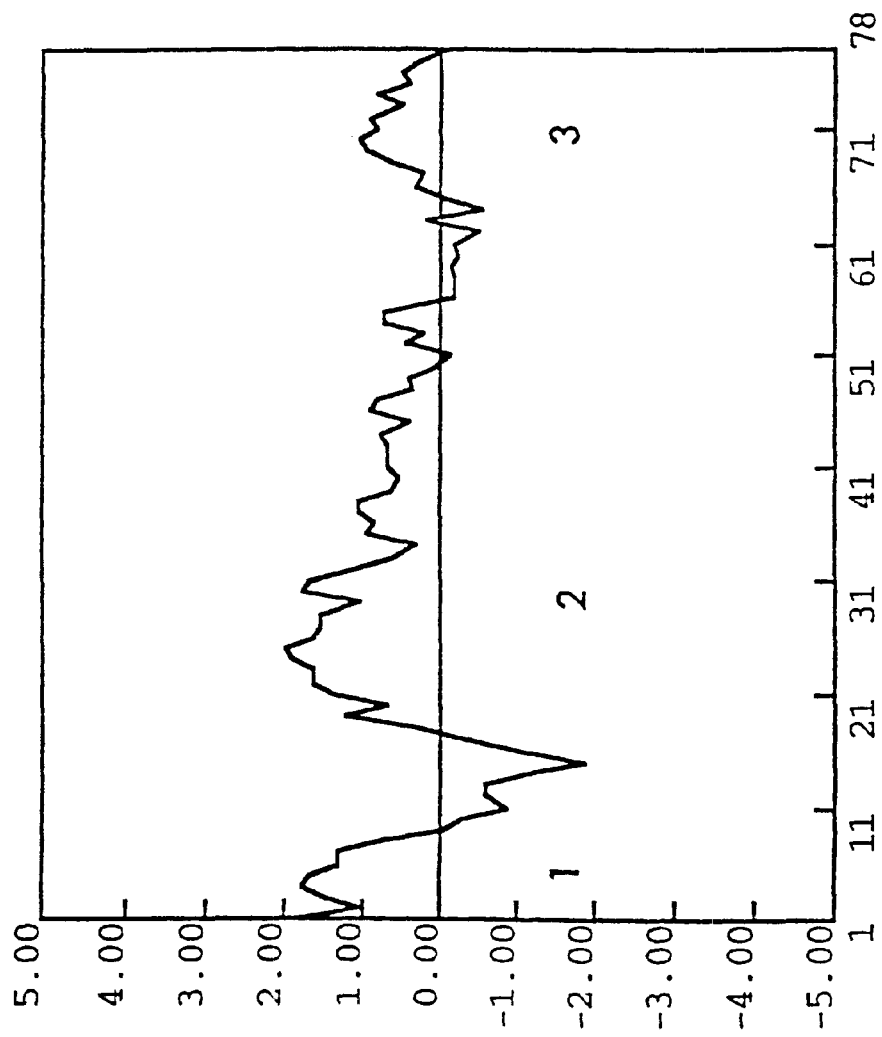
FIG. 31 is the hydrophobicity plotting profile, prepared based upon the amino acid sequence shown in FIG. 29, suggesting the presence of hydrophobic domains as designated by 1 to 3.
Figure 32:
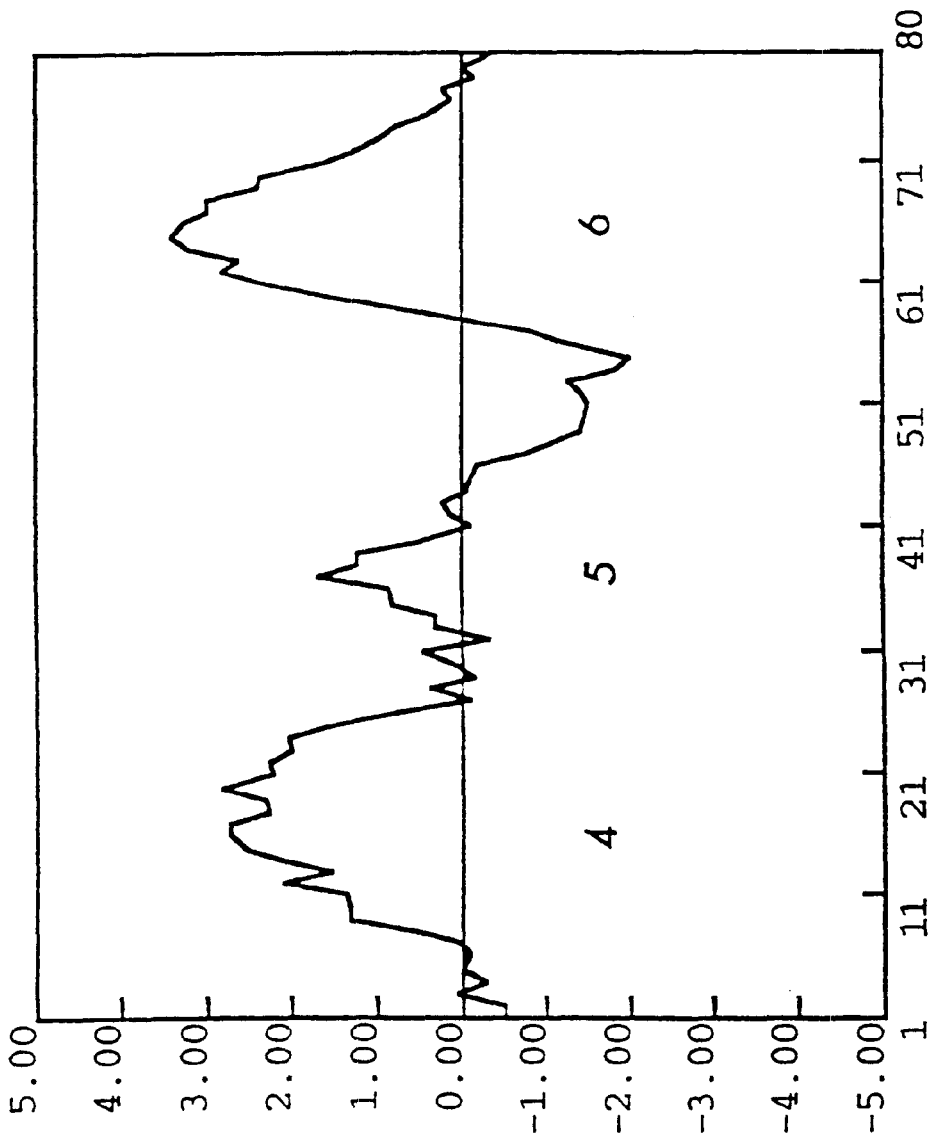
FIG. 32 is the hydrophobicity plotting profile, prepared based upon the amino acid sequence shown in FIG. 30, suggesting the presence of hydrophobic domains as designated by 4 to 6.

Isolation of Human Somatostatin Receptor Protein-Encoding DNA, Human D5 Dopamine Receptor Protein-Encoding DNA, and Rat Somatostatin Receptor Protein-Encoding DNA (1) Amplification of DNA by Polymerase Chain Reaction (PCR) cDNAs (QuickClone, CLONTECH Laboratories, Inc.) prepared from human brain amygdaloid nucleus, human pituitary gland and rat brain each in an amount of 1 ng as templates, the synthetic DNA primers prepared in Example 1 each in an amount of 1 μM, 2.5 mM dNTPs (deoxyribonucleoside triphosphates), and 2.5 units of Taq DNA polymerase (Takara Shuzo Co., Japan) were mixed together with a buffer attached to the enzyme kit such that the total amount was 100 μl. The polymerase chain reaction was carried out by using a Thermal Cycler manufactured by Perkin-Elmer Co. One cycle was set to include 96° C. for 30 sec., 45° C. for 1 min. and 60° C. for 3 min. Totally this one cycle was repeated 30 times to amplify DNAs. Amplification of DNAs was confirmed by 1.2% agarose electrophoresis [FIG. 17].

(2) Isolation of Amplified DNA and Analysis of DNA Sequence

By using a TA Cloning Kit (Invitrogen Co.), the DNA amplified by the PCR was inserted into a plasmid vector, pCR™II. The DNA was transfected into E. coli attached to the kit to form an amplified DNA library. Colonies formed by the transformants were selected under guidance based on the activity of β-galactosidase on X-gal (5-bromo-4-chloro-3-indolyl-β-D-galactoside)-added LB (Luria-Bertani) plates in order to separate only white colonies in which DNA fragments are inserted. They were cultured in an LB culture medium to which ampicillin was added and plasmid DNAs were prepared with an automatic plasmid extracting machine (Kurabo Co., Japan).

An aliquot of the DNA thus prepared was further digested with EcoRI to confirm DNA fragments that were inserted, and a DNA yield each of clones was compared with a marker. An aliquot of the plasmid DNA thus prepared was treated with RNase, extracted with phenol/chloroform, precipitated in ethanol, and the resulting product was then reacted for sequencing by using a DyeDeoxy terminator cycle sequencing kit (Applied Biosystems Co.).

Sequencing was carried out by using a 370A fluorescent automatic sequencer manufactured by Applied Biosystems Co. The nucleotide sequences obtained were analyzed by using DNASIS (Hitachi Software Engineering, Japan). The nucleotide sequences obtained are shown in FIGS. 18, 19, 20 and 21. From these Figures and the results of homology retrieval, it was learned that the DNAs obtained were DNAs encoding human somatostatin receptor protein [FIGS. 18 and 19], human D5 dopamine receptor protein [FIG. 20] and rat somatostatin receptor protein [FIG. 21] that can be classified each into a group of G protein coupled receptor proteins.

In FIG. 18 as described herein, the nucleotide sequence of the DNA is in agreement with the nucleotide sequence encoding somatostatin receptor (HUMSOMAT) and the clone, A58, is a human somatostatin receptor cDNA. The underlined part represents the 5' side synthetic DNA primer used for the PCR. Thus, even when parts of the nucleotide sequence are mismatched, amplification is effected to a sufficient degree by the PCR.

It will be understood from FIG. 19 that the clone, A58 is in good agreement with the nucleotide sequence coding for the human somatostatin receptor (HUMSOMAT) even when the sequencing is carried out from the opposite side. The underlined part represents the 3' side synthetic DNA primer used for the PCR. In this figure, the nucleotide sequences are mismatched to some extent even in the portions other than the primer portion presumably due to base substitution at the time of PCR or due to partial deviation in the sequencing reaction. It can be confirmed via sequencing of chains complementary thereto as required.

In FIG. 20 as described herein, the nucleotide sequence of the DNA is in good agreement with a nucleotide sequence coding for the human D5 dopamine receptor (HUMDRD5A) except the primer portion (underlined). It was learned that the clone, 57-A-2, is a human D5 dopamine receptor cDNA.

In FIG. 21 as described herein, the DNA is in good agreement with a nucleotide sequence coding for the rat somatostatin receptor (RNU04738) except the primer portion (underlined). It was learned that the clone, B54, is a rat somatostatin receptor cDNA.

Example 3

Isolation of Human Pituitary Gland-Derived G Protein Coupled Receptor Protein-Encoding DNA (1) Amplification of Receptor cDNA by PCR Using Human Pituitary Gland-Derived cDNA By using human pituitary gland-derived cDNA (QuickClone, CLONTECH Laboratories, Inc.) as a template, PCR amplification using the DNA primers synthesized in Example 1 was carried out. The composition of the reaction solution consisted of the synthetic DNA primers (SEQ: 5' primer sequence and 3' primer sequence) each in an amount of 1 µM, 1 ng of the template cDNA, 0.25 mM dNTPs, 1 µl of Taq DNA polymerase and a buffer attached to the enzyme kit, and the total amount of the reaction solution was made to be 100 µl. The cycle for amplification including 95° C. for 1 min., 55° C. for 1 min. and 72° C. for 1 min. was repeated 30 times by using a Thermal Cycler (Perkin-Elmer Co.). Prior to adding Taq DNA polymerase, the remaining reaction solution was mixed and was heated at 95° C. for 5 minutes and at 65° C. for 5 minutes. The amplified products were confirmed relying upon 1.2% agarose gel electrophoresis and ethidium bromide staining.

(2) Subcloning of PCR Product into Plasmid Vector and Selection of Novel Receptor Candidate Clone via Decoding Nucleotide Sequence of Inserted cDNA Region The PCR products were separated by using a 0.8% low-melting temperature agarose gel, the band parts were excised from the gel with a razor blade, and were heat-melted, extracted with phenol and precipitated in ethanol to recover DNAS. According to the protocol attached to a TA Cloning Kit (Invitrogen Co.), the recovered DNAs were subcloned into the plasmid vector, pCR™II (™ represents registered trademark). The recombinant vectors were introduced into E. coli INVα F' competent cells (Invitrogen Co.) to produce transformants. Then, transformant clones having a cDNA-inserted fragment were selected in an LB agar culture medium containing ampicillin and X-gal. Only transformant clones exhibiting white color were picked with a sterilized toothstick to obtain transformant Escherichia coli INVα F'/p19P2.

The individual clones were cultured overnight in an LB culture medium containing ampicillin and treated with an automatic plasmid extracting machine (Kurabo Co., Japan) to prepare plasmid DNAs. An aliguot of the DNA thus prepared was cut by EcoRI to confirm the size of the cDNA fragment that was inserted. An aliquot of the remaining DNA was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan). The underlined portions represent regions corresponding to the synthetic primers [FIGS. 22 and 23].

Homology retrieval was carried out based upon the determined nucleotide sequences [FIGS. 22 and 23]. As a result, it was learned that a novel G protein coupled receptor protein was encoded by the cDNA fragment insert in the plasmid, p19P2, possessed by the transformant Escherichia coli INVα F'/p19P2. To further confirm this fact, by using DNASIS (Hitachi System Engineering Co., Japan) the nucleotide sequences were converted into amino acid sequences [FIGS. 22 and 23], and homology retrieval was carried out in view of hydrophobicity plotting [FIGS. 24 and 25] and at the amino acid sequence level to find homology relative to neuropeptide Y receptor proteins [FIG. 26].

Example 4

Isolation of Mouse Pancreas-Derived G Protein Coupled Receptor Protein-Encoding DNA (1) Preparation of Poly(A)$^+$ RNA Fraction from Mouse Pancreatic β-Cell Strain, MIN6 and Synthesis of cDNA A total RNA was prepared from the mouse pancreatic β-cell strain, MIN6 (Jun-ichi Miyazaki et al., Endocrinology, Vol. 127, No. 1, p.126–132) according to the guanidine thiocyanate method (Kaplan B. B. et al., Biochem. J., 183, 181–184 (1979)) and, then, poly(A)+ RNA fractions were prepared with a mRNA purifying kit (Pharmacia Co.). Next, to 5 μg of the poly(A)+ RNA fraction was added a random DNA hexamer (BRL Co.) as a primer, and the resulting mixture was subjected to reaction with mouse Moloney Leukemia virus (MMLV) reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE buffer (10 mM Tris-HCl at pH8.0, 1 mM EDTA at pH8.0).

(2) Amplification of Receptor cDNA by PCR Using MIN6-Derived cDNA and Sequencing By using, as a template, 5 μl of cDNA prepared from the mouse pancreatic β-cell strain, MIN6 in the above step (1), PCR amplification using the DNA primers synthesized in Example 1 was carried out under the same conditions as in Example 3(2). The resulting PCR product was subcloned into the plasmid vector, pCR™II, in the same manner as in Example 2 to obtain a plasmid, pG3-2. The plasmid pG3-2 was transfected into *E. coli* INVα F' to obtain transformed *Escherichia coli* INVα F'/pG3-2.

By using, as a template, 5 μl of the cDNA prepared from the mouse pancreatic β-cell strain, MIN6, PCR amplification using DNA primers as disclosed in Libert F. et al., "Science, 244:569–572, 1989", i.e., a degenerate synthetic primer represented by the following sequence:

```
5'-CTGTG (C or T) G (C or T) (G or C) AT (C or T) GCIIT (G
     or T) GA (C or T) (A or C) G (G or C)
     TAC-3'                                    (SEQ ID NO: 60)
``` wherein I is inosine; and
a degenerate synthetic primer represented by the following sequence:

```
5'-A (G or T) G (A or T) AG (A or T) AGGGCAGCCAGCAGAI
     (G or C) (A or G) (C or T) GAA-3'        (SEQ ID NO: 61)
``` wherein I is inosine,
was carried out under the same conditions as in Working Example 1. The resulting PCR product was subcloned into the plasmid vector, pCR™II, in the same manner as described in Example 3(2) to obtain a plasmid, pG1-10.

The reaction for determining the nucleotide sequence (sequencing) was carried out with a DyeDeoxy terminator cycle sequencing kit (ABI Co.), the DNA was decoded with the fluorescent automatic sequencer (ABI Co.), and the data of the nucleotide sequence obtained were analyzed with DNASIS (Hitachi System Engineering Co., Japan).

FIG. 27 shows a mouse pancreatic β-cell strain MIN6-derived G protein coupled receptor protein-encoding DNA and an amino acid sequence encoded by the isolated DNA based upon the nucleotide sequences of plasmids pG3-2 and pG1-10 which are held by the transformant *Escherichia coli* INVα F'/pG3-2. The underlined portions represent regions corresponding to the synthetic primers.

Homology retrieval was carried out based upon the determined nucleotide sequence [FIG. 27]. As a result, it was learned that a novel G protein coupled receptor protein was encoded by the cDNA fragment obtained. To further confirm this fact, by using DNASIS (Hitachi System Engineering Co., Japan) the nucleotide sequence was converted into an amino acid sequence [FIG. 27], hydrophobicity plotting was carried out to confirm the presence of six hydrophobic regions [FIG. 28]. Upon comparing the amino acid sequence with that of p19P2 obtained in Example 3, furthermore, a high degree of homology was found as shown in [FIG. 61]. As a result, it is strongly suggested that the G protein coupled receptor proteins encoded by pG3-2 and pG1-10 recognize the same ligand as the G protein coupled receptor protein encoded by p19P2 does while the animal species from which the receptor proteins encoded by pG3-2 and pG1-10 are derived is different from that from which the receptor protein encoded by p19P2 is.

Example 5

Isolation of Human Amygdaloid Nucleus-Derived G Protein Coupled Receptor Protein-Encoding DNA (1) Amplification of Receptor cDNA by PCR Using Human Amygdaloid Nucleus-Derived cDNA By using an amplified human amygdala-derived cDNA (QuickClone, CLONTECH Laboratories, Inc.) as a template, PCR amplification using the DNA primers synthesized in Example 1 was carried out. The composition of the reaction solution consisted of the synthetic DNA primers (SEQ: 5' primer sequence and 3' primer sequence) each in an amount of 1 μM, 1 ng of the template cDNA, 0.25 mM dNTPs, 1 μl of Taq DNA polymerase and a buffer attached to the enzyme kit, and the total amount of the reaction solution was made to be 100 μl. The cycle for amplification including 95° C. for 1 min., 55° C. for 1 min. and 72° C. for 1 min. was repeated 30 times by using a Thermal Cycler (Perkin-Elmer Co.). Prior to adding Taq DNA polymerase, the remaining reaction solution was mixed and was heated at 95° C. for 5 minutes and at 65° C. for 5 minutes. The amplified products were confirmed relying upon 1.2% agarose gel electrophoresis and ethidium bromide staining.

(2) Subcloning of PCR Product into Plasmid Vector and Selection of Novel Receptor Candidate Clone via Decoding Nucleotide Sequence of Inserted cDNA Region The PCR products were separated by using a 0.8% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into *E. coli* INVα F' competent cells (Invitrogen Co.) to produce transformants. Then, transformant clones having a cDNA-inserted fragment were selected in an LB agar culture medium containing ampicillin and X-gal. Only transformant clones exhibiting white color were picked with a sterilized toothstick to obtain transformant *Escherichia coli* INVα F'/p63A2.

The individual clones were cultured overnight in an LB culture medium containing ampicillin and treated with an automatic plasmid extracting machine (Kurabo Co., Japan) to prepare plasmid DNAs. An aliquot of the DNA thus prepared was cut by EcoRI to confirm the size of the cDNA fragment that was inserted. An aliquot of the remaining DNA was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan).

Homology retrieval was carried out based upon the determined nucleotide sequences [FIGS. 29 and 30]. As a result, it was learned that a novel G protein coupled receptor protein was encoded by the cDNA fragment insert in the plasmid, p63A2 possessed by the transformant *Escherichia coli* INVα F'/p63A2. To further confirm this fact, by using DNASIS (Hitachi System,Engineering Co., Japan) the nucleotide sequences were converted into amino acid sequences [FIGS. 29 and 30], and homology retrieval was carried out in view of hydrophobicity plotting [FIGS. 31 and 32] and at the amino acid sequence level to find homology relative to mouse GIR [FIG. 33].

Example 6

Cloning of Human Pituitary Gland-Derived G Protein Coupled Receptor Protein cDNA (1) Cloning of cDNA Comprising Whole Coding Regions for Receptor Protein from Human Pituitary Gland-Derived cDNA Library The DNA library constructed by Clontech Co. wherein λ gt11 phage vector is used (CLONTECH Laboratories, Inc.; CLH L1139b) was employed as a human pituitary gland-derived cDNA library. The human pituitary gland cDNA library (2×10$^6$ pfu (plaque forming units)) was mixed with *E. coli* Y1090 treated with magnesium sulfate, and incubated at 37° C. for 15 minutes followed by addition of 0.5% agarose (Pharmacia Co.) LB. The *E. coli* was plated onto a 1.5% agar (Wako-Junyaku Co.) LB plate (containing 50 μg/ml of ampicillin). A nitrocellulose filter was placed on the plate on which plaques were formed and the plaque was transferred onto the filter. The filter was denatured with an alkali and then heated at 80° C. for 3 hours to fix DNAs.

The filter was incubated overnight at 42° C. together with the probe mentioned herein below in a buffer containing 50% formamide, 5×SSPE (20×SSPE (pH 7.4) is 3 M NaCl, 0.2 M NaH$_2$PO$_4$.H$_2$O, 25 mM EDTA), 5×Denhardt's solution (Nippon Gene, Japan), 0.1% SDS and 100 μg/ml of salmon sperm DNA for hybridization.

The probe used was obtained by cutting the DNA fragment inserted in the plasmid, p19P2, obtained in Working Example 3, with EcoRI, followed by recovery and labelling by incorporation of [$^{32}$P]dCTP (Dupont Co.) with a random prime DNA labelling kit (Amasham Co.).

It was washed with 2×SSC (20×SSC is 3 M NaCl, 0.3 M sodium citrate), 0.1% SDS at 55° C. for 1 hour and, then, subjected to an autoradiography at −80° C. to detect hybridized plaques.

In this screening, hybridization signals were recognized in three independent plaques. Each DNA was prepared from the three clones. The DNAs digested with EcoRI were subjected to an agarose electrophoresis and were analyzed by the southern blotting using the same probe as the one used in the screening. Hybridizing bands were identified at about 0.7 kb, 0.8 kb and 2.0 kb, respectively. Among them, the DNA fragment corresponding to the band at about 2.0 kb (λ hGR3) was selected. The λ hGR3-derived EcoRI fragment with a hybridizable size was subcloned to the EcoRI site of the plasmid, pUC18, and *E. coli* JM109 was transformed with the plasmid to obtain transformant *E. coli* JM109/phGR3. A restriction enzyme map of the plasmid, phGR3, was prepared relying upon a restriction enzyme map deduced from the nucleotide sequence as shown in Example 3. As a result, it was learned that it carried a full-length receptor protein-encoding DNA which was predicted from the receptor protein-encoding DNA as shown in Example 3.

(2) sequencing of Human Pituitary Gland-Derived Receptor Protein cDNA

Among the EcoRI fragments inserted in the plasmid, phGR3, obtained in the above step (1), the from EcoRI to NheI nucleotide sequence with about 1330 bp that is considered to be a receptor protein-coding region was sequenced. Concretely speaking, by utilizing restriction enzyme sites that exist in the EcoRI fragments, unnecessary parts were removed or necessary fragments were subcloned in order to prepare template plasmids for analyzing the nucleotide sequence.

The reaction for determining the nucleotide sequence (sequencing) was carried out with a DyeDeoxy terminator cycle sequencing kit (ABI Co.), the DNA was decoded with the fluorescent automatic sequencer (ABI Co.), and the data of the nucleotide sequence obtained were analyzed with DNASIS (Hitachi System Engineering Co., Japan).

Figure 36:
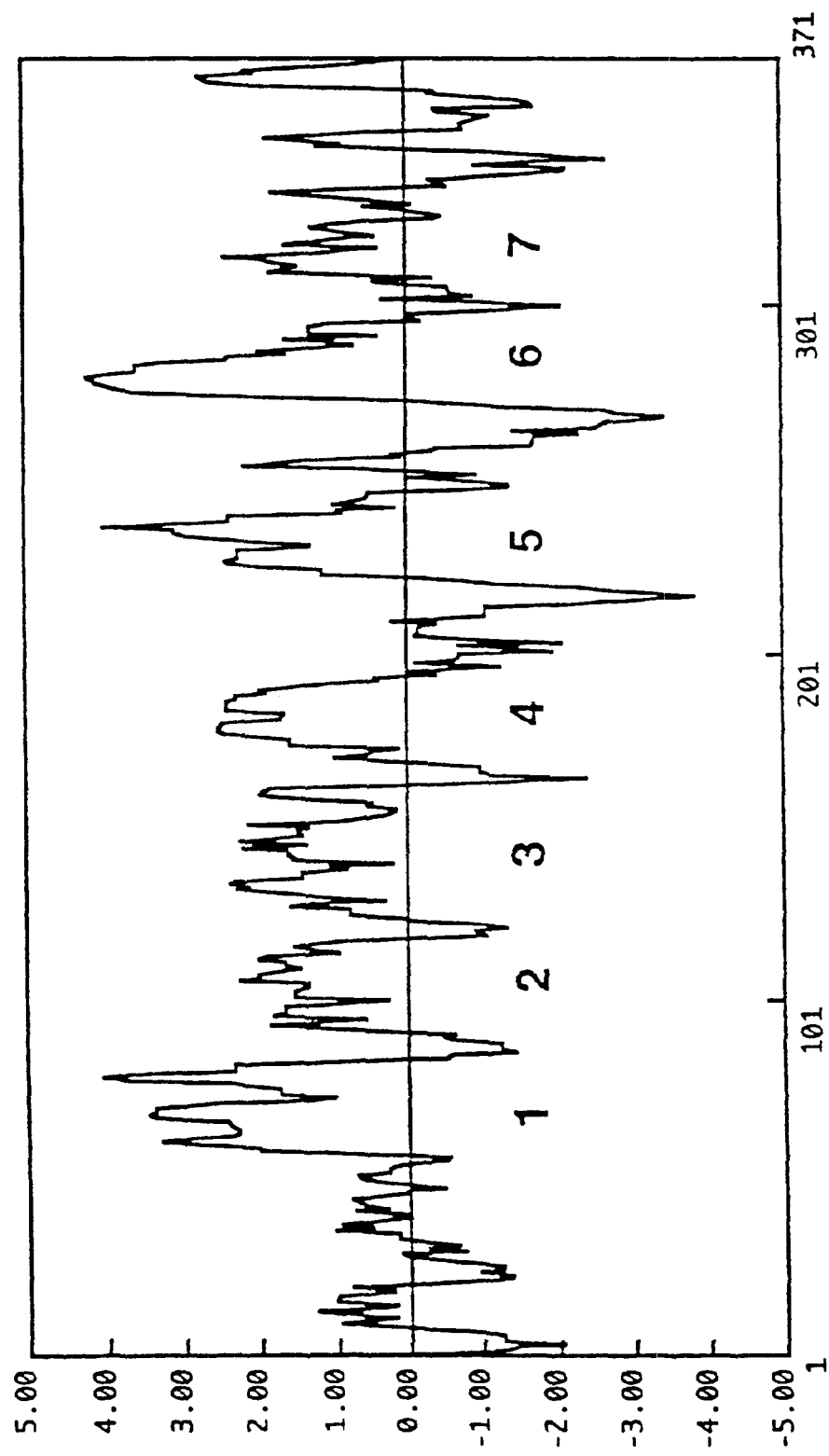
FIG. 36 is the hydrophobicity plotting profile of the protein encoded by the human pituitary gland-derived G protein coupled receptor protein cDNA included in phGR3, prepared based upon the amino acid sequence shown in FIG. 34.
Figure 38:
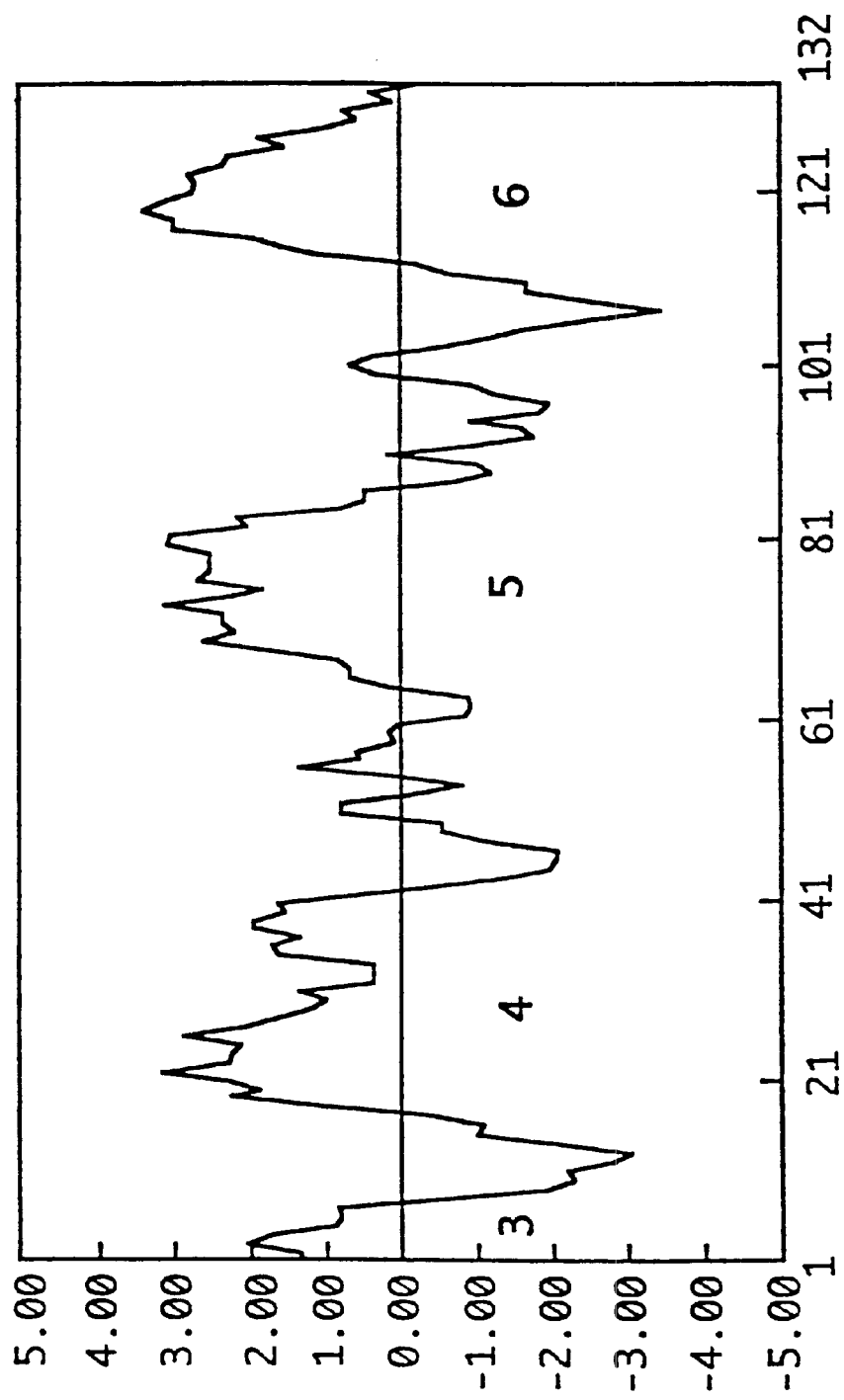
FIG. 38 is the hydrophobicity plotting profile, prepared based upon the amino acid sequence shown in FIG. 37, suggesting the presence of hydrophobic domains as designated by 3 to 6.
Figure 41:
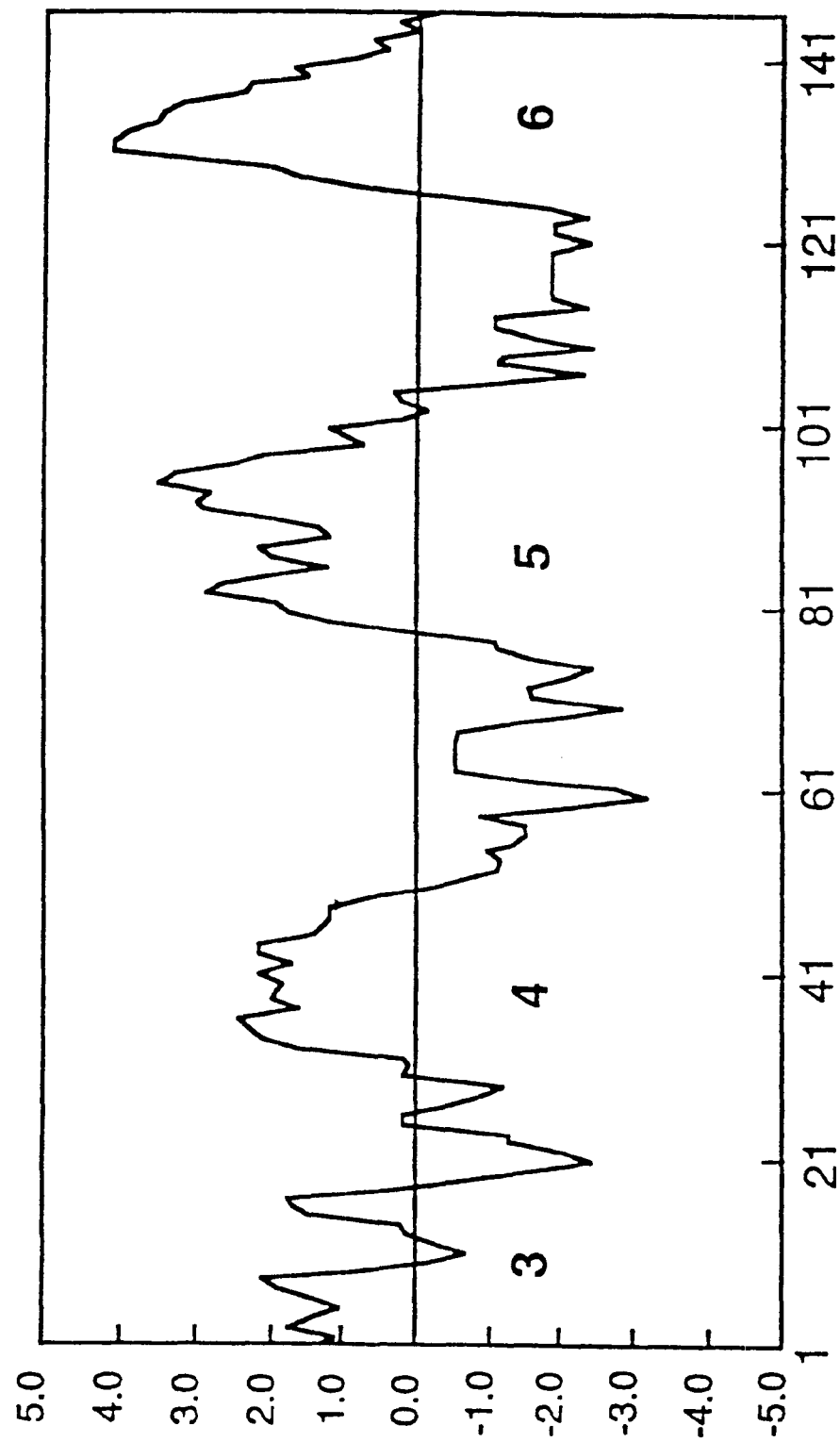
FIG. 41 is the hydrophobicity plotting profile, prepared based upon the amino acid sequence shown in FIG. 40, wherein the axis of ordinate represents an index of hydrophobicity, the axis of abscissa represents the number of amino acids and numerals 3 to 6 represent the presence of hydrophobic domains.
Figure 47:
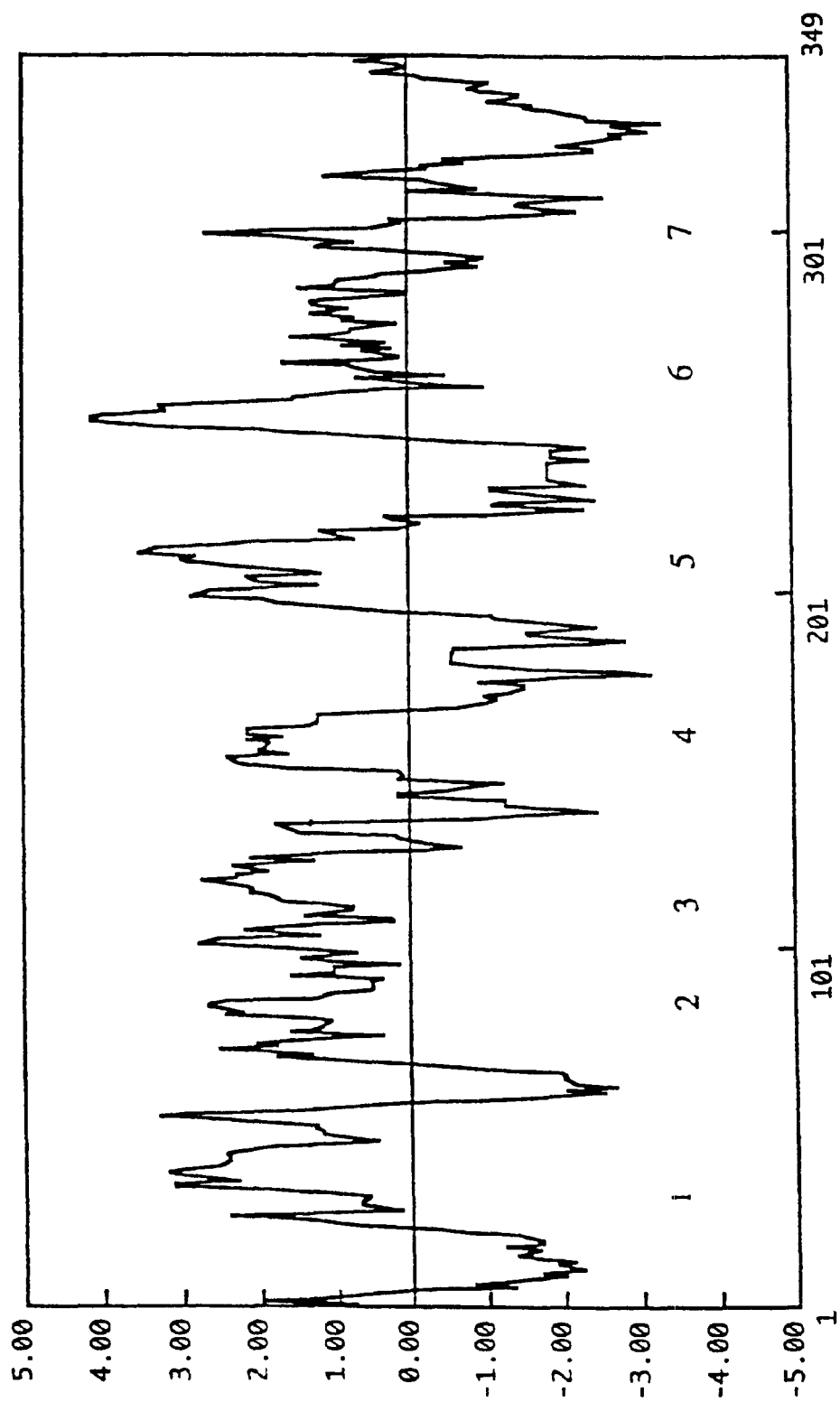
FIG. 47 is the hydrophobicity plotting profile, prepared based upon the amino acid sequence shown in FIG. 46, wherein the axis of ordinate represents an index of hydrophobic property, the axis of abscissa represents the number of amino acids, and numerals 1 to 7 represent the presence of hydrophobic domains.
Figure 53:
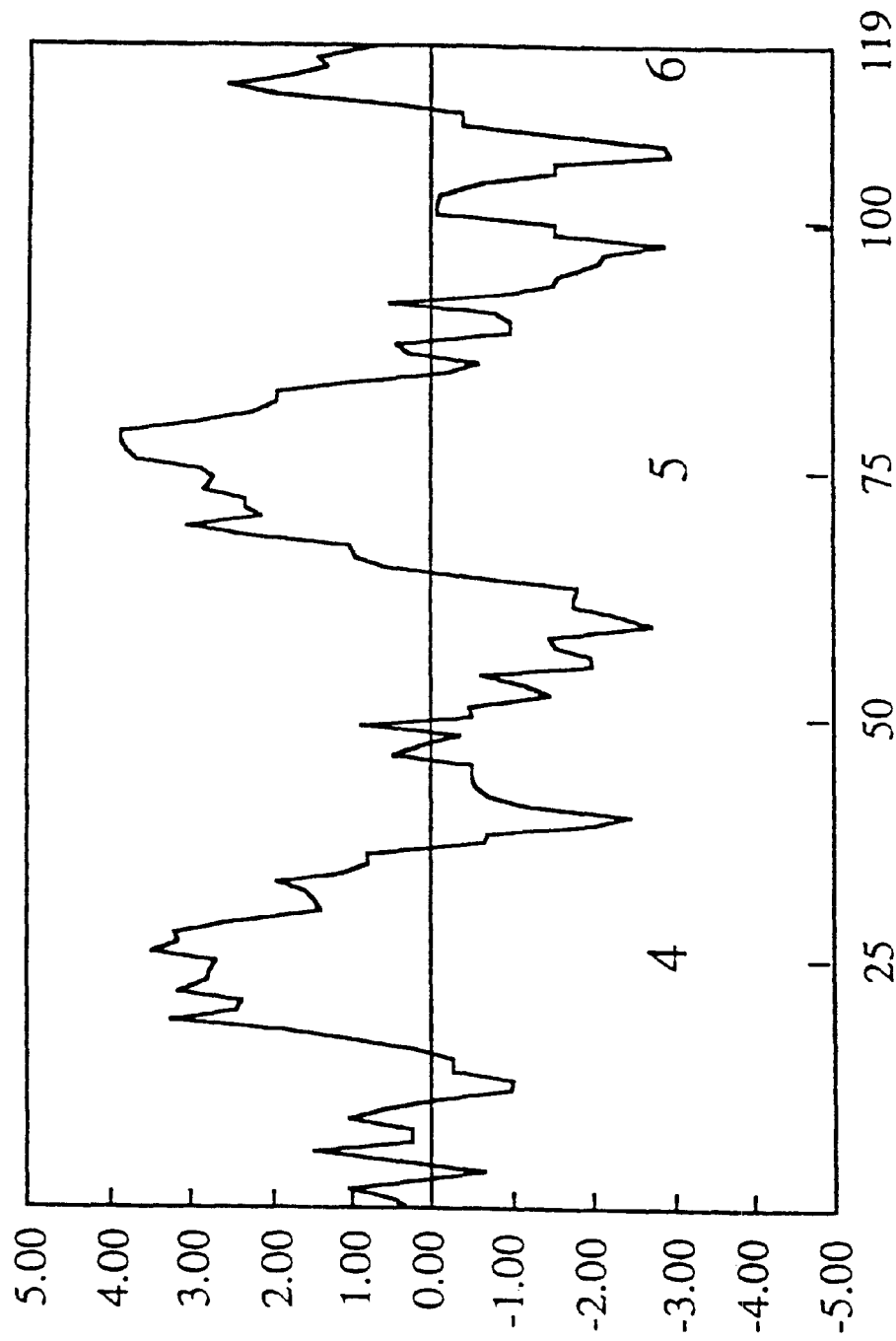
FIG. 53 is the hydrophobicity plotting profile of the protein encoded by the rabbit gastropyrolic part smooth muscle-derived G protein coupled receptor protein cDBA fragment included in pMH28, prepared based upon the amino acid sequence shown in FIG. 52, wherein numerals 4 to 6 suggest the presence of hydrophobic domains.
Figure 57:
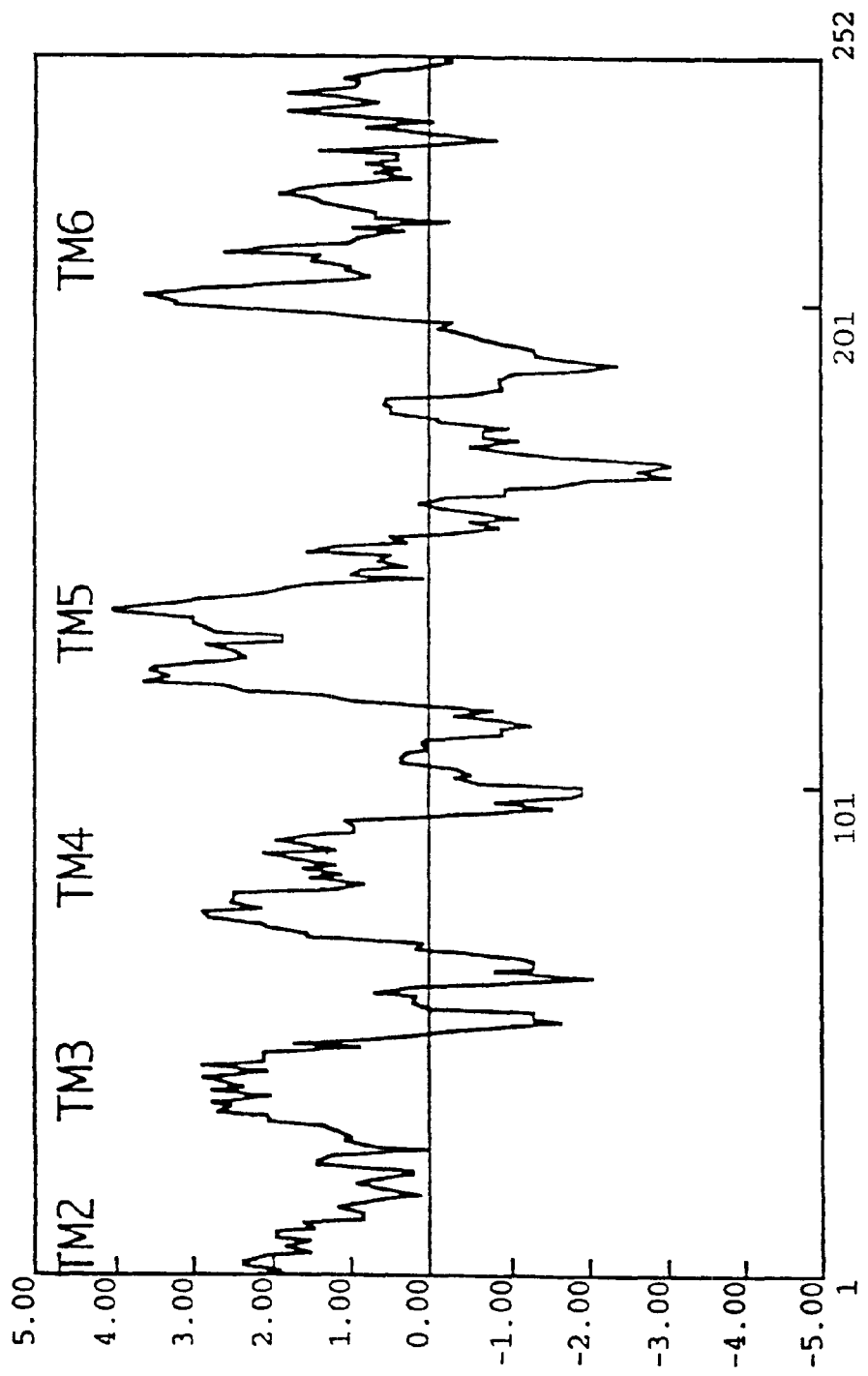
FIG. 57 is the hydrophobicity plotting profile of the protein encoded by the rabbit gastropyrolic part smooth muscle-derived G protein coupled receptor protein cDNA fragment included in pMN7, prepared based upon the amino acid sequences shown in FIGS. 55 and 56, wherein numerals TM2 to TM6 suggest the presence of hydrophobic domains.
Figure 58:
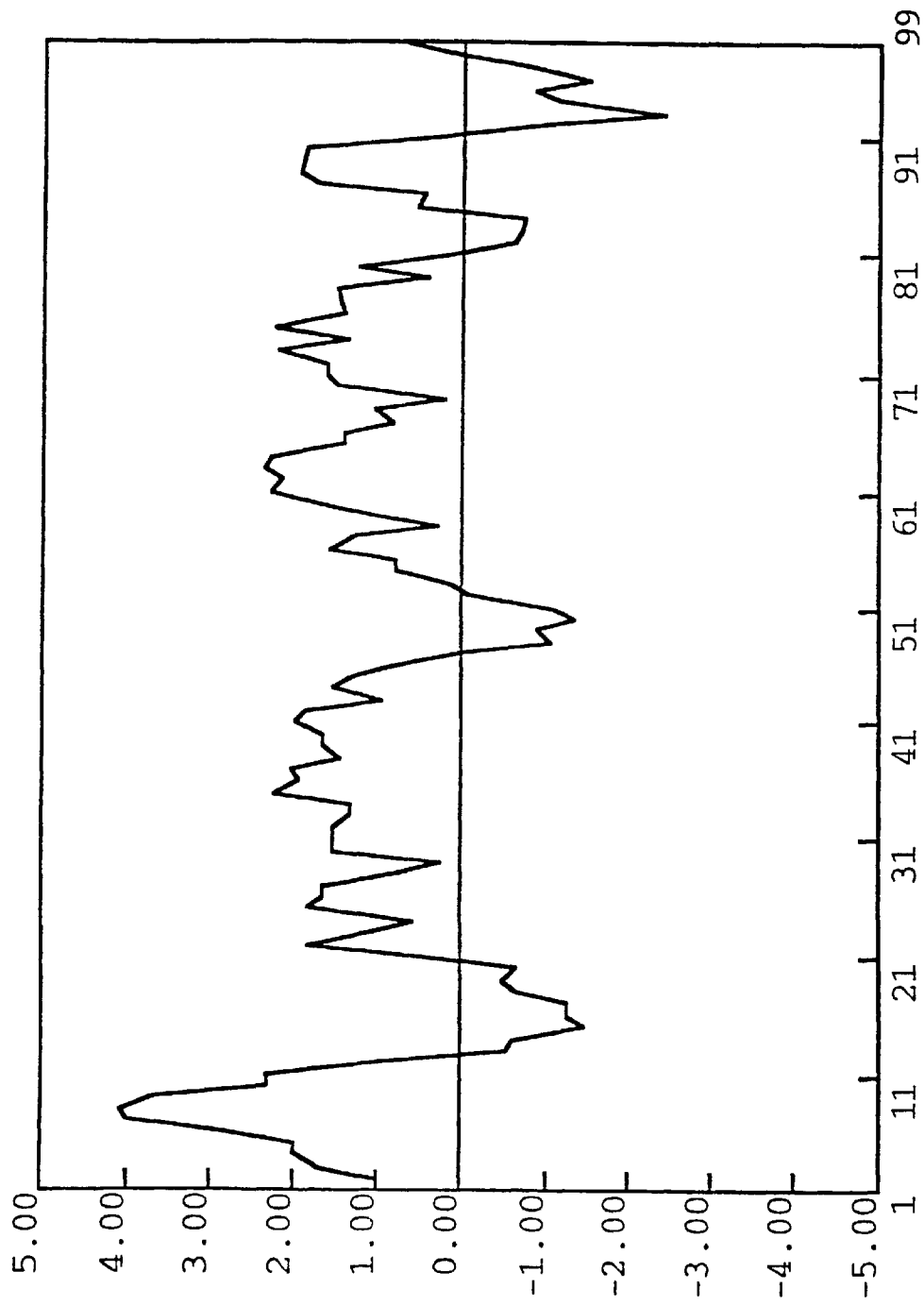
FIG. 58 is the partial hydrophobicity plotting profile of the protein encoded by the human pituitary gland-derived G protein coupled receptor protein cDNA fragment included in p19P2, prepared based upon the amino acid sequence shown in FIG. 22.
Figure 59:
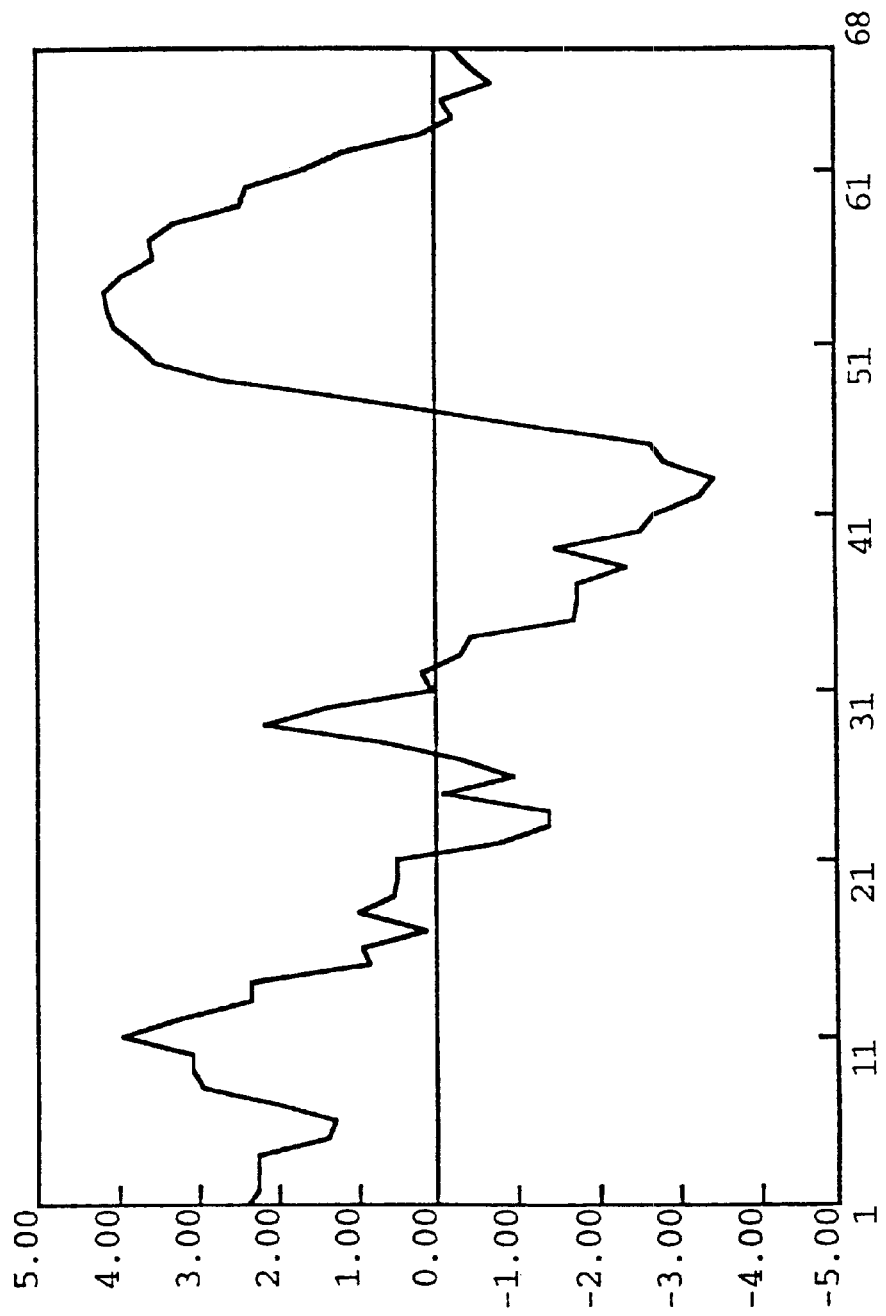
FIG. 59 is the partial hydrophobicity plotting profile of the protein encoded by the human pituitary gland-derived G protein coupled receptor protein cDNA fragment included in p19P2, prepared based upon the amino acid sequence shown in FIG. 23.
Figure 64:
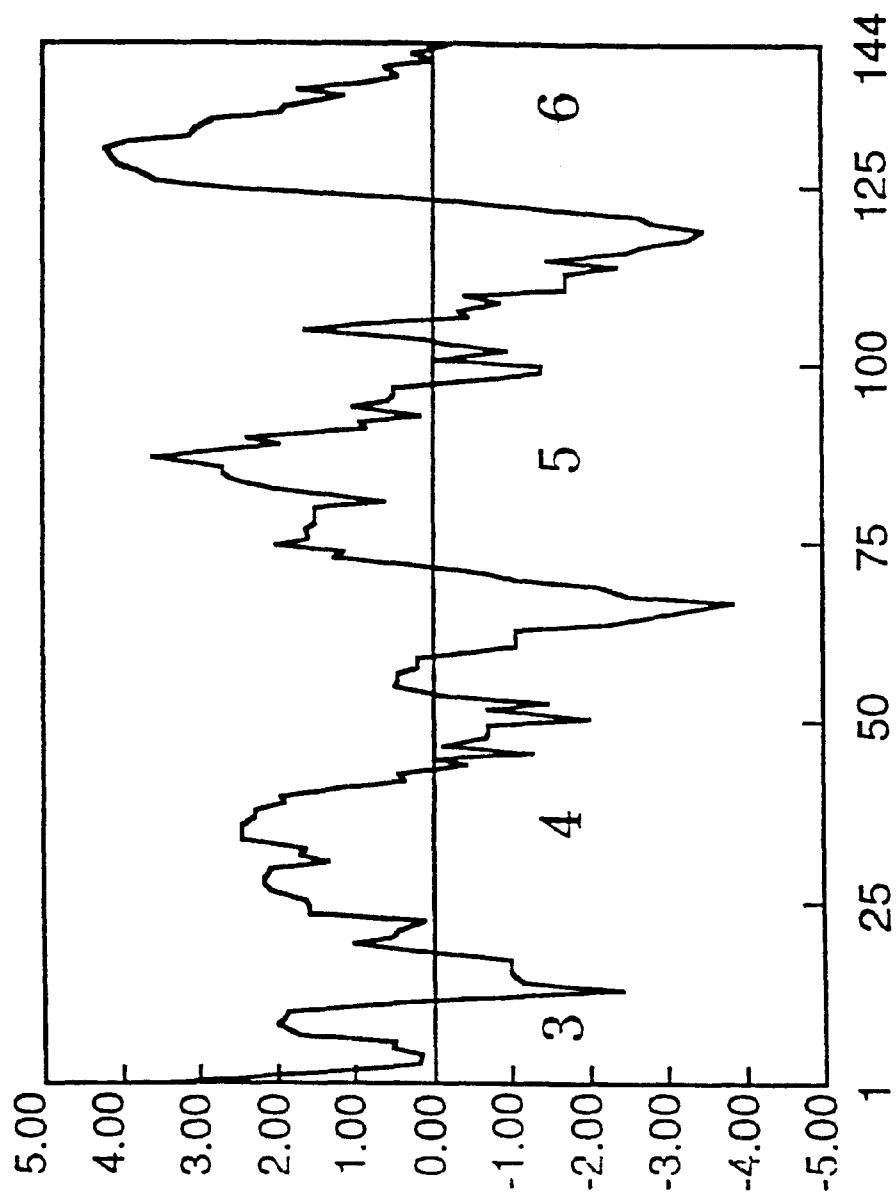
FIG. 64 is the partial hydrophobicity plotting profile of the protein encoded by the MIN6-derived G protein coupled receptor protein cDNA fragment included in p5S38, prepared based upon the amino acid sequence shown in FIG. 62.

FIG. 34 shows a nucleotide sequence of from immediate after the EcoRI site up to the NheI site encoded by phGR3. The nucleotide sequence of the human pituitary gland-derived receptor protein-encoding DNA corresponds to the nucleotide sequence of from 118th to 123rd nucleotides [FIG. 34]. An amino acid sequence of the receptor protein that is encoded by the nucleotide sequence is shown in FIG. 34. FIG. 36 shows the results of hydrophobicity plotting based upon the amino acid sequence.

(3) Northern Hybridization with Human Pituitary Gland-Derived Receptor Protein-Encoding phGR3

Northern blotting was carried out in order to detect the expression of phGR3-encoded human pituitary gland-derived receptor proteins in the pituitary gland at a mRNA level. Human pituitary gland mRNA (2.5 μg, Clontech Co.) was used as a template mRNA and the same as the probe used in Working Example 5 was used as a probe. Nylon membrane (Pall Biodyne, U.S.A.) was used as a filter for northern blotting and migration of the mRNA and adsorption (sucking) thereof with the blotting filter was carried out according to the method as disclosed in Molecular Cloning, Cold Spring Harbor Laboratory Press, 1989.

Figure 35:
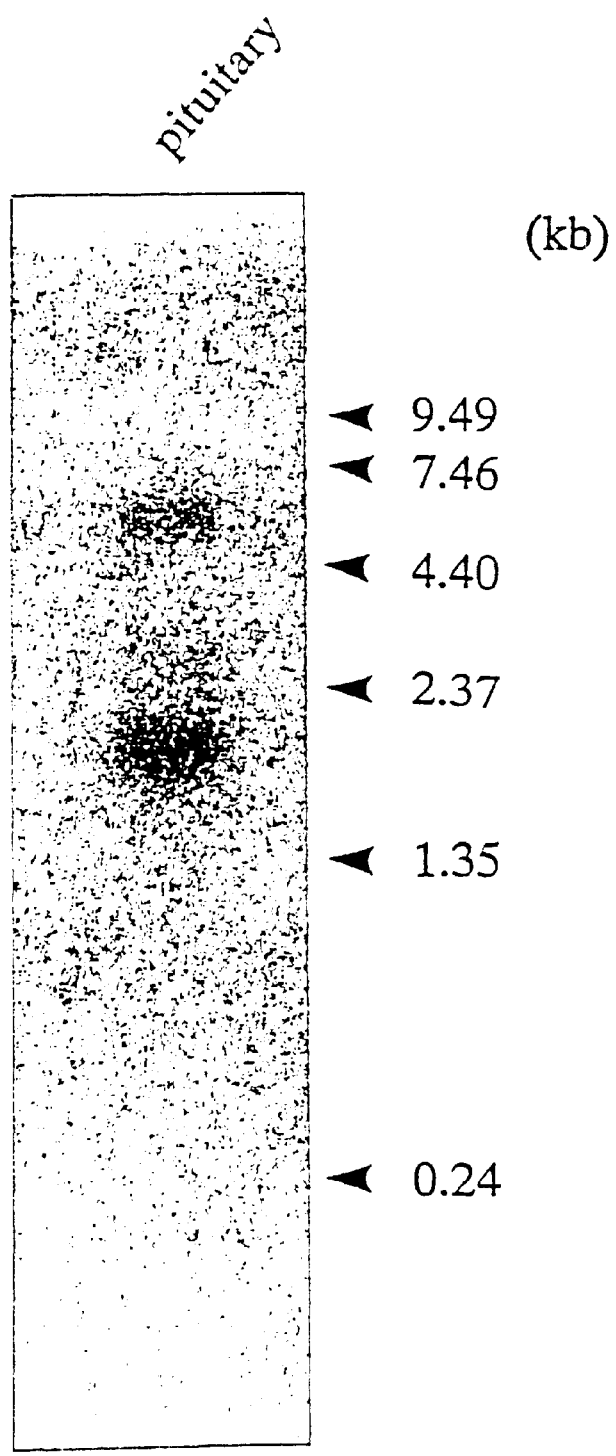
FIG. 35 is the northern blotting profile of the human pituitary gland mRNA of the receptor gene encoded by the human pituitary gland-derived cDNA clone, phGR3.

The hybridization was effected by incubating the above-mentioned filter and probe in a buffer containing 50% formamide, 5×SSPE, 5×Denhardt's solution, 0.1% SDS and 100 μg/ml of salmon sperm DNA overnight at 42° C. The filter was washed with 0.1×SSC, 0.1% SDS at 50° C. and, after drying with an air, was exposed to an X-ray film (XAR5, Kodak) for three days at −80° C. The results were as shown in FIG. 35 from which it is considered that the receptor gene encoded by phGR3is expressed in the human pituitary gland.

Example 7

Cloning of Mouse Pancreatic β-Cell Strain, MIN6-Derived G Protein Coupled Receptor Protein cDNA (1) Preparation of Poly(A)$^+$ RNA Fraction from Mouse Pancreatic β-Cell Strain, MIN6 and Synthesis of cDNA A total RNA was prepared from the mouse pancreatic β-cell strain, MIN6 (Jun-ichi Miyazaki et al., Endocrinology, Vol. 127, No. 1, p.126–132) according to the guanidine thiocyanate method (Kaplan B. B. et al., Biochem. J., 183, 181–184 (1979)) and, then, poly(A)$^+$ RNA fractions were prepared with a mRNA purifying kit (Pharmacia Co.). Next, to 5 μg of the poly(A)$^+$ RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE.

(2) Amplification of Receptor cDNA by PCR Using MIN6-Derived cDNA and Sequencing By using, as a template, 5 μl of cDNA prepared from the mouse pancreatic β-cell strain, MIN6 in the above step (1), PCR amplification using the DNA primers synthesized in Example 1 was carried out. A reaction solution was composed of the synthetic DNA primers (SEQ: 5' primer sequence and 3' primer sequence) each in an amount of 100 pM, 0.25 mM dNTPs, 1 μl of Taq DNA polymerase and 10 μl of 10×buffer attached to the enzyme kit, and the total amount of the reaction solution was made to be 100 μl. The cycle for amplification including 96° C. for 30 sec., 45° C. for 1 min. and 60° C. for 3 min. was repeated 30 times by using a Thermal Cycler (Perkin-Elmer Co.). Prior to adding Taq DNA polymerase, the remaining reaction solution was mixed and was heated at 95° C. for 5 minutes and at 65° C. for 5 minutes. The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated by using a 0.8% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into *E. coli* JM109 competent cells (Takara Shuzo Co., Japan) to produce transformants. Then, transformant clones having a cDNA-inserted fragment were selected in an LB agar culture medium containing ampicillin, IPTG (isopropylthio-β-D-galactoside) and X-gal. Only transformant clones exhibiting white color were picked with a sterilized toothstick to obtain transformant *Escherichia coli* JM109/p3H2-17.

The individual clones were cultured overnight in an LB culture medium containing ampicillin and treated with an automatic plasmid extracting machine (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan).

Homology retrieval was carried out based upon the determined nucleotide sequence [FIG. 37]. As a result, it was learned that a novel G protein coupled receptor protein was encoded by the cDNA fragment insert in the plasmid possessed by the transformant *Escherichia coli* JM109/p3H2-17. To further confirm this fact, by using DNASIS (Hitachi System Engineering Co., Japan) the nucleotide sequence were converted into an amino acid sequence [FIG. 37], and homology retrieval was carried out in view of hydrophobicity plotting [FIG. 38] and at the amino acid sequence level to find homology relative to chicken ATP receptor (P34996), human somatostatin receptor subtype 3 (A46226), human somatostatin receptor subtype 4 (JN0605) and bovine neuropeptide Y receptor (S28787) [FIG. 39]. Abbreviations in parentheses are reference numbers assigned when they are registered as data to NBRF-PIR/Swiss-PROT and are usually called "Accession Numbers".

Example 8

Cloning of Mouse Pancreatic β-Cell Strain, MIN6-Derived G Protein Coupled Receptor Protein cDNA (1) Preparation of Poly(A)$^+$ RNA Fraction from Mouse Pancreatic β-Cell Strain, MIN6 and Synthesis of cDNA A total RNA was prepared from the mouse pancreatic β-cell strain, MIN6 (Jun-ichi Miyazaki et al., Endocrinology, Vol. 127, No. 1, p.126–132) according to the guanidine thiocyanate method (Kaplan B. B. et al., Biochem. J., 183, 181–184 (1979)) and, then, poly(A)$^+$ RNA fractions were prepared with a mRNA purifying kit (Pharmacia Co.). Next, to 5 μg of the poly(A)$^+$ RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAS. The reaction product was extracted with phenol/chloroform (1:1), precipitated in ethanol, and was then dissolved in 30 μl of TE.

(2) Amplification of Receptor cDNA by PCR Using MIN6-Derived cDNA and Sequencing By using, as a template, 5 μl of cDNA prepared from the mouse pancreatic β-cell strain, MIN6, in the above step (1), PCR amplification using the DNA primers synthesized in Example 1 was carried out. A reaction solution was composed of the synthetic DNA primers (SEQ: 5' primer sequence and 3' primer sequence) each in an amount of 100 pM, 0.25 mM dNTPs, 1 μl of Taq DNA polymerase and 10 μl of 10×buffer attached to the enzyme kit, and the total amount of the reaction solution was made to be 100 μl. The cycle for amplification including 96° C. for 30 sec., 45° C. for 1 min. and 60° C. for 3 min. was repeated 30 times by using a Thermal Cycler (Perkin-Elmer Co.). Prior to adding Taq DNA polymerase, the remaining reaction solution was mixed and was heated at 95° C. for 5 minutes and at 65° C. for 5 minutes. The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated with a 0.8% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into *E. coli* JM109 competent cells (Takara Shuzo Co., Japan) to produce transformants. Then, transformant clones having a cDNA-inserted fragment were selected in an LB agar culture medium containing ampicillin, IPTG and X-gal. Only transformant clones exhibiting white color were picked with a sterilized toothstick to obtain transformant *Escherichia coli* JM109/p3H2-34.

The individual clones were cultured overnight in an LB culture medium containing ampicillin and treated with an automatic plasmid extracting machine (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan).

Figure 42:
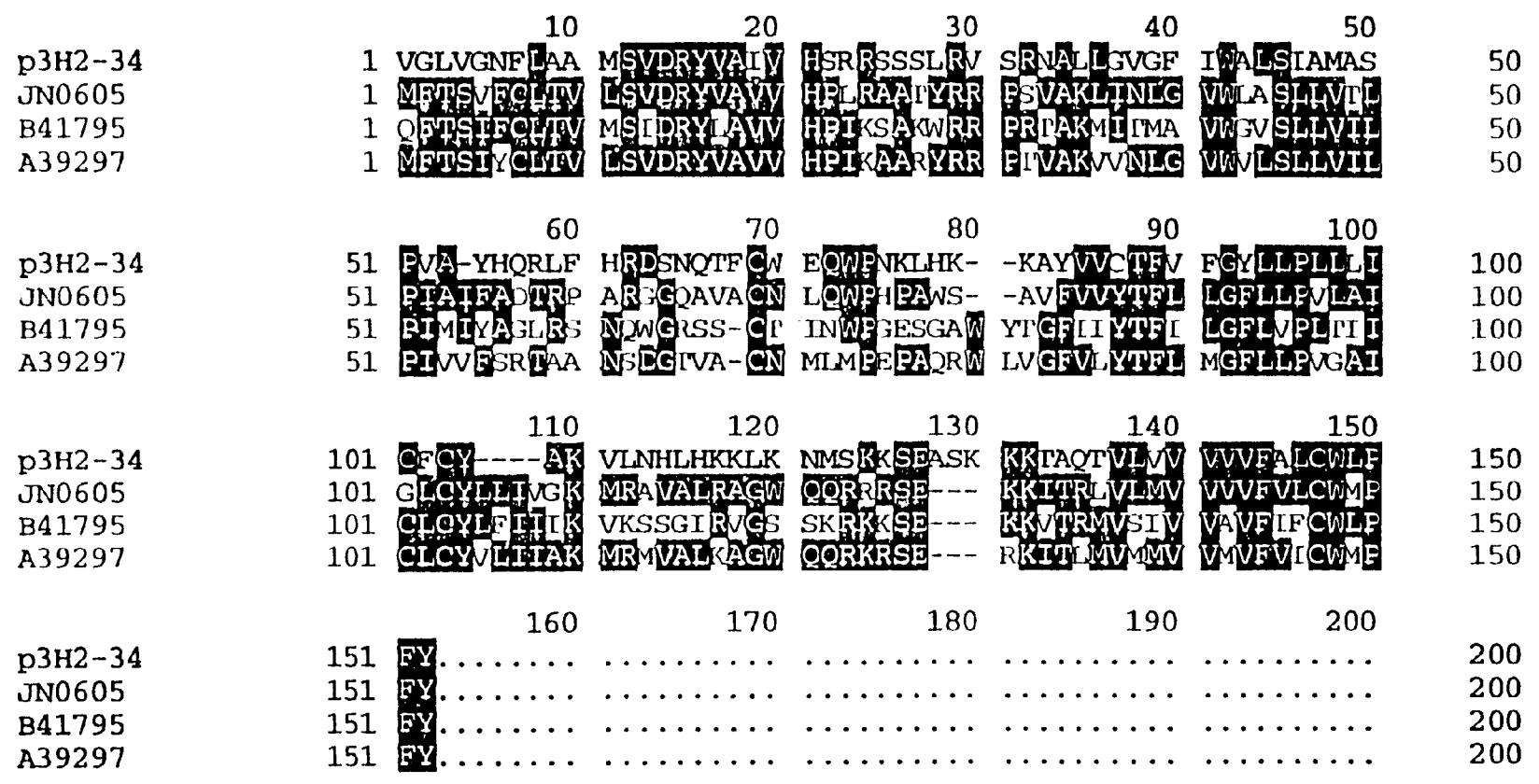

Homology retrieval was carried out based upon the determined nucleotide sequence [FIG. 40]. As a result, it was learned that a novel G protein coupled receptor protein was encoded by the cDNA fragment insert in the plasmid possessed by the transformant Escherichia coli JM109/p3H2-34. To further confirm this fact, by using DNASIS (Hitachi System Engineering Co., Japan) the nucleotide sequence were converted into an amino acid sequence [FIG. 40], and homology retrieval was carried out in view of hydrophobicity plotting [FIG. 41] and at the amino acid sequence level to find homology relative to human somatostatin receptor subtype 2 (B41795) and rat-derived ligand unknown receptor (A39297) [FIG. 42]. Abbreviations in parentheses are reference numbers assigned when they are registered as data to NBRF-PIR/Swiss-PROT and are usually called "Accession Numbers" or "Entry Names".

Example 9

Cloning of Rabbit Gastropyrolic Part Smooth Muscle-Derived G Protein Coupled Receptor Protein cDNA (1) Preparation of Poly(A)+ RNA Fraction from Rabbit Gastropyrolic Part Smooth Muscle and Synthesis of cDNA A total RNA was prepared from rabbit gastropyrolic part smooth muscles by the guanidine thiocyanate method (Kaplan B. B. et al., Biochem. J. 183, 181–184 (1979)) and, then, poly(A)+ RNA fractions were prepared with a mRNA purifying kit (Pharmacia Co.). Next, to 5 μg of the poly(A)+ RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE (Tris-EDTA solution).

(2) Amplification of Receptor cDNA by PCR Using Rabbit Gastropyrolic Part Smooth Muscle-Derived cDNA and Sequencing By using, as a template, 1 μl of cDNA prepared from the rabbit gastropyrolic part smooth muscle in the above step (1), PCR amplification using the DNA primers synthesized in Example 1 was carried out. A reaction solution was composed of the synthetic DNA primers (SEQ: 5' primer sequence and 3' primer sequence) each in an amount of 100 pM, 0.25 mM dNTPs, 1 μl of Taq DNA polymerase and 10 μl of buffer attached to the enzyme kit, and the total amount of the reaction solution was made to be 100 μl. The cycle for amplification including 96° C. for 30 sec., 45° C. for 1 min. and 60° C. for 3 min. was repeated 25 times by using a Thermal Cycler (Perkin-Elmer Co.). The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated with a 1.0% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into E. coli JM109 competent cells (Takara Shuzo Co., Japan) to produce transformants. Then, transformant clones having a cDNA-inserted fragment were selected in an LB agar culture medium containing ampicillin, IPTG and X-gal. Only transformant clones exhibiting white color were picked with a sterilized toothstick to obtain transformant Escherichia coli JM109/pMD4.

The individual clones were cultured overnight in an LB culture medium containing ampicillin and treated with an automatic plasmid extracting machine (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan). The determined nucleotide sequence was as shown in FIG. 43. It was learned from FIG. 43 that the cloned cDNA fragment was amplified from both sides with only the synthetic DNA primer having a nucleotide sequence represented by SEQ ID NO: 1 as synthesized in Example 1.

Homology retrieval was carried out based upon the determined nucleotide sequence [FIG. 43]. As a result, it was learned that a novel G protein coupled receptor protein was encoded by the cDNA fragment insert in the plasmid possessed by the transformant Escherichia coli JM109/pMD4. To further confirm this fact, by using DNASIS (Hitachi System Engineering Co., Japan) the nucleotide sequence were converted into an amino acid sequence [FIG. 43], and homology retrieval was carried out in view of hydrophobicity plotting [FIG. 44] and at the amino acid sequence level to find homology relative to rat ligand-unknown receptor protein (A35639) [FIG. 45]. Abbreviations in parentheses are reference numbers assigned when they are registered as data to NBRF-PIR/Swiss-PROT and are usually called "Accession Numbers".

Example 10

Cloning of cDNA Comprising Whole Coding Regions for Receptor Protein from Mouse Pancreatic β-Cell Strain, MIN6-Derived cDNA Library (1) Cloning of cDNA Comprising Whole Coding Regions for Receptor Protein from Mouse Pancreatic β-Cell Strain, MIN6-Derived cDNA Library Superscript™ Lambda System (BRL, Cat. 8256) distributed by BRL Co. and Glgapack II Gold (Stratagene, Cat. 200215) distributed by Stratagene Co. were used to construct MIN6-derived cDNA libraries. By using the above kits, a MIN6 cDNA library with $2.2 \times 10^6$ pfu (plaque forming units) was constructed from 10 μg of MIN6 poly(A)+ RNA. The cDNA library was mixed with E. coli Y1090⁻ treated with magnesium sulfate, and incubated at 37° C. for 15 minutes followed by addition of 0.5% agarose (Pharmacia Co.) LB. The E. coli was plated onto a 1.5% agar (Wako-Junyaku Co.) LB plate (containing 50 μg/ml of ampicillin). A nitrocellulose filter was placed on the plate on which plaques were formed and the plaque was transferred onto the filter. The filter was denatured with an alkali and then heated at 80° C. for 3 hours to fix DNAs.

The filter was incubated overnight at 42° C. together with the probe mentioned herein below in a buffer containing 50% formamide, 5×SSPE, 5×Denhardt's solution, 0.1% SDS and 100 μg/ml of salmon sperm DNA for hybridization.

The probe used was obtained by cutting the DNA fragment inserted in the plasmid, p3H2-34, obtained in Working Example 8, with EcoRI, followed by recovery and labeling by incorporation of [$^{32}$P]dCTP (Dupont Co.) with a random prime DNA labelling kit (Amasham Co.).

It was washed with 2×SSC (150 mM NaCl and 15 mM sodium citrate), 0.1% SDS at 55° C. for 1 hour and, then, subjected to an autoradiography at −80° C. to detect hybridized plaques.

In this screening, hybridization signals were recognized in two independent plaques. Each DNA was prepared from the two clones. The DNAs digested with SalI and NotI were subjected to an agarose electrophoresis and were analyzed. Inserted fragments were identified at about 2.0 kb and 3.0 kb, respectively. Between them, the DNA fragment corresponding to the band at about 3.0 kb (λ No.20) was selected. The λ No.20-derived NotI-SalI fragment with about 3.0 kb was subcloned into the NotI-SalI site of the plasmid, pBluescript II SK(+), and E. coli JM109 was transformed with the plasmid to obtain a transformant E. coli JM109/pMGR20. A restriction enzyme map of the plasmid, pMGR20, was prepared relying upon a restriction enzyme map deduced from the nucleotide sequence as shown in Working Example 8. As a result, it was learned that it carried a full-length receptor protein-encoding DNA which was predicted from the receptor protein-encoding DNA as shown in Working Example 8.

(2) Sequencing of MIN6-Derived Receptor Protein Full-Length cDNA

Among the NotI-SalI fragments inserted in the plasmid, pMGR20, obtained in the above step (1), the nucleotide sequence with total 1607 bp, including not only a region that is considered to be a receptor protein-coding region (ORF) but also a neighboring region thereof was sequenced. Concretely speaking, by utilizing restriction enzyme sites that exist in the NotI-SalI fragments, unnecessary parts were removed or necessary fragments were subcloned in order to prepare template plasmids for analyzing the nucleotide sequence thereof. As for the nucleotide sequences of part of the regions, primers for sequencing were synthesized based upon the nucleotide sequences that were determined already and used to make confirmation.

The reaction for determining the nucleotide sequence (sequencing) was carried out with a DyeDeoxy terminator cycle sequencing kit (ABI Co.), the DNA was decoded with the fluorescent automatic sequencer (ABI Co.), and the data of the nucleotide sequence obtained were analyzed with DNASIS (Hitachi System Engineering Co., Japan).

FIG. 46 shows a nucleotide sequence around an open reading frame (ORF) of a mouse galanin receptor protein encoded by the cDNA insert in pMGR20. The nucleotide sequence of mouse galanin receptor protein-encoding DNA corresponds to from the 481st to 1525th nucleotides of the nucleotide sequence in FIG. 46. The nucleotide sequence was converted into an amino acid sequence [FIG. 46] and hydrophobicity plotting was carried out [FIG. 47]. Since the amino acid sequence [FIG. 46] has 92% homology to the human-derived galanin receptor protein at the amino acid sequence level [FIG. 48], it was learned that the cDNA insert in the pMGR20 is a mouse-derived galanin receptor protein-encoding cDNA.

Example 11

Preparation of Synthetic DNA Primer for Amplifying G Protein Coupled Receptor Protein-Encoding DNA Highly homologous parts were found by comparing nucleotide sequences corresponding to or near the third membrane-spanning domain [3C and 3D in FIG. 4] and the sixth membrane-spanning domain [6C of FIG. 6] among known G protein coupled receptors, i.e., rat-derived angiotensin II receptor protein (L32840), rat-derived angiotensin Ib receptor protein (X64052), rat-derived angiotensin receptor protein subtype (M90065), human-derived angiotensin Ia receptor protein (M91464), rat-derived cholecystokinin$_A$ receptor protein (M88096), rat-derived cholecystokinin$_B$ receptor protein (M99418), human-derived cholecystokinin$_B$ receptor protein (L04473), mouse-derived low-affinity interleukin 8 receptor protein (M73969), human-derived high-affinity interleukin 8 receptor protein (X65858), mouse-derived C5a anaphylatoxin receptor protein (S46665), human-derived N-formyl peptide receptor protein (M60626), etc.

The aforementioned abbreviations in parentheses are reference numbers that are indicated when the GenBank/EMBL data base is retrieved, and are usually called "Accession Numbers".

It was planned to incorporate mixed bases relying upon the base regions that were in agreement with a large number of receptor protein cDNAs in order to enhance base agreement of sequences with as many receptor cDNAs as possible even in other regions. Based upon these sequences, the degenerate synthetic DNA (3D of FIG. 4) having a nucleotide sequence represented by SEQ ID NO: 3 which is complementary to the homologous nucleotide sequence of FIG. 4 and the degenerate synthetic DNA (nucleotide sequence complementary to 6C of FIG. 6) having a nucleotide sequence represented by SEQ ID NO: 4 were produced. Nucleotide synthesis was carried out by a DNA synthesizer.

[Synthetic DNAs]

5'-CTCGC (G or C) GC (C or T) (A or C) TI (A or G) G (C or T) ATGGA (C or T) CGITAT-3'   (SEQ ID NO:3)

5'-CATGT (A or G) G (T or A) AGGGAAICCAG (G or C) A (A or C) AI (A or G) A (A or G)(A or G) AA-3'   (SEQ ID NO:4)

The parentheses indicate the incorporation of a plurality of bases, leading to multiple oligonucleotides in the primer preparation. In other words, nucleotide residues in parentheses of the aforementioned DNAs were incorporated in the presence of a mixture of plural bases at the time of synthesis, provided that I denotes inosine.

Example 12

Cloning of Rabbit Gastropyrolic Part Smooth Muscle-Derived G Protein Coupled Receptor Protein cDNA (1) Preparation of Poly(A)$^+$ RNA Fraction from Rabbit Gastropyrolic Part Smooth Muscle and Synthesis of cDNA A total RNA was prepared frpm rabbit gastropyrolic part smooth muscles by the guanidine thiocyanate method (Kaplan B. B. et al., Biochem. J. 183, 181–184 (1979)) and, then, poly(A)$^+$ RNA fractions were prepared with a mRNA purifying kit (Pharmacia Co.). Next, to 5 μg of the poly(A)$^+$ RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE.

(2) Amplification of Receptor cDNA by PCR Using Rabbit Gastropyrolic Part Smooth Muscle-Derived cDNA and Sequencing By using, as a template, 1 µl of cDNA prepared from the rabbit gastropyrolic part smooth muscle in the above step (1), PCR amplification using the DNA primer having a nucleotide sequence represented by SEQ ID NO: 3 and the DNA primer having a nucleotide sequence represented by SEQ ID NO: 4 synthesized in Example 11 was carried out. A reaction solution was composed of the synthetic DNA primers (SEQ: 5' primer sequence and 3' primer sequence) each in an amount of 100 pM, 0.25 mM dNTPs, 1 µl of Taq DNA polymerase and 10 µl of buffer attached to the enzyme kit, and the total amount of the reaction solution was made to be 100 µl. The cycle for amplification including 96° C. for 30 sec., 45° C. for 1 min. and 60° C. for 3 min. was repeated 25 times by using a Thermal Cycler (Perkin-Elmer Co.). The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated with a 1.0% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into *E. coli* JM109 competent cells (Takara Shuzo Co., Japan) to produce transformants. Then, transformant clones having a cDNA-inserted fragment were selected in an LB agar culture medium containing ampicillin, IPTG and X-gal. Only transformant clones exhibiting white color were picked with a sterilized toothstick to obtain transformant *Escherichia coli* JM109/pMJ10.

The individual clones were cultured overnight in an LB culture medium containing ampicillin and treated with an automatic plasmid extracting machine (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan). The determined nucleotide sequence was as shown in FIG. 49.

Homology retrieval was carried out based upon the determined nucleotide sequence [FIG. 49]. As a result, it was learned that a novel G protein coupled receptor protein was encoded by the cDNA fragment insert in the plasmid possessed by the transformant *Escherichia coli* JM109/pMJ10. To further confirm this fact, by using DNASIS (Hitachi System Engineering Co., Japan) the nucleotide sequence were converted into an amino acid sequence [FIG. 49], and homology retrieval was carried out in view of hydrophobicity plotting [FIG. 50] and at the amino acid sequence level to find homology relative to human ligand unknown receptor protein (B42009), human N-formyl peptide receptor protein (JC2014), rabbit N-formyl peptide receptor protein (A46520), mouse C5a anaphylatoxin receptor protein (A46525) and bovine neuropeptide Y receptor protein (S28787) [FIG. 51]. Abbreviations in parentheses are reference numbers assigned when they are registered as data to NBRF-PIR/Swiss-PROT and are usually called "Accession Numbers".

Example 13

Preparation of Synthetic DNA Primer for Amplifying G Protein Coupled Receptor Protein-Encoding DNA A comparison of nucleotide sequences coding for regions corresponding to or near the third membrane-spanning domain among known G protein coupled receptors, i.e., mouse-derived κ-opioid receptor protein (L11064), mouse-derived δ-opioid receptor protein (L11065), rat-derived µ-opioid receptor protein (D16349), mouse-derived bradykinin B2 receptor protein (X69676), rat-derived bradykinin B2 receptor protein (M599967), mouse-derived bombesin receptor protein (M35328), human-derived neuromedin B receptor protein (M73482), human-derived gastrin releasing peptide receptor protein (M73481), human-derived bombesin receptor protein subtype 3 (L08893), mouse-derived substance K receptor protein (X62933), mouse-derived substance P receptor protein (X62934), rat-derived neurokinin 3 receptor protein (J05189), rat-derived endothelin receptor protein (M60786), rat-derived ligand unknown receptor proteins (L04672), (X61496), (X59249) and (L09249), mouse-derived ligand unknown receptor protein (P30731), human-derived ligand unknown receptor proteins (M31210) and (U03642), etc. was made. In particular, the degenerate DNA primer having a nucleotide sequence (3B in FIG. 3; SEQ ID NO: 6) with highly common bases (highly homologous nucleotides) was synthesized to enhance base agreement of sequences with as many receptor cDNAs as possible even in other regions on the basis of nucleotide sequence regions that were in agreement with a large number of receptor cDNAs. Nucleotide synthesis was carried out by a DNA synthesizer.

The nucleotide sequence represented by SEQ ID NO: 6 is:

5'-CTGAC (C or T) G (C or T) TCTI (A or G)(G or C) I (A or G)(C or T) TGAC (A or C) G (A, C or G) TAT-3'

The parentheses indicate the incorporation of a plurality of bases, leading to multiple oligonucleotides in the primer preparation. In other words, nucleotide residues in parentheses of the aforementioned DNAs were incorporated in the presence of a mixture of plural bases at the time of synthesis, provided that I denotes inosine.

Furthermore, a comparison of nucleotide sequences coding for regions corresponding to or near the sixth membrane-spanning domain among known G protein coupled receptors, i.e., mouse-derived κ-opioid receptor protein (L11064), mouse-derived δ-opioid receptor protein (L11065), rat-derived µ-opioid receptor protein (D16349), mouse-derived bradykinin B2 receptor protein (X69676), rat-derived bradykinin B2 receptor protein (M59967), mouse-derived bombesin receptor protein (M35328), human-derived neuromedin B receptor protein (M73482), human-derived gastrin releasing peptide receptor protein (M73481), human-derived bombesin receptor protein subtype 3 (L08893), mouse-derived substance K receptor protein (X62933), mouse-derived substance P receptor protein (X62934), rat-derived neurokinin 3 receptor protein (J05189), rat-derived endothelin receptor protein (M60786), rat-derived ligand unknown receptor proteins (L04672), (X61496), (X59249) and (L09249), mouse-derived ligand unknown receptor protein (P30731), human-derived ligand unknown receptor proteins (M31210) and (U03642), etc. was made. In particular, the degenerate DNA primer having a nucleotide sequence (SEQ ID NO: 8) which is complementary to the nucleotide sequence (6A in FIG. 5) with highly common bases (highly homologous nucleotides) was synthesized to enhance base agreement of sequences with as many receptor cDNAs as possible even in other portions on the basis of base regions that are in agreement with a large number of receptor cDNAs.

The nucleotide sequence represented by SEQ ID NO: 8 is:

5'-GATGTG (A or G) TA (A or G) GG (G or C)(A or G) ICCAA-CAGAIG (A or G) (C or T) AAA-3'

The parentheses indicate the incorporation of a plurality of bases, leading to multiple oligonucleotides in the primer preparation. In other words, nucleotide residues in parentheses of the aforementioned DNAs were incorporated in the presence of a mixture of plural bases at the time of synthesis, provided that I denotes inosine.

The aforementioned abbreviations in parentheses are reference numbers indicated when the GenBank/EMBL data base is retrieved and are usually called "Accession Numbers".

Example 14

Cloning of Rabbit Gastropyrolic Part Smooth Muscle-Derived G Protein Coupled Receptor Protein cDNA (1) Preparation of Poly(A)+ RNA Fraction from Rabbit Gastropyrolic Part Smooth Muscle and Synthesis of cDNA A total RNA was prepared from rabbit gastropyrolic part smooth muscles by the guanidine thiocyanate method (Kaplan B. B. et al., Biochem. J. 183, 181–184 (1979)) and, then, poly(A)+ RNA fractions were prepared with a mRNA purifying kit (Pharmacia Co.). Next, to 5 μg of the poly(A)+ RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAS. The reaction product was extracted with phenol/chloroform (1:1), precipitated in ethanol, and was then dissolved in 30 μl of TE.

(2) Amplification of Receptor cDNA by PCR Using Rabbit Gastropyrolic Part Smooth Muscle-Derived cDNA and Sequencing By using, as a template, 1 μl of cDNA prepared from the rabbit gastropyrolic part smooth muscle in the above step (1), PCR amplification using the DNA primer having a nucleotide sequence represented by SEQ ID NO: 6 and the DNA primer having a nucleotide sequence represented by SEQ ID NO: 8 synthesized in Example 13 was carried out. A reaction solution was composed of the synthetic DNA primers (SEQ: 5' primer sequence and 3' primer sequence) each in an amount of 100 pM, 0.25 mM dNTPs, 1 μl of Taq DNA polymerase and 10 μl of buffer attached to the enzyme kit, and the total amount of the reaction solution was made to be 100 μl. The cycle for amplification including 96° C. for 30 sec., 45° C. for 1 min. and 60° C. for 3 min. was repeated 25 times by using a Thermal Cycler (Perkin-Elmer Co.). The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated by using a 1.0% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into *E. coli* JM109 competent cells (Takara Shuzo Co., Japan) to produce transformants. Then, transformant clones having a cDNA-inserted fragment were selected in an LB agar culture medium containing ampicillin, IPTG and X-gal. Only transformant clones exhibiting white color were picked with a sterilized toothstick to obtain transformant *Escherichia coli* JM109/pMH28.

The individual clones were cultured overnight in an LB culture medium containing ampicillin and treated with an automatic plasmid extracting machine (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan). The determined nucleotide sequence was as shown in FIG. 52.

Homology retrieval was carried out based upon the determined nucleotide sequence [FIG. 52]. As a result, it was learned that a novel G protein coupled receptor protein was encoded by the cDNA fragment insert in the plasmid possessed by the transformant *Escherichia coli* JM109/pMH28. To further confirm this fact, by using DNASIS (Hitachi System Engineering Co., Japan) the nucleotide sequence were converted into an amino acid sequence [FIG. 52], and homology retrieval was carried out in view of hydrophobicity plotting [FIG. 53] and at the amino acid sequence level to find homology relative to mouse IL-8 receptor protein (P35343), human somatostatin receptor protein 1 (A41795) and human somatostatin receptor protein 4 (A47457)[FIG. 54]. The aforementioned abbreviations in parentheses are reference numbers assigned when they are registered as data to NBRF-PIR or SWISS-PROT and are usually called "Accession Numbers".

Example 15

Preparation of Synthetic DNA Primer for Amplifying G Protein Coupled Receptor Protein-Encoding DNA A comparison of nucleotide sequences coding for regions corresponding to or near the second membrane-spanning domain among known G protein coupled receptors, i.e., human-derived galanin receptor (HUMGALAREC), rat-derived α-1B-adrenergic receptor (RATADR1B), human-derived β-1-adrenergic receptor (HUMADRB1), rabbit-derived IL-8 receptor (RABIL8RSB), human-derived opioid receptor (HUMOPIODRE), bovine-derived substance K receptor (BTSKR), human-derived somatostatin receptor-2 (HUMSTRI2A), human-derived somatostatin receptor-3 (HUMSSTR3Y), human-derived gastrin receptor (HUMGARE), human-derived cholecystokinin A receptor (HUMCCKAR), human-derived dopamine receptor-D5 (HUMD1B), human-derived serotonin receptor 5HT1E (HUM5HT1E), human-derived dopamine receptor D4 (HUMD4C), mouse-derived serotonin receptor-2 (MMSERO), rat-derived α-1A-adrenergic receptor (RATADRA1A), rat-derived histamine H2 receptor (S57565), etc. was made. In particular, the degenerate DNA primer having a nucleotide sequence (T2A in FIG. 7, SEQ ID NO: 10) with highly common bases (highly homologous nucleotides) was synthesized to enhance base agreement of sequences with as many receptor cDNAs as possible even in other regions on the basis of nucleotide sequence regions that were in agreement with a large number of receptor cDNAs. Nucleotide synthesis was carried out by a DNA synthesizer.

The nucleotide sequence represented by SEQ ID NO: 10 is:

5'-GYCACCAACN$_2$WSTTCATCCTSWN$_2$HCTG-3' wherein S represents G or C; Y represents C or T; W represents A or T; H represents A, C or T and N$_2$ represents I.

The parentheses indicate the incorporation of a plurality of bases, leading to multiple oligonucleotides in the primer preparation. In other words, nucleotide residues in parentheses of the aforementioned DNAs were incorporated in the presence of a mixture of plural bases at the time of synthesis, provided that I denotes,inosine.

Furthermore, a comparison of nucleotide sequences coding for regions corresponding to or near the seventh membrane-spanning domain among known G protein coupled receptors, i.e., human-derived galanin receptor (HUMGALAREC), rat-derived A1 adenosine receptor (RAT1ADREC), porcine-derived angiotensin receptor (PIGA2R), rat-derived serotonin receptor (RAT5HTRTC), human-derived dopamine receptor (S58541), human-derived gastrin releasing peptide receptor (HUMGRPR), mouse-derived GRP/bombesin receptor (MUSGRPBOM), rat-derived vascular type 1 angiotensin receptor (RRVT1AIIR), human-derived muscarinic acetylcholine receptor (HSHM4), human-derived β-1 adrenergic receptor (HUMDRB1), human-derived gastrin receptor (HUMGARE), rat-derived cholecystokinin receptor (RATCCKAR), rat-derived ligand unknown receptor (S59748), human-derived somatostatin receptor (HUMSST28A), rat-derived ligand unknown receptor (RNGPROCR), mouse-derived somatostatin receptor 1 (MUSSRI1A), human-derived α-A1-adrenergic receptor (HUMA1AADR), mouse-derived delta-opioid receptor (S66181), human-derived somatostatin receptor-3 (HUMSSTR3Y), etc. was made. In particular, the degenerate DNA primer having a nucleotide sequence (T7A in FIG. 8, SEQ ID NO: 11) with highly common bases (highly homologous nucleotides) was synthesized to enhance base agreement of sequences with as many receptor cDNAs as possible even in other regions on the basis of nucleotide sequence regions that were in agreement with a large number of receptor cDNAs. Nucleotide synthesis was carried out by a DNA synthesizer.

The nucleotide sequence represented by SEQ ID NO: 11 is:

5'-ASN$_2$SAN$_2$RAAGSARTAGAN$_2$GAN$_2$RGGRTT-3' wherein R represents A or G; S represents G or C and N$_2$ represents I.

The parentheses indicate the incorporation of a plurality of bases, leading to multiple oligonucleotides in the primer preparation. In other words, nucleotide residues in parentheses of the aforementioned DNAs were incorporated in the presence of a mixture of plural bases at the time of synthesis, provided that I denotes inosine.

The aforementioned abbreviations in parentheses are reference numbers indicated when the GenBank/EMBL data base is retrieved and are usually called "Accession Numbers".

Example 16

Cloning of Rabbit Gastropyrolic Part Smooth Muscle-Derived G Protein Coupled Receptor Protein cDNA (1) Preparation of Poly(A)$^+$ RNA Fraction from Rabbit Gastropyrolic Part Smooth Muscle and Synthesis of cDNA A total RNA was prepared from rabbit gastropyrolic part smooth muscles by the guanidine thiocyanate method (Kaplan B. B. et al., Biochem. J. 183, 181–184 (1979)) and, then, poly(A)$^+$ RNA fractions were prepared with a mRNA purifying kit (Pharmacia Co.). Next, to 5 μg of the poly(A)$^+$ RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE.

(2) Amplification of Receptor cDNA by PCR Using Rabbit Gastropyrolic Part Smooth Muscle-Derived cDNA and Sequencing By using, as a template, 1 μl of cDNA prepared from the rabbit gastropyrolic part smooth muscle in the above step (1), PCR amplification using the DNA primer having a nucleotide sequence represented by SEQ ID NO: 10 and the DNA primer having a nucleotide sequence represented by SEQ ID NO: 11 synthesized in Example 15 was carried out. A reaction solution was composed of the synthetic DNA primers (SEQ: 5' primer sequence and 3' primer sequence) each in an amount of 100 pM, 0.25 mM dNTPs, 1 μl of Taq DNA polymerase and 10 μl of buffer attached to the enzyme kit, and the total amount of the reaction solution was made to be 100 μl. The cycle for amplification including 96° C. for 30 sec., 45° C. for 1 min. and 60° C. for 3 min. was repeated 25 times with a Thermal Cycler (Perkin-Elmer Co.). The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated with a 1.4% low-melting temperature agarose gel, the band parts were excised from the gel with a razor blade, and were eluted electrophoretically, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into *E. coli* JM109 competent cells (Takara Shuzo Co., Japan) to produce transformants. Then, transformant clones having a cDNA-inserted fragment were selected in an LB agar culture medium containing ampicillin, IPTG and X-gal. Only transformant clones exhibiting white color were picked with a sterilized toothstick to obtain 100 transformant clones.

The individual clones were cultured overnight in an LB culture medium containing ampicillin and treated with the automatic plasmid extracting machine PI-100 (Kurabo Co., Japan) to prepare plasmid DNAs. An aliquot of the DNA thus prepared was cut by EcoRI to confirm the size of the cDNA fragment that was inserted. An aliquot of the remaining DNA was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer.

Homology retrieval was carried out based upon the determined nucleotide sequence by using DNASIS (Hitachi System Engineering Co., Japan). As a result, it was learned that a novel G protein coupled receptor protein was encoded by the cDNA fragment insert in the plasmid possessed by the transformant Escherichia coli JM109/pMN7. FIG. 56 and FIG. 56 show the nucleotide sequences of the cDNA fragments. To further confirm this fact, by using DNASIS (Hitachi System Engineering Co., Japan), the nucleotide sequences were converted into amino acid sequences [FIG. 55] and [FIG. 56], and hydrophobicity plotting was carried out [FIG. 57]. As a result, the presence of hydrophobic domains which prove that it is a G protein coupled receptor protein were confirmed. Furthermore, homology retrieval was carried out at the amino acid sequence level to find that the DNAs were novel receptor proteins having 27% homology relative to rat-derived $\beta_3$-adrenaline receptor protein (A41679), 29% homology relative to rat-derived serotonin (5-HT6) receptor protein (JN0591), 27% homology relative to dog-derived histamine $H_2$ receptor protein (A39008), 27% homology relative to human-derived somatostatin receptor (type 4) protein (JN0605), 24% homology relative to human-derived dopamine $D_1$ receptor protein (S11377), 23% homology relative to rat-derived neurotensin receptor protein (JH0164), 31% homology relative to human-derived cholecystokinin B receptor protein (JC1352), and 30% homology relative to rat-derived gastrin receptor protein (JQ1614). The aforementioned abbreviations in parentheses are reference numbers assigned when they are registered as data to NBRF-PIR and are usually called "Accession Numbers".

Example 17

Amplification of Receptor cDNA by PCR Using MIN6-Derived cDNA and Sequencing

By using, as a template, 5 µl of cDNA prepared from the mouse pancreatic β-cell strain, MIN6 in working Example 4 (1), PCR amplification using the DNA primers synthesized in Example 4 (2) as disclosed in Libert F. et al., "Science, 244:569–572, 1989", i.e., a synthetic primer represented by the following sequence:

5'-CTGTG (C or T) G (C or T) (G or C) AT (C or T) GCIIT (G or T) GA (C or T) (A or C) G (G or C)
TAC-3'                                                                                                (SEQ ID NO: 60)

wherein I is inosine; and
a synthetic primer represented by the following sequence:

5'-A (G or T) G (A or T) AG (A or T) AGGGCAGCCAGCAGAI
(G or C) (A or G) (C or T) GAA-3'                              (SEQ ID NO: 61)

wherein I is inosine, was carried out under the same conditions as in Example 3 (1). The resulting PCR product was subcloned to the plasmid vector, pCR™II, in the same manner as in Example 3 (2) to obtain a plasmid, p5S38. The plasmid p5S38 was transfected into E. coli JM109 to obtain transformant Escherichia coli JM109/p5S38.

The reaction for determining the nucleotide sequence (sequencing) was carried out with a DyeDeoxy terminator cycle sequencing kit (ABI Co.), the DNA was decoded with the fluorescent automatic sequencer (ABI Co.), and the data of the nucleotide sequence obtained were read with DNASIS (Hitachi System Engineering Co., Japan).

FIG. 62 shows a mouse pancreatic β-cell strain MIN6-derived G protein coupled receptor protein-encoding DNA (SEQ ID NO: 33) and an amino acid sequence (SEQ ID NO: 28) encoded by the isolated DNA based upon the nucleotide sequence of plasmid, p5S38. The underlined portions represent regions corresponding to the synthetic primers.

Homology retrieval was carried out based upon the determined nucleotide sequence [FIG. 62]. As a result, it was learned that a novel G protein coupled receptor protein was encoded by the cDNA fragment obtained. To further confirm this fact, by using DNASIS (Hitachi System Engineering Co., Japan), the nucleotide sequence was converted into an amino acid sequence [FIG. 62], and hydrophobicity plotting was carried out to confirm the presence of four hydrophobic regions [FIG. 64]. Upon comparing the amino acid sequence with those encoded by p19P2 obtained in Example 3 (2) and encoded by pG3-2 obtained in Example 4 (2), furthermore, a high degree of homology was found as shown in FIG. 63. As a result, it is strongly suggested that the mouse pancreatic β-cell strain, MIN6-derived G protein coupled receptor protein encoded by p5S38 recognizes the same ligand as the human pituitary gland-derived G protein coupled receptor protein encoded by p19P2 does while the animal species from which the receptor protein encoded by p5S38 is derived is different from that from which the receptor protein encoded by p19P2 is. It is also strongly suggested that the mouse pancreatic β-cell strain, MIN6-derived G protein coupled receptor protein encoded by p5S38 recognizes the same ligand as the mouse pancreatic β-cell strain, MIN6-derived G protein coupled receptor proteins encoded by pG3-2 and pG1-10 do and they are analogous receptor proteins one another (so-called "subtype").

Example 18

Northern Hybridization with cDNA Fragment Included in MIN6-Derived Receptor Protein-Encoding p3H2-17

Mouse cell line, MIN6, Neuro-2a, poly(A)$^+$ RNA (2.5 µg) and mouse brain, spleen, thymus and pancreas poly(A)$^+$ RNAs (2.5 µg) were used as poly(A) RNAs. The DNA fragment inserted into the plasmid, p3H2-17, obtained in Example 7 (3) was recovered as a DNA fragment with about 400 bp by cutting the plasmid with EcoRI-and the resulting DNA fragment was labeled by incorporation of [$^{32}$P]dCTP (Dupont Co.) with a random prime DNA labeling kit (Amasham Co.). The about 400 bp labeled DNA fragment was used as a probe for hybridization.

Nylon membrane (PaLL Biodyne, U.S.A.) was used as a filter for northern blotting and migration of the poly(A)$^+$ RNA and adsorption (sucking) thereof with the blotting filter was carried out according to the method as disclosed in Molecular Cloning, Cold Spring Harbor Laboratory Press, 1989.

The hybridization was carried out by incubating the above-mentioned filter and probe in a buffer containing 50% formamide, 5×SSPE (20×SSPE (pH 7.4) is 3 M NaCl, 0.2 M NaH$_2$PO$_4$.H$_2$O, 25 mM EDTA), 5×Denhardt's solution (Nippon Gene, Japan), 0.1% SDS and 100 µg/ml of salmon sperm DNA overnight at 42° C. The filter was washed with 0.1×SSC (20×SSC is 3 M NaCl, 0.3 M sodium citrate), 0.1% SDS at 50° C. and, after drying with an air, was exposed to an X-ray film (XAR5, Kodak) for15 days at −80° C. The results were as shown in FIG. 65.

Figure 65:
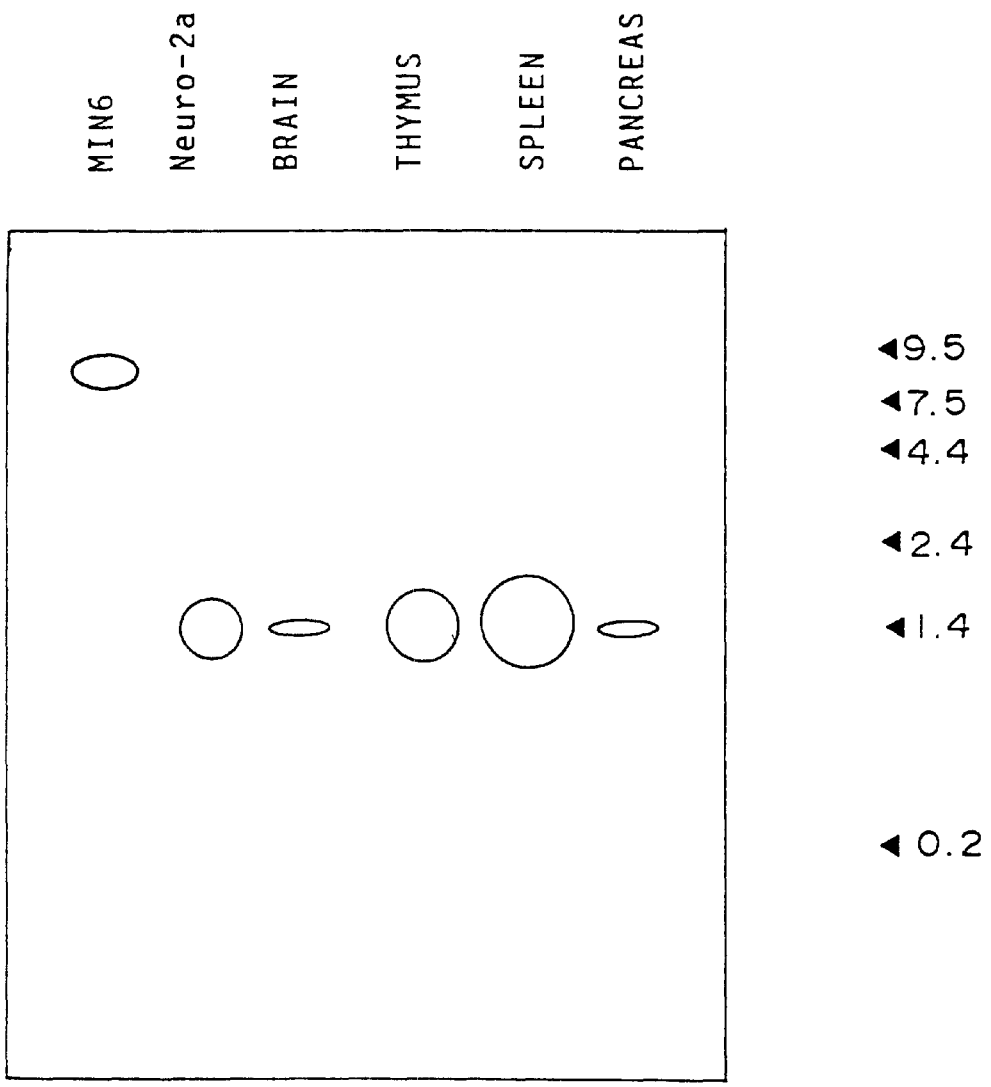
FIG. 65 shows the northern blot analysis profile of the receptor gene encoded by the cDNA included in the mouse pancreatic β-cell strain MIN6-derived novel receptor protein cDNA clone, p3H2-17, for mouse cell line, MIN6, Neuro-2a cell and mouse brain, thymus, spleen and pancreas poly(A)$^+$ RNA, wherein each arrow and number indicates the size marker position (unit of number: kb).

It is considered from FIG. 65 that mRNA for the the receptor gene encoded by the cDNA fragment included in p3H2-17 is expressed in the cell line, MIN6, Neuro-2a, and the mouse brain, pancreas, spleen and thymus and especially expressed in the mouse spleen and thymus intensely. The MIN6 signal position hybridizable in the northern hybridization plotting is different from those of other organ cells.

Example 19

PCR Cloning of cDNA Comprising Whole Coding Regions of Receptor Proteins from Mouse Spleen, Thymus-Derived Poly(A)$^+$ RNA and Sequencing (1) PCR Cloning of cDNA Comprising Whole Coding Region of Receptor Protein In order to obtain a full-length open reading frame (coding region) of the receptor protein encoded by the cDNA fragment included in p3H2-17, PCR amplification was carried out by 5'RACE and 3'RACE wherein poly(A)$^+$ RNA derived from mouse spleen and thymus was used.

Based on the nucleotide sequence of 3H2-17 which was disclosed, the following 4 primers were synthesized:

(Nucleotide sequence of synthesized primer)
① 5'-TAGTGTGTGGAGTCGTGTGGCTGGCTG-3' (SEQ ID NO: 20)
② 5'-AGTCTTTGCTGCCACAGGCATCCAGCG-3' (SEQ ID NO: 21)
③ 5'-CAAGCCAGTAAGGCTATGAAGGGCAGCAAG-3' (SEQ ID NO: 22)
④ 5'-ACAGGACCTGCTGGGCCATCCTGGCGACACA-3' (SEQ ID NO: 23)

The 5'RACE was carried out according to the protocol of 5'Ampli Finder RACE kit from ClonTech Co. (ClonTech Co.).

Figure 66:
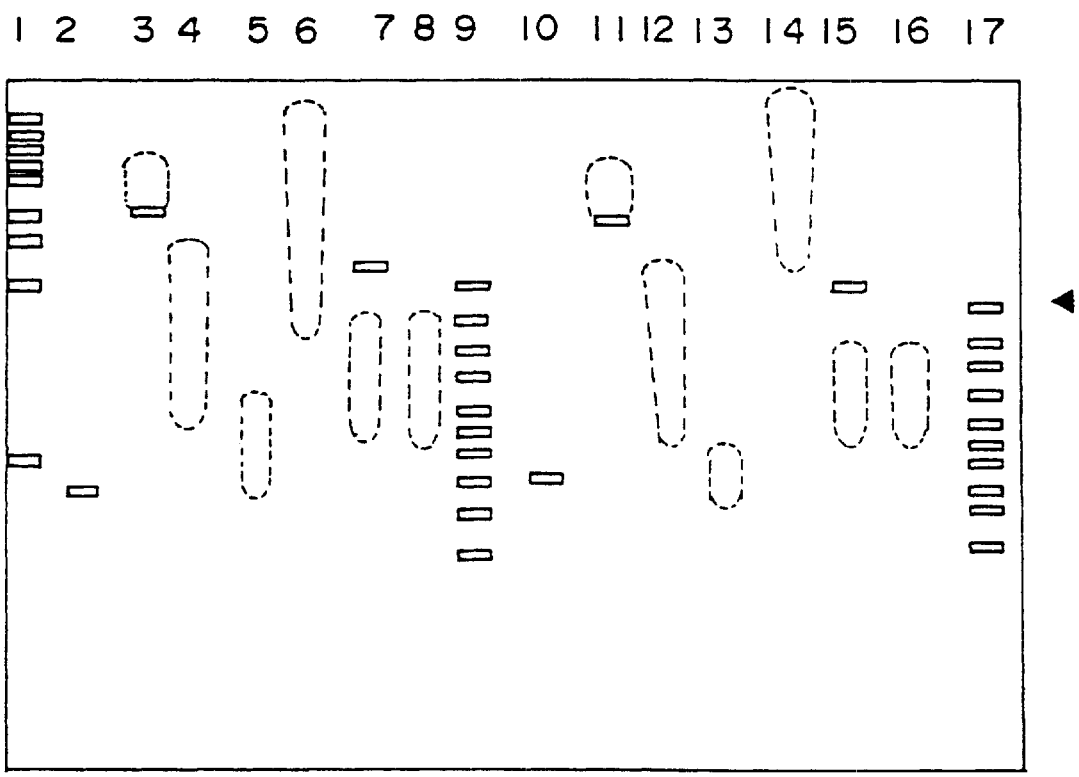
FIG. 66 shows the agarose gel electrophoresis analysis profile of the PCR products obtained by 5'RACE PCR of the receptor gene included in p3H2-17 using mouse thymus and spleen poly(A)$^+$ RNA.

In an embodiment, cDNA was prepared from 2 μg each of poly(A)$^+$ RNAs derived from mouse spleen and thymus by using the aforementioned primer ④ and ligated with an anchor attached to the 5'RACE kit. A mixture of a 1/200 amount of the cDNA thus prepared, the anchor and the aforementioned primer ③ was subjected to PCR using 4 polymerases, Taq (Takara, Japan), Ex Taq (Takara, Japan), Vent (New England Biolabs) and Pfu (Stratagene) under the following conditions: 96° C. for 30 sec., 60° C. for 60 sec., 72° C. for 90 sec. and 35 cycles. A 1/5 amount of the PCR product was subjected to agarose electrophoresis and stained with ethidium bromide (EtBr). The results are shown in FIG. 66. The amplified DNA band appeared at an about 1 kbp position and the isolated about 1 kbp DNA band which was synthesized from poly(A)$^+$ RNAs derived from mouse spleen and thymus by the 5'RACE using Ex Taq polymerase was treated with SUPREC™-01 (Takara, Japan) to recover cDNA.

The isolated DNA was subcloned into pCR™II vector by using a TA Cloning Kit (Invitrogen Co.) and the vector was transfected into E. coli JM109 to obtain 3 transformant clones, N26, N64 and N75. The clone, N26, holds the thymus-derived cDNA which is amplified by the 5'RACE and the clone, N75, holds the spleen-derived cDNA which is amplified by the 5'RACE (FIG. 68).

The 3'RACE was carried out according to the protocol of 3' RACE kit (GIBCO BRL Co.).

In an embodiment, cDNA was prepared from 1 μg each of poly(A)$^+$ RNAs derived from mouse spleen and thymus by using an adaptor primer attached to the 3' RACE kit. A mixture of the adaptor primer thus prepared and a 1/10 amount of cDNA which was prepared by using the aforementioned primer ① was subjected to 1st PCR using 4 polymerases, Taq (Takara, Japan), Ex Taq (Takara, Japan), Vent (NEB) and Pfu (Stratagene) under the following conditions: 96° C. for 30 sec., 55° C. for 60 sec., 72° C. for 120 sec. and 30 cycles. A mixture of a 1/50 amount of the 1st PCR product, the aforementioned primer ② and the adaptor primer was subjected to 2nd PCR using the aforementioned polymerases under the same conditions as aforementioned herein in the 5'RACE process. A 1/5 amount of the 2nd PCR product was subjected to agarose electrophoresis and stained with ethidium bromide. The results are shown in FIG. 67.

The amplified DNA band appeared at an about 1 kbp position (which was synthesized from poly(A)$^+$ RNAs derived from mouse thymus by the 3'RACE using Vent polymerase) and the amplified DNA band appeared at an about 1 kbp position (which was synthesized from poly(A)$^+$ RNAs derived from mouse thymus by the 3'RACE using Pfu polymerase) were treated with SUPREC™-01 (Takara, Japan) to recover cDNA, respectively.

The isolated DNAs were treated with T4 polynucleotide kinase (Wako Pure Chemical Co., Japan) to add phosphate to the end thereof and the phosphorylated DNAs were ligated with pUC18 SmaI BAP (Pharmacia) by using DNA Ligation Kit (Takara, Japan) followed by transformation of E. coli JM109 to obtain 3 transformant clones, C2, C13 and C15. The clones, C13 and C15, hold the thymus-derived cDNA which is amplified by the 3'RACE and the clone, C2, holds the thymus-derived cDNA which is amplified by the 3'RACE (FIG. 68).

Based on the nucleotide sequences of clones, N26, N64 and N75, which are considered to hold the N-terminal region of the open reading frame (ORF) of the cDNA fragment included in p3H2-17 and the nucleotide sequences of clones, C2, C13 and C15, which are considered to hold the C-terminal region of the open reading flame (ORF) of the cDNA fragment included in p3H2-17, the entire nucleotide sequence coding for the open reading flame and neighboring region of the receptor protein encoded by the cDNA included in p3H2-17 was determined. To be more specific, sequencing was carried out with the primers used in the 5'RACE and 3'RACE or synthetic primers for sequencing by using a DyeDeoxy Terminator Cycle Sequencing Kit (ABI Co.), the nucleotide sequences were decoded by using a fluorescent automatic sequencer. The obtained data of the DNA were analyzed by DNASIS (Hitachi System Engineering Co., Japan).

PCR errors which presumably happen to occur upon PCR have been corrected by a way of thinking that, when nucleotides between two clones which are independently produced by PCR are identical (e.g. those between clones, N75 and N64, are identical) each other, the identical base is considered as correct. The determined nucleotide sequence is shown in FIG. 69. The amino acid sequence is deduced based on the determined nucleotide sequence (FIG. 69). Hydrophobicity plotting was carried out based on the deduced amino acid sequence (FIG. 70). As a result, it was learned that it was a seven transmembrane G protein coupled receptor, as it is suggested from the cDNA fragment included in p3H2-17.

Homology retrieval at the amino acid level indicates that it is homologous to mouse $P_{2U}$purinoceptor and chicken $P_{2Y}$purinoceptor.

Further, the clone which are free of an error in the open reading flame (ORF) was selected and used to construct plasmids carrying the full-length ORF of the receptor protein encoded by p3H2-17. In an embodiment, the cDNA fragment held by the clone, N75, was digested with restriction enzymes, DraIII and EcoRI, to obtain cDNA fragments which are the N-terminal region of the receptor protein held by p3H2-17. The C-terminal cDNA fragment encoded by C13 was digested with restriction enzymes, DraIII and EcoRI, to delete 5'-side regions from the DraIII site of the C-terminal and the long fragment was obtained by the digestion of C13 with restriction enzymes, DraIII and EcoRI. The N75-derived N-terminal cDNA DraIII-EcoRI fragment was ligated with the long C13-derived DraIII-EcoRI fragment by using a DNA Ligation Kit (Takara, Japan) and transfected into *Escherichia coli* JM109 to obtain transformant *Escherichia coli* JM109/pMAH2-17.

(2) Electrophysiological Measurement of Receptor Encoded by pMAH2-17

The receptor encoded by pMAH2-17 was examined electrophsiologically in Xenopus oocytes. The ORF of the receptor encoded by pMAH2-17 was inserted into the XhoI-XbaI sites of pBluescript™II SK(+) (Stratagene) with directing the sequence thereof downstream from T7 promoter. The resulting plasmid as a template was treated with a mCAP™mRNA Capping kit (Stratagene) to produce cRNA of this receptor gene.

The cRNA was injected into Xenopus oocytes (50 ng cRNA/50 nl/oocyte), previously prepared according to the method disclosed in Nathan Dascal et al., Proc. Natl. Acad. Sci. USA, Vol. 90, pp.6596–6600 (1993). The cRNA-injected oocytes were incubated at 20° C. for 2 to 3 days and subjected to electrophysiological measurements. The measurement was carried out with a microelectrode-applicable high input resistance amplifier (MEz-8300, Nippon Koden, Co., Japan), and a voltage clamping amplifier (CEz −/200, Nippon Koden, Co., Japan).

The initial membrane potential of oocytes was set to −60 mV and responses (current changes of the membrane) evoked by addition of ligands were recorded with a recorder (Thermal Array recorder, Nippon Koden, Co., Japan) (Nathan Dascal et al., Proc. Natl. Acad. Sci. USA, Vol. 90, pp.6596–6600 (1993)).

Typical inward currents elicited upon activation of phospholipase C-coupled receptors were observed in oocytes injected with pMAH2-17 cRNA via stimulation by 10 $\mu$M ATP (FIG. 75). In contrast, such a current was not observed in oocytes injected with $H_2O$, instead of pMAH2-17 cRNA, by the ATP stimulation.

In conclusion, it is considered that the receptor encoded by pMAH2-17 cRNA is classified into a subtype within the ATP receptor, $P_2$ purinoceptor.

Example 20

Cloning of Rabbit Gastropyrolic Part Smooth Muscle-Derived G Protein Coupled. Receptor Protein cDNA (1) Preparation of Poly(A)$^+$ RNA Fraction from Rabbit Gastropyrolic Part Smooth Muscle and Synthesis of cDNA A total RNA was prepared from rabbit gastropyrolic part smooth muscles by the guanidine thiocyanate method (Kaplan B. B. et al., Biochem. J. 183, 181–184 (1979)) and, then, poly(A)$^+$ RNA fractions were prepared with a mRNA purifying kit (Pharmacia Co.). Next, to 5 $\mu$g of the poly(A)$^+$ RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 $\mu$l of TE.

(2) Amplification of Receptor cDNA by PCR Using Rabbit Gastropyrolic Part Smooth Muscle-Derived cDNA and Sequencing By using, as a template, 1 $\mu$l of cDNA prepared from the rabbit gastropyrolic part smooth muscle in the above step (1), PCR amplification using the DNA primer having a nucleotide sequence represented by SEQ ID NO: 10 and the DNA primer having a nucleotide sequence represented by SEQ ID NO: 4 synthesized in Example 15 was carried out. A reaction solution was composed of the synthetic DNA primers (SEQ: 5' primer sequence and 3' primer sequence) each in an amount of 100 pM, 0.25 mM dNTPs, 1 $\mu$l of Taq DNA polymerase and 10 $\mu$l of buffer attached to the enzyme kit, and the total amount of the reaction solution was made to be 100 $\mu$l. The cycle for amplification including 96° C. for 30 sec., 45° C. for 1 min. and 60° C. for 3 min. was repeated 25 times by using a Thermal Cycler (Perkin-Elmer Co.). The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated by using a 1.0% low-melting temperature agarose gel, the band parts were excised from the gel with a razor blade, and were electro-eluted, extracted with phenol and precipitated in ethanol to recover DNAS. According to the protocol attached to a TA Cloning Kit (Invitrogen Co.), the recovered DNAs were subcloned to the plasmid vector, pCR™II. The recombinant vectors were introduced into *E. coli* JM109 competent cells (Takara Shuzo Co., Japan) to produce transformants. Then, transformant clones having a cDNA-inserted fragment were selected in an LB agar culture medium containing ampicillin, IPTG and X-gal. Only transformant clones exhibiting white color were picked with a sterilized toothstick to obtain 100 transformant clones.

The individual clones were cultured overnight in an LB culture medium containing ampicillin and treated with the automatic plasmid extracting machine PI-100 (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer.

Homology retrieval was carried out based upon the determined nucleotide sequence. As a,result, it was learned that a novel G protein coupled receptor protein was been encoded by the cDNA fragment insert in the plasmid possessed by the transformant *Escherichia coli* JM109/pMN128. The nucleotide sequences of the cDNA fragments are shown in FIGS. 71 and 72. To further confirm this fact, by using DNASIS (Hitachi System Engineering Co., Japan) the nucleotide sequences were converted into amino acid sequences [FIG. 71 and FIG. 72], and homology retrieval was carried out in view of hydrophobicity plotting [FIG. 73] and at the amino acid sequence level to find a novel receptor protein which has 27% homology relative to hamster-derived $\beta_2$-adrenaline receptor protein (A03159), 20% homology relative to rat-derived bradykinin receptor (type $B_2$) protein (A41283), 24% homology relative to human-derived dopamine $D_1$ receptor protein (S11377) and 23% homology relative to human-derived blue sensitive opsin receptor protein (A03156). The aforementioned abbreviations in parentheses are reference numbers assigned when they are registered as data to NBRF-PIR and are usually called "Accession Numbers".

Example 21

Cloning of cDNA Comprising Whole Coding Regions for Receptor Protein from Human-Derived DNA Library The DNA library constructed by Clontech wherein $\lambda$ gt11 phage vector is used (CLONTECH Laboratories, Inc.; CLH L1008b) was employed as a human placenta-derived cDNA library. The human placenta cDNA library (1×10⁵ pfu (plaque forming units)) was thermally denatured. By using the human placenta-derived cDNA library, PCR amplification using the DNA primer having a nucleotide sequence represented by SEQ ID NO: 20 and the DNA primer having a nucleotide sequence represented by SEQ ID NO: 23 synthesized in Example 19 was carried out.

(Nucleotide sequence of synthesized primer)
① 5'-TAGTGTGTGGAGTCGTGTGGCTGGCTG-3' (SEQ ID NO: 20)
② 5'-ACAGGACCTGCTGGGCCATCCTGGCGACACA-3' (SEQ ID NO: 23)

The isolated DNA was subcloned using a TA Cloning Kit (Invitrogen Co.) and sequencing was carried out. FIG. 76 shows a nucleotide sequence of obtained cDNA fragment, ph3H2-17. As a result, it was learned that ph3H2-17 is highly homologous to the mouse purinoceptor cDNA fragment, p3H2-17. It is strongly suggested that the human-derived cDNA fragment is a partial nucleotide sequence of human purinoceptor.

Based on the nucleotide sequence of ph3H2-17 which was sequenced, the following 2 primers were synthesized:

(Nucleotide sequence of synthesized primer)
③ 5'-ACAGCCATCTTCGCTGCCACAGGCAT-3' (SEQ ID NO: 58)
④ 5'-AGACAGTAGCAGGCCAGCAGGGCAGCAAA-3' (SEQ ID NO: 59) The above synthetic 2 primers were each used in combination with λ gt 11 primers (Takara, Japan; catalogue 3864) for obtaining full-length human prinoceptor cDNA. Thus, using thermally denatured, human placenta-derived λ gt 11 cDNA libraries (CLONTECH; CLHL 1008b), first RCR amplification using a combination of the DNA primer having a nucleotide sequence represented by SEQ ID NO: 20 with λ gt 11 Forward primer, of the DNA primer having a nucleotide sequence represented by SEQ ID NO: 20 with λ gt 11 Reverse primer, of the DNA primer having a nucleotide sequence represented by SEQ ID NO: 23 with λ gt 11 Forward primer, and of the DNA primer having a nucleotide sequence represented by SEQ ID NO: 23 with λ gt 11 Reverse primer was carried out with Ex Taq polymerase (Takara, Japan) (30 cycles; 95° C./30 seconds, 55° C./60 seconds, and 72° C./60 seconds), respectively.

Next, by using a 1/50 of the 1st PCR product, second RCR amplification was carried in the same manner as in the first PCR except for using the DNA primer having a nucleotide sequence represented by SEQ ID NO: 58 in place of SEQ ID NO: 20 and the DNA primer having a nucleotide sequence represented by SEQ ID NO: 59 in place of SEQ ID NO: 23 (30 cycles; 95° C./30 seconds, 65° C./60 seconds and 72° C./60 seconds). The amplified product DNA was subcloned using a TA Cloning Kit (Invitrogen Co.) and sequencing was carried out for three clones each of 5' and 3' sides (FIG. 77).

Based on the amino acid sequence (FIG. 77) deduced from the determined nucleotide sequence of human purinoceptor cDNA as shown in FIG. 77, hydrophobicity plotting was carried out (FIG. 78). As a result, it was learned that the human-derived receptor is a novel seven transmembrane G protein coupled receptor, similarly to the mouse type. It was also learned that the deduced amino acid sequence of human receptor has 87% homology relative to the amino acid sequence of mouse purinoceptor and its amino acid residues are well conserved (FIG. 79).

Clones free of PCR errors which often occur in a PCR amplification were selected and restriction enzyme regions comprising overlapping areas were obtained therefrom. The restriction enzyme regions thus obtained were subjected to construction of plasmid phAH2-17 having a full-length open reading frame of human purinoceptor cDNA. The plasmid phAH2-17 is possessed by transformant *Escherichia coli* JM109/phAH2-17.

The DNA primers of the present invention allow efficient amplification of DNAs that encode G protein coupled receptor proteins. This makes it possible to efficiently screen for the DNAs coding for G protein coupled receptor proteins and to accomplish the cloning.

The G protein coupled receptor protein of the present invention and their G protein coupled receptor protein-encoding DNA are advantageously useful in:

① determining ligands,
② obtaining antibodies and an antisera,
③ constructing systems for expressing recombinant receptor proteins,
④ investigating or developing receptor-binding assay systems and screening for pharmaceutical candidate compounds, by using the above expression system
⑤ designing drugs based upon comparisons with ligands and receptors having a structure similar or analogous thereto,
⑥ preparing probes and/or PCR primers in gene diagnosis, and
⑦ gene manipulating therapy.

In particular, discovering the structure and properties of the G protein coupled receptor will lead to the development of unique pharmaceuticals acting upon these systems.

The practice of the present invention will employ, otherwise indicated, conventional techniques of molecular biology, microbiology, recombinant DNA, pharmacology, immunology, bioscience, and medical technology, which are within the skill of the art. All patents, patent applications, and publications mentioned herein, both supra and infra, are hereby incorporated herein by reference.

What is claimed is:
1. An isolated protein comprising an amino acid sequence represented by SEQ ID NO:54 or a salt thereof.

\* \* \* \* \*

SEQUENCE LISTING (1) GENERAL INFORMATION:

(iii) NUMBER OF SEQUENCES: 61

(2) INFORMATION FOR SEQ ID NO: 1:

(i) SEQUENCE CHARACTERISTICS:
      (A) LENGTH: 25
      (B) TYPE: Nucleic acid

```
        (C) STRANDEDNESS: Single
        (D) TOPOLOGY: Linear (ii) MOLECULE TYPE: Other nucleic acid
        (A) DESCRIPTION: /desc = "synthetic DNA (ix) FEATURE:
        (D) OTHER INFORMATION:/note= N is A, G, C, or T; S is G or C;
            M is A or C; Y is T or C."

(xi) SEQUENCE DESCRIPTION: SEQ ID NO: 1:

CGTGGSCMTS STGGGCAACN YCCTG                                              25

(2) INFORMATION FOR SEQ ID NO: 2:

(i) SEQUENCE CHARACTERISTICS:
        (A) LENGTH: 27
        (B) TYPE: Nucleic acid
        (C) STRANDEDNESS: Single
        (D) TOPOLOGY: Linear (ii) MOLECULE TYPE: Other nucleic acid
        (A) DESCRIPTION: /desc = "synthetic DNA (ix) FEATURE:
        (D) OTHER INFORMATION:/note= N is A, G, C, or T; W is A or T;
            R is A or G; K is G or T."

(xi) SEQUENCE DESCRIPTION: SEQ ID NO: 2:

GTNGWRRGGC ANCCAGCAGA KGGCAAA                                            27

(2) INFORMATION FOR SEQ ID NO: 3:

(i) SEQUENCE CHARACTERISTICS:
        (A) LENGTH: 27
        (B) TYPE: Nucleic acid
        (C) STRANDEDNESS: Single
        (D) TOPOLOGY: Linear (ii) MOLECULE TYPE: Other nucleic acid
        (A) DESCRIPTION: /desc = "synthetic DNA (ix) FEATURE:
        (D) OTHER INFORMATION:/note= N is inosine; S is G or C;
            Y is C or T; M is A or C; R is A or G."

(xi) SEQUENCE DESCRIPTION: SEQ ID NO: 3:

CTCGCSGCYM TNRGYATGGA YCGNTAT                                            27

(2) INFORMATION FOR SEQ ID NO: 4:

(i) SEQUENCE CHARACTERISTICS:
        (A) LENGTH: 30
        (B) TYPE: Nucleic acid
        (C) STRANDEDNESS: Single
        (D) TOPOLOGY: Linear (ii) MOLECULE TYPE: Other nucleic acid
        (A) DESCRIPTION: /desc = "synthetic DNA (ix) FEATURE:
        (D) OTHER INFORMATION:/note= N is inosine; R is A or G;
            W is T or A; S is G or C; M is A or C."

(xi) SEQUENCE DESCRIPTION: SEQ ID NO: 4:

CATGTRGWAG GGAANCCAGS AMANRARRAA                                         30

(2) INFORMATION FOR SEQ ID NO: 5:

(i) SEQUENCE CHARACTERISTICS:
        (A) LENGTH: 27
```

(B) TYPE: Nucleic acid
            (C) STRANDEDNESS: Single
            (D) TOPOLOGY: Linear (ii) MOLECULE TYPE: Other nucleic acid
            (A) DESCRIPTION: /desc = "synthetic DNA (ix) FEATURE:
            (D) OTHER INFORMATION:/note= N is inosine; Y is C or T;
                R is A or G; S is G or C; M is A or C; V is A, C or G."

(xi) SEQUENCE DESCRIPTION: SEQ ID NO: 5:

CTGACYGYTC TNRSNRYTGA CMGVTAC                                           27

(2) INFORMATION FOR SEQ ID NO: 6:

(i) SEQUENCE CHARACTERISTICS:
            (A) LENGTH: 27
            (B) TYPE: Nucleic acid
            (C) STRANDEDNESS: Single
            (D) TOPOLOGY: Linear (ii) MOLECULE TYPE: Other nucleic acid
            (A) DESCRIPTION: /desc = "synthetic DNA (ix) FEATURE:
            (D) OTHER INFORMATION:/note= N is inosine; Y is C or T;
                R is A or G; S is G or C; M is A or C; V is A, C or G."

(xi) SEQUENCE DESCRIPTION: SEQ ID NO: 6:

CTGACYGYTC TNRSNRYTGA CMGVTAT                                           27

(2) INFORMATION FOR SEQ ID NO: 7:

(i) SEQUENCE CHARACTERISTICS:
            (A) LENGTH: 27
            (B) TYPE: Nucleic acid
            (C) STRANDEDNESS: Single
            (D) TOPOLOGY: Linear (ii) MOLECULE TYPE: Other nucleic acid
            (A) DESCRIPTION: /desc = "synthetic DNA (ix) FEATURE:
            (D) OTHER INFORMATION:/note= N is inosine; S is G or C;
                Y is C or T; M is A or C; R is A or G."

(xi) SEQUENCE DESCRIPTION: SEQ ID NO: 7:

CTCGCSGCYM TNRGYATGGA YCGNTAC                                           27

(2) INFORMATION FOR SEQ ID NO: 8:

(i) SEQUENCE CHARACTERISTICS:
            (A) LENGTH: 30
            (B) TYPE: Nucleic acid
            (C) STRANDEDNESS: Single
            (D) TOPOLOGY: Linear (ii) MOLECULE TYPE: Other nucleic acid
            (A) DESCRIPTION: /desc = "synthetic DNA (ix) FEATURE:
            (D) OTHER INFORMATION:/note= N is inosine; R is A or G;
                S is G or C; Y is C or T."

(xi) SEQUENCE DESCRIPTION: SEQ ID NO: 8:

GATGTGRTAR GGSRNCCAAC AGANGRYAAA                                        30

(2) INFORMATION FOR SEQ ID NO: 9:

(i) SEQUENCE CHARACTERISTICS:

(A) LENGTH: 30
            (B) TYPE: Nucleic acid
            (C) STRANDEDNESS: Single
            (D) TOPOLOGY: Linear (ii) MOLECULE TYPE: Other nucleic acid
            (A) DESCRIPTION: /desc = "synthetic DNA (ix) FEATURE:
            (D) OTHER INFORMATION:/note= N is inosine; R is A or G;
                S is G or C; Y is C or T."

(xi) SEQUENCE DESCRIPTION: SEQ ID NO: 9:

GATGTGRTAR GGSRNCCAAC AGANGRYGAA                                        30

(2) INFORMATION FOR SEQ ID NO: 10:

(i) SEQUENCE CHARACTERISTICS:
            (A) LENGTH: 27
            (B) TYPE: Nucleic acid
            (C) STRANDEDNESS: Single
            (D) TOPOLOGY: Linear (ii) MOLECULE TYPE: Other nucleic acid
            (A) DESCRIPTION: /desc = "synthetic DNA (ix) FEATURE:
            (D) OTHER INFORMATION:/note= N is inosine; S is G or C;
                Y is C or T; W is A or T; H is A, C or T."

(xi) SEQUENCE DESCRIPTION: SEQ ID NO: 10:

GYCACCAACN WSTTCATCCT SWNHCTG                                           27

(2) INFORMATION FOR SEQ ID NO: 11:

(i) SEQUENCE CHARACTERISTICS:
            (A) LENGTH: 27
            (B) TYPE: Nucleic acid
            (C) STRANDEDNESS: Single
            (D) TOPOLOGY: Linear (ii) MOLECULE TYPE: Other nucleic acid
            (A) DESCRIPTION: /desc = "synthetic DNA (ix) FEATURE:
            (D) OTHER INFORMATION:/note= N is inosine; R is A or G;
                S is G or C."

(xi) SEQUENCE DESCRIPTION: SEQ ID NO: 11:

ASNSANRAAG SARTAGANGA NRGGRTT                                           27

(2) INFORMATION FOR SEQ ID NO: 12:

(i) SEQUENCE CHARACTERISTICS:
            (A) LENGTH: 25
            (B) TYPE: Nucleic acid
            (C) STRANDEDNESS: Single
            (D) TOPOLOGY: Linear (ii) MOLECULE TYPE: Other nucleic acid
            (A) DESCRIPTION: /desc = "synthetic DNA (ix) FEATURE:
            (D) OTHER INFORMATION:/note= N is inosine; S is G or C;
                K is G or T; M is A or C."

(xi) SEQUENCE DESCRIPTION: SEQ ID NO: 12:

TGNTSSTKMT NGSNGTKGTN GGNAA                                             25

(2) INFORMATION FOR SEQ ID NO: 13:

(i) SEQUENCE CHARACTERISTICS:
        (A) LENGTH: 25
        (B) TYPE: Nucleic acid
        (C) STRANDEDNESS: Single
        (D) TOPOLOGY: Linear (ii) MOLECULE TYPE: Other nucleic acid
        (A) DESCRIPTION: /desc = "synthetic DNA (ix) FEATURE:
        (D) OTHER INFORMATION:/note= N is inosine; Y is C or T;
            K is G or T; W is A or T."

(xi) SEQUENCE DESCRIPTION: SEQ ID NO: 13:

AYCKGTAYCK GTCCANKGWN ATKGC                                            25

(2) INFORMATION FOR SEQ ID NO: 14:

(i) SEQUENCE CHARACTERISTICS:
        (A) LENGTH: 24
        (B) TYPE: Nucleic acid
        (C) STRANDEDNESS: Single
        (D) TOPOLOGY: Linear (ii) MOLECULE TYPE: Other nucleic acid
        (A) DESCRIPTION: /desc = "synthetic DNA (ix) FEATURE:
        (D) OTHER INFORMATION:/note= N is inosine; K is G or T;
            S is G or C; Y is C or T; R is A or G."

(xi) SEQUENCE DESCRIPTION: SEQ ID NO: 14:

CATKKCCSTG GASAGNTAYN TRGC                                             24

(2) INFORMATION FOR SEQ ID NO: 15:

(i) SEQUENCE CHARACTERISTICS:
        (A) LENGTH: 24
        (B) TYPE: Nucleic acid
        (C) STRANDEDNESS: Single
        (D) TOPOLOGY: Linear (ii) MOLECULE TYPE: Other nucleic acid
        (A) DESCRIPTION: /desc = "synthetic DNA (ix) FEATURE:
        (D) OTHER INFORMATION:/note= N is inosine; W is A or T;
            S is G or C; K is G or T; R is A or G."

(xi) SEQUENCE DESCRIPTION: SEQ ID NO: 15:

GWWGGGSAKC CAGCASANGG CRAA                                             24

(2) INFORMATION FOR SEQ ID NO: 16:

(i) SEQUENCE CHARACTERISTICS:
        (A) LENGTH: 18
        (B) TYPE: Nucleic acid
        (C) STRANDEDNESS: Single
        (D) TOPOLOGY: Linear (ii) MOLECULE TYPE: Other nucleic acid
        (A) DESCRIPTION: /desc = "synthetic DNA (ix) FEATURE:
        (D) OTHER INFORMATION:/note= N at position 6, 9, 10 & 12 =
            inosine; N at position 15 = A, G, C, or T; R is A or G;
            Y is C or T."

(xi) SEQUENCE DESCRIPTION: SEQ ID NO: 16:

ARYYTNGCNN TNGCNGAY                                                    18

(2) INFORMATION FOR SEQ ID NO: 17:

(i) SEQUENCE CHARACTERISTICS:
       (A) LENGTH: 21
       (B) TYPE: Nucleic acid
       (C) STRANDEDNESS: Single
       (D) TOPOLOGY: Linear (ii) MOLECULE TYPE: Other nucleic acid
       (A) DESCRIPTION: /desc = "synthetic DNA (ix) FEATURE:
       (D) OTHER INFORMATION:/note= N at position 1, 4, & 6 =
           inosine; N at position 13, 15, 16 & 18 = A, G, C, or T;
           R is A or G."

(xi) SEQUENCE DESCRIPTION: SEQ ID NO: 17:

NGGNANCCAR CANANNRNRA A                                          21

(2) INFORMATION FOR SEQ ID NO: 18:

(i) SEQUENCE CHARACTERISTICS:
       (A) LENGTH: 27
       (B) TYPE: Nucleic acid
       (C) STRANDEDNESS: Single
       (D) TOPOLOGY: Linear (ii) MOLECULE TYPE: Other nucleic acid
       (A) DESCRIPTION: /desc = "synthetic DNA (ix) FEATURE:
       (D) OTHER INFORMATION:/note= N is inosine; S is G or C; R is
           A or G; W is A or T; M is A or C."

(xi) SEQUENCE DESCRIPTION: SEQ ID NO: 18:

GCCTSNTNRN SATGWSTGTG GANMGNT                                    27

(2) INFORMATION FOR SEQ ID NO: 19:

(i) SEQUENCE CHARACTERISTICS:
       (A) LENGTH: 27
       (B) TYPE: Nucleic acid
       (C) STRANDEDNESS: Single
       (D) TOPOLOGY: Linear (ii) MOLECULE TYPE: Other nucleic acid
       (A) DESCRIPTION: /desc = "synthetic DNA (ix) FEATURE:
       (D) OTHER INFORMATION:/note= N is inosine, W is A or T,
           S is G or C, M is A or C, Y is C or T, R is A or G."

(xi) SEQUENCE DESCRIPTION: SEQ ID NO: 19:

GAWSNTGMYN ANRTGGWAGG GNANCCA                                    27

(2) INFORMATION FOR SEQ ID NO: 20:

(i) SEQUENCE CHARACTERISTICS:
       (A) LENGTH: 27
       (B) TYPE: Nucleic acid
       (C) STRANDEDNESS: Single
       (D) TOPOLOGY: Linear (ii) MOLECULE TYPE: Other nucleic acid
       (A) DESCRIPTION: /desc = "synthetic DNA"

(xi) SEQUENCE DESCRIPTION: SEQ ID NO: 20:

TAGTGTGTGG AGTCGTGTGG CTGGCTG                                    27

(2) INFORMATION FOR SEQ ID NO: 21:

(i) SEQUENCE CHARACTERISTICS:
        (A) LENGTH: 27
        (B) TYPE: Nucleic acid
        (C) STRANDEDNESS: Single
        (D) TOPOLOGY: Linear (ii) MOLECULE TYPE: Other nucleic acid
        (A) DESCRIPTION: /desc = "synthetic DNA"

(xi) SEQUENCE DESCRIPTION: SEQ ID NO: 21:

AGTCTTTGCT GCCACAGGCA TCCAGCG                                       27

(2) INFORMATION FOR SEQ ID NO: 22:

(i) SEQUENCE CHARACTERISTICS:
        (A) LENGTH: 30
        (B) TYPE: Nucleic acid
        (C) STRANDEDNESS: Single
        (D) TOPOLOGY: Linear (ii) MOLECULE TYPE: Other nucleic acid
        (A) DESCRIPTION: /desc = "synthetic DNA"

(xi) SEQUENCE DESCRIPTION: SEQ ID NO: 22:

CAAGCCAGTA AGGCTATGAA GGGCAGCAAG                                    30

(2) INFORMATION FOR SEQ ID NO: 23:

(i) SEQUENCE CHARACTERISTICS:
        (A) LENGTH: 31
        (B) TYPE: Nucleic acid
        (C) STRANDEDNESS: Single
        (D) TOPOLOGY: Linear (ii) MOLECULE TYPE: Other nucleic acid
        (A) DESCRIPTION: /desc = "synthetic DNA"

(xi) SEQUENCE DESCRIPTION: SEQ ID NO: 23:

ACAGGACCTG CTGGGCCATC CTGGCGACAC A                                  31

(2) INFORMATION FOR SEQ ID NO: 24:

(i) SEQUENCE CHARACTERISTICS:
        (A) LENGTH: 91
        (B) TYPE: Amino acid
        (C) STRANDEDNESS: <Unknown>
        (D) TOPOLOGY: Linear (ii) MOLECULE TYPE: Peptide (xi) SEQUENCE DESCRIPTION: SEQ ID NO: 24:

Leu Val Leu Val Ile Ala Arg Val Arg Arg Leu His Asn Val Thr Asn
 1               5                  10                  15

Phe Leu Ile Gly Asn Leu Ala Leu Ser Asp Val Leu Met Cys Thr Ala
                20                  25                  30

Cys Val Pro Leu Thr Leu Ala Tyr Ala Phe Glu Pro Arg Gly Trp Val
            35                  40                  45

Phe Gly Gly Gly Leu Cys His Leu Val Phe Phe Leu Gln Pro Val Thr
        50                  55                  60

Val Tyr Val Ser Val Phe Thr Leu Thr Thr Ile Ala Val Asp Arg Tyr
65                  70                  75                  80

Val Val Leu Val His Pro Leu Arg Arg Arg Ile
                85                  90

(2) INFORMATION FOR SEQ ID NO: 25:

(i) SEQUENCE CHARACTERISTICS:
    (A) LENGTH: 59
    (B) TYPE: Amino acid
    (C) STRANDEDNESS: <Unknown>
    (D) TOPOLOGY: Linear (ii) MOLECULE TYPE: Peptide (xi) SEQUENCE DESCRIPTION: SEQ ID NO: 25:

```
Gly Leu Leu Leu Val Thr Tyr Leu Leu Pro Leu Leu Val Ile Leu Leu
 1               5                  10                  15
Ser Tyr Val Arg Val Ser Val Lys Leu Arg Asn Arg Val Val Pro Gly
                20                  25                  30
Cys Val Thr Gln Ser Gln Ala Asp Trp Asp Arg Ala Arg Arg Arg Arg
                35                  40                  45
Thr Phe Cys Leu Leu Val Val Val Val Val
            50                  55
```

(2) INFORMATION FOR SEQ ID NO: 26:

(i) SEQUENCE CHARACTERISTICS:
        (A) LENGTH: 370 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 26:

```
Met Ala Ser Ser Thr Thr Arg Gly Pro Arg Val Ser Asp Leu Phe Ser
 1               5                  10                  15
Gly Leu Pro Pro Ala Val Thr Thr Pro Ala Asn Gln Ser Ala Glu Ala
                20                  25                  30
Ser Ala Gly Asn Gly Ser Val Ala Gly Ala Asp Ala Pro Ala Val Thr
                35                  40                  45
Pro Phe Gln Ser Leu Gln Leu Val His Gln Leu Lys Gly Leu Ile Val
            50                  55                  60
Leu Leu Tyr Ser Val Val Val Val Gly Leu Val Gly Asn Cys Leu
 65                  70                  75                  80
Leu Val Leu Val Ile Ala Arg Val Arg Arg Leu His Asn Val Thr Asn
                85                  90                  95
Phe Leu Ile Gly Asn Leu Ala Leu Ser Asp Val Leu Met Cys Thr Ala
            100                 105                 110
Cys Val Pro Leu Thr Leu Ala Tyr Ala Phe Glu Pro Arg Gly Trp Val
            115                 120                 125
Phe Gly Gly Gly Leu Cys His Leu Val Phe Phe Leu Gln Pro Val Thr
            130                 135                 140
Val Tyr Val Ser Val Phe Thr Leu Thr Thr Ile Ala Val Asp Arg Tyr
145                 150                 155                 160
Val Val Leu Val His Pro Leu Arg Arg Arg Ile Ser Leu Arg Leu Ser
                165                 170                 175
Ala Tyr Ala Val Leu Ala Ile Trp Ala Leu Ser Ala Val Leu Ala Leu
                180                 185                 190
Pro Ala Ala Val His Thr Tyr His Val Glu Leu Lys Pro His Asp Val
                195                 200                 205
Arg Leu Cys Glu Glu Phe Trp Gly Ser Gln Glu Arg Gln Arg Gln Leu
            210                 215                 220
Tyr Ala Trp Gly Leu Leu Leu Val Thr Tyr Leu Leu Pro Leu Leu Val
225                 230                 235                 240
```

```
Ile Leu Leu Ser Tyr Val Arg Val Ser Val Lys Leu Arg Asn Arg Val
                245                 250                 255

Val Pro Gly Cys Val Thr Gln Ser Gln Ala Asp Trp Asp Arg Ala Arg
            260                 265                 270

Arg Arg Arg Thr Phe Cys Leu Leu Val Val Val Val Val Val Phe Ala
        275                 280                 285

Val Cys Trp Leu Pro Leu His Val Phe Asn Leu Leu Arg Asp Leu Asp
    290                 295                 300

Pro His Ala Ile Asp Pro Tyr Ala Phe Gly Leu Val Gln Leu Leu Cys
305                 310                 315                 320

His Trp Leu Ala Met Ser Ser Ala Cys Tyr Asn Pro Phe Ile Tyr Ala
                325                 330                 335

Trp Leu His Asp Ser Phe Arg Glu Glu Leu Arg Lys Leu Leu Val Ala
            340                 345                 350

Trp Pro Arg Lys Ile Ala Pro His Gly Gln Asn Met Thr Val Ser Val
        355                 360                 365

Val Ile
370

(2) INFORMATION FOR SEQ ID NO: 27:

(i) SEQUENCE CHARACTERISTICS:
        (A) LENGTH: 206 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 27:

Leu Val Leu Val Ile Ala Arg Val Arg Arg Leu Tyr Asn Val Thr Asn
1               5                   10                  15

Phe Leu Ile Gly Asn Leu Ala Leu Ser Asp Val Leu Met Cys Thr Ala
                20                  25                  30

Cys Val Pro Leu Thr Leu Ala Tyr Ala Phe Glu Pro Arg Gly Trp Val
            35                  40                  45

Phe Gly Gly Gly Leu Cys His Leu Val Phe Phe Leu Gln Ala Val Thr
        50                  55                  60

Val Tyr Val Ser Val Phe Thr Leu Thr Thr Ile Ala Val Asp Arg Tyr
65                  70                  75                  80

Val Val Leu Val His Pro Leu Arg Arg Arg Ile Ser Leu Arg Leu Ser
                85                  90                  95

Ala Tyr Ala Val Leu Ala Ile Trp Val Leu Ser Ala Val Leu Ala Leu
                100                 105                 110

Pro Ala Ala Val His Thr Tyr His Val Glu Leu Lys Pro His Asp Val
            115                 120                 125

Arg Leu Cys Glu Glu Phe Trp Gly Ser Gln Glu Arg Gln Arg Gln Leu
        130                 135                 140

Tyr Ala Trp Gly Leu Leu Leu Val Thr Tyr Leu Leu Pro Leu Leu Val
145                 150                 155                 160

Ile Leu Leu Ser Tyr Ala Arg Val Ser Val Lys Leu Arg Asn Arg Val
                165                 170                 175

Val Pro Gly Arg Val Thr Gln Ser Gln Ala Asp Trp Asp Arg Ala Arg
            180                 185                 190

Arg Arg Arg Thr Phe Cys Leu Leu Val Val Val Val Val Val
        195                 200                 205
```

(2) INFORMATION FOR SEQ ID NO: 28:

(i) SEQUENCE CHARACTERISTICS:
        (A) LENGTH: 126 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 28:

```
Val Val Leu Val His Pro Leu Arg Arg Arg Ile Ser Leu Arg Leu Ser
 1               5                  10                  15

Ala Tyr Ala Val Leu Gly Ile Trp Ala Leu Ser Ala Val Leu Ala Leu
                20                  25                  30

Pro Ala Ala Val His Thr Tyr His Val Glu Leu Lys Pro His Asp Val
                35                  40                  45

Ser Leu Cys Glu Glu Phe Trp Gly Ser Gln Glu Arg Gln Arg Gln Ile
        50                  55                  60

Tyr Ala Trp Gly Leu Leu Leu Gly Thr Tyr Leu Leu Pro Leu Leu Ala
65                  70                  75                  80

Ile Leu Leu Ser Tyr Val Arg Val Ser Val Lys Leu Arg Asn Arg Val
                85                  90                  95

Val Pro Gly Ser Val Thr Gln Ser Gln Ala Asp Trp Asp Arg Ala Arg
                100                 105                 110

Arg Arg Arg Thr Phe Cys Leu Leu Val Val Val Val
                115                 120         125
```

(2) INFORMATION FOR SEQ ID NO: 29:

(i) SEQUENCE CHARACTERISTICS:
        (A) LENGTH: 273 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 29:

```
CTGGTGCTGG TGATCGCGCG GGTGCGCCGG CTGCACAACG TGACGAACTT CCTCATCGGC      60
AACCTGGCCT TGTCCGACGT GCTCATGTGC ACCGCCTGCG TGCCGCTCAC GCTGGCCTAT     120
GCCTTCGAGC CACGCGGCTG GGTGTTCGGC GGCGGCCTGT GCCACCTGGT CTTCTTCCTG     180
CAGCCGGTCA CCGTCTATGT GTCGGTGTTC ACGCTCACCA CCATCGCAGT GGACCGGTAC     240
GTCGTGCTGG TGCACCCGCT GAGGCGGCGC ATC                                   273
```

(2) INFORMATION FOR SEQ ID NO: 30:

(i) SEQUENCE CHARACTERISTICS:
        (A) LENGTH: 177 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 30:

```
GGCCTGCTGC TGGTCACCTA CCTGCTCCCT CTGCTGGTCA TCCTCCTGTC TTACGTCCGG      60
GTGTCAGTGA AGCTCCGCAA CCGCGTGGTG CCGGGCTGCG TGACCCAGAG CCAGGCCGAC     120
TGGGACCGCG CTCGGCGCCG GCGCACCTTC TGCTTGCTGG TGGTGGTCGT GGTGGTG        177
```

(2) INFORMATION FOR SEQ ID NO: 31:

(i) SEQUENCE CHARACTERISTICS:
        (A) LENGTH: 1110 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 31:

```
ATGGCCTCAT CGACCACTCG GGGCCCCAGG GTTTCTGACT TATTTTCTGG GCTGCCGCCG      60

GCGGTCACAA CTCCCGCCAA CCAGAGCGCA GAGGCCTCGG CGGGCAACGG GTCGGTGGCT     120

GGCGCGGACG CTCCAGCCGT CACGCCCTTC CAGAGCCTGC AGCTGGTGCA TCAGCTGAAG     180

GGGCTGATCG TGCTGCTCTA CAGCGTCGTG GTGGTCGTGG GCTGGTGGG CAACTGCCTG      240

CTGGTGCTGG TGATCGCGCG GGTGCGCCGG CTGCACAACG TGACGAACTT CCTCATCGGC     300

AACCTGGCCT TGTCCGACGT GCTCATGTGC ACCGCCTGCG TGCCGCTCAC GCTGGCCTAT     360

GCCTTCGAGC CACGCGGCTG GGTGTTCGGC GGCGGCCTGT GCCACCTGGT CTTCTTCCTG     420

CAGCCGGTCA CCGTCTATGT GTCGGTGTTC ACGCTCACCA CCATCGCAGT GGACCGCTAC     480

GTCGTGCTGG TGCACCCGCT GAGGCGGCGC ATCTCGCTGC GCCTCAGCGC CTACGCTGTG     540

CTGGCCATCT GGGCGCTGTC CGCGGTGCTG GCGCTGCCCG CCGCCGTGCA CACCTATCAC     600

GTGGAGCTCA AGCCGCACGA CGTGCGCCTC TGCGAGGAGT CTGGGGCTC CCAGGAGCGC      660

CAGCGCCAGC TCTACGCCTG GGGGCTGCTG CTGGTCACCT ACCTGCTCCC TCTGCTGGTC     720

ATCCTCCTGT CTTACGTCCG GGTGTCAGTG AAGCTCCGCA ACCGCGTGGT GCCGGGCTGC     780

GTGACCCAGA GCCAGGCCGA CTGGGACCGC GCTCGGCGCC GGCGCACCTT CTGCTTGCTG     840

GTGGTGGTCG TGGTGGTGTT CGCCGTCTGC TGGCTGCCGC TGCACGTCTT CAACCTGCTG     900

CGGGACCTCG ACCCCCACGC CATCGACCCT TACGCCTTTG GCTGGTGCA GCTGCTCTGC      960

CACTGGCTCG CCATGAGTTC GGCCTGCTAC AACCCCTTCA TCTACGCCTG GCTGCACGAC    1020

AGCTTCCGCG AGGAGCTGCG CAAACTGTTG GTCGCTTGGC CCCGCAAGAT AGCCCCCCAT    1080

GGCCAGAATA TGACCGTCAG CGTGGTCATC                                    1110
```

(2) INFORMATION FOR SEQ ID NO: 32:

(i) SEQUENCE CHARACTERISTICS:
        (A) LENGTH: 618 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 32:

```
CTGGTGCTGG TGATCGCGCG GGTGCGCCGG CTGTACAACG TGACGAATTT CCTCATCGGC      60

AACCTGGCCT TGTCCGACGT GCTCATGTGC ACCGCCTGCG TGCCGCTCAC GCTGGCCTAT     120

GCCTTCGAGC CACGCGGCTG GGTGTTCGGC GGCGGCCTGT GCCACCTGGT CTTCTTCCTG     180

CAGGCGGTCA CCGTCTATGT GTCGGTGTTC ACGCTCACCA CCATCGCAGT GGACCGCTAC     240

GTCGTGCTGG TGCACCCGCT GAGGCGGCGC ATCTCGCTGC GCCTCAGCGC CTACGCTGTG     300

CTGGCCATCT GGGTGCTGTC CGCGGTGCTG GCGCTGCCCG CCGCCGTGCA CACCTATCAC     360

GTGGAGCTCA AGCCGCACGA CGTGCGCCTC TGCGAGGAGT CTGGGGCTC CCAGGAGCGC      420
```

```
CAGCGCCAGC TCTACGCCTG GGGGCTGCTG CTGGTCACCT ACCTGCTCCC TCTGCTGGTC      480

ATCCTCCTGT CTTACGCCCG GGTGTCAGTG AAGCTCCGCA ACCGCGTGGT GCCGGGCCGC      540

GTGACCCAGA GCCAGGCCGA CTGGGACCGC GCTCGGCGCC GGCGCACCTT CTGCTTGCTG      600

GTGGTGGTCG TGGTGGTG                                                   618

(2) INFORMATION FOR SEQ ID NO: 33:

(i) SEQUENCE CHARACTERISTICS:
        (A) LENGTH: 378 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 33:

GTGGTTCTGG TGCACCCGCT ACGTCGGCGC ATTTCACTGA GGCTCAGCGC CTACGCGGTG       60

CTGGGCATCT GGGCTCTATC TGCAGTGCTG GCGCTGCCGG CCGCGGTGCA CACCTACCAT      120

GTGGAGCTCA AGCCCCACGA CGTGAGCCTC TGCGAGGAGT TCTGGGGCTC GCAGGAGCGC      180

CAACGCCAGA TCTACGCCTG GGGGCTGCTT CTGGGCACCT ATTTGCTCCC CCTGCTGGCC      240

ATCCTCCTGT CTTACGTACG GGTGTCAGTG AAGCTGAGGA ACCGCGTGGT GCCTGGCAGC      300

GTGACCCAGA GTCAAGCTGA CTGGGACCGA GCGCGTCGCC GCCGCACTTT CTGTCTGCTG      360

GTGGTGGTGG TGGTAGTG                                                   378

(2) INFORMATION FOR SEQ ID NO: 34:

(i) SEQUENCE CHARACTERISTICS:
        (A) LENGTH: 70 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 34:

Val Cys His Val Ile Phe Lys Asn Gln Arg Met His Ser Ala Thr Ser
1               5                   10                  15

Leu Phe Ile Val Asn Leu Ala Val Ala Asp Ile Met Ile Thr Leu Ile
                20                  25                  30

Asn Thr Pro Phe Thr Leu Val Arg Phe Val Asn Ser Thr Trp Ile Phe
            35                  40                  45

Gly Lys Gly Met Cys His Val Ser Arg Phe Ala Gln Tyr Cys Ser Leu
        50                  55                  60

His Val Ser Ala Leu Thr
65                  70

(2) INFORMATION FOR SEQ ID NO: 35:

(i) SEQUENCE CHARACTERISTICS:
        (A) LENGTH: 71 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 35:

Glu Pro Ala Asp Leu Phe Trp Lys Asn Leu Asp Leu Pro Thr Phe Ile
1               5                   10                  15
```

```
Leu Leu Asn Ile Leu Pro Leu Leu Ile Ile Ser Val Ala Tyr Val Arg
             20                  25                  30

Val Thr Lys Lys Leu Trp Leu Cys Asn Met Ile Val Asp Val Thr Thr
         35                  40                  45

Glu Gln Tyr Phe Ala Leu Arg Pro Lys Lys Lys Thr Ile Lys Met
     50                  55                  60

Leu Met Leu Val Val Val Leu
65               70
```

(2) INFORMATION FOR SEQ ID NO: 36:

(i) SEQUENCE CHARACTERISTICS:
        (A) LENGTH: 210 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 36:

```
GTCTGTCATG TCATCTTCAA GAACCAGCGA ATGCACTCGG CCACCAGCCT CTTCATCGTC      60

AACCTGGCAG TTGCCGACAT AATGATCACG CTGCTCAACA CCCCCTTCAC TTTGGTTCGC     120

TTTGTGAACA GCACATGGAT ATTTGGGAAG GGCATGTGCC ATGTCAGCCG CTTTGCCCAG     180

TACTGCTCAC TGCACGTCTC AGCACTGACA                                     210
```

(2) INFORMATION FOR SEQ ID NO: 37:

(i) SEQUENCE CHARACTERISTICS:
        (A) LENGTH: 213 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 37:

```
GAGCCAGCTG ACCTCTTCTG GAAGAACCTG GACTTGCCCA CCTTCATCCT GCTCAACATC      60

CTGCCCCTCC TCATCATCTC TGTGGCCTAC GTTCGTGTGA CCAAGAAACT GTGGCTGTGT     120

AATATGATTG TCGATGTGAC CACAGAGCAG TACTTTGCCC TGCGGCCCAA AAAGAAGAAG     180

ACCATCAAGA TGTTGATGCT GGTGGTAGTC CTC                                 213
```

(2) INFORMATION FOR SEQ ID NO: 38:

(i) SEQUENCE CHARACTERISTICS:
        (A) LENGTH: 115 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 38:

```
Ala Ser Trp His Lys Arg Gly Arg Arg Ala Ala Trp Val Val Cys
1                5                  10                  15

Gly Val Val Trp Leu Ala Val Thr Ala Gln Cys Leu Pro Thr Ala Val
             20                  25                  30

Phe Ala Ala Thr Gly Ile Gln Arg Asn Arg Thr Val Cys Tyr Asp Leu
         35                  40                  45

Ser Pro Pro Ile Leu Ser Thr Arg Tyr Leu Pro Tyr Gly Met Ala Leu
     50                  55                  60
```

```
Thr Val Ile Gly Phe Leu Leu Pro Phe Ile Ala Leu Ala Cys Tyr
 65                  70                  75                  80

Cys Arg Met Ala Arg Arg Leu Cys Arg Gln Asp Gly Pro Ala Gly Pro
                 85                  90                  95

Val Ala Gln Glu Arg Arg Ser Lys Ala Ala Arg Met Ala Val Val Val
                100                 105                 110

Ala Ala Val
        115

(2) INFORMATION FOR SEQ ID NO: 39:

(i) SEQUENCE CHARACTERISTICS:
        (A) LENGTH: 328 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 39:

Met Glu Gln Asp Asn Gly Thr Ile Gln Ala Pro Gly Leu Pro Pro Thr
  1               5                  10                  15

Thr Cys Val Tyr Arg Glu Asp Phe Lys Arg Leu Leu Leu Thr Pro Val
                 20                  25                  30

Tyr Ser Val Val Leu Val Val Gly Leu Pro Leu Asn Ile Cys Val Ile
             35                  40                  45

Ala Gln Ile Cys Ala Ser Arg Arg Thr Leu Thr Arg Ser Ala Val Tyr
         50                  55                  60

Thr Leu Asn Leu Ala Leu Ala Asp Leu Met Tyr Ala Cys Ser Leu Pro
 65                  70                  75                  80

Leu Leu Ile Tyr Asn Tyr Ala Arg Gly Asp His Trp Pro Phe Gly Asp
                 85                  90                  95

Leu Ala Cys Arg Phe Val Arg Phe Leu Phe Tyr Ala Asn Leu His Gly
                100                 105                 110

Ser Ile Leu Phe Leu Thr Cys Ile Ser Phe Gln Arg Tyr Leu Gly Ile
                115                 120                 125

Cys His Pro Leu Ala Ser Trp His Lys Arg Gly Gly Arg Arg Ala Ala
        130                 135                 140

Trp Val Val Cys Gly Val Val Trp Leu Ala Val Thr Ala Gln Cys Leu
145                 150                 155                 160

Pro Thr Ala Val Phe Ala Ala Thr Gly Ile Gln Arg Asn Arg Thr Val
                165                 170                 175

Cys Tyr Asp Leu Ser Pro Pro Ile Leu Ser Thr Arg Tyr Leu Pro Tyr
            180                 185                 190

Gly Met Ala Leu Thr Val Ile Gly Phe Leu Leu Pro Phe Ile Ala Leu
            195                 200                 205

Leu Ala Cys Tyr Cys Arg Met Ala Arg Arg Leu Cys Arg Gln Asp Gly
        210                 215                 220

Pro Ala Gly Pro Val Ala Gln Glu Arg Arg Ser Lys Ala Ala Arg Met
225                 230                 235                 240

Ala Val Val Val Ala Ala Val Phe Ala Ile Ser Phe Leu Pro Phe His
                245                 250                 255

Ile Thr Lys Thr Ala Tyr Leu Ala Val Arg Ser Thr Pro Gly Val Ser
            260                 265                 270

Cys Pro Val Leu Glu Thr Phe Ala Ala Ala Tyr Lys Gly Thr Arg Pro
            275                 280                 285
```

```
Phe Ala Ser Val Asn Ser Val Leu Asp Pro Ile Leu Phe Tyr Phe Thr
    290                 295                 300

Gln Gln Lys Phe Arg Arg Gln Pro His Asp Leu Leu Gln Arg Leu Thr
305                 310                 315                 320

Ala Lys Trp Gln Arg Gln Arg Val
                325
```

(2) INFORMATION FOR SEQ ID NO: 40:

(i) SEQUENCE CHARACTERISTICS:
        (A) LENGTH: 345 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 40:

```
GCTTCCTGGC ACAAGCGTGG AGGTCGCCGT GCTGCTTGGG TAGTGTGTGG AGTCGTGTGG    60
CTGGCTGTGA CAGCCCAGTG CCTGCCCACG GCAGTCTTTG CTGCCACAGG CATCCAGCGC   120
AACCGCACTG TGTGCTACGA CCTGAGCCCA CCCATCCTGT CTACTCGCTA CCTGCCCTAT   180
GGTATGGCCC TCACGGTCAT CGGCTTCTTG CTGCCCTTCA TAGCCTTACT GGCTTGTTAT   240
TGTCGCATGG CCCGCCGCCT GTGTCGCCAG GATGGCCCAG CAGGTCCTGT GGCCCAAGAG   300
CGGCGCAGCA AGGCGGCTCG TATGGCTGTG GTGGTGGCAG CTGTC                   345
```

(2) INFORMATION FOR SEQ ID NO: 41:

(i) SEQUENCE CHARACTERISTICS:
        (A) LENGTH: 984 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 41:

```
ATGGAGCAGG ACAATGGCAC CATCCAGGCT CCAGGCTTGC CGCCCACCAC CTGCGTCTAC    60
CGTGAGGATT TCAAGCGACT GCTGCTAACC CCGGTATACT CGGTGGTGCT GGTGGTCGGC   120
CTGCCACTGA ACATCTGCGT CATTGCCCAG ATCTGCGCAT CCCGCCGGAC CCTGACCCGT   180
TCCGCTGTGT ACACCCTGAA CCTGGCACTG GCGGACCTGA TGTATGCCTG TTCACTACCC   240
CTACTTATCT ATAACTACGC CAGAGGGGAC CACTGGCCCT TCGGAGACCT CGCCTGCCGC   300
TTTGTACGCT TCCTCTTCTA TGCCAATCTA CATGGCAGCA TCCTGTTCCT CACCTGCATT   360
AGCTTCCAGC GCTACCTGGG CATCTGCCAC CCCCTGGCTT CCTGGCACAA GCGTGGAGGT   420
CGCCGTGCTG CTTGGGTAGT GTGTGGAGTC GTGTGGCTGG CTGTGACAGC CCAGTGCCTG   480
CCCACGGCAG TCTTTGCTGC CACAGGCATC CAGCGCAACC GCACTGTGTG CTACGACCTG   540
AGCCCACCCA TCCTGTCTAC TCGCTACCTG CCCTATGGTA TGGCCCTCAC GGTCATCGGC   600
TTCTTGCTGC CCTTCATAGC CTTACTGGCT TGTTATTGTC GCATGGCCCG CCGCCTGTGT   660
CGCCAGGATG GCCCAGCAGG TCCTGTGGCC CAAGAGCGGC GCAGCAAGGC GGCTCGTATG   720
GCTGTGGTGG TGGCAGCTGT CTTTGCCATC AGCTTCCTGC CTTTCCACAT CACCAAGACA   780
GCCTACTTGG CTGTGCGCTC CACGCCCGGT GTCTCTTGCC CTGTGCTGGA GACCTTCGCT   840
GCTGCCTACA AAGGCACTCG GCCCTTCGCC AGTGTCAACA GTGTTCTGGA CCCCATTCTC   900
TTCTACTTCA CACAACAGAA GTTCCGGCGG CAACCCCACG ATCTCTTACA GAGGCTCACA   960
```

```
GCCAAGTGGC AGAGGCAGAG AGTC                                              984
```

(2) INFORMATION FOR SEQ ID NO: 42:

(i) SEQUENCE CHARACTERISTICS:
        (A) LENGTH: 128 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 42:

```
Ala Ala Met Ser Val Asp Arg Tyr Val Ala Ile Val His Ser Arg Arg
 1               5                  10                  15
Ser Ser Ser Leu Arg Val Ser Arg Asn Ala Leu Leu Gly Val Gly Phe
                20                  25                  30
Ile Trp Ala Leu Ser Ile Ala Met Ala Ser Pro Val Ala Tyr His Gln
                35                  40                  45
Arg Leu Phe His Arg Asp Ser Asn Gln Thr Phe Cys Trp Glu Gln Trp
         50                  55                  60
Pro Asn Lys Leu His Lys Lys Ala Tyr Val Val Cys Thr Phe Val Phe
65                  70                  75                  80
Gly Tyr Leu Leu Pro Leu Leu Leu Ile Cys Phe Cys Tyr Ala Lys Val
                85                  90                  95
Leu Asn His Leu His Lys Lys Leu Lys Asn Met Ser Lys Lys Ser Glu
                100                 105                 110
Ala Ser Lys Lys Lys Thr Ala Gln Thr Val Leu Val Val Val Val Val
         115                 120                 125
```

(2) INFORMATION FOR SEQ ID NO: 43:

(i) SEQUENCE CHARACTERISTICS:
        (A) LENGTH: 384 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 43:

```
GCCGCGATGT CTGTGGATCG CTACGTGGCC ATTGTGCACT CGCGGCGCTC CTCCTCCCTC    60
AGGGTGTCCC GCAACGCACT GCTGGGCGTG GGCTTCATCT GGGCGCTGTC CATCGCCATG   120
GCCTCGCCGG TGGCCTACCA CCAGCGTCTT TTCCATCGGG ACAGCAACCA GACCTTCTGC   180
TGGGAGCAGT GGCCCAACAA GCTCCACAAG AAGGCTTACG TGGTGTGCAC TTTCGTCTTT   240
GGGTACCTTC TGCCCTTACT GCTCATCTGC TTTTGCTATG CCAAGGTCCT TAATCATCTG   300
CATAAAAAGC TGAAAAACAT GTCAAAAAAG TCTGAAGCAT CCAAGAAAAA GACTGCACAG   360
ACCGTCCTGG TGGTCGTTGT AGTA                                         384
```

(2) INFORMATION FOR SEQ ID NO: 44:

(i) SEQUENCE CHARACTERISTICS:
        (A) LENGTH: 71 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 44:

```
Val Leu Trp Phe Phe Gly Phe Ser Ile Lys Arg Thr Pro Phe Ser Val
 1               5                  10                  15

Tyr Phe Leu His Leu Ala Ser Ala Asp Gly Ala Tyr Leu Phe Ser Lys
                 20                  25                  30

Ala Val Phe Ser Leu Leu Asn Ala Gly Gly Phe Leu Gly Thr Phe Ala
             35                  40                  45

His Tyr Val Arg Ser Val Ala Arg Val Leu Gly Leu Cys Ala Phe Val
         50                  55                  60

Ala Gly Val Ser Leu Leu Pro
 65                  70
```

(2) INFORMATION FOR SEQ ID NO: 45:

(i) SEQUENCE CHARACTERISTICS:
        (A) LENGTH: 215 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 45:

```
GTGCTCTGGT TCTTCGGCTT CTCCATCAAG AGGACCCCCT TCTCCGTCTA CTTCCTGCAC      60

CTGGCCAGCG CCGACGGCGC CTACCTCTTC AGCAAGGCCG TGTTCTCCCT GCTGAACGCC     120

GGCGGCTTCC TGGGCACCTT CGCCCACTAT GTGCGCAGCG TGGCCCGGGT GCTGGGGCTC     180

TGCGCCTTCG TGGCGGGCGT GAGCCTCCTG CCGGC                                215
```

(2) INFORMATION FOR SEQ ID NO: 46:

(i) SEQUENCE CHARACTERISTICS:
        (A) LENGTH: 348 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 46:

```
Met Glu Leu Ala Met Val Asn Leu Ser Glu Gly Asn Gly Ser Asp Pro
 1               5                  10                  15

Glu Pro Pro Ala Pro Glu Ser Arg Pro Leu Phe Gly Ile Gly Val Glu
                 20                  25                  30

Asn Phe Ile Thr Leu Val Val Phe Gly Leu Ile Phe Ala Met Gly Val
             35                  40                  45

Leu Gly Asn Ser Leu Val Ile Thr Val Leu Ala Arg Ser Lys Pro Gly
 50                  55                  60

Lys Pro Arg Ser Thr Thr Asn Leu Phe Ile Leu Asn Leu Ser Ile Ala
 65                  70                  75                  80

Asp Leu Ala Tyr Leu Leu Phe Cys Ile Pro Phe Gln Ala Thr Val Tyr
                 85                  90                  95

Ala Leu Pro Thr Trp Val Leu Gly Ala Phe Ile Cys Lys Phe Ile His
             100                 105                 110

Tyr Phe Phe Thr Val Ser Met Leu Val Ser Ile Phe Thr Leu Ala Ala
         115                 120                 125

Met Ser Val Asp Arg Tyr Val Ala Ile Val His Ser Arg Arg Ser Ser
 130                 135                 140

Ser Leu Arg Val Ser Arg Asn Ala Leu Leu Gly Val Gly Phe Ile Trp
 145                 150                 155                 160
```

```
Ala Leu Ser Ile Ala Met Ala Ser Pro Val Ala Tyr His Gln Arg Leu
                165                 170                 175

Phe His Arg Asp Ser Asn Gln Thr Phe Cys Trp Glu Gln Trp Pro Asn
            180                 185                 190

Lys Leu His Lys Lys Ala Tyr Val Val Cys Thr Phe Val Phe Gly Tyr
        195                 200                 205

Leu Leu Pro Leu Leu Leu Ile Cys Phe Cys Tyr Ala Lys Val Leu Asn
    210                 215                 220

His Leu His Lys Lys Leu Lys Asn Met Ser Lys Lys Ser Glu Ala Ser
225                 230                 235                 240

Lys Lys Lys Thr Ala Gln Thr Val Leu Val Val Val Val Phe Gly
                245                 250                 255

Ile Ser Trp Leu Pro His His Val Val His Leu Trp Ala Glu Phe Gly
                260                 265                 270

Ala Phe Pro Leu Thr Pro Ala Ser Phe Phe Phe Arg Ile Thr Ala His
                275                 280                 285

Cys Leu Ala Tyr Ser Asn Ser Ser Val Asn Pro Ile Ile Tyr Ala Phe
        290                 295                 300

Leu Ser Glu Asn Phe Arg Lys Ala Tyr Lys Gln Val Phe Lys Cys His
305                 310                 315                 320

Val Cys Asp Glu Ser Pro Arg Ser Glu Thr Lys Glu Asn Lys Ser Arg
                325                 330                 335

Met Asp Thr Pro Pro Ser Thr Asn Cys Thr His Val
                340                 345

(2) INFORMATION FOR SEQ ID NO: 47:

(i) SEQUENCE CHARACTERISTICS:
        (A) LENGTH: 1044 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 47:

ATGGAACTGG CTATGGTGAA CCTCAGTGAA GGGAATGGGA GCGACCCAGA GCCGCCAGCC    60

CCGGAGTCCA GGCCGCTCTT CGGCATTGGC GTGGAGAACT TCATTACGCT GGTAGTGTTT   120

GGCCTGATTT TCGCGATGGG CGTGCTGGGC AACAGCCTGG TGATCACCGT GCTGGCGCGC   180

AGCAAACCAG GCAACCCCCG CAGCACCACC AACCTGTTTA TCCTCAATCT GAGCATCGCA   240

GACCTGGCCT ACCTGCTCTT CTGCATCCCT TTTCAGGCCA CCGTGTATGC ACTGCCCACC   300

TGGGTGCTGG GCGCCTTCAT CTGCAAGTTT ATACACTACT TCTTCACCGT GTCCATGCTG   360

GTGAGCATCT TCACCCTGGC CGCGATGTCT GTGGATCGCT ACGTGGCCAT TGTGCACTCG   420

CGGCGCTCCT CCTCCCTCAG GGTGTCCCGC AACGCACTGC TGGGCGTGGG CTTCATCTGG   480

GCGCTGTCCA TCGCCATGGC CTCGCCGGTG GCCTACCACC AGCGTCTTTT CCATCGGGAC   540

AGCAACCAGA CCTTCTGCTG GGAGCAGTGG CCCAACAAGC TCCACAAGAA GGCTTACGTG   600

GTGTGCACTT TCGTCTTTGG GTACCTTCTG CCCTTACTGC TCATCTGCTT TTGCTATGCC   660

AAGGTCCTTA ATCATCTGCA TAAAAAGCTG AAAAACATGT CAAAAAAGTC TGAAGCATCC   720

AAGAAAAAGA CTGCACAGAC CGTCCTGGTG GTCGTTGTAG TATTTGGCAT ATCCTGGCTG   780

CCCCATCATG TCGTCCACCT CTGGGCTGAG TTTGGAGCCT TCCCACTGAC GCCAGCTTCC   840

TTCTTCTTCA GAATCACCGC CCATTGCCTG GCATACAGCA ACTCCTCAGT GAACCCCATC   900
```

```
ATATATGCCT TTCTCTCAGA AAACTTCCGG AAGGCGTACA AGCAAGTGTT CAAGTGTCAT      960

GTTTGCGATG AATCTCCACG CAGTGAAACT AAGGAAAACA AGAGCCGGAT GGACACCCCG     1020

CCATCCACCA ACTGCACCCA CGTG                                           1044
```

(2) INFORMATION FOR SEQ ID NO: 48:

(i) SEQUENCE CHARACTERISTICS:
        (A) LENGTH: 125 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 48:

```
Leu Leu Thr Leu His Pro Val Trp Ser Gln Lys His Arg Thr Ser His
 1               5                  10                  15

Trp Ala Ser Arg Val Val Leu Gly Val Trp Leu Ser Ala Thr Ala Phe
            20                  25                  30

Ser Val Pro Tyr Leu Val Phe Arg Glu Thr Tyr Asp Asp Arg Lys Gly
        35                  40                  45

Arg Val Thr Cys Arg Asn Asn Tyr Ala Val Ser Thr Asp Trp Glu Ser
    50                  55                  60

Lys Glu Met Gln Thr Val Arg Gln Trp Ile His Ala Thr Cys Phe Ile
65                  70                  75                  80

Ser Arg Phe Ile Leu Gly Phe Leu Leu Pro Phe Leu Val Ile Gly Phe
                85                  90                  95

Cys Tyr Glu Arg Val Ala Arg Lys Met Lys Glu Arg Gly Leu Phe Lys
            100                 105                 110

Ser Ser Lys Pro Phe Lys Val Thr Met Thr Ala Val Ile
        115                 120                 125
```

(2) INFORMATION FOR SEQ ID NO: 49:

(i) SEQUENCE CHARACTERISTICS:
        (A) LENGTH: 377 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 49:

```
CTTCTCACCC TTCACCCAGT GTGGTCCCAA AAGCACCGAA CCTCACACTG GCTTCCAGA       60

GTCGTTCTGG GAGTCTGGCT CTCTGCCACT GCCTTCAGCG TGCCCTATTT GGTTTTCAGG     120

GAGACATATG ATGACCGTAA AGGAAGAGTG ACCTGCAGAA ATAACTACGC TGTGTCCACT     180

GACTGGGAAA GCAAAGAGAT GCAAACAGTA AGACAATGGA TTCATGCCAC CTGTTTCATC     240

AGCCGCTTCA TACTGGGCTT CCTTCTGCCT TTCTTAGTCA TTGGCTTTTG TTATGAAAGA     300

GTAGCCCGCA AGATGAAAGA GAGGGGCCTC TTTAAATCCA GCAAACCCTT CAAAGTCACG     360

ATGACTGCTG TTATCTC                                                   377
```

(2) INFORMATION FOR SEQ ID NO: 50:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 50:

Phe Lys Ile Val Lys Pro Leu Ser Thr Ser Phe Ile Gln Ser Val Asn
1               5                   10                  15

Tyr Ser Lys Leu Val Ser Leu Val Val Trp Leu Leu Met Leu Leu Leu
                20                  25                  30

Ala Val Pro Asn Val Ile Leu Thr Asn Gln Arg Val Lys Asp Val Thr
            35                  40                  45

Gln Ile Lys Cys Met Glu Leu Lys Asn Glu Leu Gly Arg Gln Trp His
        50                  55                  60

Lys Ala Ser Asn Tyr Ile Phe Val Gly Ile Phe Trp Leu Val Phe Leu
65                  70                  75                  80

Leu Leu Ile Ile Phe Tyr Thr Ala Ile Thr Arg Lys Ile Phe Lys Ser
                85                  90                  95

His Leu Lys Ser Arg Lys Asn Ser Ile Ser Val Lys Lys Lys Ser Ser
            100                 105                 110

Arg Asn Ile Phe Ser Ile Val
        115

(2) INFORMATION FOR SEQ ID NO: 51:

(i) SEQUENCE CHARACTERISTICS:
        (A) LENGTH: 357 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 51:

TTCAAGATTG TGAAGCCCCT TTCCACGTCC TTCATCCAGT CTGTGAACTA CAGCAAACTC        60

GTCTCGCTGG TGGTCTGGTT GCTCATGCTC CTCCTCGCCG TCCCCAACGT CATTCTCACC       120

AACCAGAGAG TTAAGGACGT GACGCAGATA AAATGCATGG AACTTAAAAA CGAACTGGGC       180

CGCCAGTGGC ACAAGGCGTC AAACTACATC TTTGTGGGCA TTTTCTGGCT TGTGTTCCTT       240

TTGCTAATCA TTTTCTACAC TGCTATCACC AGGAAAATCT TAAGTCCCA CCTGAAATCC        300

AGAAAGAATT CCATCTCGGT CAAAAAGAAA TCTAGCCGCA ACATCTTCAG CATCGTG          357

(2) INFORMATION FOR SEQ ID NO: 52:

(i) SEQUENCE CHARACTERISTICS:
        (A) LENGTH: 252 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 52:

Val Asp Leu Leu Ala Ala Leu Thr Leu Met Pro Leu Ala Met Leu Ser
1               5                   10                  15

Ser Ser Ala Leu Phe Asp His Ala Leu Phe Gly Glu Val Ala Cys Arg
                20                  25                  30

Leu Tyr Leu Phe Leu Ser Val Cys Phe Val Ser Leu Ala Ile Leu Ser
            35                  40                  45

Val Ser Ala Ile Asn Val Glu Arg Tyr Tyr Val Val His Pro Met
        50                  55                  60

Arg Tyr Glu Val Arg Met Lys Leu Gly Leu Val Ala Ser Val Leu Val

```
                65                  70                  75                  80
Gly Val Trp Val Lys Ala Leu Ala Met Ala Ser Val Pro Val Leu Gly
                    85                  90                  95
Arg Val Ser Trp Glu Glu Gly Pro Pro Ser Val Pro Pro Gly Cys Ser
                100                 105                 110
Leu Gln Trp Ser His Ser Ala Tyr Cys Gln Leu Phe Val Val Phe
                115                 120                 125
Ala Val Leu Tyr Phe Leu Leu Pro Leu Leu Leu Ile Leu Val Val Tyr
            130                 135                 140
Cys Ser Met Phe Arg Val Ala Arg Val Ala Ala Met Gln His Gly Pro
145                 150                 155                 160
Leu Pro Thr Trp Met Glu Thr Pro Arg Gln Arg Ser Glu Ser Leu Ser
                165                 170                 175
Ser Arg Ser Thr Met Val Thr Ser Ser Gly Ala Pro Gln Thr Thr Pro
                180                 185                 190
His Arg Thr Phe Gly Gly Gly Lys Ala Ala Val Val Leu Leu Ala Val
                195                 200                 205
Gly Gly Gln Phe Leu Leu Cys Trp Leu Pro Tyr Phe Ser Phe His Leu
            210                 215                 220
Tyr Val Ala Leu Ser Ala Gln Pro Ile Ala Ala Gly Gln Val Glu Asn
225                 230                 235                 240
Val Val Thr Trp Ile Gly Tyr Phe Cys Phe Thr Ser
                    245                 250
```

(2) INFORMATION FOR SEQ ID NO: 53:

(i) SEQUENCE CHARACTERISTICS:
        (A) LENGTH: 756 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 53:

```
GTGGACCTGC TGGCTGCCCT GACCCTCATG CCTCTGGCCA TGCTCTCCAG CTCCGCCCTC    60
TTTGACCACG CCCTCTTTGG GGAGGTGGCC TGCCGCCTCT ACTTGTTCCT GAGCGTCTGC   120
TTTGTCAGCC TGGCCATCCT CTCGGTGTCC GCCATCAATG TGGAGCGCTA CTATTATGTG   180
GTCCACCCCA TGCGCTATGA GGTGCGCATG AAACTGGGC TGGTGGCCTC TGTGCTGGTG    240
GGCGTGTGGG TGAAGGCCCT GGCCATGGCT TCTGTGCCAG TGTTGGGAAG GGTGTCCTGG   300
GAGGAAGGCC CTCCCAGTGT CCCCCCAGGC TGTTCACTCC AATGGAGCCA CAGTGCCTAC   360
TGCCAGCTTT TCGTGGTGGT CTTCGCCGTC CTCTACTTCC TGCTGCCCCT GCTCCTCATC   420
CTTGTGGTCT ACTGCAGCAT GTTCCGGGTG GCTCGTGTGG CTGCCATGCA GCACGGGCCG   480
CTGCCCACGT GGATGGAGAC GCCCCGGCAA CGCTCCGAGT CTCTCAGCAG CCGCTCCACT   540
ATGGTCACCA GCTCGGGGGC CCCGCAGACC ACCCCTCACC GGACGTTTGG CGGAGGGAAG   600
GCAGCAGTGG TCCTCCTGGC TGTGGGAGGA CAGTTCCTGC TCTGTTGGTT GCCCTACTTC   660
TCCTTCCACC TCTATGTGGC CCTGAGCGCT CAGCCCATTG CAGCGGGGCA GGTGGAGAAC   720
GTGGTGACCT GGATTGGCTA CTTCTGCTTC ACCTCC                             756
```

(2) INFORMATION FOR SEQ ID NO: 54:

(i) SEQUENCE CHARACTERISTICS:
        (A) LENGTH: 263 amino acids

-continued (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 54:

Ala Asp Val Leu Val Thr Ala Ile Cys Leu Pro Ala Ser Leu Leu Val
1               5                   10                  15

Asp Ile Thr Glu Ser Trp Leu Phe Gly His Ala Leu Cys Lys Val Ile
            20                  25                  30

Pro Tyr Leu Gln Ala Val Ser Val Ser Val Val Leu Thr Leu Ser
        35                  40                  45

Ser Ile Ala Leu Asp Arg Trp Tyr Ala Ile Cys His Pro Leu Leu Phe
    50                  55                  60

Lys Ser Thr Ala Arg Arg Ala Arg Gly Ser Ile Leu Gly Ile Trp Ala
65                  70                  75                  80

Val Ser Leu Ala Val Met Val Pro Gln Ala Ala Val Met Glu Cys Ser
                85                  90                  95

Ser Val Leu Pro Glu Leu Ala Asn Arg Thr Arg Leu Leu Ser Val Cys
            100                 105                 110

Asp Glu Arg Trp Ala Asp Asp Leu Tyr Pro Lys Ile Tyr His Ser Cys
        115                 120                 125

Phe Phe Ile Val Thr Tyr Leu Ala Pro Leu Gly Leu Met Ala Met Ala
130                 135                 140

Tyr Phe Gln Ile Phe Arg Lys Leu Trp Gly Arg Gln Ile Pro Gly Thr
145                 150                 155                 160

Thr Ser Ala Leu Val Arg Asn Trp Lys Arg Pro Ser Asp Gln Leu Asp
                165                 170                 175

Asp Gln Gly Gln Gly Leu Ser Ser Glu Pro Gln Pro Arg Ala Arg Ala
            180                 185                 190

Phe Leu Ala Glu Val Lys Gln Met Arg Ala Arg Arg Lys Thr Ala Lys
        195                 200                 205

Met Leu Met Val Val Leu Leu Val Phe Ala Leu Cys Tyr Leu Pro Ile
210                 215                 220

Ser Val Leu Asn Val Leu Lys Arg Val Phe Gly Met Phe Arg Gln Ala
225                 230                 235                 240

Ser Asp Arg Glu Ala Ile Tyr Ala Cys Phe Thr Phe Ser His Trp Leu
                245                 250                 255

Val Tyr Ala Asn Ser Ala Ala
            260

(2) INFORMATION FOR SEQ ID NO: 55:

(i) SEQUENCE CHARACTERISTICS:
        (A) LENGTH: 789 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 55:

GCCGATGTGC TGGTGACAGC CATCTGCCTG CCGGCCAGTC TGCTGGTAGA CATCACGGAA      60

TCCTGGCTCT TTGGCCATGC CCTCTGCAAG GTCATCCCCT ATCTACAGGC CGTGTCCGTG     120

TCAGTGGTCG TGCTGACTCT CAGCTCCATC GCCCTGGACC GCTGGTACGC CATCTGCCAC     180

CCGCTGTTGT TCAAGAGCAC TGCCCGGCGC GCCCGCGGCT CCATCCTCGG CATCTGGGCG     240

-continued

```
GTGTCGCTGG CTGTCATGGT GCCTCAGGCT GCTGTCATGG AGTGTAGCAG CGTGCTGCCC    300

GAGCTGGCCA ACCGCACCCG CCTCCTGTCT GTCTGTGATG AGCGCTGGGC AGACGACCTG    360

TACCCCAAGA TCTACCACAG CTGCTTCTTC ATTGTCACCT ACCTGGCCCC ACTGGGCCTC    420

ATGGCCATGG CCTATTTCCA GATCTTCCGC AAGCTCTGGG GCCGCCAGAT CCCCGGCACC    480

ACCTCGGCCC TGGTGCGCAA CTGGAAGCGG CCCTCAGACC AGCTGGACGA CCAGGGCCAG    540

GGCCTGAGCT CAGAGCCCCA GCCCCGGGCC CGCGCCTTCC TGGCCGAGGT GAAACAGATG    600

CGAGCCCGGA GGAAGACGGC CAAGATGCTG ATGGTGGTGC TGCTGGTCTT CGCCCTCTGC    660

TACCTGCCCA TCAGTGTCCT CAACGTCCTC AAGAGGGTCT TCGGGATGTT CCGCCAAGCC    720

AGCGACCGAG AGGCCATCTA CGCCTGCTTC ACCTTCTCCC ACTGGCTGGT GTACGCCAAC    780

AGCGCCGCC                                                            789
```

(2) INFORMATION FOR SEQ ID NO: 56:

(i) SEQUENCE CHARACTERISTICS:
        (A) LENGTH: 328 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 56:

```
Met Glu Trp Asp Asn Gly Thr Gly Gln Ala Leu Gly Leu Pro Pro Thr
 1               5                  10                  15

Thr Cys Val Tyr Arg Glu Asn Phe Lys Gln Leu Leu Pro Pro Val
             20                  25                  30

Tyr Ser Ala Val Leu Ala Ala Gly Leu Pro Leu Asn Ile Cys Val Ile
         35                  40                  45

Thr Gln Ile Cys Thr Ser Arg Arg Ala Leu Thr Arg Thr Ala Val Tyr
     50                  55                  60

Thr Leu Asn Leu Ala Leu Ala Asp Leu Leu Tyr Ala Cys Ser Leu Pro
 65                  70                  75                  80

Leu Leu Ile Tyr Asn Tyr Ala Gln Gly Asp His Trp Pro Phe Gly Asp
                 85                  90                  95

Phe Ala Cys Arg Leu Val Arg Phe Leu Phe Tyr Ala Asn Leu His Gly
            100                 105                 110

Ser Ile Leu Phe Leu Thr Cys Ile Ser Phe Gln Arg Tyr Leu Gly Ile
        115                 120                 125

Cys His Pro Leu Ala Pro Trp His Lys Arg Gly Arg Arg Ala Ala
    130                 135                 140

Trp Leu Val Cys Val Thr Val Trp Leu Ala Val Thr Thr Gln Cys Leu
145                 150                 155                 160

Pro Thr Ala Ile Phe Ala Ala Thr Gly Ile Gln Arg Asn Arg Thr Val
                165                 170                 175

Cys Tyr Asp Leu Ser Pro Pro Ala Leu Ala Thr His Tyr Met Pro Tyr
            180                 185                 190

Gly Met Ala Leu Thr Val Ile Gly Phe Leu Leu Pro Phe Ala Ala Leu
        195                 200                 205

Leu Ala Cys Tyr Cys Leu Leu Ala Cys Arg Leu Cys Arg Gln Asp Gly
    210                 215                 220

Pro Ala Glu Pro Val Ala Gln Glu Arg Gly Lys Ala Ala Arg Met
225                 230                 235                 240
```

```
Ala Val Val Ala Ala Ala Phe Ala Ile Ser Phe Leu Pro Phe His
            245                 250                 255

Ile Thr Lys Thr Ala Tyr Leu Ala Val Gly Ser Thr Pro Gly Val Pro
            260                 265                 270

Cys Thr Val Leu Glu Ala Phe Ala Ala Tyr Lys Gly Thr Arg Pro
            275                 280             285

Phe Ala Ser Ala Asn Ser Val Leu Asp Pro Ile Leu Phe Tyr Phe Thr
        290                 295                 300

Gln Lys Lys Phe Arg Arg Arg Pro His Glu Leu Leu Gln Lys Leu Thr
305                 310                 315                 320

Ala Lys Trp Gln Arg Gln Gly Arg
                325
```

(2) INFORMATION FOR SEQ ID NO: 57:

(i) SEQUENCE CHARACTERISTICS:
        (A) LENGTH: 984 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 57:

```
ATGGAATGGG ACAATGGCAC AGGCCAGGCT CTGGGCTTGC CACCCACCAC CTGTGTCTAC         60
CGCGAGAACT TCAAGCAACT GCTGCTGCCA CCTGTGTATT CGGCGGTGCT GGCGGCTGGC        120
CTGCCGCTGA ACATCTGTGT CATTACCCAG ATCTGCACGT CCCGCCGGGC CCTGACCCGC        180
ACGGCCGTGT ACACCCTAAA CCTTGCTCTG GCTGACCTGC TATATGCCTG CTCCCTGCCC        240
CTGCTCATCT ACAACTATGC CCAAGGTGAT CACTGGCCCT TTGGCGACTT CGCCTGCCGC        300
CTGGTCCGCT TCCTCTTCTA TGCCAACCTG CACGGCAGCA TCCTCTTCCT CACCTGCATC        360
AGCTTCCAGC GCTACCTGGG CATCTGCCAC CCGCTGGCCC CCTGGCACAA ACGTGGGGGC        420
CGCCGGGCTG CCTGGCTAGT GTGTGTAACC GTGTGGCTGG CCGTGACAAC CCAGTGCCTG        480
CCCACAGCCA TCTTCGCTGC CACAGGCATC CAGCGTAACC GCACTGTCTG CTATGACCTC        540
AGCCCGCCTG CCCTGGCCAC CCACTATATG CCCTATGGCA TGGCTCTCAC TGTCATCGGC        600
TTCCTGCTGC CCTTTGCTGC CCTGCTGGCC TGCTACTGTC TCCTGGCCTG CCGCCTGTGC        660
CGCCAGGATG GCCCGGCAGA GCCTGTGGCC CAGGAGCGGC GTGGCAAGGC GGCCCGCATG        720
GCCGTGGTGG TGGCTGCTGC CTTTGCCATC AGCTTCCTGC CTTTTCACAT CACCAAGACA        780
GCCTACCTGG CAGTGGGCTC GACGCCGGGC GTCCCCTGCA CTGTATTGGA GGCCTTTGCA        840
GCGGCCTACA AAGGCACGCG GCCGTTTGCC AGTGCCAACA GCGTGCTGGA CCCCATCCTC        900
TTCTACTTCA CCCAGAAGAA GTTCCGCCGG CGACCACATG AGCTCCTACA GAAACTCACA        960
GCCAAATGGC AGAGGCAGGG TCGC                                               984
```

(2) INFORMATION FOR SEQ ID NO: 58:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 58:

```
ACAGCCATCT TCGCTGCCAC AGGCAT                                    26

(2) INFORMATION FOR SEQ ID NO: 59:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 59:

AGACAGTAGC AGGCCAGCAG GGCAGCAAA                                 29

(2) INFORMATION FOR SEQ ID NO: 60:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc = "synthetic DNA (ix) FEATURE:
        (D) OTHER INFORMATION:/note= N is inosine; Y is C or T; S is
            G or C; K is G or T; M is A or C."

(xi) SEQUENCE DESCRIPTION: SEQ ID NO: 60:

CTGTGYGYSA TYGCNNTKGA YMGSTAC                                   27

(2) INFORMATION FOR SEQ ID NO: 61:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc = "synthetic DNA (ix) FEATURE:
        (D) OTHER INFORMATION:/note= N is inosine; S is G or C; W is
            A or T; R is A or G; K is G or T; Y is C or T."

(xi) SEQUENCE DESCRIPTION: SEQ ID NO: 61:

AKGWAGWAGG GCAGCCAGCA GANSRYGAA                                 29
```